US009056865B2

(12) United States Patent  
Nair et al.

(10) Patent No.: US 9,056,865 B2  
(45) Date of Patent: Jun. 16, 2015

(54) PYRIDINE-2-DERIVATIVES AS SMOOTHENED RECEPTOR MODULATORS

(75) Inventors: Sajiv Krishnan Nair, Vista, CA (US); Simon Paul Planken, San Diego, CA (US)

(73) Assignee: Pfizer Inc., New York, NY (US)

( * ) Notice: Subject to any disclaimer, the term of this patent is extended or adjusted under 35 U.S.C. 154(b) by 108 days.

(21) Appl. No.: 13/880,298

(22) PCT Filed: Oct. 19, 2011

(86) PCT No.: PCT/IB2011/054675
§ 371 (c)(1),
(2), (4) Date: Apr. 18, 2013

(87) PCT Pub. No.: WO2012/052948
PCT Pub. Date: Apr. 26, 2012

(65) Prior Publication Data
US 2013/0210800 A1 Aug. 15, 2013

Related U.S. Application Data

(60) Provisional application No. 61/405,101, filed on Oct. 20, 2010.

(51) Int. Cl.  
*A61K 31/337* (2006.01)  
*A61K 31/497* (2006.01)  
*A61K 31/505* (2006.01)  
*A61K 31/445* (2006.01)  
*A61K 31/4965* (2006.01)  
(Continued)

(52) U.S. Cl.  
CPC ............ *C07D 487/04* (2013.01); *C07D 401/04* (2013.01); *C07D 401/14* (2013.01); *C07D 403/04* (2013.01); *C07D 403/14* (2013.01); *C07D 405/14* (2013.01); *C07D 409/14* (2013.01); *C07D 413/14* (2013.01); *C07D 213/74* (2013.01); *C07D 498/10* (2013.01)

(58) Field of Classification Search
CPC .. C07D 487/04; C07D 401/14; C07D 413/14; C07D 405/04; C07D 409/14; C07D 213/74; C07D 498/10; A61K 31/337; A61K 31/497; A61K 31/505; A61K 31/445; A61K 31/4965
USPC ............... 514/210.18, 253.01, 275, 318, 278, 514/252.18, 316, 255.06; 544/121, 130, 544/295, 331, 364, 405; 546/19, 187, 193
See application file for complete search history.

(56) References Cited

U.S. PATENT DOCUMENTS 8,148,401 B2 4/2012 Munchhof et al.  
8,431,597 B2 4/2013 Munchhof et al.  
(Continued)

FOREIGN PATENT DOCUMENTS

WO WO 2009/154739 12/2009

OTHER PUBLICATIONS

Alcedo et al., "The *Drosophila* smoothened gene encodes a seven-pass membrane protein, a putative receptor for the hedgehog signal," Cell 86: 221-232 (1996).
Chen and Struhl, "Dual roles for patched in sequestering and transducing Hedgehog," Cell 87: 553-63 (1996).
Chidambaram et al., "Mutations in the human homologue of the *Drosophila* patched gene in Caucasian and African-American nevoid basal cell carcinoma syndrome patients," Cancer Research 56: 4599-601 (1996).
Gailani et al., "The role of the human homologue of *Drosophila* patched in sporadic basal cell carcinomas," Nature Genet. 14: 78-81 (1996).
Hahn et al., "Mutations of the human homolog of *Drosophila* patched in the nevoid basal cell carcinoma syndrome," Cell 85: 841-51 (1996).

(Continued)

*Primary Examiner* — James O Wilson  
*Assistant Examiner* — Ebenezer O Sackey  
(74) *Attorney, Agent, or Firm* — Leslie A. Robinson

(57) ABSTRACT

The present application relates to compounds of Formula (I), and Formula (II), or pharmaceutically acceptable salt thereof, wherein A, X, Y, Z, e, f, $R^1$, $R^2$, $R^3$, $R^4$, $R^5$, $R^{5b}$, $R^6$, $R^7$, $R^8$, $R^9$, $R^{10}$, $R^{11}$, $R^{20}$, $R^{21}$, $R^{22}$ and $R^{23}$ are defined herein. These novel pyridine derivatives that are useful in therapy, in particular for treating diseases or conditions mediated by Smo, including the treatment of abnormal cell growth, such as cancer, in mammals. Additional embodiments relate to methods of using such compounds in the treatment of abnormal cell growth in mammals, especially humans, and to pharmaceutical compositions containing such compounds.

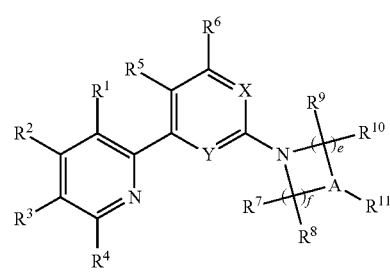

(I)

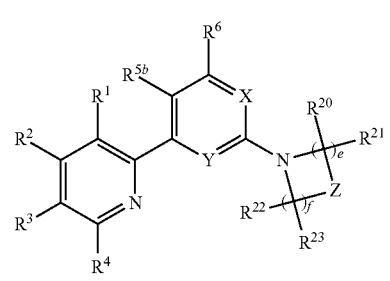

(II)

18 Claims, No Drawings

(51) Int. Cl.
  *C07D 487/04*  (2006.01)
  *C07D 401/14*  (2006.01)
  *C07D 413/14*  (2006.01)
  *C07D 409/14*  (2006.01)
  *C07D 213/74*  (2006.01)
  *C07D 498/10*  (2006.01)
  *C07D 401/04*  (2006.01)
  *C07D 403/04*  (2006.01)
  *C07D 403/14*  (2006.01)
  *C07D 405/14*  (2006.01)

(56) References Cited

U.S. PATENT DOCUMENTS

2010/0029615 A1   2/2010   Munchhof et al.
2012/0157471 A1   6/2012   Nair et al.

OTHER PUBLICATIONS

Hooper and Scott, "The *Drosophila* patched gene encodes a putative membrane protein required for segmental patterning," Cell 59: 751-65 (1989).
International Search Report for PCT/IB2011/054675, mailed Dec. 14, 2011.
International Preliminary Report on Patentability for PCT/IB2011/054675, issued Apr. 23, 2013.
Johnson et al., "Human homolog of patched, a candidate gene for the basal cell nevus syndrome," Science 272: 1668-71 (1996).
Marigo et al., "Biochemical evidence that patched is the Hedgehog receptor," Nature 384: 176-9 (1996).
Nakano et al., "A protein with several possible membrane-spanning domains encoded by the *Drosophila* segment polarity gene patched," Nature 341: 508-13 (1989).
Rohner et al., "Effective Targeting of Hedgehog Signaling in a Medulloblastoma Model with PF-5274857, a Potent and Selective Smoothened Antagonist That Penetrates the Blood-Brain Barrier," Mol. Cancer Ther., 2012; 11:57-65, published online Nov. 14, 2011.
Stevens G et al., "Toxicologic Characterization of PF-05274857, a Potent and Selective Smoothened Inhibitor for the Treatment of Advanced Cancer," Abstract No. 2268, Poster No. 226, presented at Society of Toxicology Annual Meeting 2012 on Mar 14, 2012.
Stone et al., "The tumour-suppressor gene patched encodes a candidate receptor for Sonic hedgehog," Nature 384:129-34 (1996).
Unden et al., "Mutations in the human homologue of *Drosophila* patched (PTCH) in basal cell carcinomas and the Gorlin syndrome: different in vivo mechanisms of PTCH inactivation," Cancer Res. 56: 4562-4565 (1996).
van den Heuvel & Ingham, "Smoothened encodes a receptor-like serpentine protein required for hedgehog signaling," Nature 382: 547-551 (1996).
Wicking et al., "Most germ-line mutations in the nevoid basal cell carcinoma syndrome lead to a premature termination of the Patched protein, and no genotype-phenotype correlations are evident," Am. J. Hum. Genet. 60: 21-6 (1997).
Xie et al., "Activating Smoothened mutations in sporadic basal-cell carcinoma," Nature 391: 90-92 (1998).

PYRIDINE-2-DERIVATIVES AS SMOOTHENED RECEPTOR MODULATORS

This application is the national stage filing under 35 U.S.C. 371 of Patent Cooperation Treaty Patent Application No. PCT/IB2011/054675, filed Oct. 19, 2011, which claims the benefit of U.S. Provisional Application No. 61/405,101 filed on Oct. 20, 2010, the contents of which is hereby incorporated by reference in its entirety.

FIELD OF INVENTION

Embodiments disclosed herein relate to novel pyridine derivatives that are useful in therapy, in particular for treating diseases or conditions mediated by Smo, including the treatment of abnormal cell growth, such as cancer, in mammals. Additional embodiments relate to methods of using such compounds in the treatment of abnormal cell growth in mammals, especially humans, and to pharmaceutical compositions containing such compounds.

BACKGROUND

Hedgehog (Hh) proteins are secreted morphogens that are involved in many biological processes during embryonic development. Postnatally, Hh has important roles in tissue homeostasis and aberrant Hh signaling is associated with developmental disorders and several types of cancer. At the cell surface, the Hh signal is thought to be relayed by the 12 transmembrane domain protein Patched (Ptc) (Hooper and Scott, Cell 59: 75 1-65 (1989); Nakano et al., Nature 341: 508-13 (1989)) and the G-protein-coupled-like receptor Smoothened (Smo) (Alcedo et al., Cell 86: 221-232 (1996); van den Heuvel and Tngham, Nature 382: 547-551 (1996)). Both genetic and biochemical evidence support a receptor model where Ptc and Smo are part of a multi-component receptor complex (Chen and Struhl, Cell 87: 553-63 (1996); Mango et al., Nature 384: 176-9 (1996); Stone et al., Nature 384:129-34 (1996)). Upon binding of Hh to Ptc, the normal inhibitory effect of Ptc on Smo is relieved, allowing Smo to transduce the Hh signal across the plasma membrane. However, the exact mechanism by which Ptc controls Smo activity still has yet to be clarified.

The signaling cascade initiated by Smo results in activation of Gli transcription factors that translocate into the nucleus where they control transcription of target genes. Gli has been shown to influence transcription of Hh pathway inhibitors such as Ptc and Hip I in a negative feedback loop indicating that tight control of the Hh pathway activity is required for proper cellular differentiation and organ formation. Uncontrolled activation of Hh signaling pathway is associated with malignancies in particular those of the brain, skin and muscle as well as angiogenesis. An explanation for this is that the Hh pathway has been shown to regulate cell proliferation in adults by activation of genes involved in cell cycle progression such as cyclin D which is involved in G1-S transition. Also, Sonic Hedgehog (SHh), an ortholog of Hh, blocks cell-cycle arrest mediated by p21, an inhibitor of cyclin dependent kinases. Hh signaling is further implicated in cancer by inducing components in the EGFR pathway (EGF, Her2) involved in proliferation as well as components in the PDGF (PDGFa) and VEGF pathways involved in angiogenesis. Loss of function mutations in the Ptc gene have been identified in patients with the basal cell nevus syndrome (BCNS), a hereditary disease characterized by multiple basal cell carcinomas (BCCs). Dysfunctional Ptc gene mutations have also been associated with a large percentage of sporadic basal cell carcinoma tumors (Chidambaram et al., Cancer Research 56: 4599-601 (1996); Gailani et al., Nature Genet. 14: 78-81 (1996); Hahn et al., Cell 85: 841-51 (1996); Johnson et al., Science 272: 1668-71 (1996); Unden et al., Cancer Res. 56: 4562-5; Wicking et al., Am. J. Hum. Genet. 60: 21-6 (1997)). Loss of Ptc function is thought to cause an uncontrolled Smo signaling in basal cell carcinoma. Similarly, activating Smo mutations have been identified in sporadic BCC tumors (Xie et al., Nature 391: 90-2 (1998)), emphasizing the role of Smo as the signaling subunit in the receptor complex for SHh. Various inhibitors of hedgehog signaling have been investigated such as Cyclopamine, a natural alkaloid that has been shown to arrest cell cycle at G0-GI and to induce apoptosis in SCLC. Cyclopamine is believed to inhibit Smo by binding to its heptahelical bundle. Forskolin has been shown to inhibit the Hh pathway downstream from Smo by activating protein kinase A (PKA) which maintains Gli transcription factors inactive. Despite advances with these and other compounds, there remains a need for potent inhibitors of the hedgehog signaling pathway.

SUMMARY

Each of the embodiments described below can be combined with any other embodiment described herein not inconsistent with the embodiment with which it is combined. Furthermore, each of the embodiments described herein envisions within its scope pharmaceutically acceptable salts of the compounds described herein. Accordingly, the phrase "or a pharmaceutically acceptable salt thereof" is implicit in the description of all compounds described herein.

Some embodiments described herein relate to a compound of formula (I),

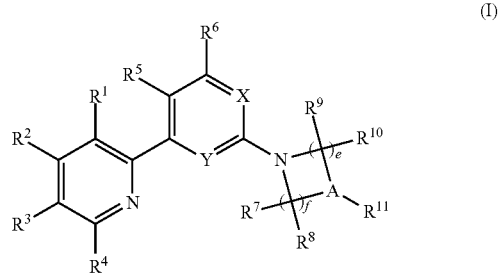

wherein:

A is selected from N and C—$R^{13}$;

X and Y are independently selected from N and C—$R^{12}$, provided that at least one of X and Y is N;

$R^1$, $R^2$, $R^3$, $R^4$, $R^6$, $R^{12}$ and $R^{13}$ are independently selected from hydrogen, —$(CR^{14}R^{15})_n$halo, —$(CR^{14}R^{15})_n$CN, —$(CR^{14}R^{15})_n$CF$_3$, —$(CR^{14}R^{15})_n$(C$_1$-C$_{10}$alkyl), —$(CR^{14}R^{15})_n$(C$_2$-C$_6$alkenyl), —$(CR^{14}R^{15})_n$(C$_2$-C$_6$alkynyl), —$(CR^{14}R^{15})_n$NR$^{16}$R$^{17}$, —$(CR^{14}R^{15})_n$OR$^{16}$, —$(CR^{14}R^{15})_n$C(O)R$^{16}$, —$(CR^{14}R^{15})_n$C(O)OR$^{16}$, —$(CR^{14}R^{15})_n$S(O)R$^{16}$, —$(CR^{14}R^{15})_n$S(O)$_2$R$^{16}$, —$(CR^{14}R^{15})_n$S(O)$_2$NR$^{16}$R$^{17}$, —$(CR^{14}R^{15})_n$NR$^{16}$S(O)$_2$R$^{17}$, —$(CR^{14}R^{15})_n$(C$_3$-C$_{10}$cycloalkyl), —$(CR^{14}R^{15})_n$(3-12 membered heterocyclyl), —$(CR^{14}R^{15})_n$(C$_6$-C$_{10}$aryl), and —$(CR^{14}R^{15})_n$(5-12 membered heteroaryl);

$R^5$ is selected from halo, C$_1$-C$_{10}$ alkyl, and —CF$_3$, each $R^7$, $R^8$, $R^9$, and $R^{10}$ is independently selected from hydrogen, —$(CR^{14}R^{15})_n$halo, —$(CR^{14}R^{15})_n$CN, —$(CR^{14}R^{15})_n$CF$_3$, —$(CR^{14}R^{15})_n$(C$_1$-C$_{10}$alkyl), —$(CR^{14}R^{15})_n$(C$_2$-C$_6$alkenyl), —$(CR^{14}R^{15})_n$(C$_2$-C$_6$alkynyl), —$(CR^{14}R^{15})_nNR^{16}R^{17}$, —$(CR^{14}R^{15})_nOR^{16}$, —$(CR^{14}R^{15})_nC(O)R^{16}$, —$(CR^{14}R^{15})_nC(O)OR^{16}$, —$(CR^{14}R^{15})_nS(O)R^{16}$, —$(CR^{14}R^{15})_nS(O)_2R^{16}$, —$(CR^{14}R^{15})_nS(O)_2NR^{16}R^{17}$, —$(CR^{14}R^{15})_nNR^{16}S(O)_2R^{17}$, —$(CR^{14}R^{15})_n(C_3-C_{10}cycloalkyl)$, —$(CR^{14}R^{15})_n(3-12\ membered\ heterocyclyl)$, —$(CR^{14}R^{15})_n(C_6-C_{10}aryl)$, and —$(CR^{14}R^{15})_n(5-12\ membered\ heteroaryl)$; or each $R^7$ and $R^8$, or $R^9$ and $R^{10}$, together with the carbon to which they are attached, may combine to form a carbonyl group; or each $R^7$ and $R^9$, or $R^8$ and $R^{10}$, may combine to form a 5 or 6 membered ring when said $R^7$ and said $R^9$, or said W and said $R^{10}$, are each —$(CR^{14}R^{15})_n(C_1-C_{10}alkyl)$.

$R^{11}$ is selected from hydrogen, —$(CR^{14}R^{15})_n$halo, —$(CR^{14}R^{15})_nCN$, —$(CR^{14}R^{15})_nCF_3$, —$(CR^{14}R^{15})_n(C_1-C_{10}alkyl)$, —$(CR^{14}R^{15})_n(C_2-C_6alkenyl)$, —$(CR^{14}R^{15})_n(C_2-C_6alkynyl)$, —$(CR^{14}R^{15})_nNR^AR^B$, —$(CR^{14}R^{15})_nNR^AOR^B$, —$(CR^{14}R^{15})_nNR^AC(O)R^B$, —$(CR^{14}R^{15})_nNR^AC(O)OR^B$, —$(CR^{14}R^{15})_nOR^A$, —$(CR^{14}R^{15})_nC(O)R^A$, —$(CR^{14}R^{15})_nC(O)OR^A$, —$(CR^{14}R^{15})_nS(O)R^A$, —$(CR^{14}R^{15})_nS(O)_2R^A$, —$(CR^{14}R^{15})_nS(O)NR^AR^B$, —$(CR^{14}R^{15})_nNR^AS(O)_2R^B$, —$(CR^{14}R^{15})_nC(O)NR^AR^B$, —$(CR^{14}R^{15})_n(C_3-C_{10}cycloalkyl)$, —$(CR^{14}R^{15})_n(3-12\ membered\ heterocyclyl)$, —$(CR^{14}R^{15})_n(C_6-C_{10}aryl)$, and —$(CR^{14}R^{15})_n(5-12\ membered\ heteroaryl)$, wherein each of said $C_3-C_{10}cycloalkyl$, said 3-12 membered heterocyclyl, said $C_6-C_{10}aryl$, and said 5-12 membered heteroaryl groups is substituted with one or more $R^{14}$ groups; or $R^{11}$ and $R^{13}$, together with the carbon to which they are attached, may combine to form a 3-12 membered heterocyclyl group which is substituted with one or more $R^{14}$ groups;

$R^A$ and $R^B$ are independently selected from hydrogen, —$(CR^{14}R^{15})_n$halo, —$(CR^{14}R^{15})_nCN$, —$(CR^{14}R^{15})_nCF_3$, —$(CR^{14}R^{15})_n(C_1-C_{10}alkyl)$, —$(CR^{14}R^{15})_n(C_2-C_6alkenyl)$, —$(CR^{14}R^{15})_n(C_2-C_6alkynyl)$, —$(CR^{14}R^{15})_nNR^{16}R^{17}$, —$(CR^{14}R^{15})_nNR^{16}OR^{17}$, —$(CR^{14}R^{15})_nNR^{16}C(O)R^{17}$, —$(CR^{14}R^{15})_nNR^{16}C(O)OR^{17}$, —$(CR^{14}R^{15})_nOR^{16}$, —$(CR^{14}R^{15})_nC(O)R^{16}$, —$(CR^{14}R^{15})_nC(O)OR^{16}$, —$(CR^{14}R^{15})_nS(O)R^{16}$, —$(CR^{14}R^{15})_nS(O)_2R^{16}$, —$(CR^{14}R^{15})_nS(O)_2NR^{16}R^{17}$, —$(CR^{14}R^{15})_nNR^{16}S(O)_2R^{17}$, —$(CR^{14}R^{15})_n(C_3-C_{10}cycloalkyl)$, —$(CR^{14}R^{15})_n(3-12\ membered\ heterocyclyl)$, —$(CR^{14}R^{15})_n(C_6-C_{10}aryl)$, and —$(CR^{14}R^{15})_n(5-12\ membered\ heteroaryl)$, wherein each of said $C_3-C_{10}cycloalkyl$, said 3-12 membered heterocyclyl, said $C_6-C_{10}aryl$, and said 5-12 membered heteroaryl groups is substituted with one or more $R^{14}$ groups;

each $R^{14}$, $R^{15}$, $R^{16}$ and $R^{17}$ is independently selected from hydrogen, —$(CR^{24}R^{25})_n$halo, —$(CR^{24}R^{25})_nCF_3$, —$(CR^{24}R^{25})_n(C_1-C_{10}alkyl)$, —$(CR^{24}R^{25})_n(C_2-C_6alkenyl)$, —$(CR^{24}R^{25})_n(C_2-C_6alkynyl)$, —$(CR^{24}R^{25})_nOR^{18}$, —$(CR^{24}R^{25})_nNR^{18}R^{19}$, —$(CR^{24}R^{28})_nCN$, —$(CR^{24}R^{25})_nS(O)_2R^{18}$, —$(CR^{24}R^{25})_nS(O)_2NR^{18}R^{19}$, —$(CR^{24}R^{25})_n(C_3-C_{10}cycloalkyl)$, —$(CR^{24}R^{25})_n(3-12\ membered\ heterocyclyl)$, —$(CR^{24}R^{25})_n(C_6-C_{10}aryl)$, and —$(CR^{24}R^{25})_n(5-12\ membered\ heteroaryl)$, wherein each of said $C_3-C_{10}cycloalkyl$, said 3-12 membered heterocyclyl, said $C_6-C_{10}aryl$, and said 5-12 membered heteroaryl groups is substituted with one or more $R^{18}$ groups;

each $R^{18}$, $R^{19}$, $R^{24}$ and $R^{25}$ is independently selected from hydrogen, —$(CH_2)_n(C_1-C_{10}alkyl)$, —$(CH_2)_n(C_3-C_{10}cycloalkyl)$, —$(CH_2)_n(3-12\ membered\ heterocyclyl)$, —$(CH_2)_n(C_6-C_{10}aryl)$, and —$(CH_2)_n(5-12\ membered\ heteroaryl)$;

e is 1 or 2;
f is 1 or 2; and
each n is independently selected from 0, 1, 2, 3, 4, 5, and 6;
or
a pharmaceutically acceptable salt thereof.

Some embodiments relate to a compound of formula (I), or a pharmaceutically acceptable salt thereof, wherein $R^1$, $R^2$, $R^3$, $R^4$, and $R^6$ are independently selected from hydrogen, —$(CR^{14}R^{15})_n$halo, —$(CR^{14}R^{15})_nCN$, —$(CR^{14}R^{15})_nCF_3$, —$(CR^{14}R^{15})_n(C_1-C_{10}alkyl)$, and —$(CR^{14}R^{15})_nOR^{16}$.

Additional embodiments relate to a compound of formula (I), or a pharmaceutically acceptable salt thereof, wherein $R^1$, $R^2$, $R^3$, $R^4$, and $R^6$ are independently selected from hydrogen, -halo, —CN, —$CF_3$, and —$(C_1-C_{10}alkyl)$.

Further embodiments relate to a compound of formula (I), or a pharmaceutically acceptable salt thereof, wherein each $R^7$, $R^8$, $R^9$, and $R^{10}$ is independently selected from hydrogen, —$(CR^{14}R^{15})''$halo, —$(CR^{14}R^{15})_nCN$, —$(CR^{14}R^{15})_nCF_3$, —$(CR^{14}R^{15})_n(C_1-C_{10}\ alkyl)$, and —$(CR^{14}R^{15})_nOR^{16}$.

Some embodiments relate to a compound of formula (I), or a pharmaceutically acceptable salt thereof, wherein each $R^7$, $R^8$, $R^9$, and $R^{10}$ is independently selected from hydrogen, -halo, —CN, —$CF_3$, and —$(C_1-C_{10}alkyl)$.

More embodiments relate to a compound of formula (I), or a pharmaceutically acceptable salt thereof, wherein e is 2 and f is 2.

Some embodiments relate to a compound of formula (I), or a pharmaceutically acceptable salt thereof, wherein $R^5$ is halo.

Additional embodiments relate to a compound of formula (I), or a pharmaceutically acceptable salt thereof, wherein X is N; Y is C—$R^{12}$; and $R^{12}$ is selected from hydrogen, -halo, —CN, —$CF_3$, and —$(C_1-C_{10}alkyl)$.

Further embodiments relate to a compound of formula (I), or a pharmaceutically acceptable salt thereof, wherein X is C—$R^{12}$; Y is N; and $R^{12}$ is selected from hydrogen, -halo, —CN, —$CF_3$, and —$(C_1-C_{10}alkyl)$.

More embodiments relate to a compound of formula (I), or a pharmaceutically acceptable salt thereof, wherein X is N and Y is N.

Some embodiments relate to a compound of formula (I), or a pharmaceutically acceptable salt thereof, wherein $R^{11}$ is selected from —$(CR^{14}R^{15})_nC(O)R^A$, —$(CR^{14}R^{15})_nNR^AC(O)R^B$, —$(CR^{14}R^{15})_nS(O)_2R^A$, —$(CR^{14}R^{15})_nS(O)_2NR^AR^B$, and —$(CR^{14}R^{15})_nNR^AS(O)_2R^B$.

Some embodiments relate to a compound of formula (I), or a pharmaceutically acceptable salt thereof, wherein A is N.

Some embodiments relate to a compound of formula (I), or a pharmaceutically acceptable salt thereof, wherein $R^{11}$ is selected from —$C(O)R^A$ and —$S(O)_2R^A$.

Additional embodiments relate to a compound of formula (I), or a pharmaceutically acceptable salt thereof, wherein $R^5$ is F or Cl; $R^{11}$ is $C(O)R^A$; and $R^A$ is —$(CR^{14}R^{15})_nS(O)_2R^{16}$.

In some embodiments, the compound of formula (I) is:

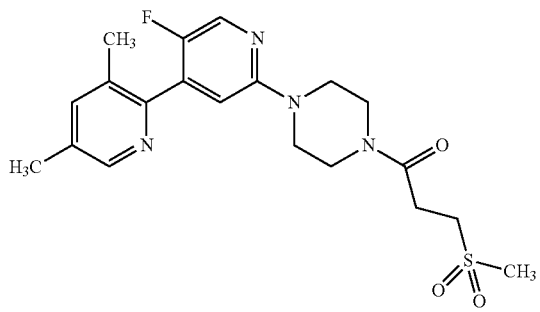

or a pharmaceutically acceptable salt thereof.

In other embodiments, the compound of formula (I) is:

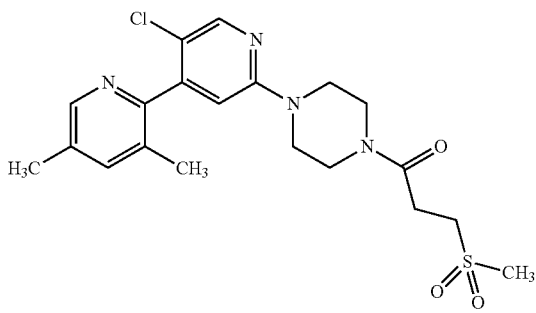

or a pharmaceutically acceptable salt thereof.

Additional embodiments relate to a compound of formula (I), or a pharmaceutically acceptable salt thereof, wherein A is $C-R^{13}$.

Further embodiments relate to a compound of formula (I), or a pharmaceutically acceptable salt thereof, wherein $R^{13}$ is hydrogen.

Some embodiments relate to a compound of formula (I), or a pharmaceutically acceptable salt thereof, wherein $R^{11}$ is selected from $-NR^{A}C(O)R^{B}$ and $-NR^{A}S(O)_{2}R^{B}$.

More embodiments relate to a compound of formula (I), or a pharmaceutically acceptable salt thereof, wherein $R^{11}$ is $NR^{A}S(O)_{2}R^{B}$.

Some embodiments relate to a compound of formula (I), or a pharmaceutically acceptable salt thereof, wherein $R^{4}$ is hydrogen and $R^{5}$ is F or Cl.

In some embodiments, the compound of formula (I) is:

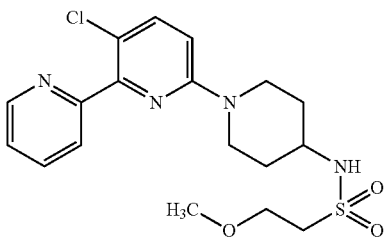 [SMILES: COCCS(=O)(=O)NC1CCN(c2ccc(Cl)c(-c3ccccn3)n2)CC1]

or a pharmaceutically acceptable salt thereof.

Some embodiments described herein relate to a compound of formula (II),

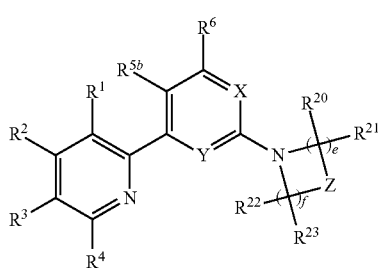

wherein:

X and Y are independently selected from N and $C-R^{12}$, provided that at least one of X and Y is N;

Z is selected from $NR^{11b}$ and $CR^{13}NR^{14}R^{11b}$;

$R^{1}$, $R^{2}$, $R^{3}$, $R^{4}$, $R^{6b}$, $R^{6}$, $R^{12}$ and $R^{13}$ are independently selected from hydrogen, $-(CR^{14}R^{15})_{n}$halo, $-(CR^{14}R^{15})_{n}$CN, $-(CR^{14}R^{15})_{n}$CF$_{3}$, $-(CR^{14}R^{15})_{n}$(C$_{1}$-C$_{10}$alkyl), $-(CR^{14}R^{15})_{n}$(C$_{2}$-C$_{6}$alkenyl), $-(CR^{14}R^{15})_{n}$(C$_{2}$-C$_{6}$alkynyl), $-(CR^{14}R^{15})_{n}$NR$^{16}$R$^{17}$, $-(CR^{14}R^{15})_{n}$OR$^{16}$, $-(CR^{14}R^{15})_{n}$C(O)R$^{16}$, $-(CR^{14}R^{15})_{n}$C(O)OR$^{16}$, $-(CR^{14}R^{15})_{n}$S(O)R$^{16}$, $-(CR^{14}R^{15})_{n}$S(O)$_{2}$R$^{16}$, $-(CR^{14}R^{15})_{n}$S(O)$_{2}$NR$^{16}$R$^{17}$, $-(CR^{14}R^{15})_{n}$NR$^{16}$S(O)$_{2}$R$^{17}$, $-(CR^{14}R^{15})_{n}$(C$_{3}$-C$_{10}$cycloalkyl), $-(CR^{14}R^{15})_{n}$(3-12 membered heterocyclyl), $-(CR^{14}R^{15})_{n}$(C$_{6}$-C$_{10}$aryl), and $-(CR^{14}R^{15})_{n}$(5-12 membered heteroaryl);

each $R^{20}$, $R^{21}$, $R^{22}$ and $R^{23}$ is independently selected from hydrogen, $-(CR^{14}R^{15})_{n}$halo, $-(CR^{14}R^{15})_{n}$CN, $-(CR^{14}R^{15})_{n}$CF$_{3}$, $-(CR^{14}R^{15})_{n}$(C$_{1}$-C$_{10}$alkyl), $-(CR^{14}R^{15})_{n}$(C$_{2}$-C$_{6}$alkenyl), $-(CR^{14}R^{15})_{n}$(C$_{2}$-C$_{6}$alkynyl), $-(CR^{14}R^{15})_{n}$NR$^{16}$R$^{17}$, $-(CR^{14}R^{15})_{n}$OR$^{16}$, $-(CR^{14}R^{15})_{n}$C(O)R$^{16}$, $-(CR^{14}R^{15})_{n}$C(O)OR$^{16}$, $-(CR^{14}R^{15})_{n}$S(O)R$^{16}$, $-(CR^{14}R^{15})_{n}$S(O)$_{2}$R$^{16}$, $-(CR^{14}R^{15})_{n}$S(O)$_{2}$NR$^{16}$R$^{17}$, $-(CR^{14}R^{15})_{n}$NR$^{16}$S(O)$_{2}$R$^{17}$, $-(CR^{14}R^{15})_{n}$(C$_{3}$-C$_{10}$cycloalkyl), $-(CR^{14}R^{15})_{n}$(3-12 membered heterocyclyl), $-(CR^{14}R^{15})_{n}$(C$_{6}$-C$_{10}$aryl), and $-(CR^{14}R^{15})_{n}$(5-12 membered heteroaryl); or each $R^{20}$ and $R^{21}$, or $R^{22}$ and $R^{23}$, together with the carbon to which they are attached, may combine to form a carbonyl group; or each $R^{20}$ and $R^{22}$, or $R^{21}$ and $R^{23}$, may combine to form a 5 or 6 membered ring when said $R^{20}$ and said $R^{22}$, or said $R^{21}$ and said $R^{23}$, are each $-(CR^{14}R^{15})_{n}$(C$_{1}$-C$_{10}$alkyl).

$R^{11b}$ is selected from C(O)R$^{A}$ and S(O)$_{2}$R$^{A}$;

$R^{A}$ is selected from $-(CR^{14}R^{15})_{n}$CF$_{3}$, $-(CR^{14}R^{15})_{n}$(C$_{1}$-C$_{10}$alkyl), $-(CR^{14}R^{15})_{n}$(C$_{2}$-C$_{6}$alkenyl), $-(CR^{14}R^{15})_{n}$(C$_{2}$-C$_{6}$alkynyl), $-(CR^{14}R^{15})_{n}$NR$^{16}$R$^{17}$, $-(CR^{14}R^{15})_{n}$NR$^{16}$OR$^{17}$, $-(CR^{14}R^{15})_{n}$NR$^{16}$C(O)R$^{17}$, $-(CR^{14}R^{15})_{n}$NR$^{16}$C(O)OR$^{17}$, $-(CR^{14}R^{15})_{n}$NR$^{16}$S(O)$_{2}$R$^{17}$, $-(CR^{14}R^{15})_{n}$(C$_{3}$-C$_{10}$cycloalkyl), $-(CR^{14}R^{15})_{n}$(3-12 membered heterocyclyl), $-(CR^{14}R^{15})_{n}$(C$_{6}$-C$_{10}$aryl), and $-(CR^{14}R^{15})_{n}$(5-12 membered heteroaryl), $-(CR^{14}R^{15})_{m}$halo, $-(CR^{14}R^{15})_{m}$CN, $-(CR^{14}R^{15})_{m}$OR$^{16}$, $-(CR^{14}R^{15})_{m}$C(O)R$^{16}$, $-(CR^{14}R^{15})_{m}$C(O)OR$^{16}$, $-(CR^{14}R^{15})_{m}$S(O)R$^{16}$, $-(CR^{14}R^{15})_{m}$S(O)$_{2}$R$^{16}$, and $-(CR^{14}R^{15})_{m}$S(O)$_{2}$NR$^{16}$R$^{17}$, wherein said C$_{3}$-C$_{10}$cycloalkyl, said 3-12 membered heterocyclyl, said C$_{6}$-C$_{10}$aryl, and said 5-12 membered heteroaryl are each substituted with one or more $R^{14}$ groups;

each $R^{14}$, $R^{15}$, $R^{16}$ and $R^{17}$ is independently selected from hydrogen, $-(CR^{24}R^{25})_{n}$halo, $-(CR^{24}R^{25})_{n}$CF$_{3}$, $-(CR^{24}R^{25})_{n}$C$_{1}$-C$_{10}$alkyl, $-(CR^{24}R^{25})_{n}$C$_{2}$-C$_{6}$alkenyl, $-(CR^{24}R^{25})_{n}$C$_{2}$-C$_{6}$alkynyl, $-(CR^{24}R^{25})_{n}$OR$^{18}$, $-(CR^{24}R^{25})_{n}$NR$^{18}$R$^{19}$, $-(CR^{24}R^{25})_{n}$CN, $(CR^{24}R^{25})_{n}$S(O)$_{2}$R$^{18}$, $-(CR^{24}R^{25})_{n}$S(O)$_{2}$NR$^{18}$R$^{19}$, $-(CR^{24}R^{25})_{n}$C$_{3}$-C$_{10}$cycloalkyl, $-(CR^{24}R^{25})_{n}$3-12 membered heterocyclyl, $-(CR^{24}R^{25})_{n}$C$_{6}$-C$_{10}$aryl, and $-(CR^{24}R^{25})_{n}$5-12 membered heteroaryl, wherein each of said C$_{3}$-C$_{10}$cycloalkyl, said 3-12 membered heterocyclyl, said C$_{6}$-C$_{10}$aryl, and said 5-12 membered heteroaryl groups is substituted with one or more $R^{18}$ groups;

each $R^{18}$, $R^{19}$, $R^{24}$ and $R^{25}$ is independently selected from hydrogen, $-(CH_{2})_{n}$(C$_{1}$-C$_{10}$alkyl), $-(CH_{2})_{n}$(C$_{3}$-C$_{10}$cycloalkyl), $-(CH_{2})_{n}$(3-12 membered heterocyclyl), $-(CH_{2})_{n}$(C$_{6}$-C$_{10}$aryl), and $-(CH_{2})_{n}$(5-12 membered heteroaryl);

e is 2;

f is 2;

each n is independently selected from 0, 1, 2, 3, 4, 5, and 6; and each m is independently selected from 1, 2, 3, 4, 5, and 6; or a pharmaceutically acceptable salt thereof.

Some embodiments relate to a compound of formula (II), or a pharmaceutically acceptable salt thereof, wherein $R^1$, $R^2$, $R^3$, $R^4$, and $R^6$ are independently selected from hydrogen, $-(CR^{14}R^{15})_n$halo, $-(CR^{14}R^{15})_n$CN, $-(CR^{14}R^{15})_n$CF$_3$, $-(CR^{14}R^{15})_n(C_1$-$C_{10}$alkyl), and $-(CR^{14}R^{15})_n$OR$^{16}$.

Additional embodiments relate to a compound of formula (II), or a pharmaceutically acceptable salt thereof, wherein $R^1$, $R^2$, $R^3$, $R^4$, and $R^6$ are independently selected from hydrogen, -halo, $-$CN, $-$CF$_3$, and $-(C_1$-$C_{10}$alkyl).

More embodiments relate to a compound of formula (II), or a pharmaceutically acceptable salt thereof, wherein each $R^{20}$, $R^{21}$, $R^{22}$, and $R^{23}$ is independently selected from hydrogen, $-(CR^{14}R^{15})_n$halo, $-(CR^{14}R^{15})_n$CN, $-(CR^{14}R^{15})_n$CF$_3$, $-(CR^{14}R^{15})_n(C_1$-$C_{10}$alkyl), and $-(CR^{14}R^{15})_n$OR$^{16}$.

Further embodiments relate to a compound of formula (II), or a pharmaceutically acceptable salt thereof, wherein each $R^{20}$, $R^{21}$, $R^{22}$, and $R^{23}$ is independently selected from hydrogen, -halo, $-$CN, $-$CF$_3$, and $-(C_1$-$C_{10}$alkyl).

Yet additional embodiments relate to a compound of formula (II), or a pharmaceutically acceptable salt thereof, wherein $R^{5b}$ is selected from hydrogen, $-(CR^{14}R^{15})_n$halo, $-(CR^{14}R^{15})_n$CN, $-(CR^{14}R^{15})_n$CF$_3$, $-(CR^{14}R^{15})_n(C_1$-$C_{10}$alkyl), and $-(CR^{14}R^{15})_n$OR$^{16}$.

Some embodiments relate to a compound of formula (II), or a pharmaceutically acceptable salt thereof, wherein $R^{5b}$ is selected from hydrogen, -halo, $-$CN, $-$CF$_3$, and $-(C_1$-$C_{10}$alkyl).

Some embodiments relate to a compound of formula (II), or a pharmaceutically acceptable salt thereof, wherein $R^{5b}$ is selected from hydrogen, bromine, chlorine, and fluorine.

Additional embodiments relate to a compound of formula (II), or a pharmaceutically acceptable salt thereof, wherein X is N; Y is C—$R^{12}$; and $R^{12}$ is selected from hydrogen, -halo, $-$CN, $-$CF$_3$, and $-(C_1$-$C_{10}$alkyl).

Further embodiments relate to a compound of formula (II), or a pharmaceutically acceptable salt thereof, wherein X is C—$R^{12}$; Y is N; and $R^{12}$ is selected from hydrogen, -halo, $-$CN, $-$CF$_3$, and $-(C_1$-$C_{10}$alkyl).

Still more embodiments relate to a compound of formula (II), or a pharmaceutically acceptable salt thereof, wherein X is N and Y is N.

Some embodiments relate to a compound of formula (II), or a pharmaceutically acceptable salt thereof, wherein Z is CR$^{13}$NR$^{14}$R$^{11b}$.

Further embodiments relate to a compound of formula (II), or a pharmaceutically acceptable salt thereof, wherein $R^{13}$ is selected from hydrogen, -halo, $-$CN, $-$CF$_3$, and $-(C_1$-$C_{10}$alkyl).

Additional embodiments relate to a compound of formula (II), or a pharmaceutically acceptable salt thereof, wherein Z is NR$^{11b}$.

Some embodiments relate to a compound of formula (II), or a pharmaceutically acceptable salt thereof, wherein $R^{5b}$ is selected from hydrogen, chlorine, and fluorine; $R^{11b}$ is S(O)$_2$R$^A$; $R^A$ is selected from $-(CR^{14}R^{15})_nC_1$-$C_{10}$alkyl), $-(CR^{14}R^{15})_m$OR$^{16}$, and $-(CR^{14}R^{15})_m$C(O)R$^{16}$; and R$^{16}$ is selected from hydrogen, $-$CF$_3$, and $C_1$-$C_{10}$alkyl.

Some embodiments relate to a compound of formula (II), or a pharmaceutically acceptable salt thereof, wherein $R^{5b}$ is selected from hydrogen, chlorine, and fluorine; $R^{11b}$ is C(O)R$^A$; and $R^A$ is $-(CR^{14}R^{15})_n(C_1$-$C_{10}$alkyl), $-(CR^{14}R^{15})_n$NR$^{16}$R$^{17}$, $-(CR^{14}R^{15})_m$OR$^{16}$, and $-(CR^{14}R^{15})_m$C(O)R$^{16}$, and $-(CR^{14}R^{15})_m$S(O)$_2$R$^{16}$.

In some embodiments, the compound of formula (II) is:

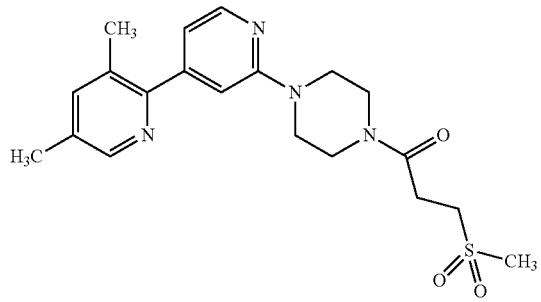

or a pharmaceutically acceptable salt thereof.

Some embodiments described herein relate to a compound of formula (III),

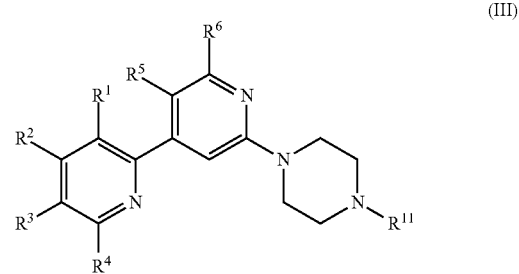

wherein:

$R^1$, $R^2$, $R^3$, $R^4$, and $R^6$ are independently selected from hydrogen, $-(CR^{14}R^{15})_n$halo, $-(CR^{14}R^{15})_n$CN, $-(CR^{14}R^{15})_n$CF$_3$, $-(CR^{14}R^{15})_n(C_1$-$C_{10}$alkyl), $-(CR^{14}R^{15})_n(C_2$-$C_6$alkenyl), $-(CR^{14}R^{15})_n(C_2$-$C_6$alkynyl), $-(CR^{14}R^{15})_n$NR$^{16}$R$^{17}$, $-(CR^{14}R^{15})_n$OR$^{16}$, $-(CR^{14}R^{15})_n$C(O)R$^{16}$, $-(CR^{14}R^{15})_n$C(O)OR$^{16}$, $-(CR^{14}R^{15})_n$S(O)R$^{16}$, $-(CR^{14}R^{15})_n$S(O)$_2$R$^{16}$, $-(CR^{14}R^{15})_n$S(O)$_2$NR$^{16}$R$^{17}$, $-(CR^{14}R^{15})_n$NR$^{16}$S(O)$_2$R$^{17}$, $-(CR^{14}R^{15})_n$C$_3$-$C_{10}$cycloalkyl), $-(CR^{14}R^{15})_n$(3-12 membered heterocyclyl), $-(CR^{14}R^{15})_n(C_6$-$C_{10}$aryl), and $-(CR^{14}R^{15})_n$(5-12 membered heteroaryl);

$R^5$ is selected from halo, $C_1$-$C_{10}$ alkyl, and $-$CF$_3$, $R^{11}$ is selected from hydrogen, $-(CR^{14}R^{15})_n$halo, $-(CR^{14}R^{15})_n$CN, $-(CR^{14}R^{15})_n$CF$_3$, $-(CR^{14}R^{15})_n(C_1$-$C_{10}$alkyl), $-(CR^{14}R^{15})_n(C_2$-$C_6$alkenyl), $-(CR^{14}R^{15})_n(C_2$-$C_6$alkynyl), $-(CR^{14}R^{15})_n$NR$^A$R$^B$, $-(CR^{14}R^{15})_n$NR$^A$OR$^B$, $-(CR^{14}R^{15})_n$NR$^A$C(O)R$^B$, $-(CR^{14}R^{15})_n$NR$^A$C(O)OR$^B$, $-(CR^{14}R^{15})_n$OR$^A$, $-(CR^{14}R^{15})_n$C(O)R$^A$, $-(CR^{14}R^{15})_n$C(O)OR$^A$, $-(CR^{14}R^{15})_n$S(O)R$^A$, $-(CR^{14}R^{15})_n$S(O)$_2$R$^A$, $-(CR^{14}R^{15})_n$S(O)$_2$NR$^A$R$^B$, $-(CR^{14}R^{15})_n$NR$^A$S(O)$_2$R$^B$, $-(CR^{14}R^{15})_n$C(O)NR$^A$R$^B$, $-(CR^{14}R^{15})_n$C$_3$-$C_{10}$cycloalkyl), $-(CR^{14}R^{15})_n$(3-12 membered heterocyclyl), $-(CR^{14}R^{15})_n(C_6$-$C_{10}$aryl), and $-(CR^{14}R^{15})_n$(5-12 membered heteroaryl), wherein each of said $C_3$-$C_{10}$cycloalkyl, said 3-12 membered heterocyclyl, said $C_6$-$C_{10}$aryl, and said 5-12 membered heteroaryl groups is substituted with one or more $R^{14}$ groups; or $R^{11}$ and $R^{13}$, together with the carbon to which they are attached, may combine to form a 3-12 membered heterocyclyl group which is substituted with one or more $R^{14}$ groups;

$R^A$ and $R^B$ are independently selected from hydrogen, —$(CR^{14}R^{15})_n$halo, —$(CR^{14}R^{15})_n$CN, —$(CR^{14}R^{15})_n$CF$_3$, —$(CR^{14}R^{15})_n$(C$_1$-C$_{10}$alkyl), —$(CR^{14}R^{15})_n$(C$_2$-C$_6$alkenyl), —$(CR^{14}R^{15})_n$(C$_2$-C$_6$alkynyl), —$(CR^{14}R^{15})_n$NR$^{16}$R$^{17}$, —$(CR^{14}R^{15})_n$NR$^{16}$OR$^{17}$, —$(CR^{14}R^{15})_n$NR$^{16}$C(O)R$^{17}$, —$(CR^{14}R^{15})_n$NR$^{16}$C(O)OR$^{17}$, —$(CR^{14}R^{15})_n$OR$^{16}$, —$(CR^{14}R^{15})_n$C(O)R$^{16}$, —$(CR^{14}R^{15})_n$C(O)OR$^{16}$, —$(CR^{14}R^{15})_n$S(O)R$^{16}$, —$(CR^{14}R^{15})_n$S(O)$_2$R$^{16}$, —$(CR^{14}R^{15})_n$S(O)$_2$NR$^{16}$R$^{17}$, —$(CR^{14}R^{15})_n$NR$^{16}$S(O)$_2$R$^{17}$, —$(CR^{14}R^{15})_n$(C$_3$-C$_{10}$cycloalkyl), —$(CR^{14}R^{15})_n$(3-12 membered heterocyclyl), —$(CR^{14}R^{15})_n$(C$_6$-C$_{10}$aryl), and —$(CR^{14}R^{15})_n$(5-12 membered heteroaryl), wherein each of said C$_3$-C$_{10}$cycloalkyl, said 3-12 membered heterocyclyl, said C$_6$-C$_{10}$aryl, and said 5-12 membered heteroaryl groups is substituted with one or more $R^{14}$ groups;

each $R^{14}$, $R^{15}$, $R^{16}$ and $R^{17}$ is independently selected from hydrogen, —$(CR^{24}R^{25})_n$halo, —$(CR^{24}R^{25})_n$CF$_3$, —$(CR^{24}R^{25})_n$(C$_1$-C$_{10}$alkyl), —$(CR^{24}R^{25})_n$(C$_2$-C$_6$alkenyl), —$(CR^{24}R^{25})_n$(C$_2$-C$_6$alkynyl), —$(CR^{24}R^{25})_n$OR$^{18}$, —$(CR^{24}R^{25})_n$NR$^{18}$R$^{19}$, —$(CR^{24}R^{25})_n$CN, —$(CR^{24}R^{25})_n$S(O)$_2$R$^{18}$, —$(CR^{24}R^{25})_n$S(O)$_2$NR$^{18}$R$^{19}$, —$(CR^{24}R^{25})_n$(C$_3$-C$_{10}$cycloalkyl), —$(CR^{24}R^{25})_n$(3-12 membered heterocyclyl), —$(CR^{24}R^{25})_n$(C$_6$-C$_{10}$aryl), and —$(CR^{24}R^{25})_n$(5-12 membered heteroaryl), wherein each of said C$_3$-C$_{10}$cycloalkyl, said 3-12 membered heterocyclyl, said C$_6$-C$_{10}$aryl, and said 5-12 membered heteroaryl groups is substituted with one or more $R^{18}$ groups;

each $R^{18}$, $R^{19}$, $R^{24}$ and $R^{25}$ is independently selected from hydrogen, —$(CH_2)_n$(C$_1$-C$_{10}$alkyl), —$(CH_2)_n$(C$_3$-C$_{10}$cycloalkyl), —$(CH_2)_n$(3-12 membered heterocyclyl), —$(CH_2)_n$(C$_6$-C$_{10}$aryl), and —$(CH_2)_n$(5-12 membered heteroaryl); and each n is independently selected from 0, 1, 2, 3, 4, 5, and 6; or a pharmaceutically acceptable salt thereof.

Some embodiments relate to a compound of formula (III), or a pharmaceutically acceptable salt thereof, wherein $R^1$, $R^2$, $R^3$, $R^4$, and $R^6$ are independently selected from hydrogen, -halo, —CN, —CF$_3$, and —(C$_1$-C$_{10}$alkyl).

Additional embodiments relate to a compound of formula (III), or a pharmaceutically acceptable salt thereof, wherein $R^5$ is halo.

More embodiments relate to a compound of formula (III), or a pharmaceutically acceptable salt thereof, wherein $R^{11}$ is selected from —$(CR^{14}R^{15})_n$C(O)R$^A$, —$(CR^{14}R^{15})_n$NR$^A$C(O)R$^B$, —$(CR^{14}R^{15})_n$S(O)$_2$R$^A$, —$(CR^{14}R^{15})_n$S(O)$_2$NR$^A$R$^B$, and —$(CR^{14}R^{15})_n$NR$^A$S(O)$_2$R$^B$.

Some embodiments relate to a compound of formula (III), or a pharmaceutically acceptable salt thereof, wherein $R^{11}$ is selected from —C(O)R$^A$ and —S(O)$_2$R$^A$.

Some embodiments relate to a compound of formula (III), or a pharmaceutically acceptable salt thereof, wherein $R^{11}$ is C(O)R$^A$.

Further embodiments relate to a compound of formula (III), or a pharmaceutically acceptable salt thereof, wherein $R^A$ is —$(CR^{14}R^{15})_n$S(O)$_2$R$^{16}$.

Additional embodiments relate to a compound of formula (III), or a pharmaceutically acceptable salt thereof, wherein $R^5$ is F or Cl; $R^{11}$ is C(O)R$^A$; and $R^A$ is —$(CR^{14}R^{15})_n$S(O)$_2$R$^{16}$.

Some embodiments described herein relate to a compound of formula (IV),

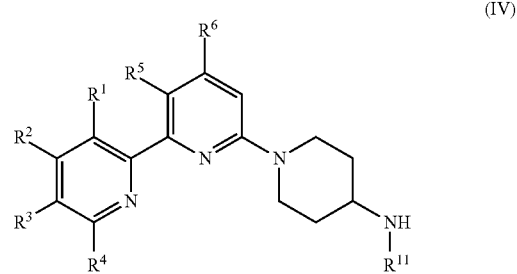

(IV)

wherein:

$R^1$, $R^2$, $R^3$, $R^4$, and $R^6$ are independently selected from hydrogen, —$(CR^{14}R^{15})_n$halo, —$(CR^{14}R^{15})_n$CN, —$(CR^{14}R^{15})_n$CF$_3$, —$(CR^{14}R^{15})_n$(C$_1$-C$_{10}$alkyl), —$(CR^{14}R^{15})_n$(C$_2$-C$_6$alkenyl), —$(CR^{14}R^{15})_n$(C$_2$-C$_6$alkynyl), —$(CR^{14}R^{15})_n$NR$^{16}$R$^{17}$, —$(CR^{14}R^{15})_n$OR$^{16}$, —$(CR^{14}R^{15})_n$C(O)R$^{16}$, —$(CR^{14}R^{15})_n$C(O)OR$^{16}$, —$(CR^{14}R^{15})_n$S(O)R$^{16}$, —$(CR^{14}R^{15})_n$S(O)$_2$R$^{16}$, —$(CR^{14}R^{15})_n$S(O)$_2$NR$^{16}$R$^{17}$, —$(CR^{14}R^{15})_n$NR$^{16}$S(O)$_2$R$^{17}$, —$(CR^{14}R^{15})_n$(C$_3$-C$_{10}$cycloalkyl), —$(CR^{14}R^{15})_n$(3-12 membered heterocyclyl), —$(CR^{14}R^{15})_n$(C$_6$-C$_{10}$aryl), and —$(CR^{14}R^{15})_n$(5-12 membered heteroaryl);

$R^5$ is selected from halo, C$_1$-C$_{10}$ alkyl, and —CF$_3$, $R^{11}$ is selected from hydrogen, —$(CR^{14}R^{15})_n$halo, —$(CR^{14}R^{15})_n$CN, —$(CR^{14}R^{15})_n$CF$_3$, —$(CR^{14}R^{15})_n$(C$_1$-C$_{10}$alkyl), —$(CR^{14}R^{15})_n$(C$_2$-C$_6$alkenyl), —$(CR^{14}R^{15})_n$(C$_2$-C$_6$alkynyl), —$(CR^{14}R^{15})_n$NR$^A$R$^B$, —$(CR^{14}R^{15})_n$NR$^A$OR$^B$, —$(CR^{14}R^{15})_n$NR$^A$C(O)R$^B$, —$(CR^{14}R^{15})_n$NR$^A$C(O)OR$^B$, —$(CR^{14}R^{15})_n$OR$^A$, —$(CR^{14}R^{15})_n$C(O)R$^A$, —$(CR^{14}R^{15})_n$C(O)OR$^A$, —$(CR^{14}R^{15})_n$S(O)R$^A$, —$(CR^{14}R^{15})_n$S(O)$_2$R$^A$, —$(CR^{14}R^{15})_n$S(O)$_2$NR$^A$R$^B$, —$(CR^{14}R^{15})_n$NR$^A$S(O)$_2$R$^B$, —$(CR^{14}R^{15})_n$C(O)NR$^A$R$^B$, —$(CR^{14}R^{15})_n$(C$_3$-C$_{10}$cycloalkyl), —$(CR^{14}R^{15})_n$(3-12 membered heterocyclyl), —$(CR^{14}R^{15})_n$(C$_6$-C$_{10}$aryl), and —$(CR^{14}R^{15})_n$(5-12 membered heteroaryl), wherein each of said C$_3$-C$_{10}$cycloalkyl, said 3-12 membered heterocyclyl, said C$_6$-C$_{10}$aryl, and said 5-12 membered heteroaryl groups is substituted with one or more $R^{14}$ groups; or $R^{11}$ and $R^{13}$, together with the carbon to which they are attached, may combine to form a 3-12 membered heterocyclyl group which is substituted with one or more $R^{14}$ groups;

$R^A$ and $R^B$ are independently selected from hydrogen, —$(CR^{14}R^{15})_n$halo, —$(CR^{14}R^{15})_n$CN, —$(CR^{14}R^{15})_n$CF$_3$, —$(CR^{14}R^{15})_n$(C$_1$-C$_{10}$alkyl), —$(CR^{14}R^{15})_n$(C$_2$-C$_6$alkenyl), —$(CR^{14}R^{15})_n$(C$_2$-C$_6$alkynyl), —$(CR^{14}R^{15})_n$NR$^{16}$R$^{17}$, —$(CR^{14}R^{15})_n$NR$^{16}$OR$^{17}$, —$(CR^{14}R^{15})_n$NR$^{16}$C(O)R$^{17}$, —$(CR^{14}R^{15})_n$NR$^{16}$C(O)OR$^{17}$, —$(CR^{14}R^{15})_n$OR$^{16}$, —$(CR^{14}R^{15})_n$C(O)R$^{16}$, —$(CR^{14}R^{15})_n$C(O)OR$^{16}$, —$(CR^{14}R^{15})_n$S(O)R$^{16}$, —$(CR^{14}R^{15})_n$S(O)$_2$R$^{16}$, —$(CR^{14}R^{15})_n$S(O)$_2$NR$^{16}$R$^{17}$, —$(CR^{14}R^{15})_n$NR$^{16}$S(O)$_2$R$^{17}$, —$(CR^{14}R^{15})_n$(C$_3$-C$_{10}$cycloalkyl), —$(CR^{14}R^{15})_n$(3-12 membered heterocyclyl), —$(CR^{14}R^{15})_n$(C$_6$-C$_{10}$aryl), and —$(CR^{14}R^{15})_n$(5-12 membered heteroaryl), wherein each of said C$_3$-C$_{10}$cycloalkyl, said 3-12 membered heterocyclyl, said C$_6$-C$_{10}$aryl, and said 5-12 membered heteroaryl groups is substituted with one or more $R^{14}$ groups;

each $R^{14}$, $R^{15}$, $R^{16}$ and $R^{17}$ is independently selected from hydrogen, —$(CR^{24}R^{25})_n$halo, —$(CR^{24}R^{25})_n$CF$_3$, —$(CR^{24}R^{25})_n$(C$_1$-C$_{10}$alkyl), —$(CR^{24}R^{25})_n$(C$_2$-C$_6$alkenyl), —$(CR^{24}R^{25})_n$(C$_2$-C$_6$alkynyl), —$(CR^{24}R^{25})_n$OR$^{18}$, —$(CR^{24}R^{25})_n$NR$^{18}$R$^{19}$, —$(CR^{24}R^{25})_n$CN, —$(CR^{24}R^{25})_n$S(O)$_2$R$^{18}$, —$(CR^{24}R^{25})_n$S(O)$_2$NR$^{18}$R$^{19}$, —$(CR^{24}R^{25})_n$(C$_3$-C$_{10}$cycloalkyl), —$(CR^{24}R^{25})_n$(3-12 membered heterocyclyl), —(CR$^{24}$R$^{25}$)$_n$(C$_6$-C$_{10}$aryl), and —(CR$^{24}$R$^{25}$)$_n$(5-12 membered heteroaryl), wherein each of said C$_3$-C$_{10}$cycloalkyl, said 3-12 membered heterocyclyl, said C$_6$-C$_{10}$aryl, and said 5-12 membered heteroaryl groups is substituted with one or more R$^{18}$ groups;

each R$^{18}$, R$^{19}$, R$^{24}$ and R$^{25}$ is independently selected from hydrogen, —(CH$_2$)$_n$(C$_1$-C$_{10}$alkyl), —(CH$_2$)$_n$(C$_3$-C$_{10}$cycloalkyl), —(CH$_2$)$_n$(3-12 membered heterocyclyl), —(CH$_2$)$_n$(C$_6$-C$_{10}$aryl), and —(CH$_2$)$_n$(5-12 membered heteroaryl); and each n is independently selected from 0, 1, 2, 3, 4, 5, and 6; or a pharmaceutically acceptable salt thereof.

Some embodiments relate to a compound of formula (IV), or a pharmaceutically acceptable salt thereof, wherein R$^1$, R$^2$, R$^3$, R$^4$, and R$^6$ are independently selected from hydrogen, -halo, —CN, —CF$_3$, and —(C$_1$-C$_{10}$alkyl).

Additional embodiments relate to a compound of formula (IV), or a pharmaceutically acceptable salt thereof, wherein R$^5$ is halo.

More embodiments relate to a compound of formula (IV), or a pharmaceutically acceptable salt thereof, wherein R$^{11}$ is selected from —(CR$^{14}$R$^{15}$)$_n$C(O)R$^A$, —(CR$^{14}$R$^{15}$)$_n$NR$^A$C(O)R$^B$, —(CR$^{14}$R$^{15}$)$_n$S(O)$_2$R$^A$, —(CR$^{14}$R$^{15}$)$_n$S(O)$_2$NR$^A$R$^B$, and —(CR$^{14}$R$^{15}$)$_n$NR$^A$S(O)$_2$R$^B$.

Some embodiments relate to a compound of formula (IV), or a pharmaceutically acceptable salt thereof, wherein R$^{11}$ is —S(O)$_2$R$^A$.

Additional embodiments relate to a compound of formula (IV), or a pharmaceutically acceptable salt thereof, wherein R$^5$ is Cl and R$^{11}$ is —S(O)$_2$R$^A$.

Additional embodiments relate to a pharmaceutical composition comprising a compound of formula (I), (II), (III), or (IV), or a pharmaceutically acceptable salt thereof, and a pharmaceutically acceptable carrier or diluent.

Further embodiments relate to a method of treating of abnormal cell growth in a mammal comprising administering to said mammal an amount of a compound of formula (I), (II), (III), or (IV), or a pharmaceutically acceptable salt thereof, that is effective in treating abnormal cell growth. In some embodiments, said abnormal cell growth is cancer. In some embodiments, said cancer is selected from the group consisting of basal cell cancer, medulloblastoma cancer, liver cancer, rhabdomyosarcoma, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma and pituitary adenoma, or a combination of one or more of the foregoing cancers.

In some embodiments, the compound is selected from:
N-[1-(5'-chloro-2,4'-bipyridin-2'-yl)piperidin-4-yl]methanesulfonamide;
N-[1-(5'-chloro-3-methyl-2,4'-bipyridin-2'-yl)piperidin-4-yl]methanesulfonamide;
N-[1-(5'-chloro-5-methyl-2,4'-bipyridin-2'-yl)piperidin-4-yl]methanesulfonamide;
N-[1-(3,5'-dichloro-2,4'-bipyridin-2'-yl)piperidin-4-yl]methanesulfonamide;
N-[1-(5,5'-dichloro-2,4'-bipyridin-2'-yl)piperidin-4-yl]methanesulfonamide;
N-[1-(3,5,5'-trichloro-2,4'-bipyridin-2'-yl)piperidin-4-yl]methanesulfonamide;
N-{1-[5'-chloro-5-(trifluoromethyl)-2,4'-bipyridin-2'-yl]piperidin-4-yl}methanesulfonamide;
N-[1-(5'-chloro-3,5-dimethyl-2,4'-bipyridin-2'-yl)piperidin-4-yl]methanesulfonamide;
N-[1-(3-chloro-2,2'-bipyridin-6-yl)piperidin-4-yl]methanesulfonamide;
N-[1-(3-chloro-3'-methyl-2,2'-bipyridin-6-yl)piperidin-4-yl]methanesulfonamide;
N-[1-(5,5'-dichloro-3-fluoro-2,4'-bipyridin-2'-yl)piperidin-4-yl]methanesulfonamide;
N-[1-(5'-chloro-5-fluoro-2,4'-bipyridin-2'-yl)piperidin-4-yl]methanesulfonamide;
6-[4-(5'-chloro-3-methyl-2,4'-bipyridin-2'-yl)piperazin-1-yl]nicotinonitrile;
8-(5'-chloro-3-methyl-2,4'-bipyridin-2'-yl)-3-methyl-1-oxa-3,8-diazaspiro[4.5]decan-2-one;
8-(5'-chloro-3-methyl-2,4'-bipyridin-2'-yl)-1-oxa-3,8-diazaspiro[4.5]decan-2-one;
5'-chloro-3-methyl-2'-[4-(methylsulfonyl)piperazin-1-yl]-2,4'-bipyridine;
2'-(4-acetylpiperazin-1-yl)-5'-chloro-3-methyl-2,4'-bipyridine;
methyl 4-(5'-chloro-3-methyl-2,4'-bipyridin-2'-yl)piperazine-1-carboxylate;
2-[4-(5'-chloro-3-methyl-2,4'-bipyridin-2'-yl)piperazin-1-yl]-2-oxoethanol;
2-(4-acetylpiperazin-1-yl)-5-chloro-4-(3-methylpyridin-2-yl)pyrimidine;
N-[1-(5'-chloro-3-methyl-2,4'-bipyridin-2'-yl)piperidin-4-yl]-3-methoxypropanamide;
5'-chloro-2'-[4-(methoxyacetyl)piperazin-1-yl]-3-methyl-2,4'-bipyridine;
5'-chloro-2'-[4-(3-methoxypropanoyl)piperazin-1-yl]-3-methyl-2,4'-bipyridine;
1-[5-chloro-4-(3-methylpyridin-2-yl)pyrimidin-2-yl]piperidin-4-ol;
N-(1-(5'-chloro-3-methyl-[2,4'-bipyridin]-2'-yl)piperidin-4-yl)-2-(dimethylamino)acetamide;
methyl [1-(5'-chloro-3-methyl-2,4'-bipyridin-2'-yl)piperidin-4-yl]carbamate;
5-chloro-4-(3-methylpyridin-2-yl)-2-[4-(methylsulfonyl)piperazin-1-yl]pyrimidine;
N-{1-[5-chloro-4-(3-methylpyridin-2-yl)pyrimidin-2-yl]piperidin-4-yl}methanesulfonamide;
N-[1-(5'-chloro-3-methyl-2,4'-bipyridin-2'-yl)piperidin-4-yl]acetamide;
methyl 4-[5-chloro-4-(3-methylpyridin-2-yl)pyrimidin-2-yl]piperazine-1-carboxylate;
5'-chloro-2'-{4-[(2-methoxyethoxy)methyl]piperidin-1-yl}-3-methyl-2,4'-bipyridine;
5'-chloro-2'-(4-isobutoxypiperidin-1-yl)-3-methyl-2,4'-bipyridine;
ethyl 4-(5'-chloro-3-methyl-2,4'-bipyridin-2'-yl)piperazine-1-carboxylate;
2-{[1-(5'-chloro-3-methyl-2,4'-bipyridin-2'-yl)piperidin-4-yl]oxy}-N-propylacetamide;
2-{[1-(5'-chloro-3-methyl-2,4'-bipyridin-2'-yl)piperidin-4-yl]oxy}-N,N-diethylacetamide;

N-tert-butyl-2-{[1-(5'-chloro-3-methyl-2,4'-bipyridin-2'-yl)piperidin-4-yl]oxy}acetamide;
5'-chloro-2'-[4-(2,2-dimethylpropanoyl)piperazin-1-yl]-3-methyl-2,4'-bipyridine;
5'-chloro-2'-(4-isobutyrylpiperazin-1-yl)-3-methyl-2,4'-bipyridine;
N-[1-(5-chloro-4-pyridin-2-ylpyrimidin-2-yl)piperidin-4-yl]methanesulfonamide;
2'-[4-(5-bromopyrimidin-2-yl)piperazin-1-yl]-5'-chloro-3-methyl-2,4'-bipyridine;
4-[4-(5'-chloro-3-methyl-2,4'-bipyridin-2'-yl)piperazin-1-yl]-2-methyl-4-oxobutan-2-ol;
N-{[1-(5'-chloro-3-methyl-2,4'-bipyridin-2'-yl)piperidin-4-yl]methyl}methanesulfonamide;
1-(5'-chloro-3-methyl-2,4'-bipyridin-2'-yl)-N-[2-(methylsulfonyl)ethyl]piperidin-4-amine;
N-{1-[4-(3-methylpyridin-2-yl)pyrimidin-2-yl]piperidin-4-yl}methanesulfonamide;
5-chloro-3-methyl-2'-{4-[(methylsulfonyl)methyl]piperidin-1-yl}-2,4'-bipyridine;
N-(1-(5'-chloro-3-methyl-[2,4'-bipyridin]-2'-yl)piperidin-4-yl)-3-hydroxy-3-methylbutanamide
3-chloro-6-{4-[(methylsulfonyl)methyl]piperidin-1-yl}-2,2'-bipyridine;
1-(5'-chloro-3-methyl-2,4'-bipyridin-2'-yl)-N-(1H-imidazol-2-ylmethyl)piperidine-4-carboxamide;
1-(5'-chloro-3-methyl-2,4'-bipyridin-2'-yl)-N-(1-pyridin-2-ylcyclopropyl)piperidine-4-carboxamide;
N-(1-{[1-(5'-chloro-3-methyl-2,4'-bipyridin-2'-yl)piperidin-4-yl]carbonyl}piperidin-4-yl)pyridin-2-amine;
1-(5'-chloro-3-methyl-2,4'-bipyridin-2'-yl)-N-[(3R)-1-(methylsulfonyl)pyrrolidin-3-yl]piperidine-4-carboxamide;
1-(5-chloro-3-methyl-2,4'-bipyridin-2'-yl)-N-[(1R,2S)-2-hydroxy-2,3-dihydro-1H-inden-1-yl]piperidine-4-carboxamide;
1-(5'-chloro-3-methyl-2,4'-bipyridin-2'-yl)-N-(5-methoxypyrazin-2-yl)piperidine-4-carboxamide;
1-(5-chloro-3-methyl-2,4'-bipyridin-2'-yl)-N-[(3S)-1-(methylsulfonyl)pyrrolidin-3-yl]piperidine-4-carboxamide;
1-(5'-chloro-3-methyl-2,4'-bipyridin-2'-yl)-N-[2-(2-oxo-2,3-dihydro-1H-indol-3-yl)ethyl]piperidine-4-carboxamide;
5'-chloro-2'-[4-({3-[(cyclopropylmethyl)sulfonyl]azetidin-1-yl}carbonyl)piperidin-1-yl]-3-methyl-2,4'-bipyridine;
1-(5-chloro-3-methyl-2,4'-bipyridin-2'-yl)-N-[(2R)-tetrahydrofuran-2-ylmethyl]piperidine-4-carboxamide;
1-(5'-chloro-3-methyl-2,4'-bipyridin-2'-yl)-N-[(1-hydroxycyclobutyl)methyl]piperidine-4-carboxamide;
5'-chloro-2'-{4-[(3-isopropyl-1-methyl-1,4,6,7-tetrahydro-5H-pyrazolo[4,3-c]pyridin-5-yl)carbonyl]piperidin-1-yl}-3-methyl-2,4'-bipyridine;
1-(5'-chloro-3-methyl-2,4'-bipyridin-2'-yl)-N-[(1R,3R)-3-hydroxycyclopentyl]piperidine-4-carboxamide;
1-(5'-chloro-3-methyl-2,4'-bipyridin-2'-yl)-N-[2-(methylsulfonyl)ethyl]piperidine-4-carboxamide;
1-(5'-chloro-3-methyl-2,4'-bipyridin-2'-yl)-N-[(3S,4S)-4-hydroxy-1,1-dioxidotetrahydro-3-thienyl]piperidine-4-carboxamide;
1-(5'-chloro-3-methyl-2,4'-bipyridin-2'-yl)-N-[(3S,4S)-4-hydroxy-1,1-dioxidotetrahydro-3-thienyl]-N-methylazetidine-3-carboxamide;
1-(5'-chloro-3-methyl-2,4'-bipyridin-2'-yl)-N-[(3S,4S)-4-hydroxy-1,1-dioxidotetrahydro-3-thienyl]-N-methylpiperidine-4-carboxamide;
1-(5'-chloro-3-methyl-2,4'-bipyridin-2'-yl)-N-(trans-4-hydroxycyclohexyl)piperidine-4-carboxamide;
1-(5'-chloro-3-methyl-2,4'-bipyridin-2'-yl)-N-(2-hydroxycyclohexyl)piperidine-4-carboxamide;
1-(5'-chloro-3-methyl-2,4'-bipyridin-2'-yl)-N-[2-(3-methyl-3H-imidazo[4,5-b]pyridin-2-yl)ethyl]piperidine-4-carboxamide;
1-(5'-chloro-3-methyl-2,4'-bipyridin-2'-yl)-N-{[4-(cyclopropylmethyl)-5-oxomorpholin-2-yl]methyl}piperidine-4-carboxamide;
1-(5'-chloro-3-methyl-2,4'-bipyridin-2'-yl)-N-[6-(hydroxymethyl)pyridin-2-yl]piperidine-4-carboxamide;
1-(5'-chloro-3-methyl-2,4'-bipyridin-2'-yl)-N-[1-(hydroxymethyl)cyclopentyl]piperidine-4-carboxamide;
1-(5'-chloro-3-methyl-2,4'-bipyridin-2'-yl)-N-(tetrahydro-2H-pyran-4-yl)piperidine-4-carboxamide;
1-(5'-chloro-3-methyl-2,4'-bipyridin-2'-yl)-N-(tetrahydrofuran-3-yl)piperidine-4-carboxamide;
1-(5'-chloro-3-methyl-2,4'-bipyridin-2'-yl)-N-(2-methoxybenzyl)piperidine-4-carboxamide;
1-(5'-chloro-3-methyl-2,4'-bipyridin-2'-yl)-N-(1,1-dioxidotetrahydro-2H-thiopyran-4-yl)piperidine-4-carboxamide;
1-(5'-chloro-3-methyl-2,4'-bipyridin-2'-yl)-N-[(1R,2R)-2-hydroxycyclohexyl]piperidine-4-carboxamide;
6-(4-{[1-(5'-chloro-3-methyl-2,4'-bipyridin-2'-yl)piperidin-4-yl]carbonyl}piperazin-1-yl)pyridazin-3-ol;
1-(5'-chloro-3-methyl-2,4'-bipyridin-2'-yl)-N-(tetrahydro-2H-pyran-2-ylmethyl)piperidine-4-carboxamide;
1-(5'-chloro-3-methyl-2,4'-bipyridin-2'-yl)-N-(9-methyl-1-oxa-9-azaspiro[5.5]undec-4-yl)piperidine-4-carboxamide;
[(2S)-1-{[1-(5'-chloro-3-methyl-2,4'-bipyridin-2'-yl)piperidin-4-yl]carbonyl}piperidin-2-yl]methanol;
1-{[1-(5'-chloro-3-methyl-2,4'-bipyridin-2'-yl)piperidin-4-yl]carbonyl}-2-(hydroxymethyl)piperidin-3-ol;
1-(5'-chloro-3-methyl-2,4'-bipyridin-2'-yl)-N-[2-(1H-imidazol-4-yl)ethyl]piperidine-4-carboxamide;
1-(5'-chloro-3-methyl-2,4'-bipyridin-2'-yl)-N-(2-methyl-2H-1,2,3-triazol-4-yl)piperidine-4-carboxamide;
1-(5'-chloro-3-methyl-2,4'-bipyridin-2'-yl)-N-[trans-4-(hydroxymethyl)cyclohexyl]piperidine-4-carboxamide;
4-[4-(3-chloro-2,2'-bipyridin-6-yl)piperazin-1-yl]-2-methyl-4-oxobutan-2-ol;
1-[1-(3-chloro-2,2'-bipyridin-6-yl)piperidin-4-yl]methanesulfonamide;
5-chloro-2-{4-[(methylsulfonyl)methyl]piperidin-1-yl}-4-pyridin-2-ylpyrimidine;
5-chloro-3-methyl-2'-{4-[3-(methylsulfonyl)propanoyl]piperazin-1-yl}-2,4'-bipyridine;
1-(5'-chloro-3,5-dimethyl-2,4'-bipyridin-2'-yl)piperidin-4-ol;
N-[1-(5'-chloro-3-methyl-2,4'-bipyridin-2'-yl)piperidin-4-yl]-3-(methylsulfonyl)propanamide;
N-{[1-(5'-chloro-3-methyl-2,4'-bipyridin-2'-yl)piperidin-4-yl]methyl}-2-(methylsulfonyl)ethanamine;
5-chloro-4-(3-methylpyridin-2-yl)-2-{4-[(methylsulfonyl)methyl]piperidin-1-yl}pyrimidine;
5'-chloro-3,5-dimethyl-2'-{4-[(methylsulfonyl)methyl]piperidin-1-yl}-2,4'-bipyridine;
3-chloro-6-{4-[3-(methylsulfonyl)propanoyl]piperazin-1-yl}-2,2'-bipyridine;
2'-(4-acetylpiperazin-1-yl)-5'-chloro-3,5-dimethyl-2,4'-bipyridine;
methyl 4-(5'-chloro-3,5-dimethyl-2,4'-bipyridin-2'-yl)piperazine-1-carboxylate;
2-[4-(5'-chloro-3,5-dimethyl-2,4'-bipyridin-2'-yl)piperazin-1-yl]-2-oxoethanol;
4-[4-(5'-chloro-3,5-dimethyl-2,4'-bipyridin-2'-yl)piperazin-1-yl]-2-methyl-4-oxobutan-2-ol;

5'-chloro-3,5-dimethyl-2'-[4-(methylsulfonyl)piperazin-1-yl]-2,4'-bipyridine;
2-[4-(5'-chloro-3,5-dimethyl-2,4'-bipyridin-2'-yl)piperazin-1-yl]-N,N-dimethyl-2-oxoethanamine;
3-[4-(5'-chloro-3,5-dimethyl-2,4'-bipyridin-2'-yl)piperazin-1-yl]-3-oxopropan-1-ol;
1-[(1R,5S)-8-(5'-chloro-3-methyl-2,4'-bipyridin-2'-yl)-3,8-diazabicyclo[3.2.1]oct-3-yl]-3-hydroxy-3-methylbutan-1-one;
N-[1-(5'-chloro-5-fluoro-3-methyl-2,4'-bipyridin-2'-yl)piperidin-4-yl]methanesulfonamide;
N-[1-(5,5'-dichloro-3-methyl-2,4'-bipyridin-2'-yl)piperidin-4-yl]methanesulfonamide;
5'-chloro-2'-{4-[(2-methoxyethyl)sulfonyl]piperazin-1-yl}-3,5-dimethyl-2,4'-bipyridine;
2-{[4-(5'-chloro-3,5-dimethyl-2,4'-bipyridin-2'-yl)piperazin-1-yl]sulfonyl}ethanol;
5'-chloro-3,5-dimethyl-2'-{4-[2-(methylsulfonyl)ethyl]piperazin-1-yl}-2,4'-bipyridine;
N-[1-(5'-chloro-3,5-dimethyl-2,4'-bipyridin-2'-yl)piperidin-4-yl]-2-hydroxyacetamide;
N-(1-(5'-chloro-3,5-dimethyl-[2,4'-bipyridin]-2'-yl)piperidin-4-yl)-2-(dimethylamino)acetamide;
N-[1-(5'-methyl-2,2'-bipyridin-6-yl)piperidin-4-yl]methanesulfonamide;
5'-chloro-3,5-dimethyl-2'-{4-[3-(methylsulfonyl)propanoyl]piperazin-1-yl}-2,4'-bipyridine;
N-[1-(3-chloro-5'-methyl-2,2'-bipyridin-6-yl)piperidin-4-yl]methanesulfonamide;
1-[1-(5'-chloro-3,5-dimethyl-2,4'-bipyridin-2'-yl)piperidin-4-yl]methanesulfonamide;
N-{1-[5-chloro-4-(5-methylpyridin-2-yl)pyrimidin-2-yl]piperidin-4-yl}methanesulfonamide;
N-[1-(3-bromo-5'-methyl-2,2'-bipyridin-6-yl)piperidin-4-yl]methanesulfonamide;
N-[1-(5'-chloro-3,5-dimethyl-2,4'-bipyridin-2'-yl)piperidin-4-yl]ethanesulfonamide;
N-[1-(5'-chloro-3,5-dimethyl-2,4'-bipyridin-2'-yl)piperidin-4-yl]-3-(methylsulfonyl)propanamide;
N-[1-(3-chloro-2,2'-bipyridin-6-yl)piperidin-4-yl]-2-methoxyethanesulfonamide;
N-[(3-endo)-8-(5'-chloro-3-methyl-2,4'-bipyridin-2'-yl)-8-azabicyclo[3.2.1]oct-3-yl]methanesulfonamide;
N-[1-(5'-chloro-5-cyano-3-methyl-2,4'-bipyridin-2'-yl)pipendin-4-yl]methanesulfonamide;
N-[1-(5'-chloro-3,5-dimethyl-2,4'-bipyridin-2'-yl)pipendin-4-yl]cyclopropanesulfonamide;
N-[1-(5'-chloro-3,5-dimethyl-2,4'-bipyridin-2'-yl)pipendin-4-yl]cyclopropanesulfonamide;
1N-[1-(3-chloro-2,2'-bipyridin-6-yl)pipendin-4-yl]-3-(methylsulfonyl)propanamide;
N-(1-(3-chloro-[2,2'-bipyridin]-6-yl)pipendin-4-yl)-2-(dimethylamino)acetamide;
N-[1-(3-chloro-2,2'-bipyridin-6-yl)pipendin-4-yl]-3-hydroxypropanamide;
N-[1-(3-chloro-2,2'-bipyridin-6-yl)pipendin-4-yl]-3-hydroxy-3-methylbutanamide;
N-[1-(3-chloro-2,2'-bipyridin-6-yl)pipendin-4-yl]ethanesulfonamide;
N-[1-(3-chloro-2,2'-bipyridin-6-yl)pipendin-4-yl]cyclopropanesulfonamide;
15'-chloro-3,5-dimethyl-2'-[4-(methylsulfonyl)pipendin-1-yl]-2,4'-bipyridine;
N-[1-(5'-chloro-3,5-dimethyl-2,4'-bipyridin-2'-yl)pipendin-4-yl]-2-methoxyacetamide;
3-chloro-6-{4-[(2-methoxyethyl)sulfonyl]piperazin-1-yl}-2,2'-bipyridine;
2-{[4-(3-chloro-2,2'-bipyridin-6-yl)piperazin-1-yl]sulfonyl}ethanol;
N-(1-(5'-chloro-3'-fluoro-2,4'-bipyridin-2'-yl)pipendin-4-yl)methanesulfonamide;
N-(1-(5'-chloro-3'-fluoro-3,5-dimethyl-2,4'-bipyridin-2'-yl)pipendin-4-yl)-3-(methylsulfonyl)propanamide;
N-[1-(3-chloro-3',5'-dimethyl-2,2'-bipyridin-6-yl)pipendin-4-yl]-2-hydroxyacetamide;
1-[4-(3,5-dimethyl-2,4'-bipyridin-2'-yl)piperazin-1-yl]-3-(methylsulfonyl)propan-1-one;
1-[4-(5'-fluoro-3,5-dimethyl-2,4'-bipyridin-2'-yl)piperazin-1-yl]-3-(methylsulfonyl)propan-1-one;
N-[1-(3,5-dimethyl-2,4'-bipyridin-2'-yl)pipendin-4-yl]methanesulfonamide;
N-[1-(5'-chloro-5-fluoro-3-methyl-2,4'-bipyridin-2'-yl)pipendin-4-yl]-3-(methylsulfonyl)propanamide;
N-[1-(5'-chloro-5-fluoro-3-methyl-2,4'-bipyridin-2'-yl)pipendin-4-yl]-N2,N2-dimethylglycinamide;
N-[1-(5'-chloro-5-fluoro-3-methyl-2,4'-bipyridin-2'-yl)piperidin-4-yl]-3-hydroxy-3-methylbutanamide;
1-[4-(3-chloro-5'-methyl-2,2'-bipyridin-6-yl)piperazin-1-yl]-3-(methylsulfonyl)propan-1-one;
1-[4-(3-chloro-5'-methyl-2,2'-bipyridin-6-yl)piperazin-1-yl]-3-(methylsulfonyl)propan-1-one;
N-[1-(5'-chloro-5-fluoro-3-methyl-2,4'-bipyridin-2'-yl)piperidin-4-yl]-2-hydroxyethanesulfonamide;
2-{[4-(5'-chloro-5-fluoro-3-methyl-2,4'-bipyridin-2'-yl)piperazin-1-yl]sulfonyl}ethanol;
1-[4-(5'-chloro-5-fluoro-3-methyl-2,4'-bipyridin-2'-yl)piperazin-1-yl]-3-(methylsulfonyl)propan-1-one;
1-{[4-(5-chloro-5-fluoro-3-methyl-2,4'-bipyridin-2'-yl)piperazin-1-yl]sulfonyl}-2-methylpropan-2-ol;
N-[1-(5'-chloro-5-fluoro-3-methyl-2,4'-bipyridin-2'-yl)piperidin-4-yl]-2-hydroxy-2-methylpropane-1-sulfonamide;
N-[1-(3-chloro-5'-fluoro-3'-methyl-2,2'-bipyridin-6-yl)piperidin-4-yl]methanesulfonamide;
2'-{4-[(2-methoxyethyl)sulfonyl]piperazin-1-yl}-3,5-dimethyl-2,4'-bipyridine;
1-[4-(3,5-dimethyl-2,4'-bipyridin-2'-yl)piperazin-1-yl]-2-[(2R,6S)-2,6-dimethylmorpholin-4-yl]ethanone; and
1-[4-(3,5-dimethyl-2,4'-bipyridin-2'-yl)piperazin-1-yl]-2-(morpholin-4-yl)ethanone;
or a pharmaceutically acceptable salt thereof.

Definitions

The term "$C_1$-$C_{10}$alkyl", as used herein refers to saturated monovalent hydrocarbon radicals containing from one to ten carbon atoms, having straight or branched moieties.

As used herein, the term "$C_3$-$C_{10}$cycloalkyl" refers to a mono, fused or bridged bicyclic or tricyclic carbocyclic rings containing from three to ten carbon atoms, (e.g., cyclopropyl, cyclobutyl, cyclopentyl, cyclohexyl, cycloheptyl, cyclopentenyl, cyclohexenyl, bicyclo[2.2.1]heptanyl, bicyclo[3.2.1]octanyl and bicyclo[5.2.0]nonanyl, norbornyl, adamantanyl, etc.); said rings may optionally contain 1 or 2 double bonds. The term "cycloalkyl" also includes spiro cycloalkyl groups, including multi-ring systems joined by a single atom.

The terms "carbocycle", "carbocyclyl", "carbocyclo", or "carbocyclic" as used herein refers to an aliphatic ring system having three to twelve members. The terms "carbocycle", "carbocyclyl", "carbocyclo", or "carbocyclic", whether saturated or partially unsaturated, also refers to rings that are optionally substituted. The terms "carbocycle", "carbocyclyl", "carbocyclo", or "carbocyclic" also include aliphatic rings that are fused to one or more aromatic or non-aromatic rings, such as in a decahydronaphthyl or tetrahydronaphthyl, where the radical or point-of-attachment is on the aliphatic ring.

The term "C$_2$-C$_6$alkenyl" used alone or as part of a larger moiety shall include both straight and branched chains containing two to six carbon atoms having at least one carbon-carbon double bond. The term "C$_2$-C$_6$alkenyl" used alone or as part of a larger moiety shall include both straight and branched chains containing two to ten carbon atoms having at least one carbon-carbon triple bond.

The term "halo" is used herein interchangeably with the term "halogen", which denotes F, Cl, Br, or I. Preferred halo groups are F, Cl, and Br.

The term "heteroatom" refers to nitrogen, oxygen, or sulfur and includes any oxidized form of nitrogen and sulfur, and the quaternized form of any basic nitrogen. Also, the term "nitrogen" includes a substitutable nitrogen of a heterocyclic ring. As an example, in a saturated or partially unsaturated ring having 0 to 3 heteroatoms selected from oxygen, sulfur or nitrogen, the nitrogen may be N (as in 3,4-dihydro-2H-pyrrolyl), NH (as in pyrrolidinyl) or NOR (as in N-substituted pyrrolidinyl).

The term "C$_6$-C$_{10}$aryl", as used herein, refers to a group derived from an aromatic hydrocarbon containing from 6 to 10 carbon atoms. Examples of such groups include, but are not limited to, phenyl and naphthyl. The terms "Ph" and "phenyl," as used herein, refer to a —C$_6$H$_5$ group. The term "benzyl," as used herein, refers to a —CH$_2$C$_6$H$_5$ group. The term "C$_6$-C$_{10}$aryl" also includes fused polycyclic aromatic ring systems in which an aromatic ring is fused to one or more rings. Examples include 1-naphthyl, 2-naphthyl, 1-anthracyl and 2-anthracyl. Also included within the scope of the term "C$_6$-C$_{10}$aryl", as it is used herein, is a group in which an aromatic ring is fused to one or more non-aromatic rings, such as in an indanyl, phenanthridinyl, or tetrahydronaphthyl, where the radical or point of attachment is on the aromatic ring. The term "C$_6$-C$_{10}$aryl" also refers to rings that are optionally substituted.

The term "5-12 membered heteroaryl", used alone or as part of a larger moiety as in "heteroaralkyl" or "heteroaralkoxy", refers to an aromatic heterocyclic group having a total of from 5 to 12 atoms in its ring, and containing from 2 to 9 carbon atoms and from one to four heteroatoms each independently selected from O, S and N, with the proviso that the ring of said group does not contain two adjacent O atoms or two adjacent S atoms. The heterocyclic groups include benzo-fused ring systems. Examples of aromatic heterocyclic groups include, but are not limited to, pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl.

Also included within the scope of the term "5-12 membered heteroaryl", as it is used herein, is a group in which a heteroatomic ring is fused to one or more aromatic or non-aromatic rings where the radical or point of attachment is on the heteroaromatic ring. Examples include tetrahydroquinolinyl, tetrahydroisoquinolinyl, and pyrido[3,4-d]pyrimidinyl.

The term "3-12 membered heterocyclyl" (also known as heterocycle, or heteroalicyclic) refers to a non-aromatic, monocyclic, bicyclic, tricyclic or spirocyclic ring group having a total of 3 to 12 ring atoms, in which 1 to 4 ring atoms are heteroatoms selected from N, O, and S, and wherein the S atom may be optionally oxidized with one or two oxygen atoms, the remaining ring atoms being C, with the proviso that such ring systems may not contain two adjacent O atoms or two adjacent S atoms. The heterocyclic ring may also be substituted by an oxo (=O) group at any available C atom. The rings may also have one or more double bonds. Furthermore, such groups may be bonded to the remainder of the compounds of embodiments disclosed herein through either a carbon atom or a heteroatom, if possible. In addition, the heterocylic ring may also be benzo-fused, where the point of attachment is on the heterocyclic ring. Examples of suitable saturated heterocyclyl groups include, but are not limited to:

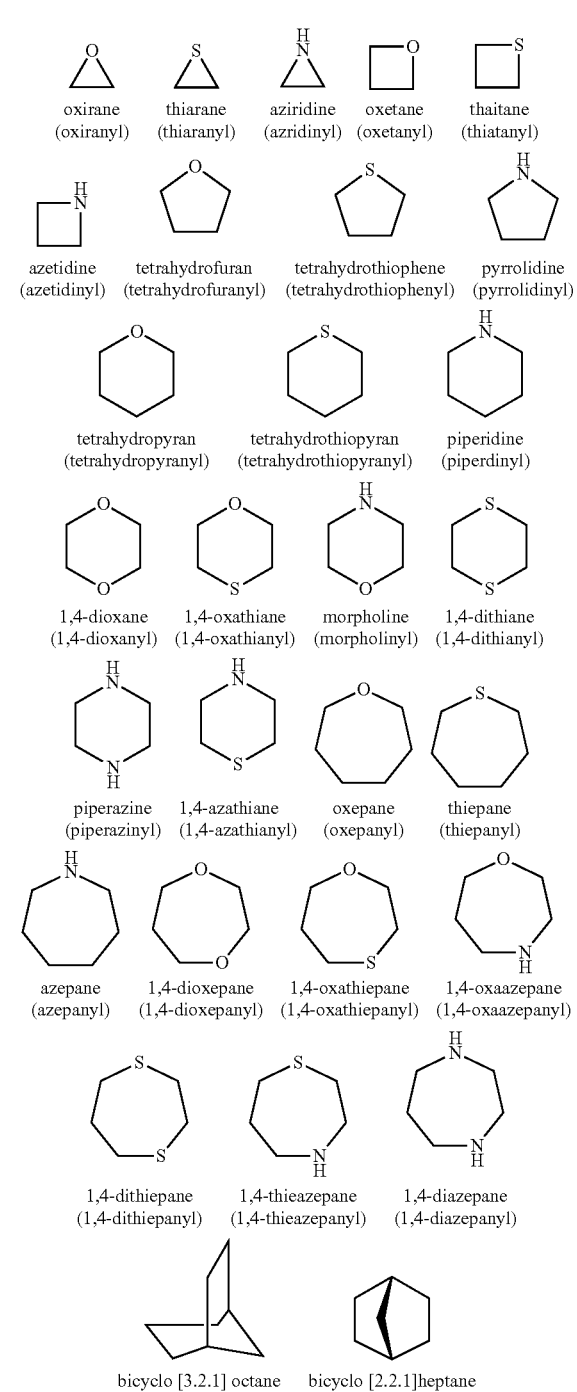

Examples of suitable partially unsaturated heterocyclyl groups include, but are not limited to:

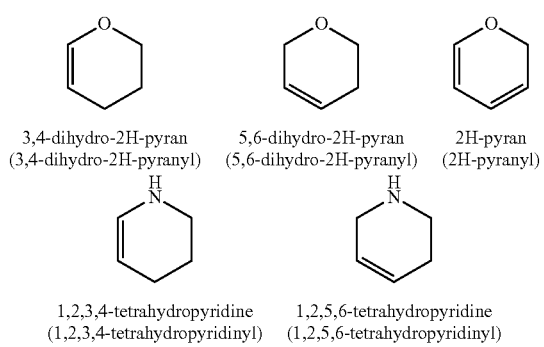

3,4-dihydro-2H-pyran (3,4-dihydro-2H-pyranyl)

5,6-dihydro-2H-pyran (5,6-dihydro-2H-pyranyl)

2H-pyran (2H-pyranyl)

1,2,3,4-tetrahydropyridine (1,2,3,4-tetrahydropyridinyl)

1,2,5,6-tetrahydropyridine (1,2,5,6-tetrahydropyridinyl)

The term "3-12 membered heterocyclyl" or "heterocycle", as previously noted, also includes spirocyclic moieties containing at least one heteroatom in one or more of the spirocyclic rings (also known as "heterospirocyclic" or "heterospirocyclic ring"). Such heterospirocyclic moieties may be optionally substituted at any ring position, including substitution on the heteroatom(s) within the spirocyclic ring(s). Examples of spirocyclic moieties include, but are not limited to:

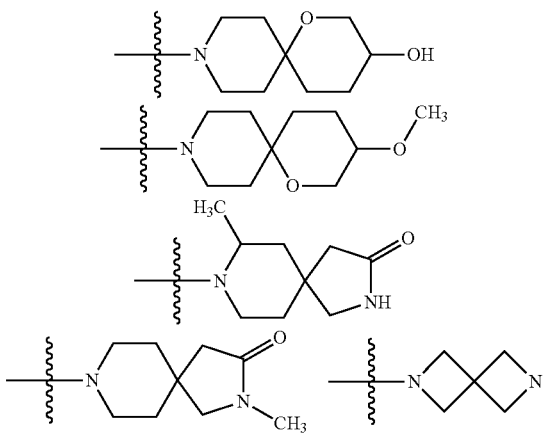

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above.

As used herein, an "effective" amount refers to an amount of a substance, agent, compound, or composition that is of sufficient quantity to result in a decrease in severity of disease symptoms, an increase in frequency and duration of disease symptom-free periods, or a prevention of impairment or disability due to the disease affliction—either as a single dose or according to a multiple dose regimen, alone or in combination with other agents or substances. One of ordinary skill in the art would be able to determine such amounts based on such factors as the subject's size, the severity of the subject's symptoms, and the particular composition or route of administration selected. The subject may be a human or non-human mammal (e.g., rabbit, rat, mouse, monkey or other lower-order primate).

Embodiments disclosed herein include isotopically-labeled compounds, which are identical to those recited in formula I or formula II, but for the fact that one or more atoms are replaced by an atom having an atomic mass or mass number different from the atomic mass or mass number usually found in nature. Examples of isotopes that can be incorporated into compounds of the embodiments disclosed herein include isotopes of hydrogen, carbon, nitrogen, oxygen, phosphorous, fluorine and chlorine, such as, but not limited to, $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds described herein and pharmaceutically acceptable salts of said compounds which contain the aforementioned isotopes and/or other isotopes of other atoms are within the scope of the present embodiments. Certain isotopically-labeled compounds of the embodiments disclosed herein, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically-labeled compounds of embodiments disclosed herein can generally be prepared by carrying out the procedures disclosed in the Schemes and/or in the Examples and Preparations below, by substituting a readily available isotopically-labeled reagent for a non-isotopically-labeled reagent.

Some embodiments also relate to the pharmaceutically acceptable acid addition salts of the compounds described herein. The acids which are used to prepare the pharmaceutically acceptable acid addition salts of the aforementioned base compounds are those which form nontoxic acid addition salts, i.e., salts containing pharmacologically acceptable anions, such as, but not limited to, the chloride, bromide, iodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1' methylene bis(2 hydroxy 3 naphthoate)]salts.

Additional embodiments relate to base addition salts of the compounds described herein. The chemical bases that may be used as reagents to prepare pharmaceutically acceptable base salts of those compounds of the compounds described herein that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

The phrase "pharmaceutically acceptable salt(s)", as used herein, unless otherwise indicated, includes salts of acidic or basic groups which may be present in the compounds of described herein. The compounds described herein that are basic in nature are capable of forming a wide variety of salts with various inorganic and organic acids. The acids that may be used to prepare pharmaceutically acceptable acid addition salts of such basic compounds described herein are those that form non-toxic acid addition salts, e.g., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts. The compounds described herein that include a basic moiety, such as an amino group, may form pharmaceutically acceptable salts with various amino acids, in addition to the acids mentioned above.

The compounds of the embodiments described herein include all stereoisomers (e.g., cis and trans isomers) and all optical isomers of compounds described herein (e.g., R and S enantiomers), as well as racemic, diastereomeric and other mixtures of such isomers. While all stereoisomers are encompassed within the scope of our claims, one skilled in the art will recognize that particular stereoisomers may be preferred.

In some embodiments, the compounds described herein can exist in several tautomeric forms, including the enol and imine form, and the keto and enamine form and geometric isomers and mixtures thereof. All such tautomeric forms are included within the scope of the present embodiments. Tautomers exist as mixtures of a tautomeric set in solution. In solid form, usually one tautomer predominates. Even though one tautomer may be described, the present embodiments includes all tautomers of the present compounds.

The present embodiments also include atropisomers of the compounds described herein. Atropisomers refer to compounds that can be separated into rotationally restricted isomers.

Further embodiments relate to methods for making intermediate compounds that are useful for making the compounds described herein.

As noted above, some embodiments also relate to the pharmaceutically acceptable salts of the compounds described herein. Pharmaceutically acceptable salts of the compounds described herein include the acid addition and base salts thereof.

Suitable acid addition salts are formed from acids which form non-toxic salts. Non-limiting examples of suitable acid addition salts include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

Suitable base salts are formed from bases which form non-toxic salts. Non-limiting examples of suitable base salts include the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulphate and hemicalcium salts.

For a review on suitable salts, see Handbook of Pharmaceutical Salts: Properties, Selection, and Use by Stahl and Wermuth (Wiley-VCH, 2002). Methods for making pharmaceutically acceptable salts of compounds described herein are known to one of skill in the art.

The compounds described herein may also exist in unsolvated and solvated forms. Accordingly, some embodiments relate to the hydrates and solvates of the compounds described herein.

The term "solvate" is used herein to describe a molecular complex comprising a compound described herein and one or more pharmaceutically acceptable solvent molecules, for example, ethanol.

Compounds described herein containing one or more asymmetric carbon atoms can exist as two or more stereoisomers. Where a compound described herein contains an alkenyl or alkenylene group, geometric cis/trans (or Z/E) isomers are possible. Where structural isomers are interconvertible via a low energy barrier, tautomeric isomerism ('tautomerism') can occur. This can take the form of proton tautomerism in compounds described herein containing, for example, an imino, keto, or oxime group, or so-called valence tautomerism in compounds which contain an aromatic moiety. A single compound may exhibit more than one type of isomerism.

Included within the scope of the present embodiments are all stereoisomers, geometric isomers and tautomeric forms of the compounds described herein, including compounds exhibiting more than one type of isomerism, and mixtures of one or more thereof. Also included are acid addition or base salts wherein the counterion is optically active, for example, d-lactate or l-lysine, or racemic, for example, dl-tartrate or dl-arginine.

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where a compound described herein contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person.

Further embodiments relate to methods of treating abnormal cell growth in a mammal. Additional embodiments relate to a method of treating abnormal cell growth in a mammal comprising administering to said mammal an amount of a compound described herein that is effective in treating abnormal cell growth.

In other embodiments, the abnormal cell growth is cancer.

In some embodiments, the cancer is selected from the group consisting of lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of two or more of the foregoing cancers.

Additional embodiments relate to methods of treating cancer solid tumors in a mammal. Some embodiments relate to the treatment of cancer solid tumor in a mammal comprising administering to said mammal an amount of a compound described herein that is effective in treating said cancer solid tumor.

In other embodiments, the cancer solid tumor is breast, lung, colon, brain, prostate, stomach, pancreatic, ovarian, skin (melanoma), endocrine, uterine, testicular, or bladder.

Further embodiments relate to methods of treating abnormal cell growth in a mammal which comprises administering to said mammal an amount of a compound described herein that is effective in treating abnormal cell growth in combination with an anti-tumor agent selected from the group consisting of mitotic inhibitors, alkylating agents, anti-metabolites, intercalating antibiotics, growth factor inhibitors, radiation, cell cycle inhibitors, enzymes, topoisomerase inhibitors, biological response modifiers, antibodies, cytotoxics, anti-hormones, and anti-androgens.

More embodiments relate to pharmaceutical compositions for treating abnormal cell growth in a mammal comprising an amount of a compound described herein that is effective in treating abnormal cell growth, and a pharmaceutically acceptable carrier.

Additional embodiments relate to a method of treating abnormal cell growth in a mammal, including a human, comprising administering to said mammal an amount of a compound described herein, or a pharmaceutically acceptable salt, solvate, hydrate or prodrug thereof, that is effective in treating abnormal cell growth. In one embodiment of this method, the abnormal cell growth is cancer, including, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers. In one embodiment the method comprises comprising administering to a mammal an amount of a compound described herein that is effective in treating said cancer solid tumor. In one preferred embodiment the solid tumor is breast, lung, colon, brain, prostate, stomach, pancreatic, ovarian, skin (melanoma), endocrine, uterine, testicular, and bladder cancer.

In another embodiment of said method, said abnormal cell growth is a benign proliferative disease, including, but not limited to, psoriasis, benign prostatic hypertrophy or restinosis.

Some embodiments relate to a method of treating abnormal cell growth in a mammal which comprises administering to said mammal an amount of a compound described herein, or a pharmaceutically acceptable salt, solvate, hydrate or prodrug thereof, that is effective in treating abnormal cell growth in combination with an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, antibodies, cytotoxics, anti-hormones, and anti-androgens.

Additional embodiments relate to a pharmaceutical composition for treating abnormal cell growth in a mammal, including a human, comprising an amount of a compound described herein, or a pharmaceutically acceptable salt, solvate, hydrate or prodrug thereof, that is effective in treating abnormal cell growth, and a pharmaceutically acceptable carrier. In one embodiment of said composition, said abnormal cell growth is cancer, including, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers. In another embodiment of said pharmaceutical composition, said abnormal cell growth is a benign proliferative disease, including, but not limited to, psoriasis, benign prostatic hypertrophy or restinosis.

Further embodiments relate to a method of treating abnormal cell growth in a mammal which comprises administering to said mammal an amount of a compound described herein, or a pharmaceutically acceptable salt, solvate, or hydrate thereof, that is effective in treating abnormal cell growth in combination with another anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, antibodies, cytotoxics, anti-hormones, and anti-androgens. Some embodiments contemplate a pharmaceutical composition for treating abnormal cell growth wherein the composition includes a compound described herein, or a pharmaceutically acceptable salt, solvate, or hydrate thereof, that is effective in treating abnormal cell growth, and another anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, antibodies, cytotoxics, anti-hormones, and anti-androgens.

Yet more embodiments relate to a method of treating a disorder associated with angiogenesis in a mammal, including a human, comprising administering to said mammal an amount of a compound described herein, as defined above, or a pharmaceutically acceptable salt, solvate, hydrate or prodrug thereof, that is effective in treating said disorder in combination with one or more anti-tumor agents listed above. Such disorders include cancerous tumors such as melanoma; ocular disorders such as age-related macular degeneration, presumed ocular histoplasmosis syndrome, and retinal neovascularization from proliferative diabetic retinopathy; rheumatoid arthritis; bone loss disorders such as osteoporosis, Paget's disease, humoral hypercalcemia of malignancy, hypercalcemia from tumors metastatic to bone, and osteoporosis induced by glucocorticoid treatment; coronary restenosis; and certain microbial infections including those associated with microbial pathogens selected from adenovirus, hantaviruses, *Borrelia burgdorferi, Yersinia* spp., *Bordetella pertussis*, and group A *Streptococcus*.

Some embodiments relate to a method of (and to a pharmaceutical composition for) treating abnormal cell growth in a mammal which comprise an amount of a compound described herein, or a pharmaceutically acceptable salt, solvate, or hydrate thereof, in combination with an amount of one or more substances selected from anti-angiogenesis agents, signal transduction inhibitors inhibitor (e.g., inhibiting the means by which regulatory molecules that govern the fundamental processes of cell growth, differentiation, and survival communicated within the cell), and antiproliferative agents, which amounts are together effective in treating said abnormal cell growth.

Anti-angiogenesis agents, such as MMP-2 (matrix-metalloprotienase 2) inhibitors, MMP-9 (matrix-metalloprotienase 9) inhibitors, and COX-II (cyclooxygenase II) inhibitors, can be used in conjunction with a compound described herein in the methods and pharmaceutical compositions described herein. Examples of useful COX-II inhibitors include CELEBREX™ (celecoxib), Bextra (valdecoxib), paracoxib, Vioxx (rofecoxib), and Arcoxia (etoricoxib). Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 331, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain patent application number 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are herein incorporated by reference in their entirety. Preferred MMP-2 and MMP-9 inhibitors are those that have little or no activity inhibiting MMP-1. More preferred, are those that selectively inhibit MMP-2 and/or MMP-9 relative to the other matrix-metalloproteinases (i.e. MMP-1, MMP-3, MMP-4, MMP-5, MMP-6, MMP-7, MMP-8, MMP-10, MMP-11, MMP-12, and MMP-13).

Some specific examples of MMP inhibitors useful in combination with the compounds described herein are AG-3340, RO 32-3555, RS 13-0830, and the following compounds:
3-[[4-(4-fluoro-phenoxy)-benzenesulfonyl]-(1-hydroxycarbamoyl-cyclopentyl)-amino]-propionic acid;
3-exo-3-[4-(4-fluoro-phenoxy)-benzenesulfonylamino]-8-oxa-bicyclo[3.2.1]octane-3-carboxylic acid hydroxyamide;
(2R,3R) 1-[4-(2-chloro-4-fluoro-benzyloxy)-benzenesulfonyl]-3-hydroxy-3-methyl-piperidine-2-carboxylic acid hydroxyamide;
4-[4-(4-fluoro-phenoxy)-benzenesulfonylamino]-tetrahydro-pyran-4-carboxyl is acid hydroxyamide;
3-[[4-(4-fluoro-phenoxy)-benzenesulfonyl]-(1-hydroxycarbamoyl-cyclobutyl)-amino]-propionic acid;
4-[4-(4-chloro-phenoxy)-benzenesulfonylamino]-tetrahydro-pyran-4-carboxylic acid hydroxyamide;
3-[4-(4-chloro-phenoxy)-benzenesulfonylamino]-tetrahydro-pyran-3-carboxylic acid hydroxyamide;
(2R,3R) 1-[4-(4-fluoro-2-methyl-benzyloxy)-benzenesulfonyl]-3-hydroxy-3-methyl-piperidine-2-carboxylic acid hydroxyamide;
3-[[4-(4-fluoro-phenoxy)-benzenesulfonyl]-(1-hydroxycarbamoyl-1-methyl-ethyl)-amino]-propionic acid;
3-[[4-(4-fluoro-phenoxy)-benzenesulfonyl]-(4-hydroxycarbamoyl-tetrahydro-pyran-4-yl)-amino]-propionic acid;
3-exo-3-[4-(4-chloro-phenoxy)-benzenesulfonylamino]-8-oxa-bicyclo[3.2.1]octane-3-carboxylic acid hydroxyamide;
3-endo-3-[4-(4-fluoro-phenoxy)-benzenesulfonylamino]-8-oxa-bicyclo[3.2.1]octane-3-carboxylic acid hydroxyamide; and
3-[4-(4-fluoro-phenoxy)-benzenesulfonylamino]-tetrahydro-furan-3-carboxylic acid hydroxyamide;
and pharmaceutically acceptable salts and solvates of said compounds.

VEGF inhibitors, for example, SU-11248, SU-5416 and SU-6668 (Sugen Inc. of South San Francisco, Calif., USA), can also be combined with a compound described herein. VEGF inhibitors are described in, for example in WO 99/24440 (published May 20, 1999), PCT International Application PCT/IB99/00797 (filed May 3, 1999), in WO 95/21613 (published Aug. 17, 1995), WO 99/61422 (published Dec. 2, 1999), U.S. Pat. No. 5,834,504 (issued Nov. 10, 1998), WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), U.S. Pat. No. 6,653,308 (issued Nov. 25, 2003), WO 99/10349 (published Mar. 4, 1999), WO 97/32856 (published Sep. 12, 1997), WO 97/22596 (published Jun. 26, 1997), WO 98/54093 (published Dec. 3, 1998), WO 98/02438 (published Jan. 22, 1998), WO 99/16755 (published Apr. 8, 1999), and WO 98/02437 (published Jan. 22, 1998), all of which are herein incorporated by reference in their entirety. Other examples of some specific VEGF inhibitors are IM862 (Cytran Inc. of Kirkland, Wash., USA); Avastin, an anti-VEGF monoclonal antibody of Genentech, Inc. of South San Francisco, Calif.; and angiozyme, a synthetic ribozyme from Ribozyme (Boulder, Colo.) and Chiron (Emeryville, Calif.).

ErbB2 receptor inhibitors, such as GW-282974 (Glaxo Wellcome plc), and the monoclonal antibodies AR-209 (Aronex Pharmaceuticals Inc. of The Woodlands, Tex., USA) and 2B-1 (Chiron), may be administered in combination with a compound described herein. Such erbB2 inhibitors include Herceptin, 2C4, and pertuzumab. Such erbB2 inhibitors include those described in WO 98/02434 (published Jan. 22, 1998), WO 99/35146 (published Jul. 15, 1999), WO 99/35132 (published Jul. 15, 1999), WO 98/02437 (published Jan. 22, 1998), WO 97/13760 (published Apr. 17, 1997), WO 95/19970 (published Jul. 27, 1995), U.S. Pat. No. 5,587,458 (issued Dec. 24, 1996), and U.S. Pat. No. 5,877,305 (issued Mar. 2, 1999), each of which is herein incorporated by reference in its entirety. ErbB2 receptor inhibitors useful in the embodiments described herein are also described in U.S. Provisional Application No. 60/117,341, filed Jan. 27, 1999, and in U.S. Provisional Application No. 60/117,346, filed Jan. 27, 1999, both of which are herein incorporated by reference in their entirety. Other erbb2 receptor inhibitors include TAK-165 (Takeda) and GW-572016 (Glaxo-Wellcome).

Various other compounds, such as styrene derivatives, have also been shown to possess tyrosine kinase inhibitory properties, and some of tyrosine kinase inhibitors have been identified as erbB2 receptor inhibitors. More recently, five European patent publications, namely EP 0 566 226 A1 (published Oct. 20, 1993), EP 0 602 851 A1 (published Jun. 22, 1994), EP 0 635 507 A1 (published Jan. 25, 1995), EP 0 635 498 A1 (published Jan. 25, 1995), and EP 0 520 722 A1 (published Dec. 30, 1992), refer to certain bicyclic derivatives, in particular quinazoline derivatives, as possessing anti-cancer properties that result from their tyrosine kinase inhibitory properties. Also, World Patent Application WO 92/20642 (published Nov. 26, 1992), refers to certain bis-mono and bicyclic aryl and heteroaryl compounds as tyrosine kinase inhibitors that are useful in inhibiting abnormal cell proliferation. World Patent Applications WO96/16960 (published Jun. 6, 1996), WO 96/09294 (published Mar. 6, 1996), WO 97/30034 (published Aug. 21, 1997), WO 98/02434 (published Jan. 22, 1998), WO 98/02437 (published Jan. 22, 1998), and WO 98/02438 (published Jan. 22, 1998), also refer to substituted bicyclic heteroaromatic derivatives as tyrosine kinase inhibitors that are useful for the same purpose. Other patent applications that refer to anti-cancer compounds are World Patent Application WO00/44728 (published Aug. 3, 2000), EP 1029853A1 (published Aug. 23, 2000), and WO01/98277 (published Dec. 12, 2001) all of which are incorporated herein by reference in their entirety.

Other antiproliferative agents that may be used with the compounds described herein include inhibitors of the enzyme farnesyl protein transferase and inhibitors of the receptor tyrosine kinase PDGFr, including the compounds disclosed and claimed in the following U.S. patent application Ser. Nos. 09/221,946 (filed Dec. 28, 1998); 09/454,058 (filed Dec. 2, 1999); 09/501,163 (filed Feb. 9, 2000); 09/539,930 (filed Mar. 31, 2000); 09/202,796 (filed May 22, 1997); 09/384,339 (filed Aug. 26, 1999); and 09/383,755 (filed Aug. 26, 1999); and the compounds disclosed and claimed in the following U.S. provisional patent applications 60/168,207 (filed Nov. 30, 1999); 60/170,119 (filed Dec. 10, 1999); 60/177,718 (filed Jan. 21, 2000); 60/168,217 (filed Nov. 30, 1999), and 60/200,834 (filed May 1, 2000). Each of the foregoing patent applications and provisional patent applications is herein incorporated by reference in their entirety.

A compound described herein may also be used with other agents useful in treating abnormal cell growth or cancer, including, but not limited to, agents capable of enhancing antitumor immune responses, such as CTLA4 (cytotoxic lymphocyte antigen 4) antibodies, and other agents capable of blocking CTLA4; and anti-proliferative agents such as other farnesyl protein transferase inhibitors, for example the farnesyl protein transferase inhibitors described in the references cited in the "Background" section, supra. Specific CTLA4 antibodies that can be used in the present embodiments include those described in U.S. Provisional Application 60/113,647 (filed Dec. 23, 1998) which is herein incorporated by reference in its entirety.

A compound described herein may be applied as a sole therapy or may involve one or more other anti-tumor substances, for example those selected from, for example, mitotic inhibitors, for example vinblastine; alkylating agents, for example cis-platin, oxaliplatin, carboplatin and cyclophosphamide; anti-metabolites, for example 5-fluorouracil, capecitabine, cytosine arabinoside and hydroxyurea, or, for example, one of the preferred anti-metabolites disclosed in European Patent Application No. 239362 such as N-(5-[N-(3,4-dihydro-2-methyl-4-oxoquinazolin-6-ylmethyl)-N-methylamino]-2-thenoyl)-L-glutamic acid; growth factor inhibitors; cell cycle inhibitors; intercalating antibiotics, for example adriamycin and bleomycin; enzymes, for example interferon; and anti-hormones, for example anti-estrogens such as Nolvadex (tamoxifen) or, for example anti-androgens such as Casodex (4'-cyano-3-(4-fluorophenylsulphonyl)-2-hydroxy-2-methyl-3'-(trifluoromethyl)propionanilide).

The compounds described herein may be used alone or in combination with one or more of a variety of anti-cancer agents or supportive care agents. For example, the compounds described herein may be used with cytotoxic agents, e.g., one or more selected from the group consisting of a camptothecin, irinotecan HCl (Camptosar), edotecarin, SU-11248, epirubicin (Ellence), docetaxel (Taxotere), paclitaxel, rituximab (Rituxan) bevacizumab (Avastin), imatinib mesylate (Gleevac), Erbitux, gefitinib (Iressa), and combinations thereof. Some embodiments also contemplate the use of the compounds described herein together with hormonal therapy, e.g., exemestane (Aromasin), Lupron, anastrozole (Arimidex), tamoxifen citrate (Nolvadex), Trelstar, and combinations thereof. Further, some embodiments provide a compound described herein alone or in combination with one or more supportive care products, e.g., a product selected from the group consisting of Filgrastim (Neupogen), ondansetron (Zofran), Fragmin, Procrit, Aloxi, Emend, or combinations thereof. Such conjoint treatment may be achieved by way of the simultaneous, sequential or separate dosing of the individual components of the treatment.

The compounds described herein may be used with anti-tumor agents, alkylating agents, antimetabolites, antibiotics, plant-derived antitumor agents, camptothecin derivatives, tyrosine kinase inhibitors, antibodies, interferons, and/or biological response modifiers. In this regard, the following is a non-limiting list of examples of secondary agents that may be used with the compounds described herein.

Alkylating agents include, but are not limited to, nitrogen mustard N-oxide, cyclophosphamide, ifosfamide, melphalan, busulfan, mitobronitol, carboquone, thiotepa, ranimustine, nimustine, temozolomide, AMD-473, altretamine, AP-5280, apaziquone, brostallicin, bendamustine, carmustine, estramustine, fotemustine, glufosfamide, ifosfamide, KW-2170, mafosfamide, and mitolactol; platinum-coordinated alkylating compounds include but are not limited to, cisplatin, carboplatin, eptaplatin, lobaplatin, nedaplatin, oxaliplatin or satrplatin.

Antimetabolites include but are not limited to, methotrexate, 6-mercaptopurine riboside, mercaptopurine, 5-fluorouracil (5-FU) alone or in combination with leucovorin, tegafur, UFT, doxifluridine, carmofur, cytarabine, cytarabine ocfosfate, enocitabine, S-1, gemcitabine, fludarabin, 5-azacitidine, capecitabine, cladribine, clofarabine, decitabine, eflornithine, ethynylcytidine, cytosine arabinoside, hydroxyurea, TS-1, melphalan, nelarabine, nolatrexed, ocfosfate, disodium premetrexed, pentostatin, pelitrexol, raltitrexed, triapine, trimetrexate, vidarabine, vincristine, vinorelbine; or for example, one of the preferred anti-metabolites disclosed in European Patent Application No. 239362 such as N-(5-[N-(3,4-dihydro-2-methyl-4-oxoquinazolin-6-ylmethyl)-N-methylamino]-2-thenoyl)-L-glutamic acid.

Antibiotics include but are not limited to: aclarubicin, actinomycin D, amrubicin, annamycin, bleomycin, daunorubicin, doxorubicin, elsamitrucin, epirubicin, galarubicin, idarubicin, mitomycin C, nemorubicin, neocarzinostatin, peplomycin, pirarubicin, rebeccamycin, stimalamer, streptozocin, valrubicin or zinostatin.

Hormonal therapy agents, e.g., exemestane (Aromasin), Lupron, anastrozole (Arimidex), doxercalciferol, fadrozole, formestane, anti-estrogens such as tamoxifen citrate (Nolvadex) and fulvestrant, Trelstar, toremifene, raloxifene, lasofoxifene, letrozole (Femara), or anti-androgens such as bicalutamide, flutamide, mifepristone, nilutamide, Casodex® (4'-cyano-3-(4-fluorophenylsulphonyl)-2-hydroxy-2-methyl-3'-(trifluoromethyl)propionanilide) and combinations thereof.

Plant derived anti-tumor substances include for example those selected from mitotic inhibitors, for example vinblastine, docetaxel (Taxotere) and paclitaxel.

Cytotoxic topoisomerase inhibiting agents include one or more agents selected from the group consisting of aclarubicn, amonafide, belotecan, camptothecin, 10-hydroxycamptothecin, 9-aminocamptothecin, diflomotecan, irinotecan HCl (Camptosar), edotecarin, epirubicin (Ellence), etoposide, exatecan, gimatecan, lurtotecan, mitoxantrone, pirarubicin, pixantrone, rubitecan, sobuzoxane, SN-38, tafluposide, and topotecan, and combinations thereof.

Immunologicals include interferons and numerous other immune enhancing agents. Interferons include interferon alpha, interferon alpha-2a, interferon, alpha-2b, interferon beta, interferon gamma-1a or interferon gamma-n1. Other agents include PF3512676, filgrastim, lentinan, sizofilan, TheraCys, ubenimex, WF-10, aldesleukin, alemtuzumab, BAM-002, dacarbazine, daclizumab, denileukin, gemtuzumab ozogamicin, ibritumomab, imiquimod, lenograstim, lentinan, melanoma vaccine (Corixa), molgramostim, OncoVAX-CL, sargramostim, tasonermin, tecleukin, thymalasin, tositumomab, Virulizin, Z-100, epratuzumab, mitumomab, oregovomab, pemtumomab, Provenge.

Biological response modifiers are agents that modify defense mechanisms of living organisms or biological responses, such as survival, growth, or differentiation of tissue cells to direct them to have anti-tumor activity. Such agents include krestin, lentinan, sizofiran, picibanil, or ubenimex.

Other anticancer agents include alitretinoin, ampligen, atrasentan bexarotene, bortezomib. Bosentan, calcitriol, exisulind, finasteride, fotemustine, ibandronic acid, miltefosine, mitoxantrone, I-asparaginase, procarbazine, dacarbazine, hydroxycarbamide, pegaspargase, pentostatin, tazarotne, TLK-286, Velcade, Tarceva, or tretinoin.

Other anti-angiogenic compounds include acitretin, fenretinide, thalidomide, zoledronic acid, angiostatin, aplidine, cilengtide, combretastatin A-4, endostatin, halofuginone, rebimastat, removab, Revlimid, squalamine, ukrain and Vitaxin.

Platinum-coordinated compounds include but are not limited to, cisplatin, carboplatin, nedaplatin, or oxaliplatin.

Camptothecin derivatives include but are not limited to camptothecin, 10-hydroxycamptothecin, 9-aminocamptothecin, irinotecan, SN-38, edotecarin, and topotecan.

Tyrosine kinase inhibitors include, for example, Iressa and SU5416.

Antibodies include, for example, Herceptin, Erbitux, Avastin, and Rituximab.

Interferons include, for example, interferon alpha, interferon alpha-2a, interferon, alpha-2b, interferon beta, interferon gamma-1a and interferon gamma-n1.

Biological response modifiers include agents that modify defense mechanisms of living organisms or biological responses, such as survival, growth, or differentiation of tissue cells to direct them to have anti-tumor activity. Such agents include, for example, krestin, lentinan, sizofiran, picibanil, and ubenimex.

Other antitumor agents include, for example, mitoxantrone, 1-asparaginase, procarbazine, dacarbazine, hydroxycarbamide, pentostatin, and tretinoin.

"Abnormal cell growth", as used herein, unless otherwise indicated, refers to cell growth that is independent of normal regulatory mechanisms (e.g., loss of contact inhibition). This includes the abnormal growth of: (1) tumor cells (tumors) that proliferate by expressing a mutated tyrosine kinase or over-expression of a receptor tyrosine kinase; (2) benign and malignant cells of other proliferative diseases in which aberrant tyrosine kinase activation occurs; (3) any tumors that proliferate by receptor tyrosine kinases; (4) any tumors that proliferate by aberrant serine/threonine kinase activation; and (5) benign and malignant cells of other proliferative diseases in which aberrant serine/threonine kinase activation occurs.

The compounds described herein are potent inhibitors of Smo, and thus are all adapted to therapeutic use as antiproliferative agents (e.g., anticancer), antitumor (e.g., effective against solid tumors), antiangiogenesis (e.g., stop or prevent proliferation of blood vessels) in mammals, particularly in humans. In particular, the compounds described herein are useful in the prevention and treatment of a variety of human hyperproliferative disorders such as malignant and benign tumors of the liver, kidney, bladder, breast, gastric, ovarian, colorectal, prostate, pancreatic, lung, vulval, thyroid, hepatic carcinomas, sarcomas, glioblastomas, head and neck, and other hyperplastic conditions such as benign hyperplasia of the skin (e.g., psoriasis) and benign hyperplasia of the prostate (e.g., BPH). It is, in addition, expected that a compound described herein may possess activity against a range of leukemias and lymphoid malignancies.

In one embodiment, cancer is lung cancer, bone cancer, pancreatic cancer, gastric, skin cancer, cancer of the head or neck, cutaneous or intraocular melanoma, uterine cancer, ovarian cancer, gynecological, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, squamous cell, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain, pituitary adenoma, or a combination of one or more of the foregoing cancers.

In another embodiment, cancer is selected a solid tumor, such as, but not limited to, breast, lung, colon, brain (e.g., glioblastoma), prostate, stomach, pancreatic, ovarian, skin (melanoma), endocrine, uterine, testicular, and bladder.

The methods described herein include the use of small molecules which inhibit Smo, in the regulation of repair and/or functional performance of a wide range of cells, tissues and organs, including normal cells, tissues, and organs, as well as those having the phenotype of ptc loss-of-function, hedgehog gain-of-function, or smoothened gain-of-function. For instance, the subject method has therapeutic and cosmetic applications ranging from regulation of neural tissues, bone and cartilage formation and repair, regulation of spermatogenesis, regulation of smooth muscle, regulation of lung, liver and other organs arising from the primative gut, regulation of hematopoietic function, regulation of skin and hair growth, etc. Moreover, the subject methods can be performed on cells that are provided in culture (in vitro), or on cells in a whole animal (in vivo). See, for example, PCT publications WO 95/18856 and WO 96/17924.

Some embodiments also relate to a pharmaceutical composition comprising a compound of formula I or formula II, or a pharmaceutically acceptable salt or solvate thereof, as hereinbefore defined in association with a pharmaceutically acceptable adjuvant, diluent or carrier.

Further embodiments relate to a pharmaceutical composition which comprises mixing a compound of formula I or formula II, or a pharmaceutically acceptable salt or solvate thereof, as hereinbefore defined with a pharmaceutically acceptable adjuvant, diluent or carrier.

For the above-mentioned therapeutic uses the dosage administered will, of course, vary with the compound employed, the mode of administration, the treatment desired and the disorder indicated. The daily dosage of the compound of formula I or formula II, or pharmaceutically acceptable salt thereof, may be in the range from 1 mg to 1 gram, preferably 1 mg to 250 mg, more preferably 10 mg to 100 mg.

The present embodiments also encompass sustained release compositions.

Administration of the compounds described herein (hereinafter the "active compound(s)") can be effected by any method that enables delivery of the compounds to the site of action. These methods include oral routes, intraduodenal routes, parenteral injection (including intravenous, subcutaneous, intramuscular, intravascular or infusion), topical, and rectal administration.

The active compound may be applied as a sole therapy or may involve one or more other anti-tumor substances, for example those selected from, for example, mitotic inhibitors, for example vinblastine; alkylating agents, for example cisplatin, carboplatin and cyclophosphamide; anti-metabolites, for example 5-fluorouracil, cytosine arabinoside and hydroxyurea, or, for example, one of the preferred anti-metabolites disclosed in European Patent Application No. 239362 such as N-(5-[N-(3,4-dihydro-2-methyl-4-oxoquinazolin-6-ylmethyl)-N-methylamino]-2-thenoyl)-L-glutamic acid; growth factor inhibitors; cell cycle inhibitors; intercalating antibiotics, for example adriamycin and bleomycin; enzymes, for example interferon; and anti-hormones, for example anti-estrogens such as Nolvadex® (tamoxifen) or, for example anti-androgens such as Casodex® (4'-cyano-3-(4-fluorophenylsulphonyl)-2-hydroxy-2-methyl-3'-(trifluoromethyl)propionanilide). Such conjoint treatment may be achieved by way of the simultaneous, sequential or separate dosing of the individual components of the treatment.

The pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound described herein as an active ingredient. In addition, it may include other medicinal or pharmaceutical agents, carriers, adjuvants, etc.

Exemplary parenteral administration forms include solutions or suspensions of active compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefor, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

DETAILED DESCRIPTION

The examples and preparations provided below further illustrate and exemplify the compounds described herein and methods of preparing such compounds. The scope of the embodiments described herein is not limited in any way by the following examples and preparations. In the following examples, molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

In general, the compounds described herein may be prepared by processes known in the chemical arts, particularly in light of the description contained herein. Certain processes for the manufacture of the compounds described herein are provided as further features of the embodiments and are illustrated in the reaction schemes provided below and in the experimental section.

The following abbreviations may be used herein: $Et_2O$ (diethyl ether); DMF (N,N-dimethylformamide); THF (tetrahydrofuran); DCM (dichloromethane); DMA (dimethyl acetal); DBU (1,8-diazabicyclo[5.4.0]undec-7-ene); HATU (2-(1H-7-azabenzotriazol-1-yl)-1,1,3,3-tetramethyl uronium hexafluorophosphate methanaminium); LDA (lithium diisopropylamide); DMSO (dimethylsulfoxide); DIPEA (N,N-diisopropylethylamine); mCPBA (meta-chloroperoxybenzoic acid); TFA (trifluoroacetic acid); N—BOC(N-tert-butoxycarbonyl); dppf (1,1'-bis(diphenylphosphino)ferrocene); TLC (thin layer chromatagrophy); HOBt (hydroxybenzotriazole); NMM (N-methylmorpholine); EDCI (1-ethyl-3-(3-dimethylaminopropyl)carbodiimide); HOAc (acetic acid); $Ac_2O$ (acetic anhydride); NCS (N-chlorosuccinimide); i-pr (isopropyl); TMS (trimethylsilyl); OTf (trifluoromethanesulfonate); APCI (atmospheric pressure chemical ionization); LRMS (low resolution mass spectrometry); DDQ (2,3-dichloro-5,6-dicyano-p-benzoquinone); Tol (toluene); MeOH (methanol); EtOH (ethanol); EtOAc (ethyl acetate); Ac (acetyl); Bu (butyl); Me (methyl); Et (ethyl); MEM (minimal essential medium); PBS (phosphate-buffered saline); FBS (fetal bovine serum); R.T. or rt (room temperature); mins (minutes); conc. (concentrated); CV (column volume); and ND (not determined). As used herein, the symbol "~" refers to "approximately" or "to approximately".

Methods of preparing various pharmaceutical compositions with a specific amount of active compound are known, or will be apparent, to those skilled in this art. For examples, see Remington's Pharmaceutical Sciences, Mack Publishing Company, Easter, Pa., 15th Edition (1975).

The compounds described herein can be prepared by the following general methods and by methods described in detail as follows.

protected or unprotected amines (6-8) in the presence of a base such as cesium fluoride in a suitable solvent (such as DMSO) can yield products A-1-A-3. In the case of the protected amines, deprotection and subsequent treatment with acylating agents (under standard conditions known in the art)

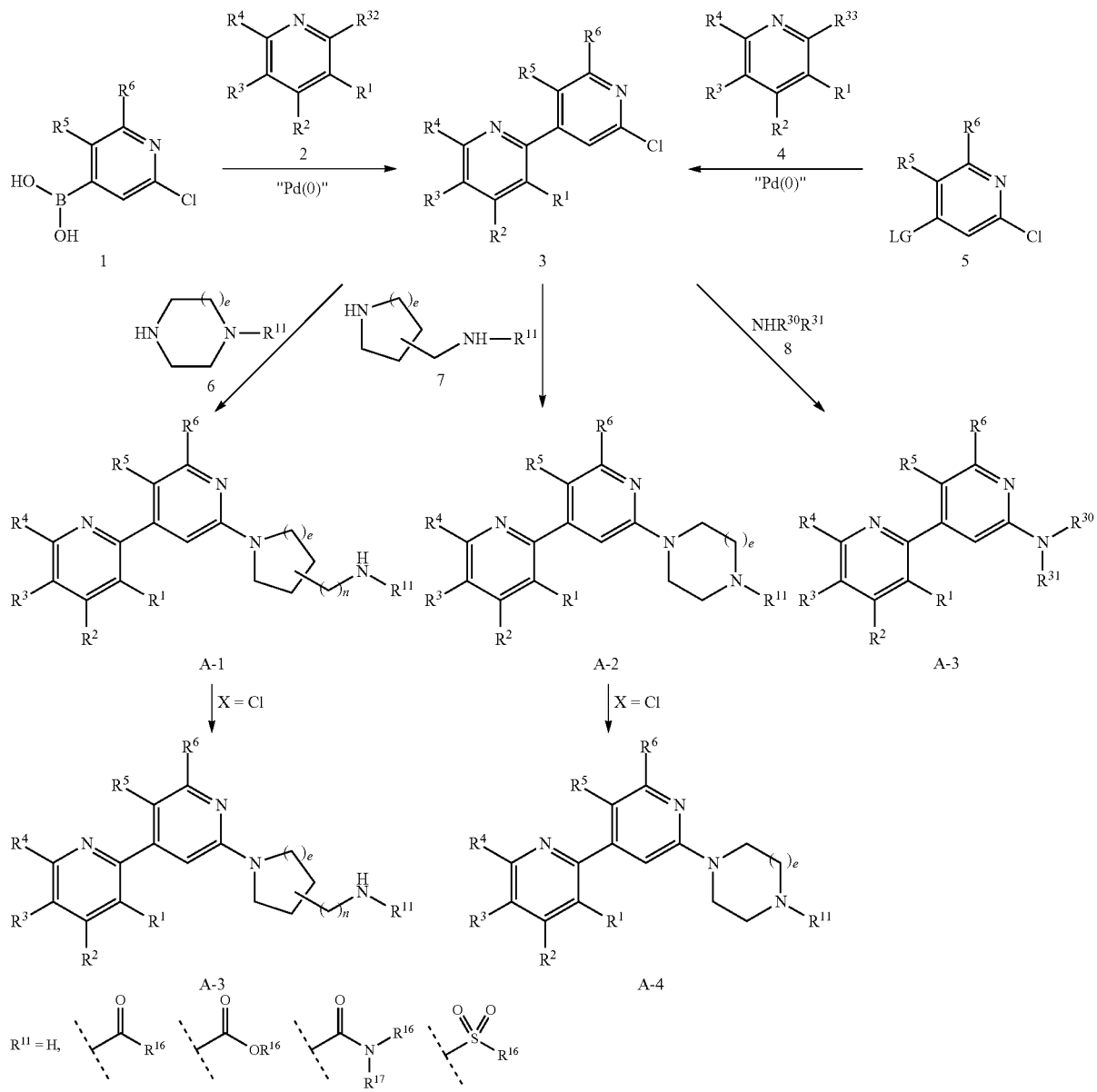

As illustrated in Scheme A1, heteroaryl boronic acid 1 can be treated with an aryl- or heteroaryl halide or aryl- or heteroaryl trifluoromethylsulfonate 2 in a transition metal mediated Suzuki coupling to provide chloropyridine 3. Alternatively, heteroaryl halide or trifluoromethane sulfonate 5 can be reacted with an aryl- or heteroaryl boronic acid or boronic ester, an aryl- or heteroaryl stannane, or an aryl- or heteroaryl zincate 4 in a transition metal catalyzed Suzuki, Stille or Negishi coupling to provide 3. Treatment of 3 with suitable such as activated carboxylic acids or acyl chlorides, carbamoyl chlorides, isocyanates and sulfonyl chlorides can provide amides, carbamates, ureas, and sulfonamides A-1 and A-2. The des-chloro analogs of A-1 and A-2 can be prepared by hydrogenation of the corresponding A1 and A-2 analogs. In Scheme A1, $R^5$ can be Cl, F, Br, Alkyl, or OR; $R^{33}$ can be $B(OR)_2$, $SnR_3$, or ZnX; LG can be Br, I or OTf; $R^{32}$ can be Br, I or OTf; and $R^{30}$ and $R^{31}$, together with the nitrogen to which they are attached, may combine to form a heterocycle as depicted in formula (I) or formula (II).

EXPERIMENTALS

Preparation of 1-(4-(5'-chloro-3,5-dimethyl-2,4'-bipyridin-2'-yl)piperazin-1-yl)-3-(methylsulfonyl)propan-1-one (Example A-116)

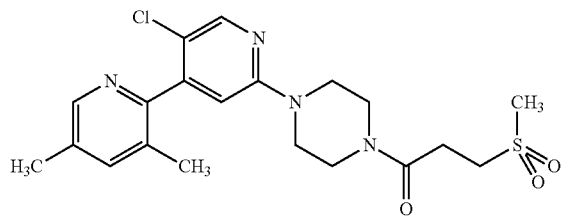 [SMILES: Cc1cnc(-c2cc(N3CCN(C(=O)CCS(C)(=O)=O)CC3)ncc2Cl)c(C)c1]

Step 1: 2',5'-dichloro-3,5-dimethyl-2,4'-bipyridine

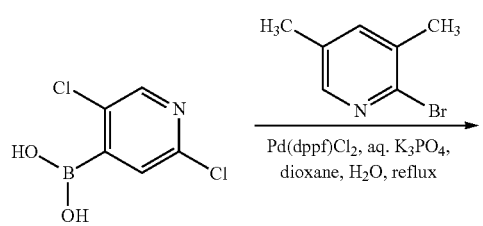

A mixture of 2,5-dichloropyridin-4-ylboronic acid (75.6 g, 0.4 mol), 2-bromo-3,5-dimethylpyridine (56.2 g, 0.3 mol), Pd(dppf)Cl$_2$ (13.5 g, 17 mmol) and K$_3$PO$_4$·3H$_2$O (162 g, 0.6 mol) in dioxane (600 mL) and H$_2$O (120 mL) was stirred at reflux under N$_2$ atmosphere overnight. TLC (petroleum ether/EtOAc=10:1) showed that the reaction was complete. After cooling to room temperature, the mixture was filtered. Water (500 mL) was then added to the filtrate. The mixture was extracted with dichloromethane (500 mL×3). The combined organic layers were washed with brine (300 mL), dried over Na$_2$SO$_4$, filtered and concentrated. The residue was purified by chromatography on silica gel (petroleum ether/EtOAc=50:1 to 30:1) to give title compound (20 g, 26%) as a yellow solid. $^1$H NMR (400 MHz, MeOD): δ 8.54 (s, 1H), 8.31 (s, 1H), 7.68 (s, 1H), 7.50 (s, 1H), 2.41 (s, 3H), 2.15 (s, 3H); m/z for C$_{12}$H$_{10}$Cl$_2$N$_2$ 253.1 (M+H)+.

Step 2: Tert-butyl 4-(5'-chloro-3,5-dimethyl-2,4'-bipyridin-2'-yl)piperazine-1-carboxylate

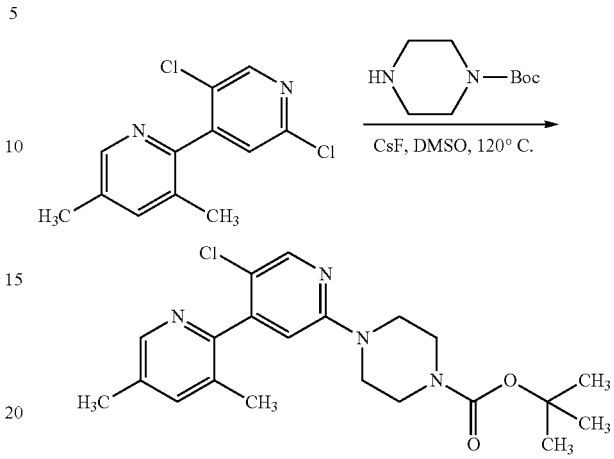

To a solution of 2',5'-dichloro-3,5-dimethyl-2,4'-bipyridine (4.5 g, 17.8 mmol) and tert-butyl piperazine-1-carboxylate (4.0 g, 21.4 mmol) in DMSO (80 mL) was added CsF (5.4 g, 35.6 mmol). Then the mixture was heated at 120° C. for 18 hours. TLC (petroleum ether/EtOAc=2:1) showed that the reaction was complete. It was diluted with EtOAc (200 mL), washed with H$_2$O (70 mL) and brine (70 mL), dried over Na$_2$SO$_4$ and concentrated in vacuo. The residue was purified by chromatography on silica gel (petroleum ether/EtOAc=3:1) to afford title compound (5.6 g, 78%) as white solid.

Step 3: 5'-chloro-3,5-dimethyl-2'-(piperazin-1-yl)-2,4'-bipyridine

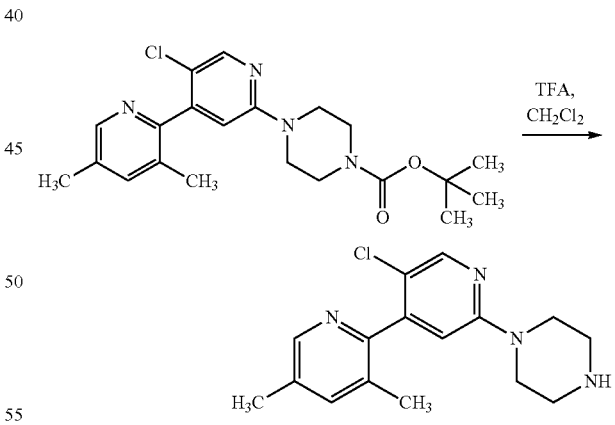

To a solution of tert-butyl 4-(5'-chloro-3,5-dimethyl-2,4'-bipyridin-2'-yl)piperazine-1-carboxylate (5.6 g, 14 mmol) in CH$_2$Cl$_2$ (50 mL) was added TFA (25 mL). Then the mixture was stirred for 18 hours. TLC (CH$_2$Cl$_2$/MeOH=10:1) showed the starting material was consumed completely. After removal of the solvent, the residue was dissolved in CH$_2$Cl$_2$ (180 mL), basified with 3 N aq. NaOH until pH=11, washed with brine (40 mL), dried over Na$_2$SO$_4$, filtered and concentrated in vacuo to afford title compound (4.1 g, 97%) as orange oil.

Step 4: 1-(4-(5'-chloro-3,5-dimethyl-2,4'-bipyridin-2'-yl)piperazin-1-yl)-3-(methylsulfonyl)propan-1-one

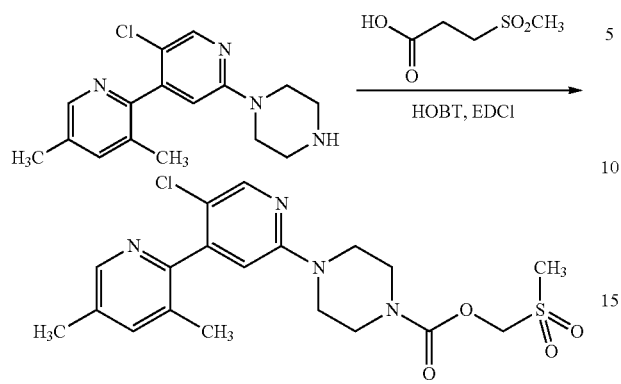

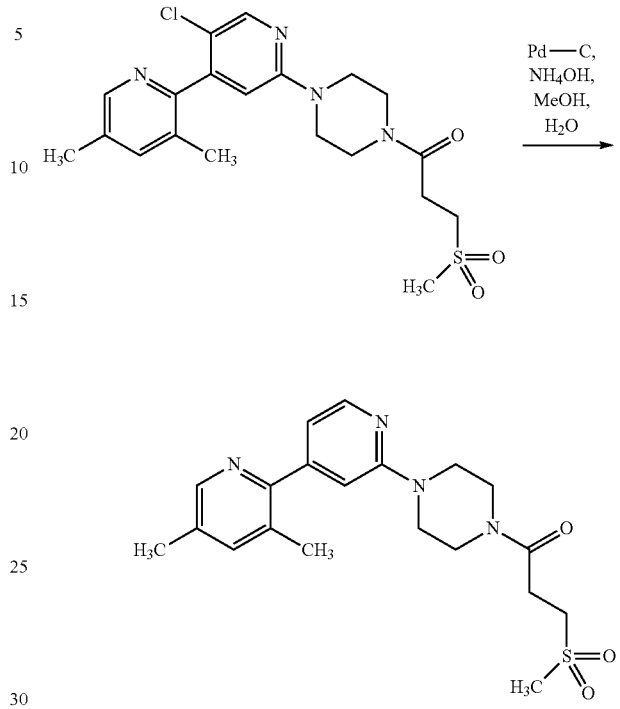

To a solution of 5'-chloro-3,5-dimethyl-2'-(piperazin-1-yl)-2,4'-bipyridine (2.3 g, 15.1 mmol) and HOBT (2.55 g, 18.9 mmol) in $CH_2Cl_2$ (60 mL) was added NMM (5.67 g, 56.7). After stirring for 30 min at room temperature, EDCI (3.63 g, 18.9 mmol) and 3-(methylsulfonyl)propanoic acid (3.9 g, 12.6 mmol) were added and the mixture was stirred at 30° C. for 18 hours. TLC ($CH_2Cl_2$/MeOH=10:1) showed the starting material was consumed completely. After removal of the solvent in vacuo, the residue was dissolved in $CH_2Cl_2$ (180 mL), washed with saturated aq. $NaHCO_3$ (40 mL), saturate aq. $NH_4Cl$ (40 mL) and brine (40 mL). The resulting material was dried over $Na_2SO_4$ and concentrated in vacuo to give title compound (4.8 g, 90%) as white solid. $^1$H NMR (400 MHz, $CDCl_3$): δ 8.28 (s, 1H), 8.15 (s, 1H), 7.36 (s, 1H), 6.53 (s, 1H), 3.69-3.66 (m, 2H), 3.58-5.53 (m, 4H), 3.48-3.46 (m, 2H), 3.41-3.37 (m, 2H), 2.94 (s, 3H) 2.89-2.86 (m, 2H), 2.31 (s, 3H), 2.10 (s, 3H); m/z for $C_{20}H_{25}ClN_4O_3S$ 437.3 $(M+H)^+$.

Preparation of 1-(4-(3,5-dimethyl-2,4'-bipyridin-2'-yl)piperazin-1-yl)-3-(methylsulfonyl)propan-1-one (Example A-141)

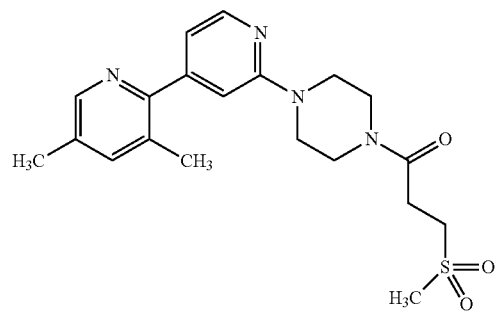

To 1-[4-(5'-chloro-3,5-dimethyl-2,4'-bipyridin-2'-yl)piperazin-1-yl]-3-(methylsulfonyl)propan-1-one (44 mg, 0.10 mmol) was added MeOH/Water 6:1 (5 mL, 0.02M), then 10% Pd/C (25 μL=20 w/w % relative to substrate) followed by $NH_4OH$ (1.0 mL, 5 eq, 0.5M solution in MeOH). The reaction of mixture was stirred at ambient temperature at 25° C. under balloon $H_2$ for 12 hrs. After filtering off catalyst through celite, the concentrated crude product was diluted with EtOAc (25 mL), washed with water (10 mL), then brine (10 mL), dried over $MgSO_4$, filtered. The solution was concentrated in vacuo. The residue was purified by chromatography on silica gel (EtOAc/heptane=1:3) to give the title compound (36 mg, 90%) as a yellow solid. $^1$H NMR (400 MHz, $CDCl_3$) δ ppm 8.36 (s, 1 H) 8.24-8.29 (m, 1 H) 7.42 (s, 1 H) 6.79-6.84 (m, 2 H) 3.75-3.81 (m, 4 H) 3.58-3.66 (m, 4 H) 3.47 (t, J=7.33 Hz, 2 H) 3.00 (s, 3H) 2.93-2.99 (m, 2 H) 2.37 (s, 3 H) 2.33 (s, 3 H); m/z for $C_{20}H_{26}N_4O_3S$ 403.1 (M+H)+.

Scheme A-2

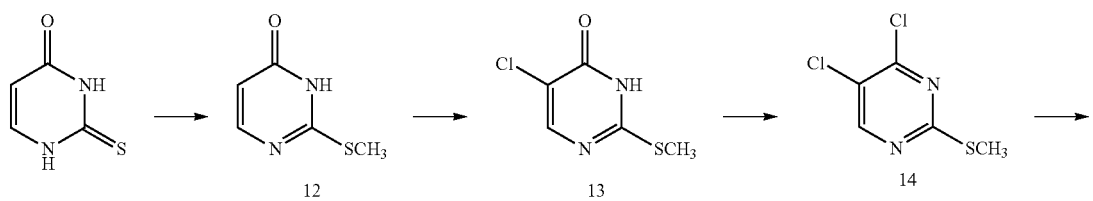

-continued

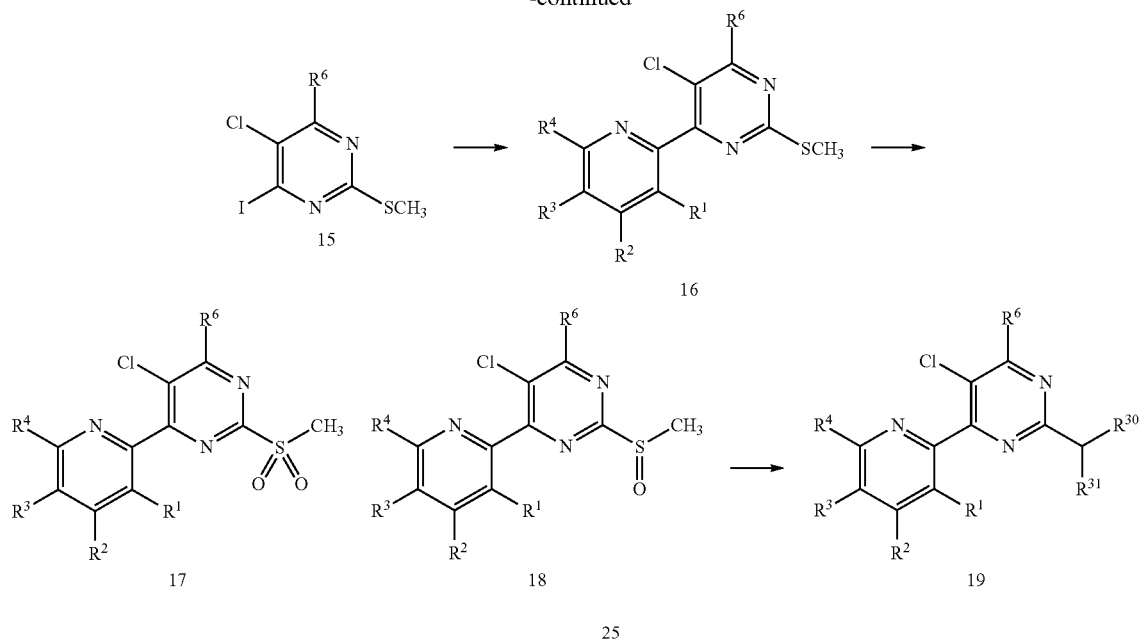

As shown in Scheme A-2, treatment of 2-thioxo-2,3-dihydropyrimidin-4(1H)-one with methyl iodide in presence of sodium hydroxide provided the thioether 12. Treatment of 12 with N-chlorosuccinimide in acetic acid and acetic anhydride provides 13 which on reaction with phosphoryl chloride (POCl$_3$) followed by aqueous hydriodic acid (HI) gives the iodide 15. Coupling of the corresponding 2-bromopyridine under Negishi conditions provides the thioether 16. Oxidation of this thioether with potassium peroxomonosulfate (Oxone) gives a mixture of the sulfone 17 and the sulfoxide 18 which can be used as is in the subsequent amination with various amines in the presence of a base such as cesium fluoride in a suitable solvent (such as DMSO) to provide the amines 19. Alternatively as shown in Scheme A-3, 2-chloropyrimidine can be treated with 2-bromopyridine in presence of n-butyl lithium followed by 2,3-dichloro-5,6-dicyano-p-benzoquinone (DDQ) to provide the chloropyrimidines 20. Amination of 20 with various functionalized amines in the presence of a base such as cesium fluoride in a suitable solvent (such as DMSO) gives amines 21. Alternatively treatment of an unfunctionalized amine such as piperazine with the chloride 20 followed by acylating agents (under standard conditions known in the art) such as activated carboxylic acids or acyl chlorides, carbamoyl chlorides, isocyanates and sulfonyl chlorides also provides amines 21. Chlorination of amines 21 with N-chlorosuccinimide provides the chloropyrimidines 22. In Schemes A-2 and A-3, R$^{30}$ and R$^{31}$, together with the nitrogen to which they are attached, may combine to form a heterocycle as depicted in formula (I) or formula (II).

Scheme A-3

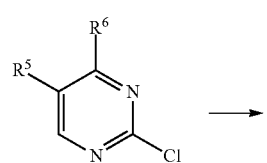

-continued

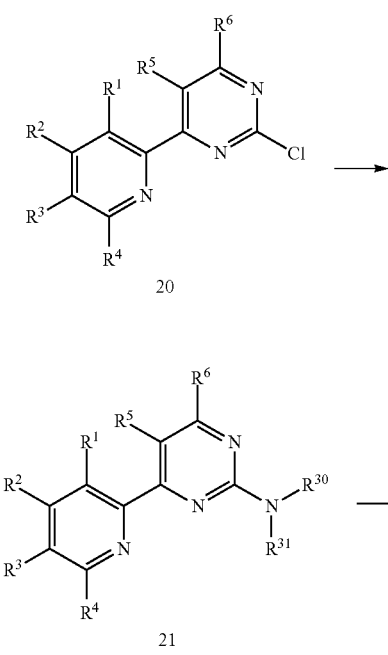

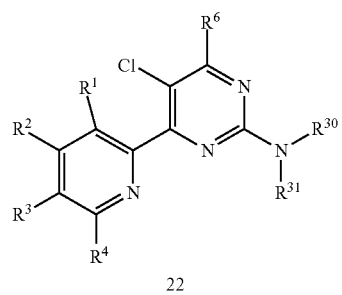

Preparation of 5-chloro-4-(3-methylpyridin-2-yl)-2-(4-(methylsulfonylmethyl)piperidin-1-yl)pyrimidine (Example A-97)

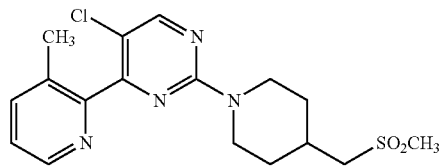 [SMILES: Cc1cccnc1-c1nc(N2CCC(CS(C)(=O)=O)CC2)ncc1Cl]

Step 1: 2-(methylthio)pyrimidin-4(3H)-one

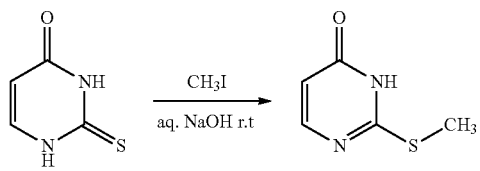

2-thioxo-2,3-dihydropyrimidin-4(1H)-one (66.7 g, 0.497 mol) was dissolved in aq. NaOH (41.6 g of solid in 365 mL of H$_2$O). The mixture was then treated with CH$_3$I (100.1 g, 0.704 mol) and was stirred at room temperature for 18 h. TLC (petroleum ether: EtOAc=4:1) indicated that the reaction was complete. The resulting mixture was adjusted to pH=5~6 with HOAc (30 mL). The solid formed was collected and dried on vacuum to give title compound (40 g, 54%) as a white solid.

Step 2: 5-chloro-2-(methylthio)pyrimidin-4(3H)-one

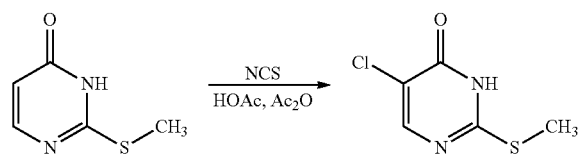

To a mixture of HOAc (500 mL) and Ac$_2$O (10 mL) was added compound 2-(methylthio)pyrimidin-4(3H)-one (40 g, 0.28 mol). The resulting mixture was heated at 80° C. for 30 min to remove any moisture. Then NCS (49 g, 0.37 mol) was added at 50~60° C. The resulting mixture was stirred at 50~60° C. for 24 h. The mixture was then cooled to room temperature and was poured into ice-water (500 mL). The solid formed was collected and was treated with MeOH (100 mL) at reflux. Then the solid was filtered and dried on vacuum to give title compound (24 g, 48%) as a white solid.

Step 3: 4,5-dichloro-2-(methylthio)pyrimidine

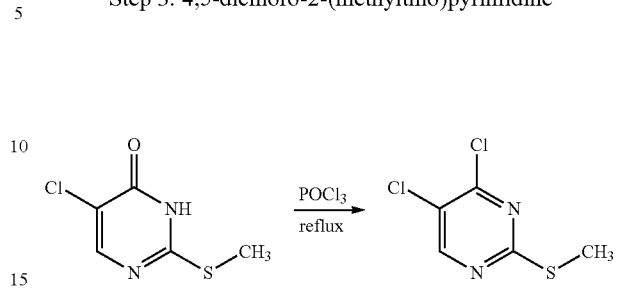

A suspension of 5-chloro-2-(methylthio)pyrimidin-4(3H)-one (24 g, 0.136 mol) in POCl$_3$ (200 mL) was heated at reflux for 2 hrs. The reaction mixture was then cooled to room temperature and was concentrated to remove excessive of POCl$_3$. The residue was then treated with H$_2$O (150 mL) and was adjusted to pH=7~8 with aq. K$_2$CO$_3$. The resulting mixture was extracted with CH$_2$Cl$_2$ (50 mL×4). The combined organic layers were washed with brine (50 mL), dried over Na$_2$SO$_4$ and filtered. The filtrate was concentrated and dried on vacuum to give title compound (23 g, 86%) as a light brown solid.

Step 4: 5-chloro-4-iodo-2-(methylthio)pyrimidine

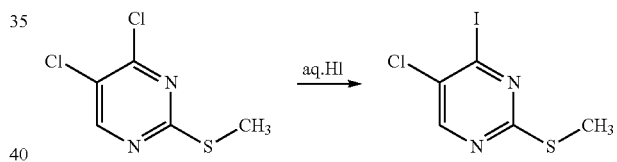

4,5-dichloro-2-(methylthio)pyrimidine (23 g, 0.118 mol) was added to aq. HI (250 mL). The resulting mixture was stirred at room temperature for 24 h. TLC (Petroleum ether: EtOAc=4:1) indicated that the reaction was complete. The solid formed was collected and was treated with H$_2$O (250 mL). The mixture was then adjusted to pH=7~8 with solid K$_2$CO$_3$ and was extracted with CH$_2$Cl$_2$ (100 mL×4). The combined organic layers were washed with brine (50 mL), dried over Na$_2$SO$_4$ and filtered. The filtrate was concentrated and dried on vacuum to give title compound (29 g, 86%) as a light yellow solid.

Step 5: 5-chloro-4-(3-methylpyridin-2-yl)-2-(methylthio)pyrimidine

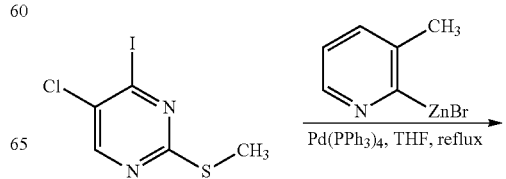

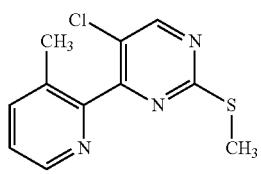

A solution of 5-chloro-4-iodo-2-(methylthio)pyrimidine (5 g, 17.4 mmol) and Pd(PPh₃)₄ (1 g, 0.87 mmol) in dry THF (120 mL) was degassed under N₂ three times. Then a solution of (3-methylpyridin-2-yl)zinc(II) bromide in THF (0.5 M, 53 mL, 26.3 mmol) was added. The resulting mixture was heated at reflux overnight. The mixture was then cooled to room temperature and was treated with EtOAc (80 mL) and H₂O (100 mL). The layers were separated and the aqueous layer was extracted with EtOAc (50 mL×3). The combined organic layers were washed with brine (50 mL), dried over Na₂SO₄ and filtered. The filtrate was concentrated and filtered. The filtrate was concentrated and the residue was purified via column chromatography (petroleum ether: EtOAc=9:1) to give the title compound (2.8 g, 64%) as a yellow syrup.

Step 6: 5-chloro-4-(3-methylpyridin-2-yl)-2-(methylsulfonyl)pyrimidine and 5-chloro-4-(3-methylpyridin-2-yl)-2-(methylsulfinyl)pyrimidine

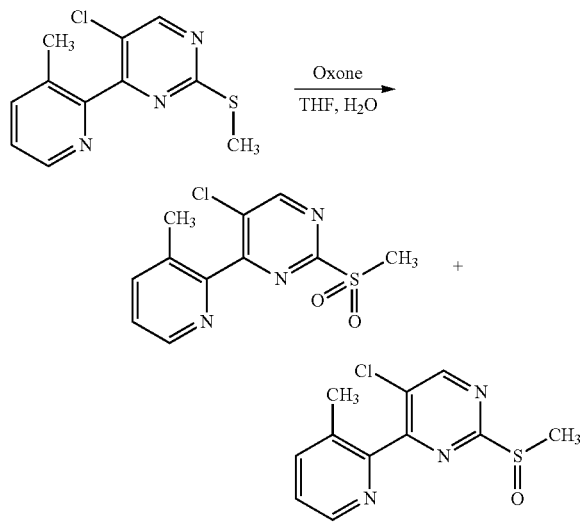

To a solution of 5-chloro-4-(3-methylpyridin-2-yl)-2-(methylthio)pyrimidine (2.5 g, 9.9 mmol) in THF/H₂O (1:1 100 mL) was added oxone (9.18 g, 15 mmol). The resulting mixture was stirred at room temperature for 3 h. TLC (petroleum ether:EtOAc=1:5) indicated that the reaction was complete. Then the mixture was diluted with EtOAc (100 mL) and H₂O (100 mL). The layers were separated and the aqueous layer was extracted with EtOAc (50 mL×5). The combined organic layers were washed with aq. NaHCO₃ (50 mL) and brine (50 mL), dried over Na₂SO₄ and filtered. The filtrate was concentrated to give the mixture of title compounds (2.5 g, 93.98%) as a yellow solid, which was directly used for the next stage without further purification.

Step 7: 5-chloro-4-(3-methylpyridin-2-yl)-2-(4-(methylsulfonylmethyl)piperidin-1-yl)pyrimidine

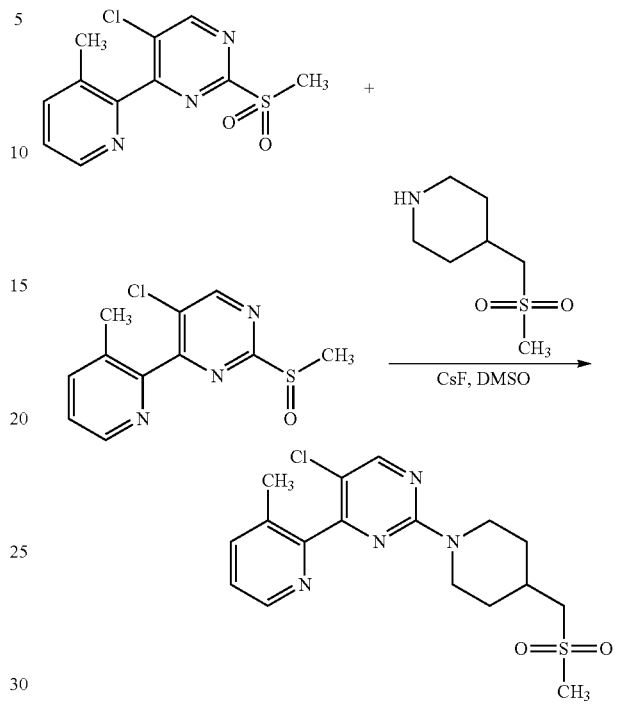

To a mixture of 5-chloro-4-(3-methylpyridin-2-yl)-2-(methylsulfonyl)pyrimidine and 5-chloro-4-(3-methylpyridin-2-yl)-2-(methylsulfinyl)pyrimidine (300 mg, 1.05 mmol) in DMSO (15 mL) was added 4-(methylsulfonylmethyl)piperidine (440 mg, 1.65 mmol) and CsF (640 mg, 4.2 mmol). The resulting mixture was heated at 100° C. at microwave for 30 min. TLC (CH₂Cl₂:MeOH=10:1) indicated that the reaction was complete. The mixture was then treated with EtOAc (50 mL) and H₂O (50 mL). The layers were separated and the aqueous layer was then extracted with EtOAc (30 mL×3). The combined organic layers were washed with brine (30 mL), dried over Na₂SO₄ and filtered. The filtrate was concentrated and the residue was purified via prep. HPLC to give title compound (183 mg, 46%) as a white solid. $^1$H NMR (400 MHz, CDCl₃): δ 8.47-8.48 (d, 1H), 8.28 (s, 1H), 7.55-7.56 (dd, 1H), 7.20-7.24 (m, 1H), 4.66-4.69 (d, 1H), 2.88-2.92 (m, 7H), 2.30-2.34 (m, 1H), 2.18 (s, 3H), 1.94-1.97 (m, 2 H), 1.26-1.37 (m, 2H); m/z for $C_{17}H_{21}ClN_4O_2S$ 381.4 (M+H)⁺.

Preparation of N-(1-(5-chloro-4-(pyridin-2-yl)pyrimidin-2-yl)piperidin-4-yl)methanesulfonamide (Example A-45)

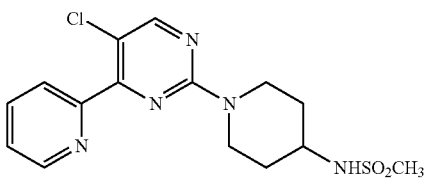

Step 1: 2-chloro-4-(pyridin-2-yl)pyrimidine

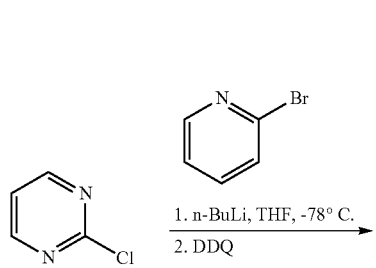

To a solution of 2-chloropyrimidine (8.0 g, 50 mmol) in THF (100 mL) at −78° C., n-BuLi (24 mL, 60 mmol) was added dropwise under N₂. After addition, the reaction solution was stirred for 30 min, a solution of 2-bromopyridine (5.75 g, 50 mmol) in THF (50 mL) was added in portions. The reaction mixture was stirred at −30° C. for 30 min and at 0° C. for 45 min., then quenched with AcOH (5 mL) and water (1 mL). A solution of DDQ (16.3 g, 80 mmol) in THF (50 mL) was added in portions and the mixture was stirred at room temperature for 45 min. TLC (petroleum:EtOAc=5:1) indicated the reaction was complete. The reaction mixture was cooled to 0° C. and 3N NaOH (142 mL) was added and stirred for 30 min. The aqueous layer was extracted with EtOAc (50 mL×3). The combined extract was dried over Na₂SO₄, concentrated and purified by chromatography, eluted with petroleum ether:EtOAc (10:1 to 5:1) to give title compound (4.8 g, 50%) as a light yellow solid.

Step 2: N-(1-(4-(pyridin-2-yl)pyrimidin-2-yl)piperidin-4-yl)methanesulfonamide

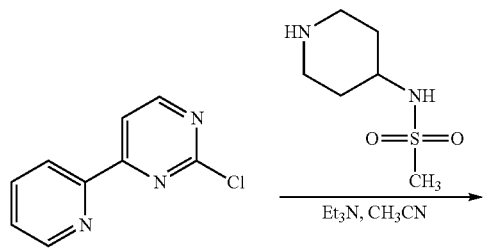

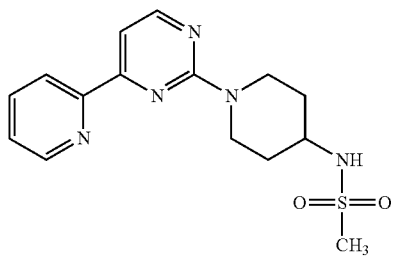

A solution of 2-chloro-4-(pyridin-2-yl)pyrimidine (0.576 g, 3 mmol), N-(piperidin-4-yl)methanesulfonamide (0.64 g, 3.6 mmol) and Et₃N (0.77 mL, 6 mmol) in CH₃CN (15 mL) was refluxed for 2 h and TLC (petroleum:EtOAc=5:1) showed the reaction was complete. The reaction mixture was concentrated and purified by chromatography, eluted with CH₂Cl₂:MeOH (10:1 to 5:1) to give the title compound (0.78 g, 78%) as a yellow oil.

Step 3: N-(1-(5-chloro-4-(pyridin-2-yl)pyrimidin-2-yl)piperidin-4-yl)methanesulfonamide

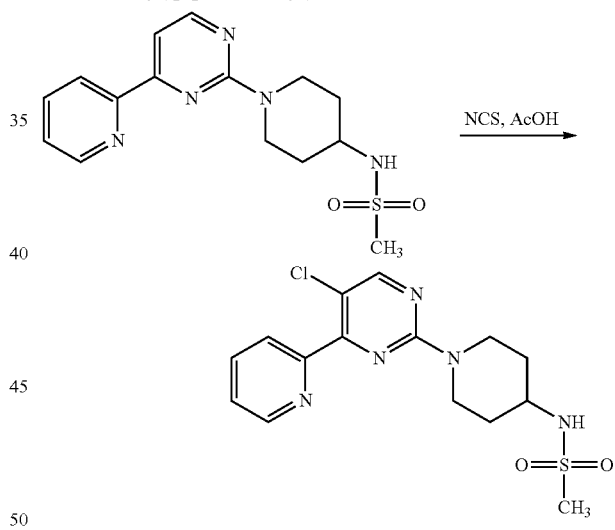

NCS (370 mg, 2.83 mmol) was added to a solution of N-(1-(4-(pyridin-2-yl)pyrimidin-2-yl)piperidin-4-yl)methanesulfonamide (180 mg, 2.36 mmol) in AcOH (10 mL) at 60° C. and the reaction solution was stirred for 2 h. LC-MS indicated the reaction was almost complete. The reaction solution was concentrated and purified by chromatography, eluted with CH₂Cl₂:MeOH (6:1) to give crude product, which was further purified by Prep-HPLC to give title compound (251 mg, 29%) as a yellow solid. $^1$H NMR (400 MHz, CDCl₃): δ 8.68-8.70 (d, 1H), 8.29 (s, 1H), 7.75-7.79 (m, 1H), 7.70-7.72 (d, 1H), 7.31-7.34 (t, 1H), 4.60-4.63 (d, 2H), 4.18-4.20 (d, 1H), 3.53-3.57 (t, 1H), 2.94 (s, 3H), 1.99-2.02 (d, 1H), 1.39-1.49 (m, 1H); m/z for $C_{15}H_{18}ClN_5O_2S$ 390.1 (M+Na)⁺.

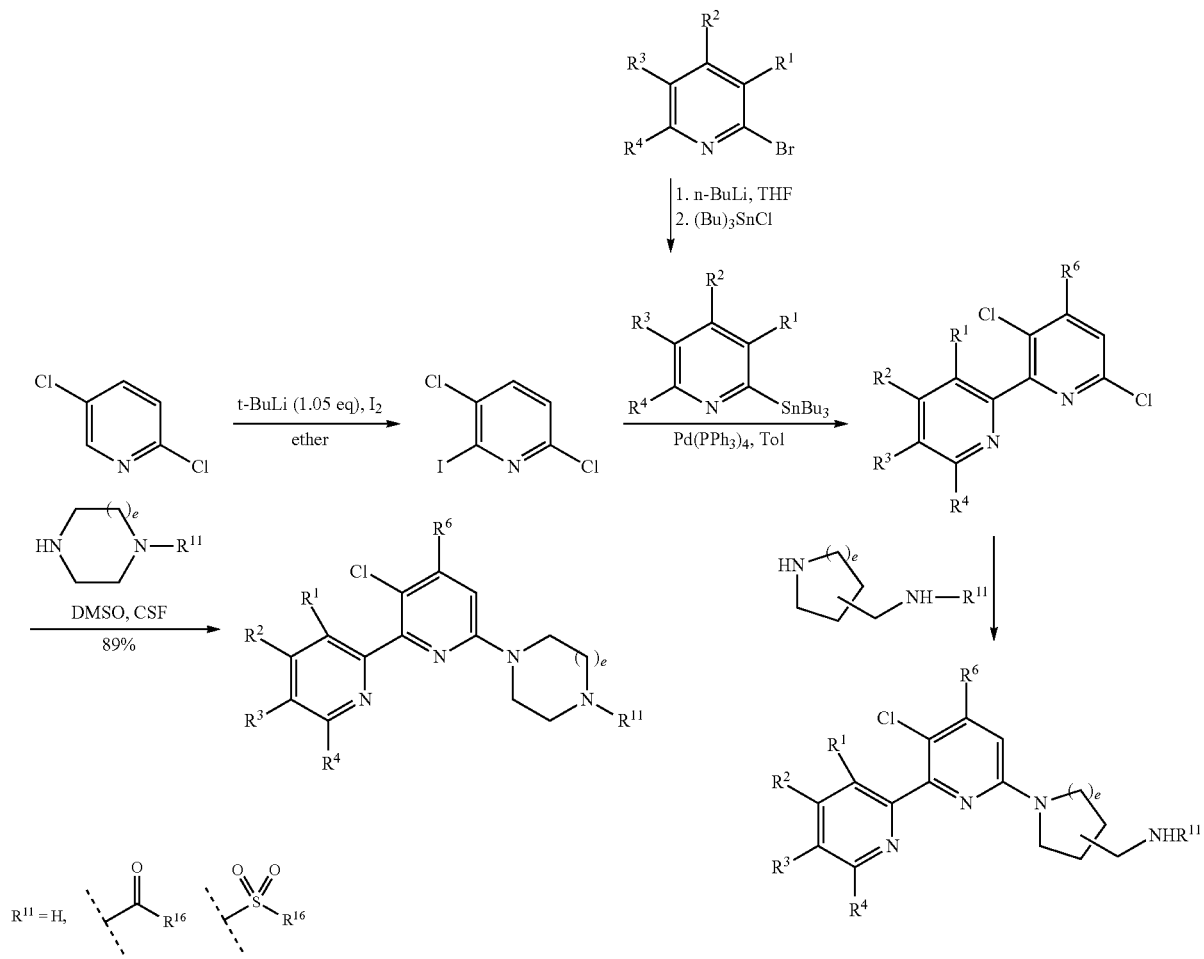

Scheme A-4

As illustrated in Scheme A-4 ortho-metalation of 2,5-dichloropyridine and quenching with iodine provides 3,6-dichloro-2-iodopyridine which on coupling with 2-(tributylstannyl)pyridine under Stille conditions gives 3,6-dichloro-2,2'-bipyridine. Treatment of 3,6-dichloro-2,2'-bipyridine with suitable protected or unprotected amines in the presence of a base such as cesium fluoride in a suitable solvent (such as DMSO) yields the corresponding amines. In the case of the protected amines, deprotection and subsequent treatment with acylating agents (under standard conditions known in the art) such as activated carboxylic acids or acyl chlorides, carbamoyl chlorides, isocyanates and sulfonyl chlorides can provide amides, carbamates, ureas, and sulfonamides.

Preparation of 2-{[4-(3-chloro-2,2'-bipyridin-6-yl)piperazin-1-yl]sulfonyl}ethanol (Example A-137)

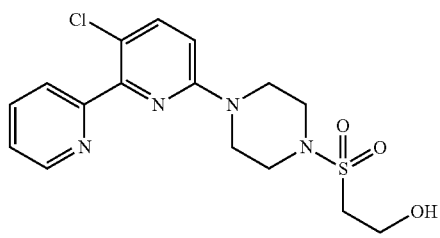 [SMILES: O=S(=O)(CCO)N1CCN(c2ccc(Cl)c(-c3ccccn3)n2)CC1]

Step 1: 3,6-dichloro-2-iodopyridine

To a solution of 2,5-dichloropyridine (95 g, 0.64 mol) in 1 L of dry ether was added dropwise t-BuLi (1.3 M, 500 mL, 0.65 mol) at −65° C. After addition, the mixture was stirred at −65° C. for 2 hrs, then the mixture was poured into a solution of iodine (180 g, 0.71 mol) in dry ether (700 mL) cooled at −60° C. Then the mixture was stirred at −65° C. for 1 hour and warmed to room temperature for another 1 hour. The mixture was quenched with $H_2O$ (400 mL), then extracted with EtOAc (200 mL). The organic phase was washed with sat. $Na_2SO_3$ (250 mL×3), sat. NaCl and dried over $Na_2SO_4$. Concentrated and the residue was purified via silica gel column (petroleum ether) to give title compound (57 g, ~77% purity, 25% yield) as a light yellow solid, which was used directly in the next step.

Step 2: 2-(tributylstannyl)pyridine

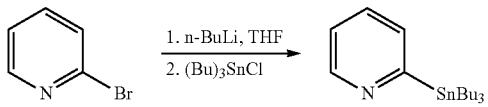

n-BuLi (200 mL, 0.5 mol) was added dropwise to 2-bromopyridine (79 g, 0.5 mol) under N₂ with continuous stirring at −78° C. This solution was stirred at −78° C. for 1 h and (Bu)₃SnCl (178.8 g, 0.55 mol) was added dropwise to the reaction solution. After addition, the reaction solution was stirred at −78° C. for 1 h and room temperature for 1 h. TLC (petroleum:EtOAc=10:1) indicated the reaction was complete. The reaction solution was quenched with sat. NH₄Cl and extracted with EtOAc (350 mL×3). The combined extracts were washed with water, dried over Na₂SO₄, concentrated and purified by chromatography, eluted with (petroleum:EtOAc=10:1) to give title compound (110 g, 60%) as a yellow liquid.

Step 3: 3,6-dichloro-2,2'-bipyridine

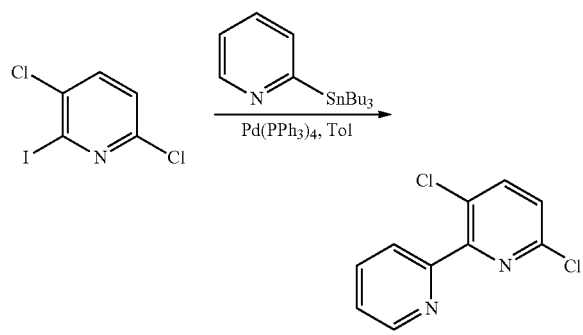

The mixture of 3,6-dichloro-2-iodopyridine (21 g, 77% purity, 58.8 mmol), 2-(tributylstannyl)pyridine (37 g, 80% purity, 80 mmol) in toluene (300 mL) was degassed, then Pd(PPh₃)₄ (730 mg) was added, the mixture was degassed again and stirred at reflux under N₂ overnight. The mixture was concentrated and the residue was purified via silica gel column (petroleum ether:EtOAc=10:1~5:1) to give title compound (10 g, 76%) as a gray solid.

¹H NMR (400 MHz, CDCl₃): δ 8.76-8.75 (d, 1H), 7.85-7.75 (m, 3H), 7.38-7.31 (m, 2H); m/z for C₁₀H₆Cl₂N₂ 225.1 (M+H)⁺.

Step 4: 3-chloro-6-piperazin-1-yl-2,2'-bipyridine

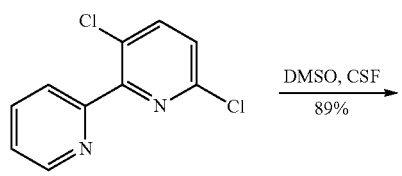

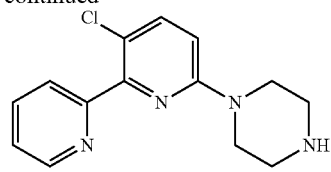

To a solution of the chloropyridine (500 mg, 2.22 mmol) in DMSO (11 mL), piperazine (1.53 g, 17.8 mmol) and CsF (844 mg, 5.55 mmol) were added and heated at 94° C. (oil bath temp) for 24 h. The reaction mixture was cooled to RT, diluted with H₂O (75 mL), extracted with ethyl acetate (5×75 mL) and the combined organics were washed with brine (50 mL), dried over sodium sulfate, filtered and concentrated under reduced pressure to a greenish gum. The crude mixture was purified by column chromatography (1 to 10%/MeOH/NH₃ (1%)/CH₂Cl₂) and obtained the title compound as a colorless gum (543 mg, 89% yield). ¹H NMR (400 MHz, DMSO-d₆) δ ppm 8.64 (d, J=4.80 Hz, 1 H) 7.91 (td, J=7.71, 1.77 Hz, 1 H) 7.65-7.71 (m, 2 H) 7.43 (ddd, J=6.88, 5.49, 1.26 Hz, 1 H) 6.90 (d, J=9.09 Hz, 1 H) 3.40-3.48 (m, 4 H) 2.75-2.84 (m, 4 H). LCMS (M+H)⁺: 270.15.

Step 5: 3-chloro-6-[4-(vinylsulfonyl)piperazin-1-yl]-2,2'-bipyridine

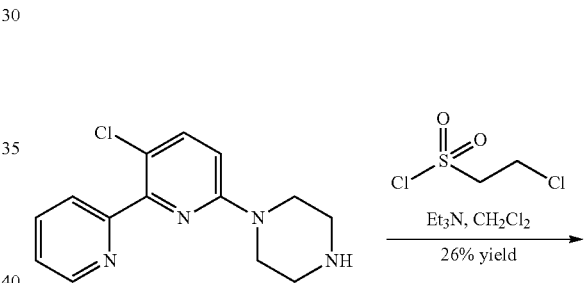

To a solution of 3-chloro-6-(piperazin-1-yl)-2,2'-bipyridine (197 mg, 0.717 mmol) in CH₂Cl₂ (7 mL) was added methanesulfonylchloride (0.0820 mL, 0.789 mmol) followed by triethylamine (0.110 mL, 0.789 mmol) and stirred at RT for 2 h. The reaction mixture was diluted with H₂O (30 mL) and extracted with dichloromethane (2×30 mL), dried over sodium sulfate, and concentrated under reduced pressure. The crude mixture was purified by column chromatography (10-50% ethyl acetate/heptane) and obtained the title compound as a white solid (68 mg, 26% yield). LCMS (M+H)⁺: 365.0.

Step 6: 3-chloro-6-{4-[(2-methoxyethyl)sulfonyl]piperazin-1-yl}-2,2'-bipyridine

Step 7: 2-{[4-(3-chloro-2,2'-bipyridin-6-yl)piperazin-1-yl]sulfonyl}ethanol

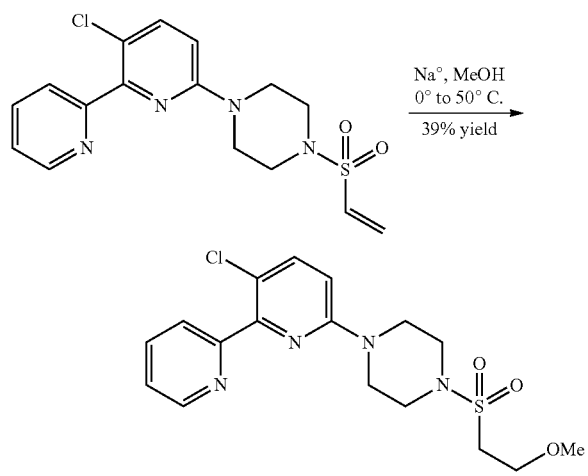 [SMILES: C=CS(=O)(=O)N1CCN(c2ccc(Cl)c(-c3ccccn3)n2)CC1 ; COCCS(=O)(=O)N1CCN(c2ccc(Cl)c(-c3ccccn3)n2)CC1]

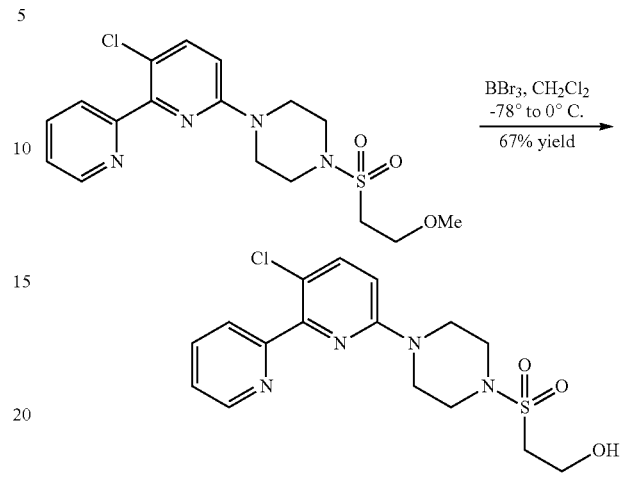

To a 0° C. solution of 3-chloro-6-(4-(vinylsulfonyl)piperazin-1-yl)-2,2'-bipyridine (68 mg, 0.190 mL) in methanol (1.8 mL), Na metal (47.5 mg, 2.05 mmol) washed in heptane was added and stirred for 15 min at 0° C. The reaction mixture was heated to 50° C. and stirred for 2 h and was cooled to RT, diluted with H$_2$O (20 mL), extracted with ethyl acetate (3×20 mL). The combined organic layer was washed with brine (15 mL), dried over sodium sulfate, filtered and concentrated under reduced pressure and purified by column chromatography (30 to 75% ethyl acetate/heptane) to obtain pure product (29 mg, 39% yield). $^1$H NMR (400 MHz, DMSO-d$_6$) δ ppm 8.65 (d, J=4.80 Hz, 1 H) 7.92 (td, J=7.71, 1.77 Hz, 1 H) 7.75 (d, J=9.09 Hz, 1 H) 7.69 (d, J=7.83 Hz, 1 H) 7.44 (ddd, J=7.52, 4.86, 1.01 Hz, 1 H) 7.00 (d, J=8.84 Hz, 1 H) 3.57-3.70 (m, 8 H) 3.35 (t, J=5.94 Hz, 2 H) 3.30 (s, 3 H) 3.22-3.27 (m, 2 H). LCMS (M+H)$^+$: 397.0.

To a cooled −78° C. solution of 3-chloro-6-(4-((2-methoxyethyl)sulfonyl)piperazin-1-yl)-2,2'-bipyridine (134 mg, 0.338 mL) in (2 mL), boron tribromide (0.139 mL, 0.737 mmol) was added. After 1 h, the reaction mixture was warmed to 0° C. and stirred for an additional 1 h. Saturated aqueous bicarbonate (10 mL) was added and extracted with CH$_2$Cl$_2$ (2×10 mL). The combined organic layer was washed with brine (10 mL), dried over sodium sulfate, filtered and concentrated under reduced pressure and purified by column chromatography (60 to 100% ethyl acetate/heptane) to obtain pure product (87 mg, 67% yield). $^1$H NMR (400 MHz, DMSO-d$_6$) δ ppm 8.65 (d, J=4.80 Hz, 1 H) 7.92 (td, J=7.71, 1.77 Hz, 1 H) 7.75 (d, J=9.09 Hz, 1 H) 7.69 (d, J=7.83, 1 H) 7.44 (td, J=6.19, 1.01 Hz, 1 H) 6.99 (d, J=8.84 Hz, 1 H) 5.02 (t, J=5.43 Hz, 1 H) 3.75 (q, J=6.06 Hz, 2 H) 3.59-3.67 (m, 4 H) 3.24-3.30 (m, 4 H) 3.21 (t, J=6.19 Hz, 2 H). LCMS (M+H)$^+$: 383.0.

Scheme A-5

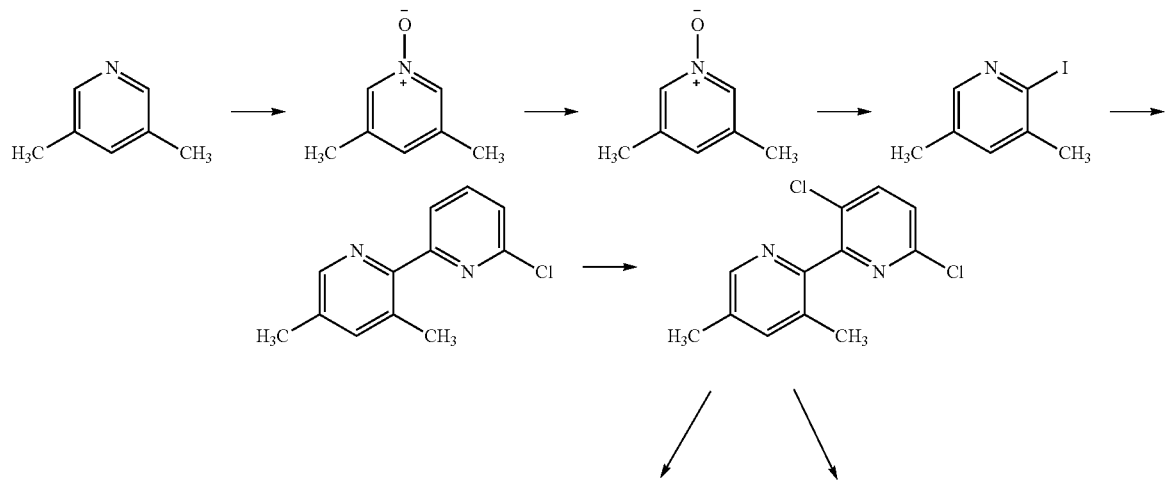

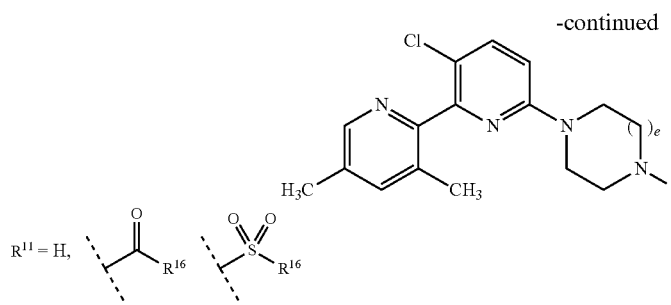

An alternative approach to amino pyridines similar to those highlighted in Scheme A-4 is illustrated in Scheme A-5. Treatment of 3,5-dimethylpyridine with m-CPBA gives the corresponding pyridine N-oxide. Deprotonation of the N-oxide followed by iodination and subsequent reduction of the N-oxide moiety with phosphorous tribromide provides 2-iodo-3,5-dimethylpyridine. Cross-coupling of this iodide with 2-bromo-6-chloropyridine under Negishi coupling conditions gives 6'-chloro-3,5-dimethyl-2,2'-bipyridine. A palladium-catalyzed C—H halogenation of this 2,2'-bipyridine using palladium acetate and N-chlorosuccinimide provides the 3',6'-dichloro-3,5-dimethyl-2,2'-bipyridine. Treatment of this dichloride with suitably protected or unprotected amines in the presence of a base such as cesium fluoride in a suitable solvent (such as DMSO) can yield final products. In the case of the protected amines, deprotection and subsequent treatment with acylating agents (under standard conditions known in the art) such as activated carboxylic acids or acyl chlorides and sulfonyl chlorides can provide amides and sulfonamides.

Preparation of N-[1-(3-chloro-3',5'-dimethyl-2,2'-bipyridin-6-yl)piperidin-4-yl]-2-hydroxyacetamide (Example A-140)

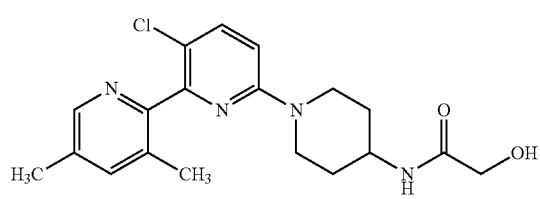

Step 1: 3,5-dimethylpyridine 1-oxide

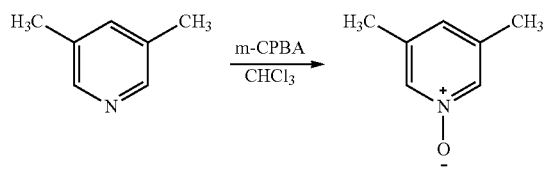

To a solution of 3,5-dimethylpyridine (85 g, 0.8 mol) in CHCl$_3$ (1500 mL) was added m-CPBA (180 g, 0.88 mol) in portions at 0° C. Then the mixture was stirred at room temperature for 18 hr. TLC (petroleum ether:EtOAc=1:1) showed the starting material was consumed almost. After diluting with CH$_2$Cl$_2$ (1200 mL), the solution was washed with Na$_2$S$_2$O$_3$(aq.) (600 mL), NaHCO$_3$(aq.) (600 mL) and brine (600 mL). The resulting material was dried over Na$_2$SO$_4$ and concentrated in vacuo to give crude material which was purified by chromatography on silica gel with EtOAc:CH$_2$Cl$_2$=4:1 to afford 3,5-dimethylpyridine 1-oxide (92 g, 93%) as light yellow solid.

Step 2: 2-iodo-3,5-dimethylpyridine 1-oxide

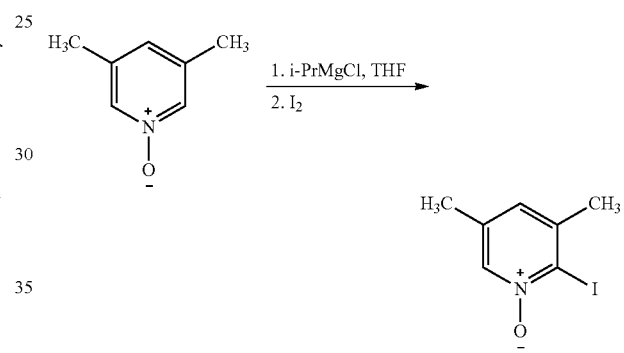

To a solution of 3,5-dimethylpyridine 1-oxide (92 g, 0.75 mol) in THF (1300 mL) was added dropwise i-PrMgCl (600 mL, 1.2 mol) at −72° C. After stirring for 2 hr at the same temperature, a solution of iodine (350 g, 1.38 mol) in THF (500 mL) was added dropwise. After stirring for 1 hr, TLC (petroleum ether:EtOAc=1:4) showed the starting material was consumed almost. After quenching with Na$_2$S$_2$O$_3$(aq.) (400 mL), THF was removed in vacuo and the residue was diluted with EtOAc (1500 mL). The solution was washed with water (400 mL) and brine (400 mL) and dried over Na$_2$SO$_4$. The resulting material was concentrated in vacuo to give crude material which was purified by chromatography on silica gel with petroleum ether:EtOAc=1:4 to afford 2-iodo-3,5-dimethylpyridine 1-oxide (68 g, 36.3%) as white solid.

Step 3: 2-iodo-3,5-dimethylpyridine

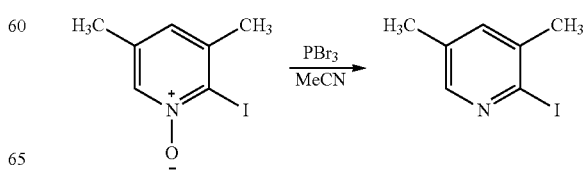

To a solution of 3,5-dimethylpyridine 1-oxide (68 g, 0.272 mol) in MeCN (800 mL) was added dropwise PBr$_3$ (160 mL) at 0° C. Then the mixture was heated at 45° C. for 6 hr. TLC (petroleum ether:EtOAc=2:1) showed there was about 15% of starting material. PBr$_3$ (34 mL) was added dropwise at 0° C. and stirred for 18 hr at 45° C. TLC (petroleum ether:EtOAc=2:1) showed the starting material was consumed completely. It was poured into the mixture of ice/H$_2$O and basified to pH=11. The aqueous layer was extracted with EtOAc (1000 mL×3). The combined organic layer was dried over Na$_2$SO$_4$ and concentrated in vacuo to give crude material which was purified by chromatography on silica gel with Petroleum Ether:EtOAc=10:1 to afford 2-iodo-3,5-dimethylpyridine (36 g, 57%) as a white solid.

Step 4: 6'-chloro-3,5-dimethyl-2,2'-bipyridine

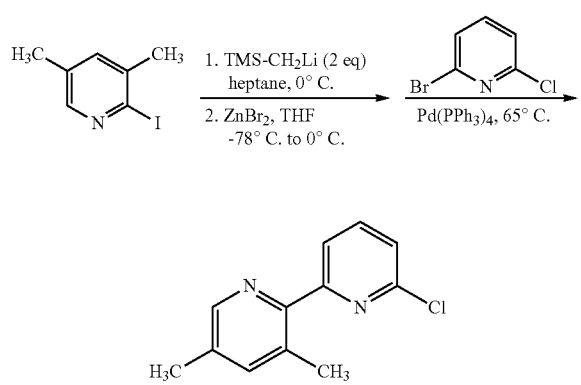

An oven-dried flask under N$_2$ was charged with TMS-CH$_2$Li (2.57 mmol, 1M in pentane) and cooled to 0° C. Then a solution of the 2-iodo-3,5-dimethylpyridine (300 mg, 1.29 mmol) in heptane (4.3 mL) was added dropwise, and the resulting mixture was stirred at 0° C. for 1 h. The solution was cooled to −78° C., and 2 mL THF was added. A solution of ZnBr$_2$ (435 mg, 1.53 mmol) in THF (4.3 mL, cooled to 0° C.) was added dropwise. The resulting mixture was stirred vigorously at −78° C. for 30 min, then warmed to 0° C. for 1 h. Solid 2-bromo-6-chloropyridine (371 mg, 1.93 mmol) and Pd(PPh$_3$)$_4$ (74 mg, 5 mol %) were added. The reaction flask was evacuated and back-filled with N$_2$ (3×) then heated to 65° C. After 20 h, the reaction was removed from heat and quenched with saturated aqueous ammonium chloride. The biphasic mixture was transferred to a separation funnel and extracted with EtOAc (3×). The combined organics were washed with 1M Na$_2$S$_2$O$_3$, saturated aqueous sodium bicarbonate, water, and brine, then dried over MgSO$_4$, filtered, and concentrated to get crude product. Purified on Biotage 40S column, eluting with 0-20% EtOAc/heptane to afford 166 mg (59%) of the title compound as an orange oil. LCMS and NMR showed desired product >95% pure. m/z (APCI+) for C$_{12}$H$_{11}$N$_2$Cl=219.00 (M+H)$^+$. $^1$H NMR (400 MHz, DMSO-d6) δ ppm 8.36 (s, 1 H) 7.95-8.01 (m, 1 H) 7.88-7.94 (m, 1 H) 7.58 (s, 1 H) 7.53 (d, J=7.83 Hz, 1 H) 2.47 (s, 3 H) 2.33 (s, 3 H).

Step 5: 3',6'-dichloro-3,5-dimethyl-2,2'-bipyridine

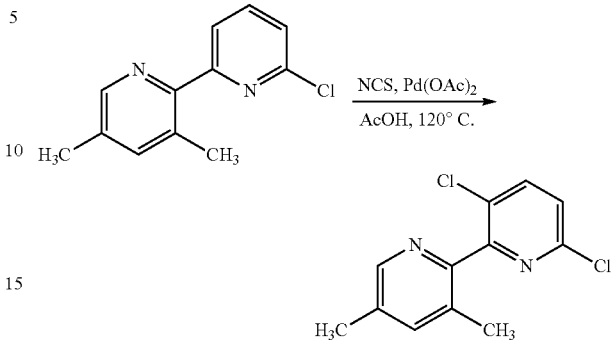

A mixture of 6'-chloro-3,5-dimethyl-2,2'-bipyridine (300 mg, 1.37 mmol), NCS (202 mg, 1.51 mmol), and Pd(OAc)$_2$ (31.4 mg, 0.137 mmol) in AcOH (9.15 mL) was heated to 120° C. in a sealed microwave vial using an oil bath. After 20 h, the reaction was removed from heat and concentrated. Took up the residue in EtOAc, filtered off the solid through a glass fiber filter, and washed with 1:1 EtOAc/heptane. The filtrate was concentrated and purified on Biotage 25S column, eluting with 0-25% EtOAc/heptane to get 240 mg (69%) of the title compound as an off-white solid. m/z (APCI+) for C$_{12}$H$_{10}$N$_2$Cl$_2$ 253.00 (M+H)$^+$. $^1$H NMR (400 MHz, DMSO-d6) δ ppm 8.33 (s, 1 H) 8.16 (d, J=8.59 Hz, 1 H) 7.66 (d, J=8.59 Hz, 1 H) 7.61 (s, 1 H) 2.34 (s, 3 H) 2.08 (s, 3 H).

Step 6: tert-butyl [1-(3-chloro-3',5'-dimethyl-2,2'-bipyridin-6-yl)piperidin-4-yl]carbamate

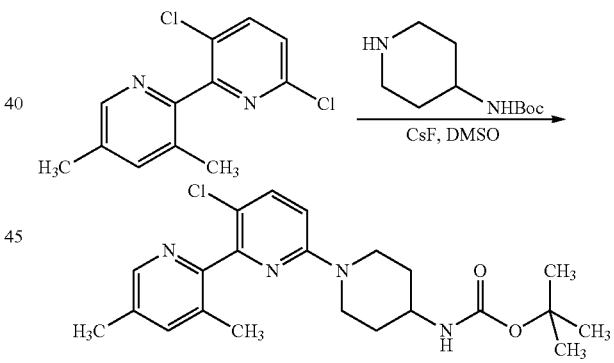

To a solution of the 3',6'-dichloro-3,5-dimethyl-2,2'-bipyridine (560 mg, 2.21 mmol) and 4-(N-Boc)-aminopiperidine (1.33 g, 6.64 mmol) in DMSO (22 mL) was added CsF (2.0 g, 13.3 mmol). The mixture was heated at 80° C. for 3 days. After cooling the reaction mixture to room temperature, water and EtOAc were added. The layers were separated, and the aqueous was extracted with EtOAc (3×). The combined organics were washed with water (3×) and brine, dried over MgSO$_4$, filtered, and concentrated. Purified on Biotage 25S column, eluting with 1:19:80 NH$_4$OH/EtOH/EtOAc in heptane (10-25%) to get 222 mg (24%) of the title compound as a white solid. m/z (APCI+) for C$_{22}$H$_{29}$N$_4$O$_2$Cl 417.20 (M+H)$^+$. $^1$H NMR (400 MHz, DMSO-d6) δ ppm 8.26 (s, 1 H) 7.66 (d, J=9.09 Hz, 1 H) 7.53 (s, 1 H) 6.91 (d, J=9.09 Hz, 1 H) 6.83 (d, J=7.33 Hz, 1 H) 4.14 (d, J=13.39 Hz, 2 H) 3.42-3.56 (m, 1 H) 2.89 (t, J=11.62 Hz, 2 H) 2.32 (s, 3 H) 2.07 (s, 3 H) 1.74 (d, J=10.36 Hz, 2 H) 1.38 (s, 9 H) 1.26-1.35 (m, 2 H).

Step 7: 1-(3-chloro-3',5'-dimethyl-2,2'-bipyridin-6-yl)piperidin-4-amine (hydrochloride salt)

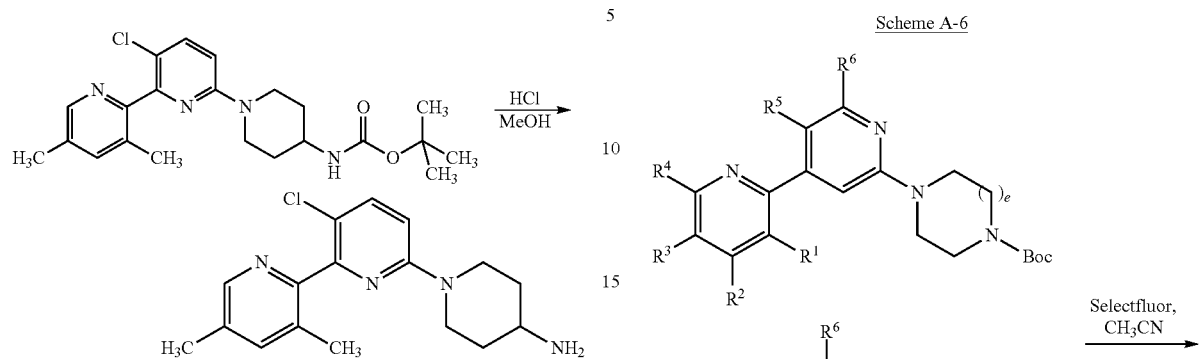

To a suspension of tert-butyl [1-(3-chloro-3',5'-dimethyl-2,2'-bipyridin-6-yl)piperidin-4-yl]carbamate (220 mg, 0.528 mmol) in MeOH (5.28 mL) was added HCl (2.64 mL, 4M in dioxane, 2.64 mmol). The resulting yellow solution was stirred at rt for 4 h and concentrated to get 242 mg (99%) of the title compound as a yellow solid. m/z (APCI+) for $C_{17}H_{21}N_4Cl$ 317.20 (M+H)+. 1H NMR (400 MHz, DMSO-d6) δ ppm 8.65 (s, 1H) 8.30 (br. s., 3 H) 8.28 (br. s., 1 H) 7.84 (d, J=9.09 Hz, 1 H) 7.14 (d, J=9.35 Hz, 1 H) 4.29 (d, J=13.39 Hz, 2 H) 3.22-3.34 (m, 1 H) 2.95 (t, J=12.25 Hz, 2 H) 2.48 (s, 3 H) 2.24 (s, 3 H) 1.96 (d, J=10.86 Hz, 2 H) 1.48-1.60 (m, 2 H).

Step 8: N-[1-(3-chloro-3',5'-dimethyl-2,2'-bipyridin-6-yl)piperidin-4-yl]-2-hydroxyacetamide To a mixture of 1-(3-chloro-3',5'-dimethyl-2,2'-bipyridin-6-yl)piperidin-4-amine (hydrochloride salt) (60 mg, 0.13 mmol) and 2-hydroxyacetic acid (14.8 mg, 0.20 mmol) in DMF (1.3 mL) were added (in this order) NMM (105 mg, 1.0 mmol), HOBT (26.3 mg, 0.20 mmol), and EDCI (38.5 mg, 0.20 mmol). The resulting solution was stirred at rt for 3.5 h. Water was added, and the mixture was stirred at rt overnight. Filtered off the solid that had crashed out, washed with water, and dried to get 23 mg (47%) of the title compound as a white solid. m/z (APCI+) for $C_{19}H_{23}N_4O_2Cl$ 375.10 (M+H)+. 1H NMR (400 MHz, DMSO-d6) δ ppm 8.26 (s, 1 H) 7.67 (d, J=9.09 Hz, 1 H) 7.62 (d, J=8.34 Hz, 1H) 7.53 (s, 1 H) 6.93 (d, J=9.35 Hz, 1 H) 5.37 (t, J=5.94 Hz, 1 H) 4.18 (d, J=13.64 Hz, 2H) 3.82-3.94 (m, 1 H) 3.78 (d, J=5.81 Hz, 2 H) 2.91 (t, J=11.49 Hz, 2 H) 2.32 (s, 3 H) 2.08 (s, 3 H) 1.72 (dd, J=12.76, 2.91 Hz, 2 H) 1.41-1.54 (m, 2 H).

Scheme A-6

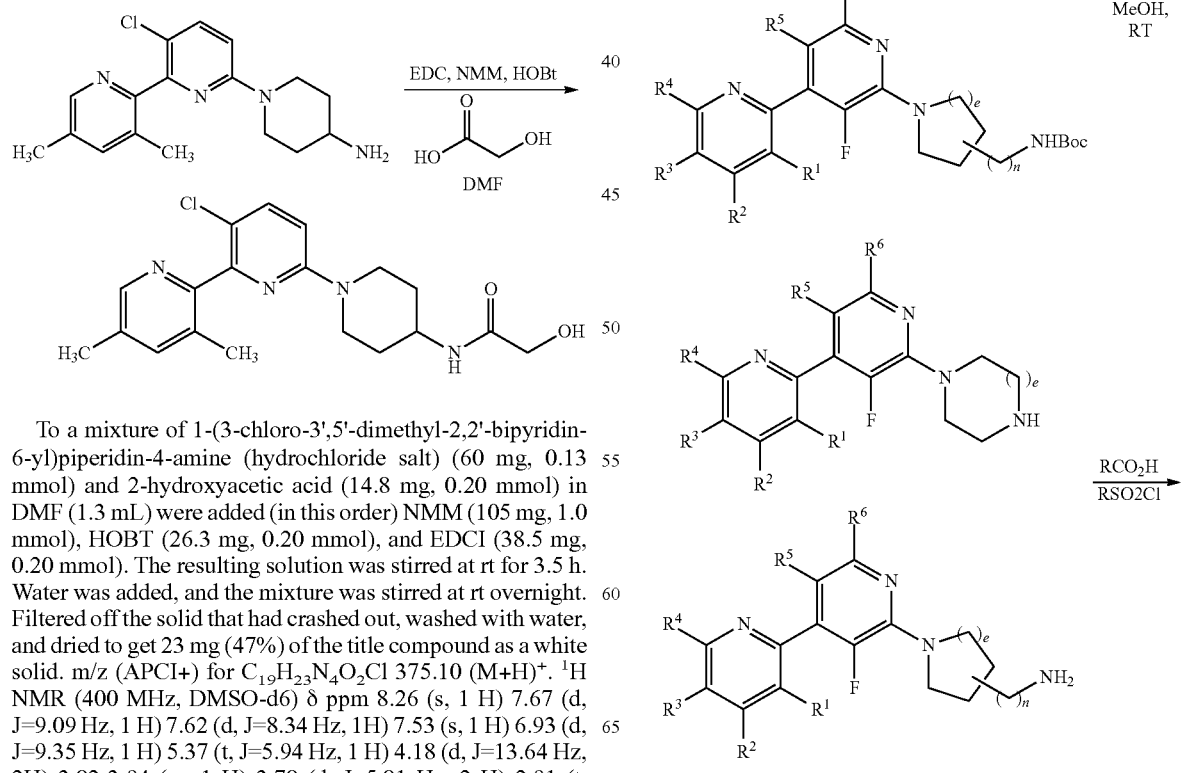

59

-continued

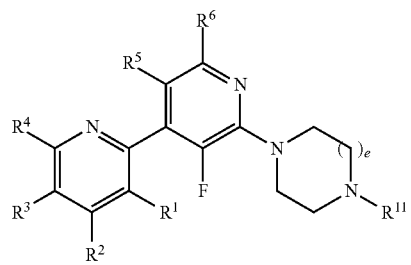

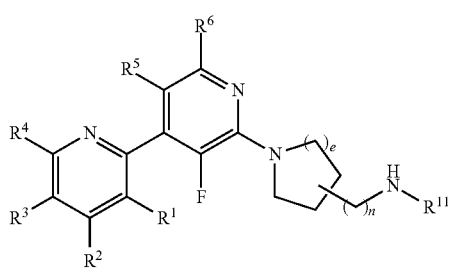

As shown in Scheme A-6, treatment of amino pyridine derivatives, obtained using methods described in Scheme A-1, with a fluorinating reagent such as Selectfluor® (1-chloromethyl-4-fluoro-1,4-diazoniabicyclo[2.2.2]octane bis(tetrafluoroborate)) leads to the introduction of a fluorine atom ortho to the amino substituent. Subsequent deprotection and subsequent treatment with acylating agents (under standard conditions known in the art) such as activated carboxylic acids or acyl chlorides and sulfonyl chlorides can provide the corresponding amides and sulfonamides.

Preparation of N-(1-(5'-chloro-3'-fluoro-3,5-dimethyl-2,4'-bipyridin-2'-yl)piperidin-4-yl)-3-(methylsulfonyl)propanamide (Example A-139)

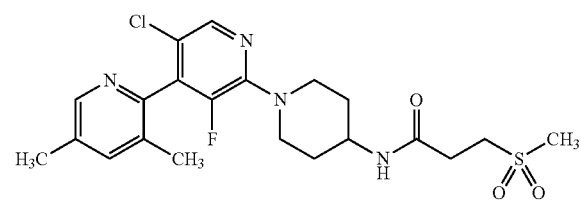

Step 1: Tert-butyl 1-(5'-chloro-3'-fluoro-3,5-dimethyl-2,4'-bipyridin-2'-yl)piperidin-4-ylcarbamate

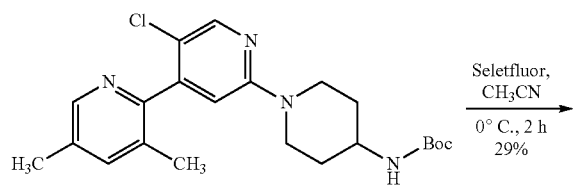

60

-continued

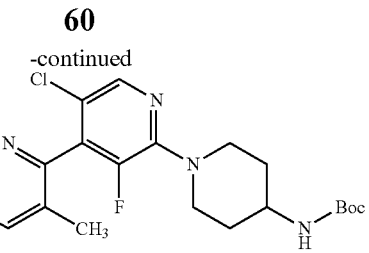

A cooled (0° C.), stirred suspension of tert-butyl (1-(5'-chloro-3,5-dimethyl-[2,4'-bipyridin]-2'-yl)piperidin-4-yl) carbamate (550 mg, 1.32 mmol) in acetonitrile (13 mL) was treated with Selectfluor® (827 mg, 2.24 mmol) portionwise. A light yellow solution was obtained and stirring was continued for 2 h. LC-MS showed the reaction was ~70% complete. The reaction was quenched with water at this point to avoid more by-product formation. EtOAc was added and layers were separated. The aqueous layer was extracted with EtOAc (2×). The organic extract was dried over sodium sulfate and concentrated to give the crude product, which was purified on ISCO separation system with a 12-gram column using 0-40% EtOAc in heptane to afford 164 mg (29%) of white foam: LRMS (M+H)+: 435.1; $^1$H NMR (400 MHz, CDCl$_3$) δ 1.43-1.50 (m, 11 H), 2.03 (d, J=12.13 Hz, 2 H), 2.14 (s, 3 H), 2.39 (s, 3 H), 2.90-3.12 (m, 2 H), 3.69 (br. s., 1 H), 3.87-4.08 (m, 2 H), 4.48 (br. s., 1 H), 7.46 (s, 1 H), 8.09 (s, 1 H), 8.40 (s, 1 H).

Step 2: 1-(5'-Chloro-3'-fluoro-3,5-dimethyl-2,4'-bipyridin-2'-yl)piperidin-4-amine

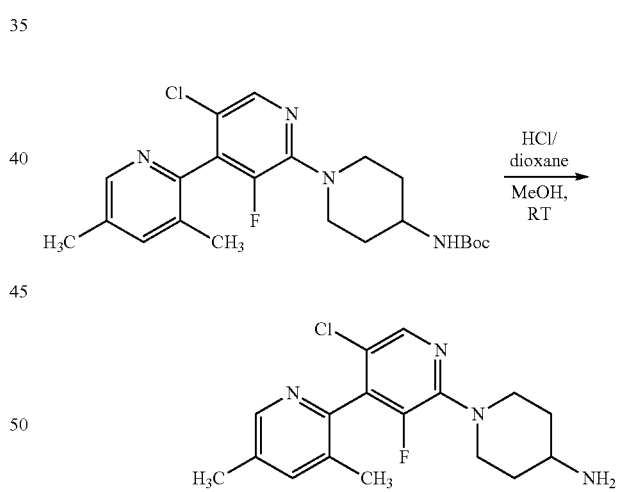

A solution of tert-butyl (1-(5'-chloro-3'-fluoro-3,5-dimethyl-[2,4'-bipyridin]-2'-yl)piperidin-4-yl)carbamate (160 mg, 0.368 mmol) in 4 M HCl in dioxane (3.0 mL, 12.0 mmol) and MeOH (1.0 mL) was stirred at rt for 2 h. After concentration, the residue was further dried under vacuum to give 150 mg (100%) of pale yellow solid as a di-HCl salt: LRMS (M+H)+: 335.0; $^1$H NMR (400 MHz, DMSO-d6) δ 1.50-1.72 (m, 2 H), 1.94-2.03 (m, 2 H), 2.10 (s, 3 H), 2.37 (s, 3 H), 2.89-3.12 (m, 2 H), 3.20-3.33 (m, 1 H), 3.92-4.08 (m, 2 H), 6.62 (br. s., 1 H), 7.77 (s, 1 H), 8.12-8.31 (m, 4 H), 8.44 (s, 1 H).

Step 3: N-(1-(5'-chloro-3'-fluoro-3,5-dimethyl-2,4'-bipyridin-2'-yl)piperidin-4-yl)-3-(methylsulfonyl)propanamide

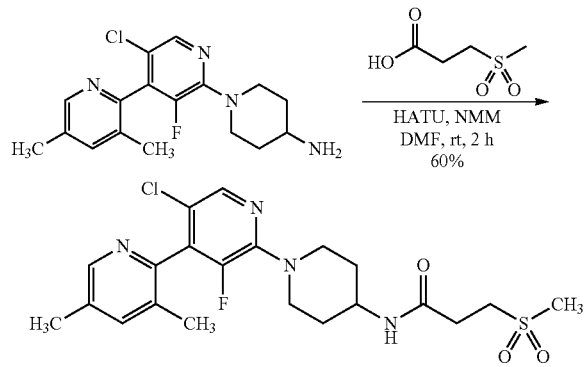

A stirred solution of 1-(5'-chloro-3'-fluoro-3,5-dimethyl-[2,4'-bipyridin]-2'-yl)piperidin-4-amine (81.5 mg, 0.20 mmol), 3-(methylsulfonyl)propanoic acid (45.7 mg. 0.30 mmol), and NMM (80.9 mg, 0.80 mmol) in DMF (2 mL) was treated with HATU (91.3 mg, 0.24 mmol) portionwise. The reaction solution was stirred at rt under nitrogen for 2 h. EtOAc (30 mL) and brine (10 mL) were added and layers were separated. The organic layer was washed with brine (2×), dried over sodium sulfate, and concentrated. Purification on ISCO separation system with a 4-gram column using 0-8% MeOH in EtOAc afforded a colorless gum, which was sonicated in heptane/EtOAc to furnish a solid. After solvent removal, 56 mg (60%) of waxy, white solid was obtained: LRMS (M+H)+: 469.1; $^1$H NMR (400 MHz, CDCl$_3$) δ 1.52 (dd, J=12.51, 3.66 Hz, 2 H), 2.02 (d, J=12.38 Hz, 2 H), 2.15 (s, 3 H), 2.39 (s, 3 H), 2.74 (t, J=6.95 Hz, 2 H), 2.96 (s, 3 H), 2.97-3.12 (m, 2 H), 3.42 (t, J=7.07 Hz, 2 H), 3.89-4.12 (m, 3 H), 5.63 (d, J=7.33 Hz, 1H), 7.47 (d, J=0.76 Hz, 1 H), 8.10 (s, 1 H), 8.40 (d, J=1.26 Hz, 1 H).

The following examples were prepared with appropriate substitutions with non-critical method changes in analogous ways to the examples described above:

TABLE 1

| Example Number | Structure | Compound Name | LRMS m/z (M + H) | $^1$H NMR |
|---|---|---|---|---|
| A-7 | 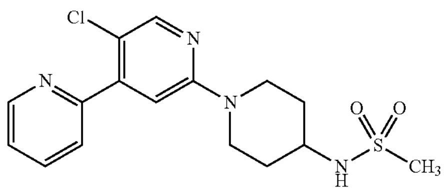 [SMILES: CS(=O)(=O)NC1CCN(c2cc(-c3ccccn3)c(Cl)cn2)CC1] | N-[1-(5'-chloro-2,4'-bipyridin-2'-yl)piperidin-4-yl]methanesulfonamide | 367.3 | $^1$H NMR (400 MHz, DMSO-d$_6$) δ ppm 8.75-8.74 (d, 1H), 8.25 (s, 1H), 7.80 (t, 1H), 7.72-7.51 (d, 1H), 7.51-7.50 (m, 1H), 7.15-7.13 (m, 1H), 7.01 (s, 1H), 4.25-4.22 (d, 2H), 3.45 (m, 1H), 3.07-3.02 (m, 2H), 2.972 (s, 3H), 1.92-1.90 (d, 2H), 1.45-1.42 (m, 2H) |
| A-8 | 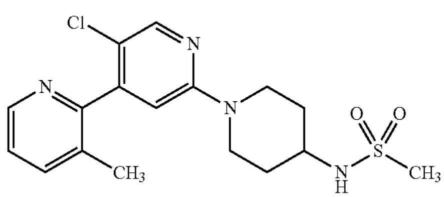 [SMILES: Cc1cccnc1-c1cc(N2CCC(NS(C)(=O)=O)CC2)ncc1Cl] | N-[1-(5'-chloro-3-methyl-2,4'-bipyridin-2'-yl)piperidin-4-yl]methanesulfonamide | 381.3 | $^1$H NMR (400 MHz, CD$_3$OD) δ ppm 8.44-8.43 (d, 1H), 8.18 (s, 1H), 7.83-7.81 (m, 1H), 7.45-7.42 (m, 1H), 6.79 (s, 1H), 4.26-4.23 (d, 2H), 3.55-3.48 m, 1H), 3.10-3.04 (m, 2H), 2.99 (s, 3H), 2.21 (s, 3H), 2.04-2.01 (d, 2H), 1.57-1.54 (m, 2H) |
| A-9 | 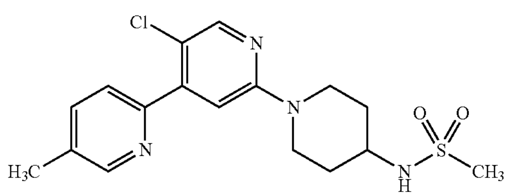 | N-[1-(5'-chloro-5-methyl-2,4'-bipyridin-2'-yl)piperidin-4-yl]methanesulfonamide | 381.2 | $^1$H NMR (400 MHz, CD$_3$OD) δ ppm 8.90 (s, 1H), 8.56-8.54 (d, 1H), 8.28 (s, 1H), 8.18-8.16 (d, 1H), 7.59 (s, 1H), 4.26-4.22 (d, 2H), 3.63-3.60 (m, 1H), 3.43-3.37 (m, 2H), 2.99 (s, 3H), 2.64 (s, 3H), 2.14-2.11 (d, 2H), 1.73-1.65 (m, 2H) |
| A-10 | 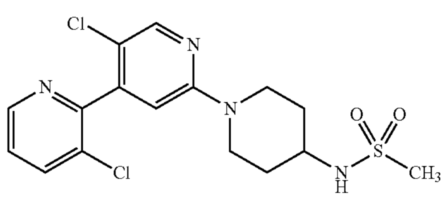 [SMILES: CS(=O)(=O)NC1CCN(c2cc(-c3ncccc3Cl)c(Cl)cn2)CC1] | N-[1-(3,5'-dichloro-2,4'-bipyridin-2'-yl)piperidin-4-yl]methanesulfonamide | 401.2 | $^1$H NMR (400 MHz, DMSO-d$_6$) δ ppm 8.64-8.63 (d, 1H), 8.22 (s, 1H), 8.11-8.09 (d, 1H), 7.56-7.53 (m, 1H), 7.12-7.10 (d, 1H), 6.92 (s, 1H), 4.21-4.18 (d, 2H), 3.43-3.41 (m, 1H), 3.03-2.97 (m, 2H), 2.93 (s, 3H), 1.88-1.84 (d, 2H), 1.40-1.38 (m, 2H) |

TABLE 1-continued

| Example Number | Structure | Compound Name | LRMS m/z (M + H) | ¹H NMR |
|---|---|---|---|---|
| A-11 | 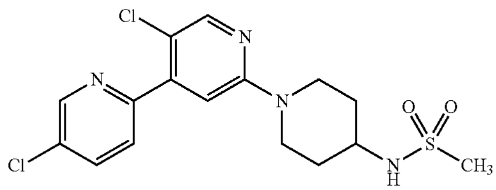 [SMILES: CS(=O)(=O)NC1CCN(c2cc(-c3ccc(Cl)cn3)c(Cl)cn2)CC1] | N-[1-(5,5'-dichloro-2,4'-bipyridin-2'-yl)piperidin-4-yl]methanesulfonamide | 401.1 | ¹H NMR (400 MHz, DMSO-d$_6$) δ ppm 8.77 (d, 1H), 8.22 (s, 1H), 8.10-8.07 (m, 1H), 7.75-7.73 (d, 1H), 7.11-7.10 (d, 1H), 6.99 (s, 1H), 4.21-4.18 (d, 2H), 3.04-2.98 (m, 2H), 2.93 (s, 3H), 1.88-1.86 (d, 2H), 1.40-1.38 (m, 2H) |
| A-12 | 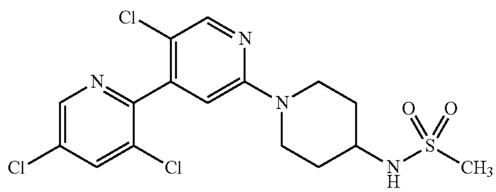 [SMILES: CS(=O)(=O)NC1CCN(c2cc(-c3ncc(Cl)cc3Cl)c(Cl)cn2)CC1] | N-[1-(3,5,5'-trichloro-2,4'-bipyridin-2'-yl)piperidin-4-yl]methanesulfonamide | 434.9 | ¹H NMR (400 MHz, DMSO-d$_6$) δ ppm 8.78 (s, 1H), 8.49-8.48 (s, 1H), 8.27 (s, 1H), 7.15-7.14 (d, 1H), 6.70 (s, 1H), 4.24-4.20 (d, 2H), 3.47-3.46 (m, 1H), 3.08-3.02 (t, 2H), 2.97 (s, 3H), 1.92-1.89 (d, 2H), 1.48-1.40 (m, 2H) |
| A-13 | 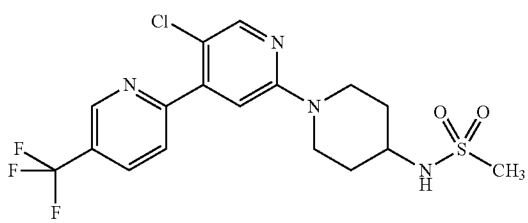 [SMILES: CS(=O)(=O)NC1CCN(c2cc(-c3ccc(C(F)(F)F)cn3)c(Cl)cn2)CC1] | N-{1-[5'-chloro-5-(trifluoromethyl)-2,4'-bipyridin-2'-yl]piperidin-4-yl}methanesulfonamide | 435.0 | ¹H NMR (400 MHz, DMSO-d$_6$) δ ppm 9.14 (s, 1H), 8.41-8.38 (d, 1H), 8.26 (s, 1H), 7.94-7.92 (d, 1H), 7.14-7.18 (d, 1H), 7.06 (s, 1H), 4.24-4.21 (d, 2H), 3.46-3.43 (m, 1H), 3.06-3.00 (t, 2H), 2.95 (s, 3H), 1.90-1.87 (d, 2H), 1.45-1.37 (m, 2H) |
| A-14 | 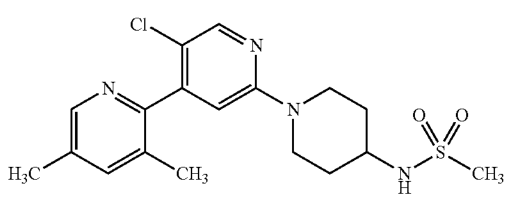 | N-[1-(5'-chloro-3,5-dimethyl-2,4'-bipyridin-2'-yl)piperidin-4-yl]methanesulfonamide | 395.3 | ¹H NMR (400 MHz, DMSO-d$_6$) δ ppm 8.31 (s, 1H), 8.20 (s, 1H), 7.58 (s, 1H), 7.13-7.12 (d, 1H), 6.79 (s, 1H), 4.21-4.17 (d, 2H), 3.43-3.40 (m, 1H), 3.02-2.94 (m, 5H), 2.33 (s, 3H), 2.09 (s, 3H), 1.88-1.85 (d, 2H), 1.45-1.36 (m, 2H) |
| A-15 | 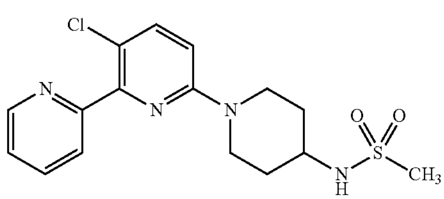 [SMILES: CS(=O)(=O)NC1CCN(c2ccc(Cl)c(-c3ccccn3)n2)CC1] | N-[1-(3-chloro-2,2'-bipyridin-6-yl)piperidin-4-yl]methanesulfonamide | 367.2 | ¹H NMR (400 MHz, DMSO) δ ppm 8.64-8.63 (d, 1H), 7.93-7.89 (m, 1H), 7.68-7.66 (d, 2H), 7.45-7.41 (m, 1H), 7.12-7.10 (d, 1H), 6.97-6.94 (d, 1H), 4.21-4.17 (d, 2H), 3.43-3.40 (m, 1H), 3.02-2.96 (m, 2H), 2.93 (s, 3H), 1.89-1.86 (m, 2H), 1.45-1.36 (m, 2H) |
| A-16 | 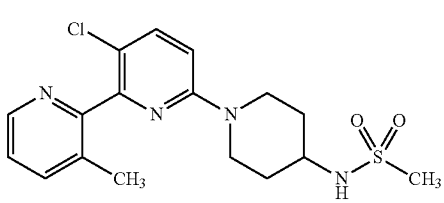 [SMILES: Cc1cccnc1-c1nc(N2CCC(NS(C)(=O)=O)CC2)ccc1Cl] | N-[1-(3-chloro-3'-methyl-2,2'-bipyridin-6-yl)piperidin-4-yl]methanesulfonamide | 381.4 | ¹H NMR (400 MHz, DMSO) δ ppm 8.45-8.44 (d, 1H), 7.74-7.68 (m, 2H), 7.37-7.34 (m, 1H), 7.14-7.12 (d, 1H), 6.97-6.94 (d, 1H), 4.15-4.12 (d, 2H), 2.30-2.94 (m, 5H), 2.11 (s, 3H), 1.88-1.85 (m, 2H), 1.43-1.35 (m, 2H) |
| A-17 | 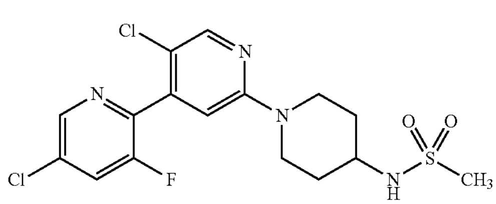 [SMILES: CS(=O)(=O)NC1CCN(c2cc(-c3ncc(Cl)cc3F)c(Cl)cn2)CC1] | N-[1-(5,5'-dichloro-3-fluoro-2,4'-bipyridin-2'-yl)piperidin-4-yl]methanesulfonamide | 419.3 | ¹H NMR (400 MHz, DMSO) δ ppm 8.68 (d, 1H), 8.33-8.30 (m, 1H), 8.24 (s, 1H), 7.13-7.11 (d, 1H), 7.00 (s, 1H), 4.20-4.17 (d, 2H), 3.43-3.41 (m, 1H), 3.04-3.98 (m, 2H), 2.93 (s, 3H), 1.88-1.85 (d, 2H), 1.42-1.36 (m, 2H) |

TABLE 1-continued

| Example Number | Structure | Compound Name | LRMS m/z (M + H) | ¹H NMR |
|---|---|---|---|---|
| A-18 | 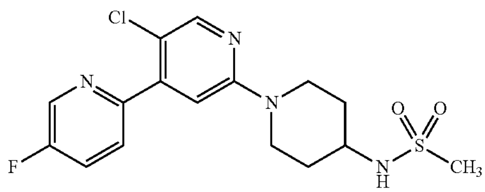 [SMILES: CS(=O)(=O)NC1CCN(c2cc(-c3ccc(F)cn3)c(Cl)cn2)CC1] | N-[1-(5'-chloro-5-fluoro-2,4'-bipyridin-2'-yl)piperidin-4-yl]methanesulfonamide | 385.1 | ¹H NMR (400 MHz, DMSO) δ ppm 8.73 (d, 1H), 8.23 (d, 1H), 7.93-7.88 (m, 1H), 7.79-7.77 (m, 1H), 7.14-7.12 (d, 1H), 6.99 (s, 1H), 4.23-4.19 (d, 2H), 3.05-2.99 (m, 2H), 2.95 (s, 3H), 1.90-1.87 (d, 2H), 1.45-1.39 (m, 2H) |
| A-19 | 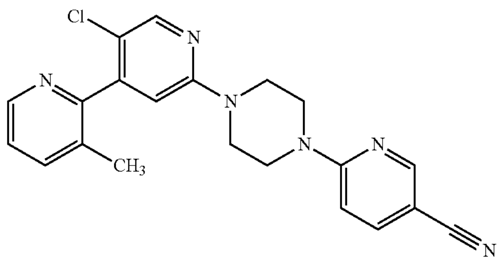 [SMILES: Cc1cccnc1-c1cc(N2CCN(c3ccc(C#N)cn3)CC2)ncc1Cl] | 6-[4-(5'-chloro-3-methyl-2,4'-bipyridin-2'-yl)piperazin-1-yl]nicatinonitrile | 391.1 | ¹H NMR (400 MHz, chloroform-d) d ppm 8.54 (d, J = 3.79 Hz, 1 H) 8.44 (d, J = 2.27 Hz, 1 H) 8.25 (s, 1 H) 7.66 (dd, J = 8.97, 2.40 Hz, 1 H) 7.63 (d, J = 7.58 Hz, 1 H) 7.29 (dd, J = 7.83, 4.80 Hz, 1 H) 6.48-6.69 (m, 2 H) 3.80-3.88 (m, 4 H) 3.66-3.78 (m, 4 H) 2.22 (s, 3 H) |
| A-20 | 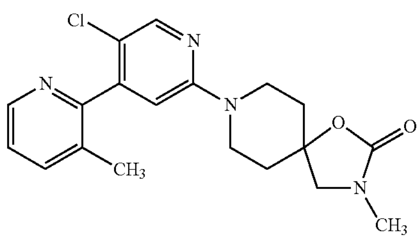 [SMILES: Cc1cccnc1-c1cc(N2CCC3(CC2)CN(C)C(=O)O3)ncc1Cl] | 8-(5'-chloro-3-methyl-2,4'-bipyridin-2'-yl)-3-methyl-1-oxa-3,8-diazaspiro[4.5]decan-2-one | 373.20 | ¹H NMR (400 MHz, DMSO-d6) δ ppm 8.47 (d, J = 4.0 Hz, 1 H) 8.22 (s, 1 H) 7.76 (d, J = 7.6 Hz, 1 H) 7.38 (dd, J = 7.8, 4.8 Hz, 1 H) 6.88 (s, 1 H) 3.75-3.89 (m, 2 H) 3.43-3.57 (m, 2 H) 3.35 (s, 2 H) 2.76 (s, 3 H) 2.13 (s, 3 H) 1.69-1.84 (m, 4 H) |
| A-21 | 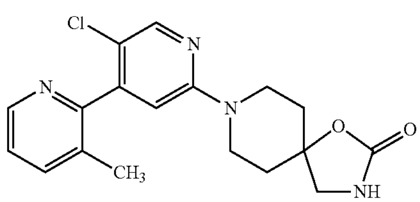 [SMILES: Cc1cccnc1-c1cc(N2CCC3(CC2)CNC(=O)O3)ncc1Cl] | 8-(5'-chloro-3-methyl-2,4'-bipyridin-2'-yl)-1-oxa-3,8-diazaspiro[4.5]decan-2-one | 359.00 | ¹H NMR (400 MHz, DMSO-d6) δ ppm 8.47 (d, J = 4.0 Hz, 1 H) 8.22 (s, 1 H) 7.76 (d, J = 7.1 Hz, 1 H) 7.52 (s, 1 H) 7.38 (dd, J = 7.6, 4.8 Hz, 1 H) 6.87 (s, 1 H) 3.71-3.89 (m, 2 H) 3.48 (ddd, J = 13.3, 9.2, 3.5 Hz, 2 H) 3.31 (s, 2 H) 2.12 (s, 3 H) 1.68-1.86 (m, 4 H) |
| A-22 | 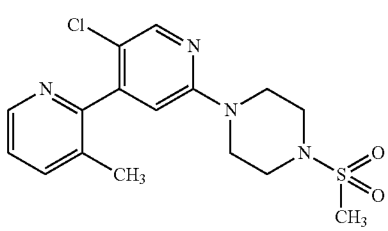 [SMILES: Cc1cccnc1-c1cc(N2CCN(S(C)(=O)=O)CC2)ncc1Cl] | 5'-chloro-3-methyl-2'-[4-(methylsulfonyl)piperazin-1-yl]-2,4'-bipyridine | 367.00 | ¹H NMR (400 MHz, DMSO-d6) δ ppm 8.48 (d, J = 3.8 Hz, 1 H) 8.26 (s, 1 H) 7.77 (d, J = 7.1 Hz, 1 H) 7.39 (dd, J = 7.7, 4.7 Hz, 1 H) 6.89 (s, 1 H) 3.58-3.75 (m, 4 H) 3.08-3.25 (m, 4 H) 2.90 (s, 3 H) 2.13 (s, 3 H) |
| A-23 | 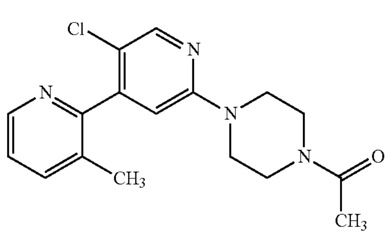 [SMILES: CC(=O)N1CCN(c2cc(-c3ncccc3C)c(Cl)cn2)CC1] | 2'-(4-acetylpiperazin-1-yl)-5'-chloro-3-methyl-2,4'-bipyridine | 330.82 | ¹H NMR (400 MHz, DMSO-d6) δ ppm 8.41-8.54 (m, 1 H) 8.25 (s, 1 H) 7.76 (d, J = 7.1 Hz, 1 H) 7.38 (dd, J = 7.8, 4.8 Hz, 1 H) 6.83 (s, 1 H) 3.56-3.65 (m, 2 H) 3.43-3.55 (m, 6 H) 2.12 (s, 3 H) 2.03 (s, 3 H) |

TABLE 1-continued

| Example Number | Structure | Compound Name | LRMS m/z (M + H) | ¹H NMR |
|---|---|---|---|---|
| A-24 | 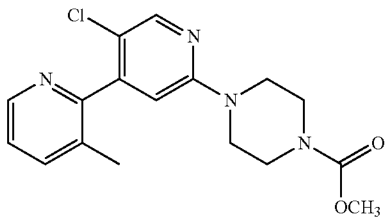 [SMILES: COC(=O)N1CCN(c2cc(-c3ncccc3C)c(Cl)cn2)CC1] | methyl 4-(5'-chloro-3-methyl-2,4'-bipyridin-2'-yl)piperazine-1-carboxylate | 347.00 | ¹H NMR (400 MHz, DMSO-d6) δ ppm 8.47 (d, J = 3.8 Hz, 1 H) 8.24 (s, 1 H) 7.76 (d, J = 7.3 Hz, 1 H) 7.38 (dd, J = 7.6, 4.8 Hz, 1 H) 6.82 (s, 1 H) 3.62 (s, 3 H) 3.50-3.59 (m, 4 H) 3.41-3.50 (m, 4 H) 2.12 (s, 3 H) |
| A-25 | 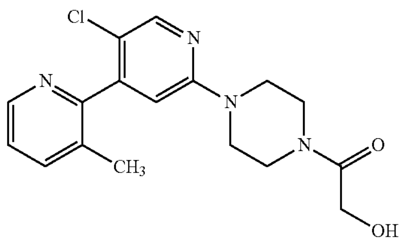 [SMILES: Cc1cccnc1-c1cc(N2CCN(C(=O)CO)CC2)ncc1Cl] | 2-[4-(5'-chloro-3-methyl-2,4'-bipyridin-2'-yl)piperazin-1-yl]-2-oxoethanol | 347.00 | ¹H NMR (400 MHz, DMSO-d6) δ ppm 8.34-8.55 (m, 1 H) 8.25 (s, 1 H) 7.76 (d, J = 7.6 Hz, 1 H) 7.38 (dd, J = 7.8, 4.8 Hz, 1 H) 6.84 (s, 1 H) 4.62 (t, J = 5.6 Hz, 1 H) 4.13 (d, 2 H) 3.56 (br. s., 6 H) 3.40-3.49 (m, 2 H) 2.12 (s, 3 H) |
| A-26 | 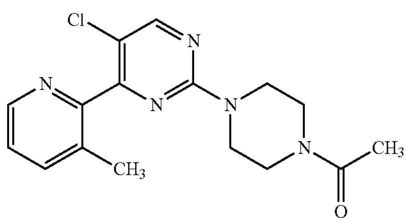 [SMILES: CC(=O)N1CCN(c2ncc(Cl)c(-c3ncccc3C)n2)CC1] | 2-(4-acetylpiperazin-1-yl)-5-chloro-4-(3-methylpyridin-2-yl)pyrimidine | 332.3 | ¹H NMR (400 MHz, CDCl₃) δ ppm 8.46-8.47 (d, 1H), 8.31 (s, 1H), 7.55-7.57 (d, 1H), 7.21-7.24 (m, 1H), 3.73-3.80 (m, 4H), 3.59-3.62 (m, 2H), 3.43-3.46 (m, 2H), 2.18 (s, 3H), 2.62 (s, 3H) |
| A-27 | 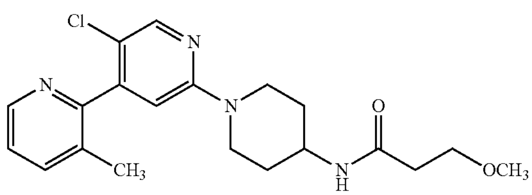 [SMILES: COCCC(=O)NC1CCN(c2cc(-c3ncccc3C)c(Cl)cn2)CC1] | N-[1-(5'-chloro-3-methyl-2,4'-bipyridin-2'-yl)piperidin-4-yl]-3-methoxypropanamide | 389.2 | ¹H NMR (400 MHz, DMSO-d₆) δ ppm 8.47 (d, J = 3.79 Hz, 1 H) 8.21 (s, 1 H) 7.81 (d, J = 7.83 Hz, 1 H) 7.76 (d, J = 7.07 Hz, 1 H) 7.38 (dd, J = 7.71, 4.67 Hz, 1 H) 6.81 (s, 1 H) 4.18 (d, J = 13.39 Hz, 2 H) 3.76-3.87 (m, 1 H) 3.51 (t, J = 6.32 Hz, 2 H) 3.20 (s, 3 H) 2.95-3.04 (m, 2 H) 2.28 (t, J = 6.44 Hz, 2 H) 2.12 (s, 3 H) 1.75 (dd, J = 13.14, 3.28 Hz, 2 H) 1.28-1.40 (m, 2 H) |
| A-28 | 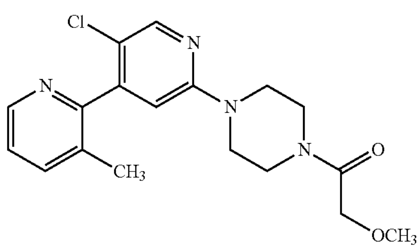 [SMILES: COCC(=O)N1CCN(c2cc(-c3ncccc3C)c(Cl)cn2)CC1] | 5'-chloro-2'-[4-(methoxyacetyl)piperazin-1-yl]-3-methyl-2,4'-bipyridine | 361.20/363.00 | ¹H NMR (400 MHz, DMSO-d6) δ ppm 8.42-8.56 (m, 1 H) 8.25 (s, 1 H) 7.76 (d, J = 7.1 Hz, 1 H) 7.38 (dd, J = 7.6, 4.8 Hz, 1 H) 6.84 (s, 1 H) 4.12 (s, 2 H) 3.41-3.66 (m, 8 H) 3.29 (s, 3 H) 2.12 (s, 3 H) |
| A-29 | 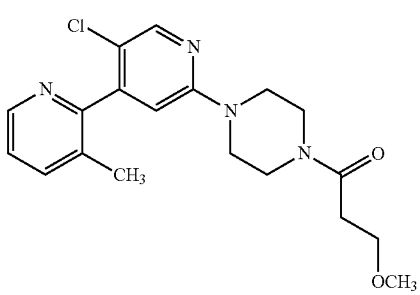 [SMILES: COCCC(=O)N1CCN(c2cc(-c3ncccc3C)c(Cl)cn2)CC1] | 5'-chloro-2'-[4-(3-methoxypropanoyl)piperazin-1-yl]-3-methyl-2,4'-bipyridine | 375.20 | ¹H NMR (400 MHz, DMSO-d6) δ ppm 8.42-8.55 (m, 1 H) 8.25 (s, 1 H) 7.76 (d, J = 7.1 Hz, 1 H) 7.38 (dd, J = 7.6, 4.8 Hz, 1 H) 6.84 (s, 1 H) 4.12 (s, 2 H) 3.41-3.68 (m, 10 H) 3.29 (s, 3 H) 2.12 (s, 3 H) |

TABLE 1-continued

| Example Number | Structure | Compound Name | LRMS m/z (M + H) | ¹H NMR |
|---|---|---|---|---|
| A-30 | 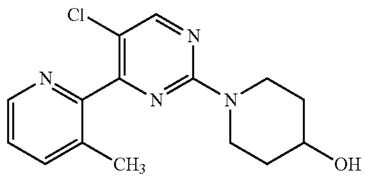 [SMILES: Cc1cccnc1-c1nc(N2CCC(O)CC2)ncc1Cl] | 1-[5-chloro-4-(3-methylpyridin-2-yl)pyrimidin-2-yl]piperidin-4-ol | 304.78 | ¹H NMR (400 MHz, CDCl₃) δ ppm 8.42-8.48 (m, 1H), 8.28 (s, 1H), 7.45-7.57 (dd, 1H), 7.22-7.30 (m, 1H), 4.23-4.33 (m, 2H), 3.87-3.88 (m, 1H), 3.10-3.46 (m, 3H), 2.19 (s, 3H), 1.78-1.88 (m, 2H), 1.44-1.52 (m, 2H) |
| A-31 | 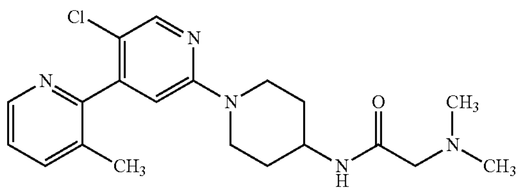 [SMILES: Cc1cccnc1-c1cc(N2CCC(NC(=O)CN(C)C)CC2)ncc1Cl] | N-(1-(5'-chloro-3-methyl-[2,4'-bipyridin]-2'-yl)piperidin-4-yl)-2-(dimethylamino)acetamide | 388.2 | ¹H NMR (400 MHz, DMSO-d₆) δ ppm 8.47 (d, J = 4.55 Hz, 1 H) 8.21 (s, 1 H) 7.76 (d, J = 7.58 Hz, 1 H) 7.64 (d, J = 8.08 Hz, 1 H) 7.37 (dd, J = 7.83, 4.80 Hz, 1 H) 6.81 (s, 1 H) 4.23 (d, J = 13.39 Hz, 2 H) 3.80-3.93 (m, 1 H) 2.95 (t, J = 11.62 Hz, 2 H) 2.83 (s, 2 H) 2.18 (s, 6 H) 2.13 (s, 3 H) 1.68-1.77 (m, 2 H) 1.45 (qd, J = 12.00, 11.81, 3.79 Hz, 2 H) |
| A-32 | 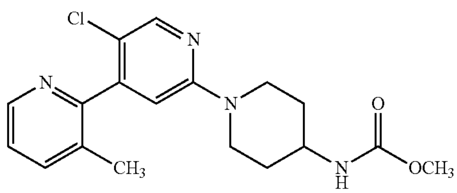 [SMILES: COC(=O)NC1CCN(c2cc(-c3ncccc3C)c(Cl)cn2)CC1] | methyl [1-(5'-chloro-3-methyl-2,4'-bipyridin-2'-yl)piperidin-4-yl]carbamate | 361.2 | ¹H NMR (400 MHz, DMSO-d₆) δ ppm 8.47 (dd, J = 4.67, 0.88 Hz, 1 H) 8.20 (s, 1 H) 7.75 (d, J = 7.07 Hz, 1 H) 7.37 (dd, J = 7.83, 4.80 Hz, 1 H) 7.14 (d, J = 7.58 Hz, 1 H) 6.80 (s, 1 H) 4.20 (d, J = 13.14 Hz, 2 H) 3.52 (s, 3 H) 3.47-3.61 (m, 1 H) 2.97 (t, J = 11.75 Hz, 2 H) 2.12 (s, 3 H) 1.77 (dd, J = 12.76, 2.91 Hz, 2 H) 1.29-1.41 (m, 2 H) |
| A-33 | 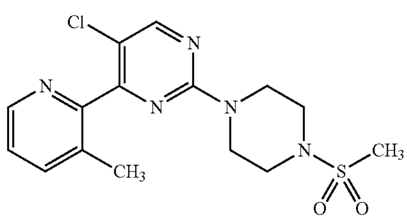 [SMILES: Cc1cccnc1-c1nc(N2CCN(S(C)(=O)=O)CC2)ncc1Cl] | 5-chloro-4-(3-methylpyridin-2-yl)-2-[4-(methylsulfonyl)piperazin-1-yl]pyrimidine | 367.86 | ¹H NMR (400 MHz, CDCl₃): δ ppm 8.38-8.56 (d, 1H), 8.31 (s, 1H), 7.52-7.64 (d, 1H), 7.17-7.27 (m, 1H), 3.89-4.00 (m, 4H), 3.11-3.31 (m, 4H), 2.68 (s, 1H), 2.18 (s, 3H). |
| A-34 | 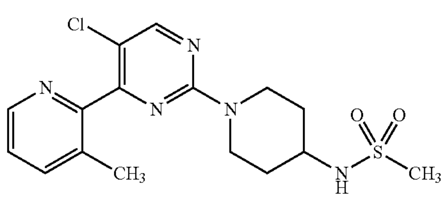 [SMILES: Cc1cccnc1-c1nc(N2CCC(NS(C)(=O)=O)CC2)ncc1Cl] | N-{1-[5-chloro-4-(3-methylpyridin-2-yl)pyrimidin-2-yl]piperidin-4-yl}methanesulfonamide | 381.89 | ¹H NMR (400 MHz, CDCl₃): δ ppm 8.53-8.62 (dd, 1H), 8.39-8.40 (d, 1H), 7.61-7.63 (d, 1H), 7.41-7.48 (m, 1H), 6.93-7.00 (d, 1H), 4.63-4.81 (m, 2H), 4.39-4.46 (m, 2H), 3.51-3.69 (m, 1H), 3.03-3.12 (m, 2H), 2.95 (s, 3H), 2.51 (s, 3H), 1.92-2.03 (m, 2H), 1.41-1.51 (m, 2H). |
| A-35 | 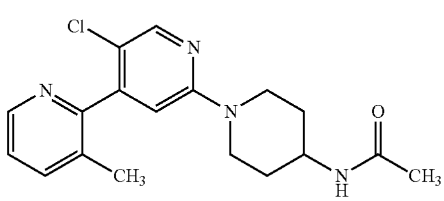 [SMILES: CC(=O)NC1CCN(c2cc(-c3ncccc3C)c(Cl)cn2)CC1] | N-[1-(5'-chloro-3-methyl-2,4'-bipyridin-2'-yl)piperidin-4-yl]acetamide | 345.2 | ¹H NMR (400 MHz, DMSO-d₆) δ ppm 8.47 (dd, J = 4.80, 1.01 Hz, 1 H) 8.21 (s, 1 H) 7.79 (d, J = 7.58 Hz, 1 H) 7.76 (d, J = 7.07 Hz, 1 H) 7.38 (dd, J = 7.83, 4.80 Hz, 1 H) 6.81 (s, 1 H) 4.18 (d, J = 13.39 Hz, 2 H) 3.74-3.86 (m, 1 H) 2.95-3.05 (m, 2 H) 2.12 (s, 3 H) 1.78 (s, 3 H) 1.71-1.80 (m, 2 H) 1.27-1.39 (m, 2 H) |

TABLE 1-continued

| Example Number | Structure | Compound Name | LRMS m/z (M + H) | ¹H NMR |
|---|---|---|---|---|
| A-36 | 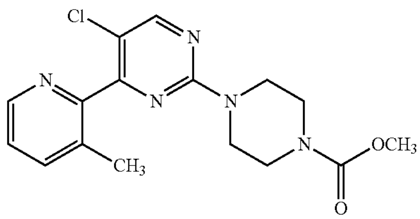 [SMILES: COC(=O)N1CCN(c2ncc(Cl)c(-c3ncccc3C)n2)CC1] | methyl 4-[5-chloro-4-(3-methylpyridin-2-yl)pyrimidin-2-yl]piperazine-1-carboxylate | 348.3 | ¹H NMR (400 MHz, CDCl₃): δ ppm 8.47-8.48 (d, 1H), 8.30 (s, 1H), 7.55-7.57 (d, 1H), 7.20-7.24 (m, 1H), 3.73-3.76 (m, 4H), 3.66 (s,, 3H), 3.40-3.46 (m, 4H), 2.18 (s, 3H). |
| A-37 | 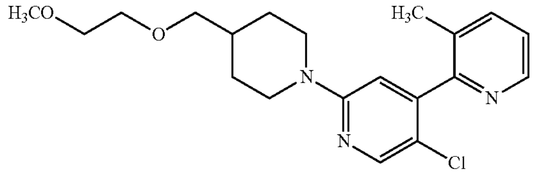 [SMILES: COCCOCC1CCN(c2cc(-c3ncccc3C)c(Cl)cn2)CC1] | 5'-chloro-2'-{4-[(2-methoxyethoxy)methyl]piperidin-1-yl}-3-methyl-2,4'-bipyridine | 376 | ND |
| A-38 | 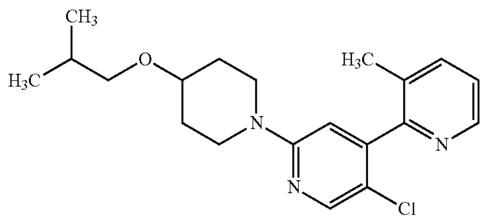 [SMILES: Cc1cccnc1-c1cc(N2CCC(OCC(C)C)CC2)ncc1Cl] | 5'-chloro-2'-(4-isobutoxypiperidin-1-yl)-3-methyl-2,4'-bipyridine | 360 | ND |
| A-39 | 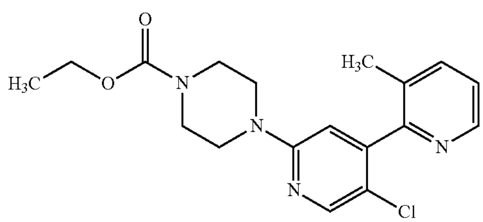 [SMILES: CCOC(=O)N1CCN(c2cc(-c3ncccc3C)c(Cl)cn2)CC1] | ethyl 4-(5'-chloro-3-methyl-2,4'-bipyridin-2'-yl)piperazine-1-carboxylate | 361 | ND |
| A-40 | 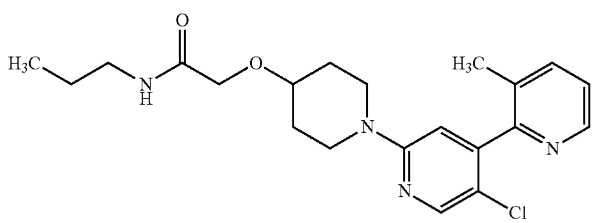 [SMILES: CCCNC(=O)COC1CCN(c2cc(-c3ncccc3C)c(Cl)cn2)CC1] | 2-{[1-(5'-chloro-3-methyl-2,4'-bipyridin-2'-yl)piperidin-4-yl]oxy}-N-propylacetamide | 403 | ND |
| A-41 | 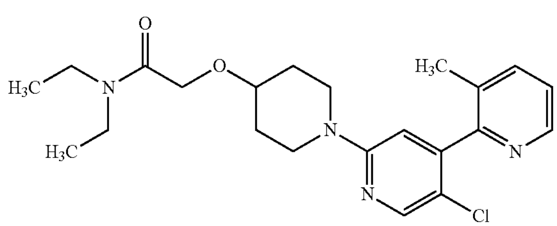 [SMILES: CCN(CC)C(=O)COC1CCN(c2cc(-c3ncccc3C)c(Cl)cn2)CC1] | 2-{[1-(5'-chloro-3-methyl-2,4'-bipyridin-2'-yl)piperidin-4-yl]oxy}-N,N-diethylacetamide | 417 | ND |
| A-42 | 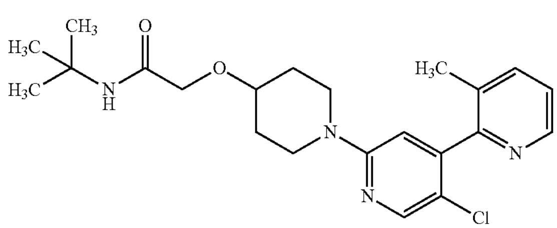 [SMILES: Cc1cccnc1-c1cc(N2CCC(OCC(=O)NC(C)(C)C)CC2)ncc1Cl] | N-tert-butyl-2-{[1-(5'-chloro-3-methyl-2,4'-bipyridin-2'-yl)piperidin-4-yl]oxy}acetamide | 417 | ND |

TABLE 1-continued

| Example Number | Structure | Compound Name | LRMS m/z (M + H) | ¹H NMR |
|---|---|---|---|---|
| A-43 | 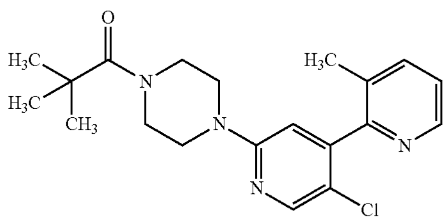 [SMILES: Cc1cccnc1-c1cc(N2CCN(C(=O)C(C)(C)C)CC2)ncc1Cl] | 5'-chloro-2'-[4-(2,2-dimethylpropanoyl)piperazin-1-yl]-3-methyl-2,4'-bipyridine | 373 | ND |
| A-44 | 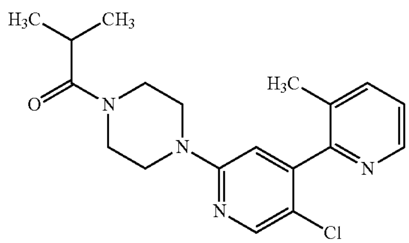 [SMILES: Cc1cccnc1-c1cc(N2CCN(C(=O)C(C)C)CC2)ncc1Cl] | 5'-chloro-2'-(4-isobutyrylpiperazin-1-yl)-3-methyl-2,4'-bipyridine | 359 | ND |
| A-45 | 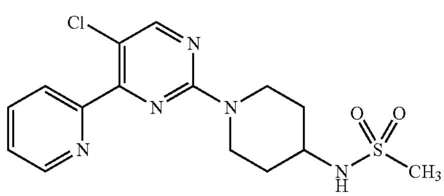 [SMILES: CS(=O)(=O)NC1CCN(c2ncc(Cl)c(-c3ccccn3)n2)CC1] | N-[1-(5-chloro-4-pyridin-2-ylpyrimidin-2-yl)piperidin-4-yl]methanesulfonamide | 390.1 (M + Na) | ¹H NMR (400 MHz, CDCl₃): δ ppm 8.68-8.70 (d, 1H), 8.29 (s, 1H), 7.75-7.79 (m, 1H), 7.70-7.72 (d, 1H), 7.31-7.34 (t, 1H), 4.60-4.63 (d, 2H), 4.18-4.20 (d, 1H), 3.53-3.57 (t, 1H), 2.94 (s, 3H), 1.99-2.02 (d, 1H), 1.39-1.49 (m, 1H) |
| A-46 | 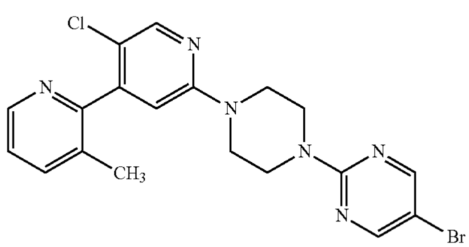 [SMILES: Cc1cccnc1-c1cc(N2CCN(c3ncc(Br)cn3)CC2)ncc1Cl] | 2'-[4-(5-bromopyrimidin-2-yl)piperazin-1-yl]-5'-chloro-3-methyl-2,4'-bipyridine | 446.0 | ¹H NMR (400 MHz, DMSO-d₆) d ppm 8.49-8.56 (m, 2 H) 8.25 (s, 1 H) 7.77 (d, J = 7.83 Hz, 1 H) 7.39 (dd, J = 7.83, 4.80 Hz, 1 H) 6.85 (s, 1 H) 3.81 (dd, J = 6.32, 4.04 Hz, 4 H) 3.64 (d, J = 5.56 Hz, 4 H) 2.13 (s, 3 H) |
| A-47 | 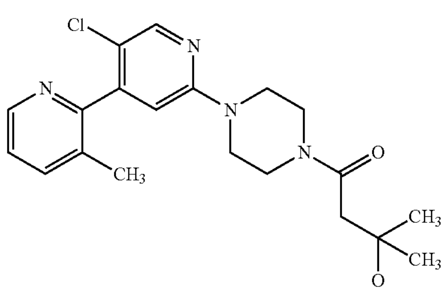 [SMILES: Cc1cccnc1-c1cc(N2CCN(C(=O)CC(C)(C)O)CC2)ncc1Cl] | 4-[4-(5'-chloro-3-methyl-2,4'-bipyridin-2'-yl)piperazin-1-yl]-2-methyl-4-oxobutan-2-ol | 389.20 | ¹H NMR (400 MHz, DMSO-d₆) δ ppm 8.48 (d, J = 3.5 Hz, 1 H) 8.25 (s, 1 H) 7.77 (d, J = 7.1 Hz, 1 H) 7.39 (dd, J = 7.6, 4.8 Hz, 1 H) 6.83 (s, 1 H) 4.80 (s, 1 H) 3.54-3.67 (m, 6 H) 3.45-3.54 (m, 2 H) 2.12 (s, 3 H) 1.18 (s, 6 H) |
| A-48 | 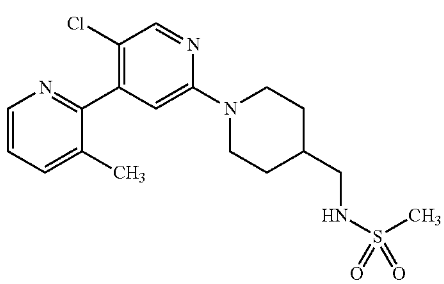 [SMILES: Cc1cccnc1-c1cc(N2CCC(CNS(C)(=O)=O)CC2)ncc1Cl] | N-{[1-(5'-chloro-3-methyl-2,4'-bipyridin-2'-yl)piperidin-4-yl]methyl}methanesulfonamide | 395.10 | ¹H NMR (400 MHz, CDCl₃): δ ppm 8.43-8.62 (m, 1 H) 8.21 (s, 1 H) 7.62 (d, J = 7.07 Hz, 1 H) 7.28-7.30 (m, 1 H) 6.60 (s, 1 H) 4.41-4.56 (m, 1 H) 4.31-4.34 (d, J = 13.59 Hz, 2H) 3.03 (t, J = 6.57 Hz, 2 H) 2.97 (s, 3 H) 2.85 (td, J = 12.69, 2.40 Hz, 2 H) 2.21 (s, 3 H) 1.79-1.92 (m, 3 H) 1.20-1.29 (m, 2 H) |

TABLE 1-continued

| Example Number | Structure | Compound Name | LRMS m/z (M + H) | ¹H NMR |
|---|---|---|---|---|
| A-49 | 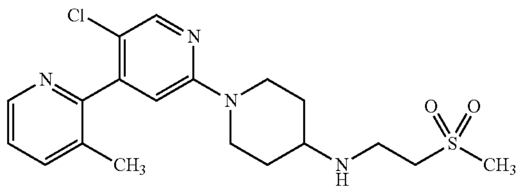 [SMILES: Cc1cccnc1-c1cc(N2CCC(NCCS(C)(=O)=O)CC2)ncc1Cl] | 1-(5'-chloro-3-methyl-2,4'-bipyridin-2'-yl)-N-[2-(methylsulfonyl)ethyl]piperidin-4-amine | 409.2 | ¹H NMR (400 MHz, DMSO-d₆) δ ppm 8.47 (d, J = 4.04 Hz, 1 H) 8.20 (s, 1 H) 7.76 (d, J = 7.33 Hz, 1 H) 7.37 (dd, J = 7.58, 4.80 Hz, 1 H) 6.80 (s, 1 H) 4.16 (d, J = 13.39 Hz, 2 H) 3.22 (t, J = 6.57 Hz, 2 H) 3.02 (s, 3 H) 2.87-3.01 (m, 4 H) 2.72 (t, J = 8.84 Hz, 1 H) 2.12 (s, 3 H) 1.84 (d, J = 10.61 Hz, 2 H) 1.19-1.29 (m, 2 H) 1.16 (t, J = 7.20 Hz, 1 H) |
| A-50 | 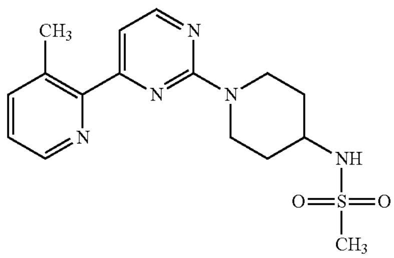 [SMILES: Cc1cccnc1-c1ccnc(N2CCC(NS(C)(=O)=O)CC2)n1] | N-{1-[4-(3-methylpyridin-2-yl)pyrimidin-2-yl]piperidin-4-yl}methanesulfonamide | 348.3 | ¹H NMR (400 MHz, CDCl₃): δ ppm 8.53-8.62 (dd, 1H), 8.39-8.40 (d, 1H), 7.61-7.63 (d, 1H), 7.41-7.48 (m, 1H), 6.93-7.00 (d, 1H), 4.63-4.81 (m, 2H), 4.39-4.46 (m, 2H), 3.51-3.69 (m, 1H), 3.03-3.12 (m, 2H), 2.95 (s, 3H), 2.51 (s, 3H), 1.92-2.03 (m, 2H), 1.41-1.51 (m, 2H). |
| A-51 | 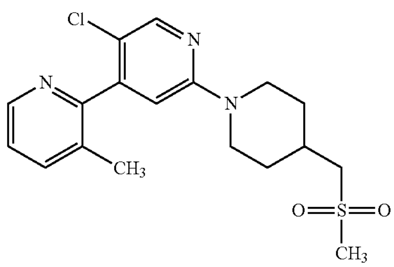 [SMILES: Cc1cccnc1-c1cc(N2CCC(CS(C)(=O)=O)CC2)ncc1Cl] | 5'-chloro-3-methyl-2'-{4-[(methylsulfonyl)methyl]piperidin-1-yl}-2,4'-bipyridine | 380.1 | ¹H NMR (500 MHz, DMSO-d₆) δ ppm 1.26-1.38 (m, 2 H) 1.88 (br. s., 2 H) 2.12 (s, 3 H) 2.22 (s, 1 H) 2.87-2.96 (m, 2 H) 2.98 (s, 3 H) 3.12 (d, J = 5.86 Hz, 2 H) 4.25 (d, J = 12.69 Hz, 2 H) 6.78 (s, 1 H) 7.37 (dd, J = 7.81, 4.88 Hz, 1 H) 7.75 (d, J = 7.81 Hz, 1 H) 8.20 (s, 1 H) 8.47 (d, J = 4.39 Hz, 1 H) |
| A-52 | 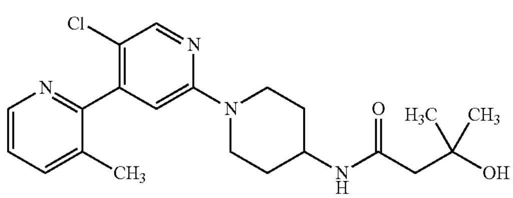 [SMILES: Cc1cccnc1-c1cc(N2CCC(NC(=O)CC(C)(C)O)CC2)ncc1Cl] | N-(1-(5'-chloro-3-methyl-[2,4'-bipyridin]-2'-yl)piperidin-4-yl)-3-hydroxy-3-methylbutanamide | 403.2 | ¹H NMR (400 MHz, DMSO-d₆) δ ppm 8.47 (dd, J = 4.80, 1.01 Hz, 1 H) 8.21 (s, 1 H) 7.84 (d, J = 7.83 Hz, 1 H) 7.74-7.78 (m, 1 H) 7.38 (dd, J = 7.83, 4.80 Hz, 1 H) 6.82 (s, 1 H) 4.80 (s, 1 H) 4.14-4.21 (m, 2 H) 3.78-3.91 (m, 1 H) 2.97-3.06 (m, 2 H) 2.17 (s, 2 H) 2.12 (s, 3 H) 1.74-1.80 (m, 2 H) 1.29-1.42 (m, 2 H) 1.13 (s, 6 H) |
| A-53 | 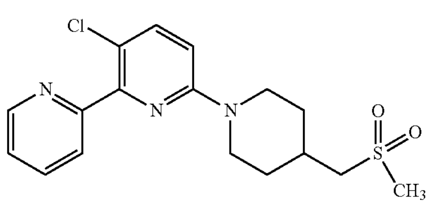 [SMILES: CS(=O)(=O)CC1CCN(c2ccc(Cl)c(-c3ccccn3)n2)CC1] | 3-chloro-6-{4-[(methylsulfonyl)methyl]piperidin-1-yl}-2,2'-bipyridine | 366.1 | ¹H NMR (400 MHz, DMSO-d₆) δ ppm 8.64 (d, J = 4.80 Hz, 1 H) 7.91 (td, J = 7.71, 1.77 Hz, 1 H) 7.63-7.71 (m, 2 H) 7.43 (ddd, J = 7.58, 4.80, 1.01 Hz, 1 H) 6.94 (d, J = 8.84 Hz, 1 H) 4.25 (d, J = 13.39 Hz, 2 H) 3.17 (d, J = 5.31 Hz, 1 H) 3.13 (d, J = 6.57 Hz, 1 H) 2.97-3.02 (m, 3 H) 2.86-2.97 (m, 2 H) 2.13-2.28 (m, 1 H) 1.84-1.95 (m, 2 H) 1.24-1.39 (m, 2 H) |

TABLE 1-continued

| Example Number | Structure | Compound Name | LRMS m/z (M + H) | ¹H NMR |
|---|---|---|---|---|
| A-54 | 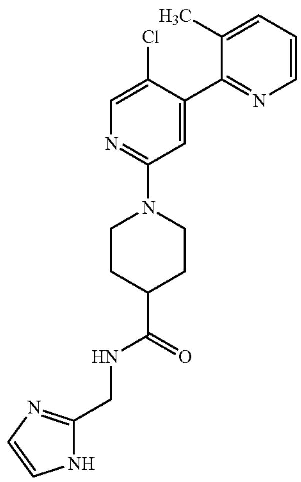 [SMILES: Cc1cccnc1-c1cc(N2CCC(C(=O)NCc3ncc[nH]3)CC2)ncc1Cl] | 1-(5'-chloro-3-methyl-2,4'-bipyridin-2'-yl)-N-(1H-imidazol-2-ylmethyl)piperidine-4-carboxamide | 411 | ND |
| A-55 | 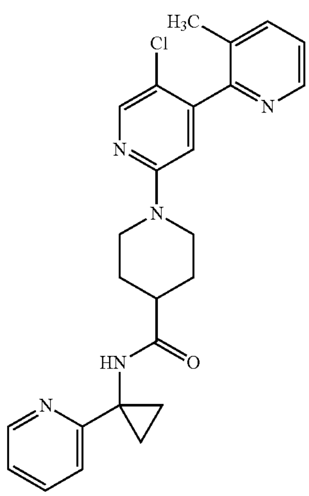 [SMILES: Cc1cccnc1-c1cc(N2CCC(C(=O)NC3(c4ccccn4)CC3)CC2)ncc1Cl] | 1-(5'-chloro-3-methyl-2,4'-bipyridin-2'-yl)-N-(1-pyridin-2-ylcyclopropyl)piperidine-4-carboxamide | 448 | ND |
| A-56 | 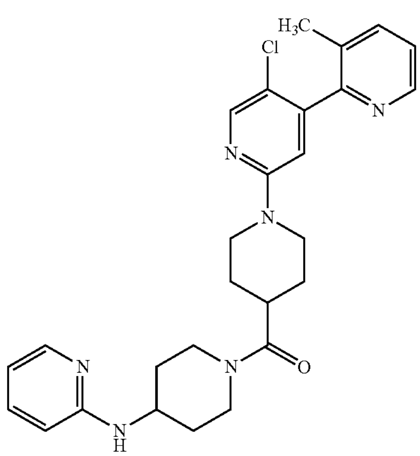 [SMILES: Cc1cccnc1-c1cc(N2CCC(C(=O)N3CCC(Nc4ccccn4)CC3)CC2)ncc1Cl] | N-(1-{[1-(5'-chloro-3-methyl-2,4'-bipyridin-2'-yl)piperidin-4-yl]carbonyl}piperidin-4-yl)pyridin-2-amine | 491 | ND |

TABLE 1-continued
| Example Number | Structure | Compound Name | LRMS m/z (M + H) | $^1$H NMR |
|---|---|---|---|---|
| A-57 | 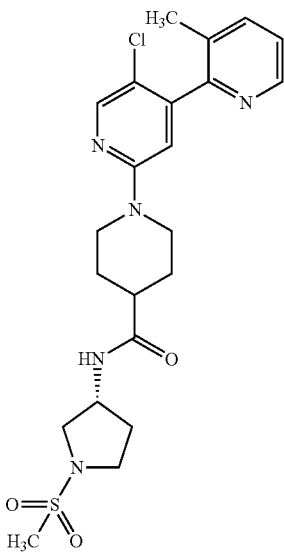 [SMILES: Cc1cccnc1-c1cc(N2CCC(C(=O)N[C@@H]3CCN(S(C)(=O)=O)C3)CC2)ncc1Cl] | 1-(5'-chloro-3-methyl-2,4'-bipyridin-2'-yl)-N-[(3R)-1-(methylsulfonyl)pyrrolidin-3-yl]piperidine-4-carboxamide | 478 | ND |
| A-58 | 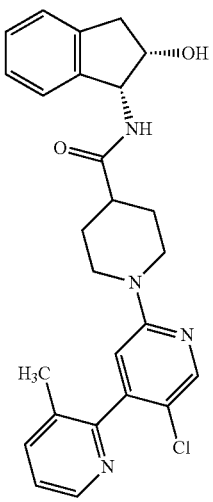 [SMILES: Cc1cccnc1-c1cc(N2CCC(C(=O)N[C@@H]3c4ccccc4C[C@@H]3O)CC2)ncc1Cl] | 1-(5'-chloro-3-methyl-2,4'-bipyridin-2'-yl)-N-[(1R,2S)-2-hydroxy-2,3-dihydro-1H-inden-1-yl]piperidine-4-carboxamide | 463 | ND |

TABLE 1-continued
| Example Number | Structure | Compound Name | LRMS m/z (M + H) | ¹H NMR |
|---|---|---|---|---|
| A-59 | 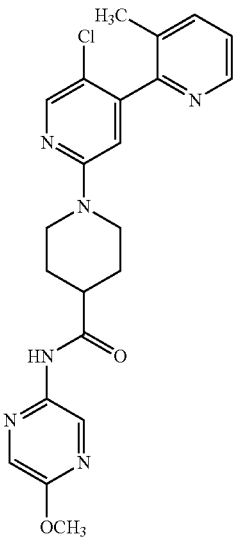 [SMILES: COc1cnc(NC(=O)C2CCN(c3cc(-c4ncccc4C)c(Cl)cn3)CC2)cn1] | 1-(5'-chloro-3-methyl-2,4'-bipyridin-2'-yl)-N-(5-methoxypyrazin-2-yl)piperidine-4-carboxamide | 439 | ND |
| A-60 | 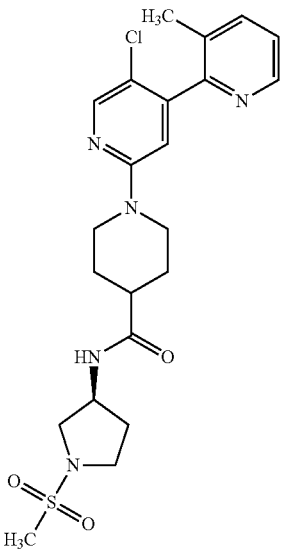 [SMILES: Cc1cccnc1-c1cc(N2CCC(C(=O)N[C@H]3CCN(S(C)(=O)=O)C3)CC2)ncc1Cl] | 1-(5'-chloro-3-methyl-2,4'-bipyridin-2'-yl)-N-[(3S)-1-(methylsulfonyl)pyrrolidin-3-yl]piperidine-4-carboxamide | 478 | ND |

TABLE 1-continued

| Example Number | Structure | Compound Name | LRMS m/z (M + H) | ¹H NMR |
|---|---|---|---|---|
| A-61 | 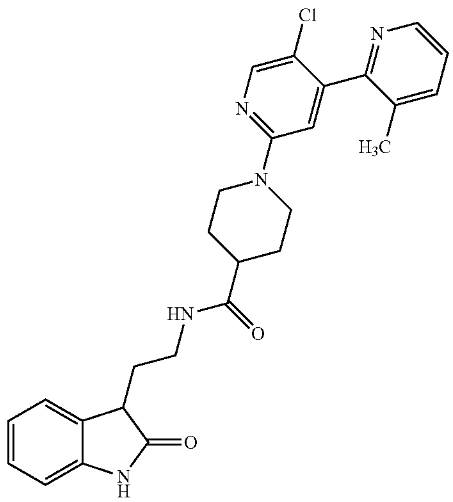 [SMILES: Cc1cccnc1-c1cc(N2CCC(C(=O)NCCC3C(=O)Nc4ccccc43)CC2)ncc1Cl] | 1-(5'-chloro-3-methyl-2,4'-bipyridin-2'-yl)-N-[2-(2-oxo-2,3-dihydro-1H-indol-3-yl)ethyl]piperidine-4-carboxamide | 490 | ND |
| A-62 | 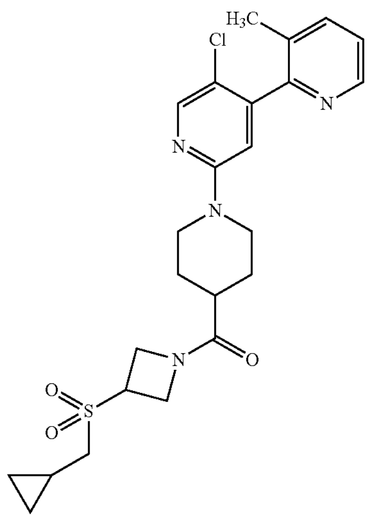 [SMILES: Cc1cccnc1-c1cc(N2CCC(C(=O)N3CC(S(=O)(=O)CC4CC4)C3)CC2)ncc1Cl] | 5'-chloro-2'-[4-({3-[(cyclopropylmethyl)sulfonyl]azetidin-1-yl}carbonyl)piperidin-1-yl]-3-methyl-2,4'-bipyridine | 489 | ND |
| A-63 | 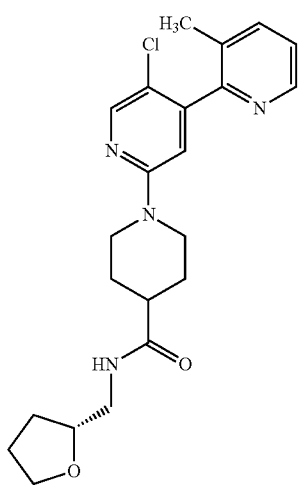 [SMILES: Cc1cccnc1-c1cc(N2CCC(C(=O)NC[C@H]3CCCO3)CC2)ncc1Cl] | 1-(5'-chloro-3-methyl-2,4'-bipyridin-2'-yl)-N-[(2R)-tetrahydrofuran-2-ylmethyl]piperidine-4-carboxamide | 415 | ND |

TABLE 1-continued

| Example Number | Structure | Compound Name | LRMS m/z (M + H) | ¹H NMR |
|---|---|---|---|---|
| A-64 | 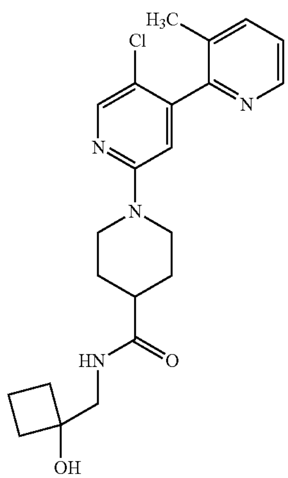 [SMILES: Cc1cccnc1-c1cc(N2CCC(C(=O)NCC3(O)CCC3)CC2)ncc1Cl] | 1-(5'-chloro-3-methyl-2,4'-bipyridin-2'-yl)-N-[(1-hydroxycyclobutyl)methyl]piperidine-4-carboxamide | 415 | ND |
| A-65 | 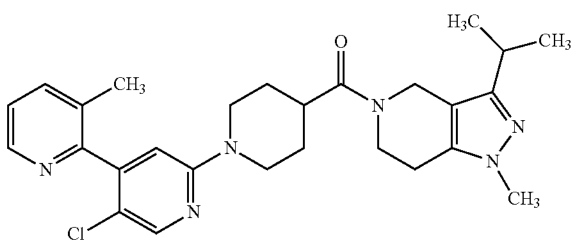 [SMILES: Cc1cccnc1-c1cc(N2CCC(C(=O)N3CCc4c(c(C(C)C)nn4C)C3)CC2)ncc1Cl] | 5'-chloro-2'-{4-[(3-isopropyl-1-methyl-1,4,6,7-tetrahydro-5H-pyrazolo[4,3-c]pyridin-5-yl)carbonyl]piperidin-1-yl}-3-methyl-2,4'-bipyridine | 493 | ND |
| A-66 | 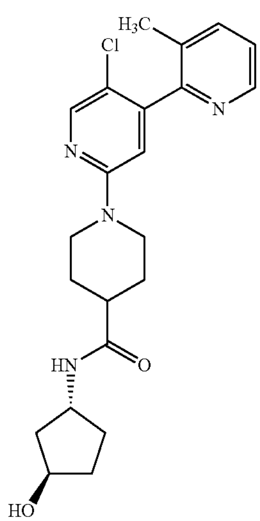 [SMILES: Cc1cccnc1-c1cc(N2CCC(C(=O)N[C@@H]3CC[C@@H](O)C3)CC2)ncc1Cl] | 1-(5'-chloro-3-methyl-2,4'-bipyridin-2'-yl)-N-[(1R,3R)-3-hydroxycyclopent-yl]piperidine-4-carboxamide | 415 | ND |

TABLE 1-continued

| Example Number | Structure | Compound Name | LRMS m/z (M + H) | ¹H NMR |
|---|---|---|---|---|
| A-67 | 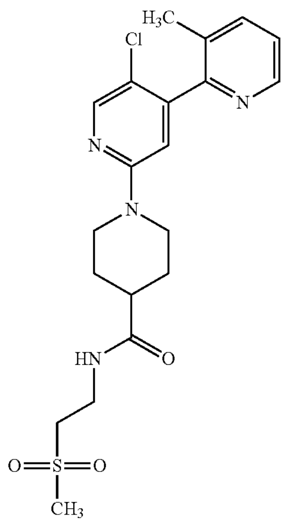 [SMILES: Cc1cccnc1-c1cc(N2CCC(C(=O)NCCS(C)(=O)=O)CC2)ncc1Cl] | 1-(5'-chloro-3-methyl-2,4'-bipyridin-2'-yl)-N-[2-(methylsulfonyl)ethyl]piperidine-4-carboxamide | 437 | ND |
| A-68 | 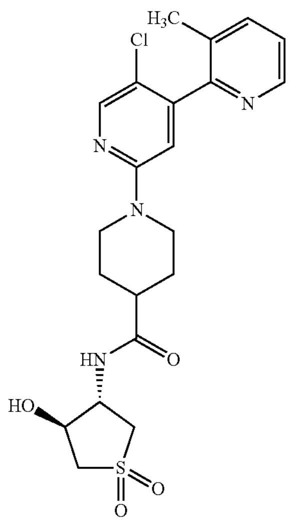 [SMILES: Cc1cccnc1-c1cc(N2CCC(C(=O)N[C@@H]3CS(=O)(=O)C[C@H]3O)CC2)ncc1Cl] | 1-(5'-chloro-3-methyl-2,4'-bipyridin-2'-yl)-N-[(3S,4S)-4-hydroxy-1,1-dioxidotetrahydro-3-thienyl]piperidine-4-carboxamide | 465 | ND |
| A-69 | 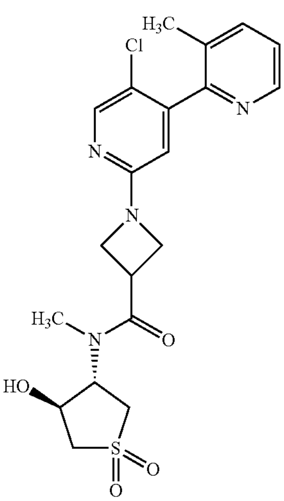 [SMILES: Cc1cccnc1-c1cc(N2CC(C(=O)N(C)[C@@H]3CS(=O)(=O)C[C@H]3O)C2)ncc1Cl] | 1-(5'-chloro-3-methyl-2,4'-bipyridin-2'-yl)-N-[(3S,4S)-4-hydroxy-1,1-dioxidotetrahydro-3-thienyl]-N-methylazetidine-3-carboxamide | 451 | ND |

TABLE 1-continued

| Example Number | Structure | Compound Name | LRMS m/z (M + H) | ¹H NMR |
|---|---|---|---|---|
| A-70 | 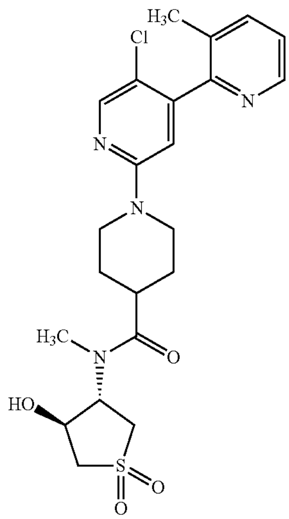 [SMILES: Cc1cccnc1-c1cc(N2CCC(C(=O)N(C)[C@@H]3CS(=O)(=O)C[C@H]3O)CC2)ncc1Cl] | 1-(5'-chloro-3-methyl-2,4'-bipyridin-2'-yl)-N-[(3S,4S)-4-hydroxy-1,1-dioxidotetrahydro-3-thienyl]-N-methylpiperidine-4-carboxamide | 479 | ND |
| A-71 | 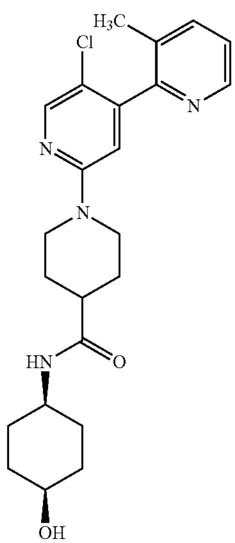 [SMILES: Cc1cccnc1-c1cc(N2CCC(C(=O)N[C@H]3CC[C@@H](O)CC3)CC2)ncc1Cl] | 1-(5'-chloro-3-methyl-2,4'-bipyridin-2'-yl)-N-(trans-4-hydroxycyclohexyl)piperidine-4-carboxamide | 429 | ND |
| A-72 | 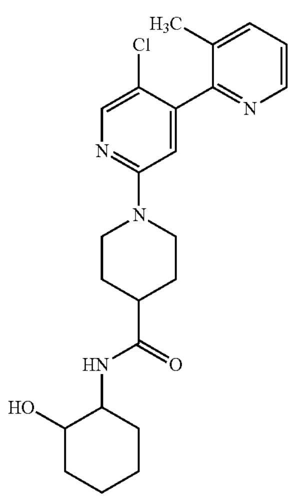 [SMILES: Cc1cccnc1-c1cc(N2CCC(C(=O)NC3CCCCC3O)CC2)ncc1Cl] | 1-(5'-chloro-3-methyl-2,4'-bipyridin-2'-yl)-N-(2-hydroxycyclohexyl)piperidine-4-carboxamide | 429 | ND |

TABLE 1-continued

| Example Number | Structure | Compound Name | LRMS m/z (M + H) | ¹H NMR |
|---|---|---|---|---|
| A-73 | 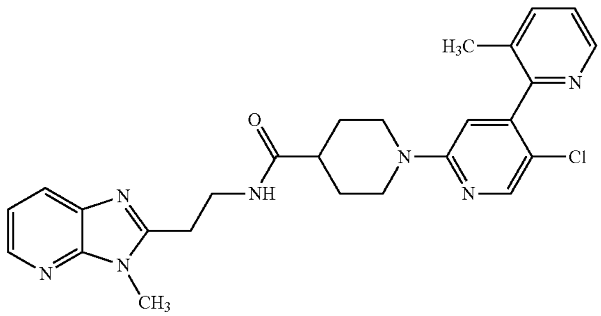 [SMILES: Cc1cccnc1-c1cc(N2CCC(C(=O)NCCc3nc4cccnc4n3C)CC2)ncc1Cl] | 1-(5'-chloro-3-methyl-2,4'-bipyridin-2'-yl)-N-[2-(3-methyl-3H-imidazo[4,5-b]pyridin-2-yl)ethyl]piperidine-4-carboxamide | 490 | ND |
| A-74 | 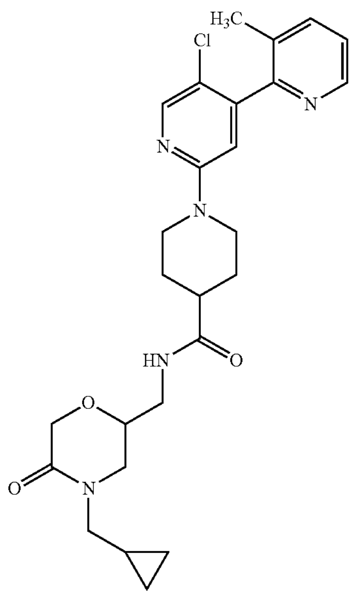 [SMILES: Cc1cccnc1-c1cc(N2CCC(C(=O)NCC3CN(CC4CC4)C(=O)CO3)CC2)ncc1Cl] | 1-(5'-chloro-3-methyl-2,4'-bipyridin-2'-yl)-N-{[4-(cyclopropyl-methyl)-5-oxomorpholin-2-yl]methyl}piperidine-4-carboxamide | 498 | ND |
| A-75 | 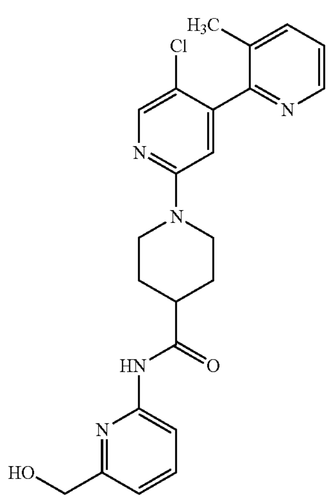 [SMILES: Cc1cccnc1-c1cc(N2CCC(C(=O)Nc3cccc(CO)n3)CC2)ncc1Cl] | 1-(5'-chloro-3-methyl-2,4'-bipyridin-2'-yl)-N-[6-(hydroxymethyl)pyridin-2-yl]piperidine-4-carboxamide | 438 | ND |

TABLE 1-continued

| Example Number | Structure | Compound Name | LRMS m/z (M + H) | ¹H NMR |
|---|---|---|---|---|
| A-76 | 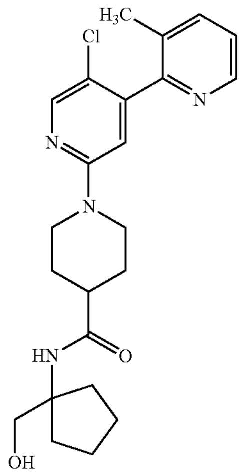 [SMILES: Cc1cccnc1-c1cc(N2CCC(C(=O)NC3(CO)CCCC3)CC2)ncc1Cl] | 1-(5'-chloro-3-methyl-2,4'-bipyridin-2'-yl)-N-[1-(hydroxymethyl)cyclopentyl]piperidine-4-carboxamide | 429 | ND |
| A-77 | 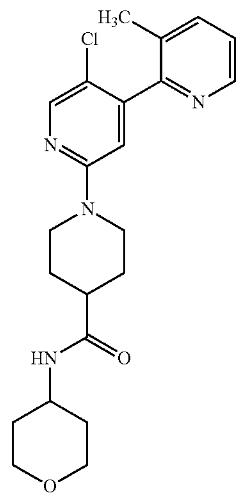 [SMILES: Cc1cccnc1-c1cc(N2CCC(C(=O)NC3CCOCC3)CC2)ncc1Cl] | 1-(5'-chloro-3-methyl-2,4'-bipyridin-2'-yl)-N-(tetrahydro-2H-pyran-4-yl)piperidine-4-carboxamide | 415 | ND |
| A-78 | 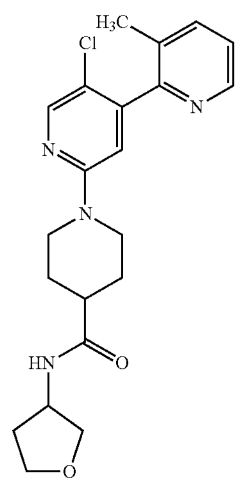 [SMILES: Cc1cccnc1-c1cc(N2CCC(C(=O)NC3CCOC3)CC2)ncc1Cl] | 1-(5'-chloro-3-methyl-2,4'-bipyridin-2'-yl)-N-(tetrahydrofuran-3-yl)piperidine-4-carboxamide | 401 | ND |

TABLE 1-continued
| Example Number | Structure | Compound Name | LRMS m/z (M + H) | ¹H NMR |
|---|---|---|---|---|
| A-79 | 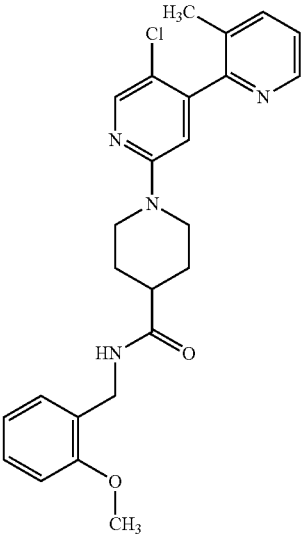 [SMILES: COc1ccccc1CNC(=O)C1CCN(c2cc(-c3ncccc3C)c(Cl)cn2)CC1] | 1-(5'-chloro-3-methyl-2,4'-bipyridin-2'-yl)-N-(2-methoxybenzyl)piperidine-4-carboxamide | 451 | ND |
| A-80 | 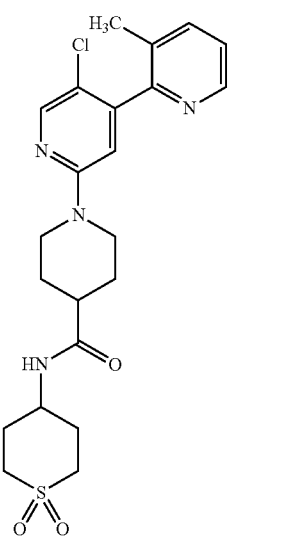 [SMILES: Cc1cccnc1-c1cc(N2CCC(C(=O)NC3CCS(=O)(=O)CC3)CC2)ncc1Cl] | 1-(5'-chloro-3-methyl-2,4'-bipyridin-2'-yl)-N-(1,1-dioxidotetrahydro-2H-thiopyran-4-yl)piperidine-4-carboxamide | 463 | ND |
| A-81 | 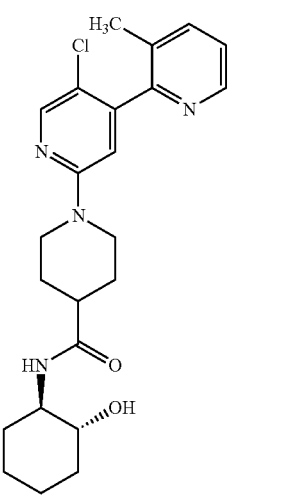 [SMILES: Cc1cccnc1-c1cc(N2CCC(C(=O)N[C@@H]3CCCC[C@H]3O)CC2)ncc1Cl] | 1-(5'-chloro-3-methyl-2,4'-bipyridin-2'-yl)-N-[(1R,2R)-2-hydroxycyclohexyl]piperidine-4-carboxamide | 429 | ND |

TABLE 1-continued

| Example Number | Structure | Compound Name | LRMS m/z (M + H) | ¹H NMR |
|---|---|---|---|---|
| A-82 | 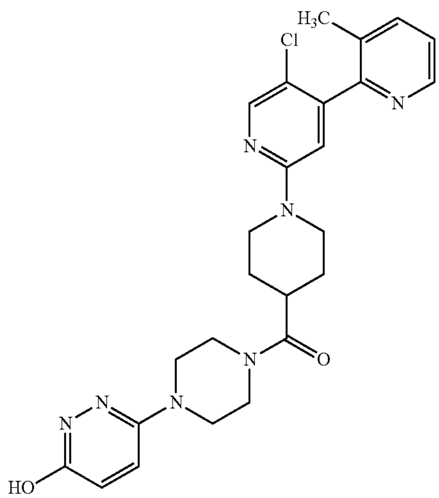 [SMILES: Cc1cccnc1-c1cc(N2CCC(C(=O)N3CCN(c4ccc(O)nn4)CC3)CC2)ncc1Cl] | 6-(4-{[1-(5'-chloro-3-methyl-2,4'-bipyridin-2'-yl)piperidin-4-yl]carbonyl}piperazin-1-yl)pyridazin-3-ol | 494 | ND |
| A-83 | 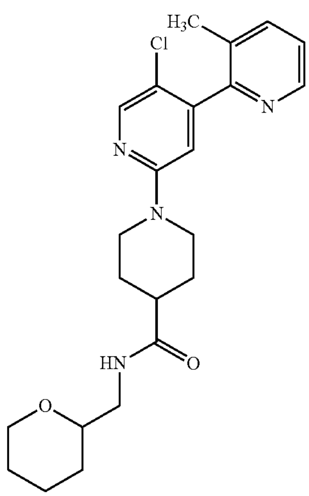 [SMILES: Cc1cccnc1-c1cc(N2CCC(C(=O)NCC3CCCCO3)CC2)ncc1Cl] | 1-(5'-chloro-3-methyl-2,4'-bipyridin-2'-yl)-N-(tetrahydro-2H-pyran-2-ylmethyl)piperidine-4-carboxamide | 429 | ND |
| A-84 | 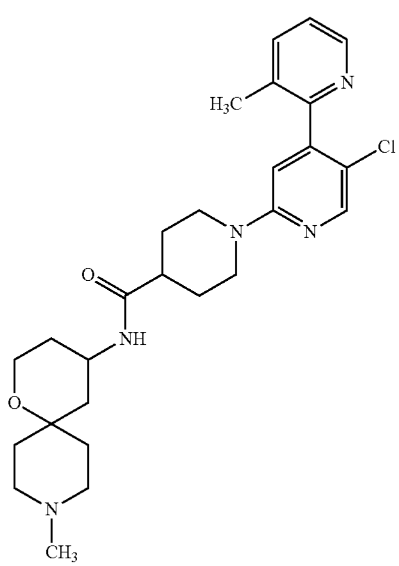 [SMILES: Cc1cccnc1-c1cc(N2CCC(C(=O)NC3CCOC4(CCN(C)CC4)C3)CC2)ncc1Cl] | 1-(5'-chloro-3-methyl-2,4'-bipyridin-2'-yl)-N-(9-methyl-1-oxa-9-azaspiro[5.5]undec-4-yl)piperidine-4-carboxamide | 498 | ND |

TABLE 1-continued

| Example Number | Structure | Compound Name | LRMS m/z (M + H) | ¹H NMR |
|---|---|---|---|---|
| A-85 | 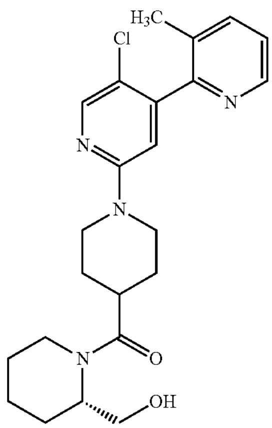 [SMILES: Cc1cccnc1-c1cc(N2CCC(C(=O)N3CCCC[C@H]3CO)CC2)ncc1Cl] | [(2S)-1-{[1-(5'-chloro-3-methyl-2,4'-bipyridin-2'-yl)piperidin-4-yl]carbonyl}piperidin-2-yl]methanol | 429 | ND |
| A-86 | 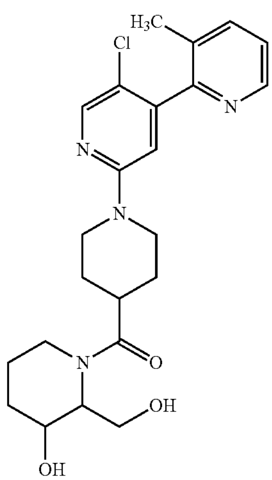 [SMILES: Cc1cccnc1-c1cc(N2CCC(C(=O)N3CCCC(O)C3CO)CC2)ncc1Cl] | 1-{[1-(5'-chloro-3-methyl-2,4'-bipyridin-2'-yl)piperidin-4-yl]carbonyl}-2-(hydroxymethyl)piperidin-3-ol | 445 | ND |
| A-87 | 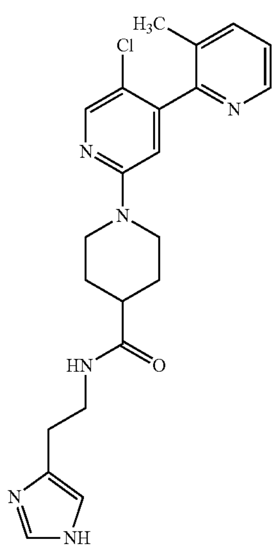 [SMILES: Cc1cccnc1-c1cc(N2CCC(C(=O)NCCc3c[nH]cn3)CC2)ncc1Cl] | 1-(5'-chloro-3-methyl-2,4'-bipyridin-2'-yl)-N-[2-(1H-imidazol-4-yl)ethyl]piperidine-4-carboxamide | 425 | ND |

TABLE 1-continued

| Example Number | Structure | Compound Name | LRMS m/z (M + H) | ¹H NMR |
|---|---|---|---|---|
| A-88 | 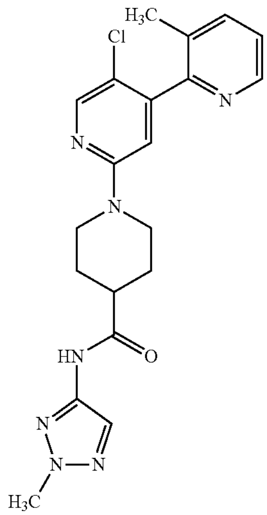 [SMILES: Cc1cccnc1-c1cc(N2CCC(C(=O)Nc3cnn(C)n3)CC2)ncc1Cl] | 1-(5'-chloro-3-methyl-2,4'-bipyridin-2'-yl)-N-(2-methyl-2H-1,2,3-triazol-4-yl)piperidine-4-carboxamide | 412 | ND |
| A-89 | 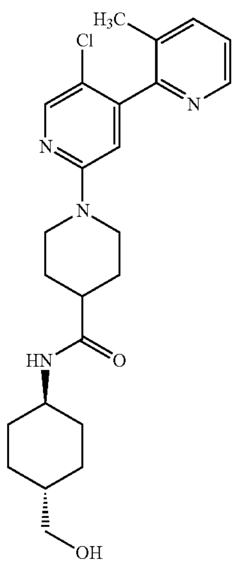 [SMILES: Cc1cccnc1-c1cc(N2CCC(C(=O)N[C@H]3CC[C@H](CO)CC3)CC2)ncc1Cl] | 1-(5'-chloro-3-methyl-2,4'-bipyridin-2'-yl)-N-[trans-4-(hydroxymethyl)cyclohexyl]piperidine-4-carboxamide | 443 | ND |
| A-90 | 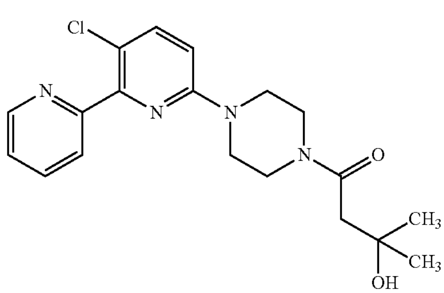 [SMILES: CC(C)(O)CC(=O)N1CCN(c2ccc(Cl)c(-c3ccccn3)n2)CC1] | 4-[4-(3-chloro-2,2'-bipyridin-6-yl)piperazin-1-yl]-2-methyl-4-oxobutan-2-ol | 375.1 | ¹H NMR (400 MHz, DMSO-d₆) δ ppm 8.66 (d, J = 3.90 Hz, 1 H) 7.92 (t, J = 7.56 Hz, 1 H) 7.68-7.77 (m, 2 H) 7.42-7.48 (m, 1 H) 6.96 (d, J = 8.78 Hz, 1 H) 4.77 (br. s., 1 H) 3.60-3.70 (m, 5 H) 3.51-3.60 (m, 5 H) 1.20 (s, 6 H) |

TABLE 1-continued

| Example Number | Structure | Compound Name | LRMS m/z (M + H) | ¹H NMR |
|---|---|---|---|---|
| A-91 | 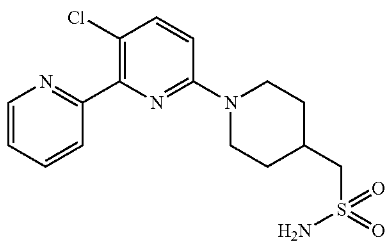 [SMILES: NS(=O)(=O)CC1CCN(c2ccc(Cl)c(-c3ccccn3)n2)CC1] | 1-[1-(3-chloro-2,2'-bipyridin-6-yl)piperidin-4-yl]methanesulfonamide | 367.0 | ¹H NMR (400 MHz, DMSO-d₆) δ ppm 8.64 (d, J = 4.04 Hz, 1 H) 7.91 (td, J = 7.71, 1.77 Hz, 1 H) 7.63-7.71 (m, 2 H) 7.43 (ddd, J = 7.58, 4.80, 1.26 Hz, 1 H) 6.94 (d, J = 9.09 Hz, 1 H) 6.82 (s, 2 H) 4.26 (d, J = 13.39 Hz, 2 H) 2.95 (d, J = 6.32 Hz, 2 H) 2.88 (m, J = 12.88, 12.88 Hz, 2 H) 2.07-2.19 (m, 1 H) 1.92 (m, J = 3.79 Hz, 2 H) 1.21-1.37 (m, 2 H) |
| A-92 | 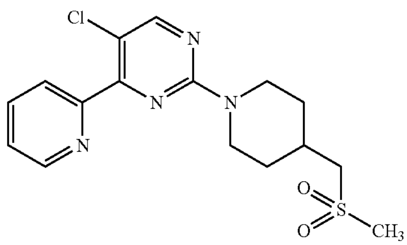 [SMILES: CS(=O)(=O)CC1CCN(c2ncc(Cl)c(-c3ccccn3)n2)CC1] | 5-chloro-2-{4-[(methylsulfonyl)methyl]piperidin-1-yl}-4-pyridin-2-ylpyrimidine | 367.2 | ¹H NMR (400 MHz, CDCl₃): δ 8.68-8.69 (t, 1H), 8.50 (s, 1H), 7.94-7.97 (m, 1H), 7.79-7.81 (d, 1H), 7.50-7.53 (m, 1H), 4.55-4.59 (d, 2H), 3.11-3.13 (m, 4H), 2.99-3.04 (m, 2H), 2.35 (s, 1H), 1.89-1.92 (d, 2H), 1.27-1.30 (m, 2H) |
| A-93 | 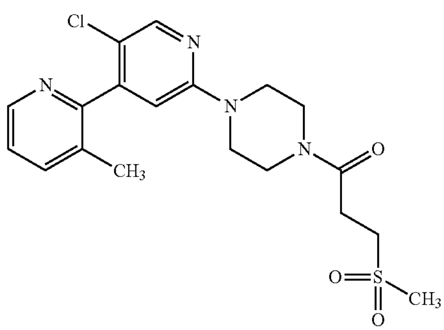 [SMILES: Cc1cccnc1-c1cc(N2CCN(C(=O)CCS(C)(=O)=O)CC2)ncc1Cl] | 5'-chloro-3-methyl-2'-{4-[3-(methylsulfonyl)propanoyl]piperazin-1-yl}-2,4'-bipyridine | 423 | ¹H NMR (400 MHz, DMSO-d₆) δ ppm 8.44-8.52 (m, 1 H) 8.25 (s, 1 H) 7.77 (d, J = 6.8 Hz, 1 H) 7.39 (dd, J = 7.6, 4.8 Hz, 1 H) 6.85 (s, 1 H) 3.49-3.70 (m, 8 H) 3.32-3.38 (m, 2 H) 3.02 (s, 3 H) 2.80-2.90 (m, 2 H) 2.13 (s, 3 H) |
| A-94 | 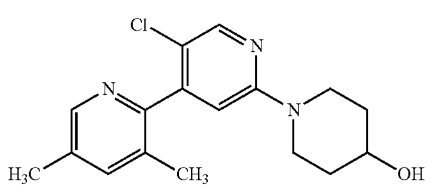 [SMILES: Cc1cnc(-c2cc(N3CCC(O)CC3)ncc2Cl)c(C)c1] | 1-(5'-chloro-3,5-dimethyl-2,4'-bipyridin-2'-yl)piperidin-4-ol | 318.3 | ¹H NMR (400 MHz, CD₃OD) δ ppm 8.24 (s, 1H), 8.13 (s, 1H), 7.62 (s, 1H), 6.74 (s, 1H), 4.09-4.04 (m, 2H), 3.83-3.80 (brs, 1H), 3.17-3.11(m, 2H), 2.37(s, 3H), 2.15 (s, 3H), 1.92-1.87 (m, 2H), 1.54-1.45 (m, 2H) |
| A-95 | 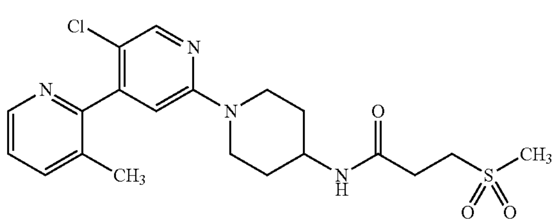 [SMILES: Cc1cccnc1-c1cc(N2CCC(NC(=O)CCS(C)(=O)=O)CC2)ncc1Cl] | N-[1-(5'-chloro-3-methyl-2,4'-bipyridin-2'-yl)piperidin-4-yl]-3-(methylsulfonyl)propanamide | 437.0 | ¹H NMR (400 MHz, DMSO-d₆) δ ppm 8.47 (d, J = 4.29 Hz, 1 H) 8.21 (s, 1 H) 8.04 (d, J = 7.58 Hz, 1 H) 7.76 (d, J = 7.58 Hz, 1 H) 7.38 (dd, J = 7.58, 4.80 Hz, 1 H) 6.82 (s, 1 H) 4.18 (d, J = 13.39 Hz, 2 H) 3.77-3.90 (m, 1 H) 3.31 (t, J = 7.70 Hz, 2 H) 3.02 (t, J = 11.37 Hz, 2 H) 2.97 (s, 3 H) 2.51-2.57 (m, 2 H) 2.12 (s, 3 H) 1.78 (dd, J = 12.51, 2.65 Hz, 2 H) 1.29-1.42 (m, 2 H) |

TABLE 1-continued

| Example Number | Structure | Compound Name | LRMS m/z (M + H) | ¹H NMR |
|---|---|---|---|---|
| A-96 | 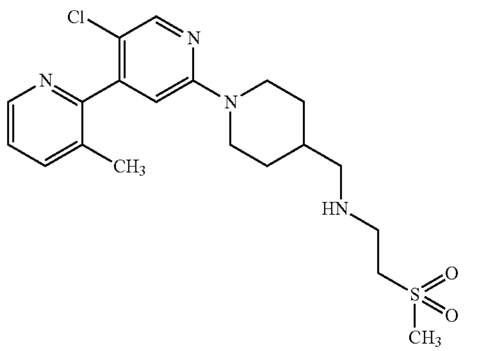 [SMILES: Cc1cccnc1-c1cc(N2CCC(CNCCS(C)(=O)=O)CC2)ncc1Cl] | N-{[1-(5'-chloro-3-methyl-2,4'-bipyridin-2'-yl)piperidin-4-yl]methyl}-2-(methylsulfonyl)ethanamine | 423.15 | ¹H NMR (500 MHz, DMSO-d₆) δ ppm 8.46 (s., 1H) 8.18 (s, 1 H) 7.75 (d, J = 7.32 Hz, 1H) 7.27-7.46 (m, 1H) 6.76 (s, 1 H) 4.22-4.34 (m, 2 H) 3.01 (s, 3H) 2.94-2.99 (m, 3 H) 2.73-2.91 (m, 3 H) 2.12 (s, 3 H) 1.72-1.80 (m, 2 H) 1.62-1.69 (m, 1H)1.09-1.19-1.24 (m, 4 H) 0.76-0.96 (m, 1 H) |
| A-97 | 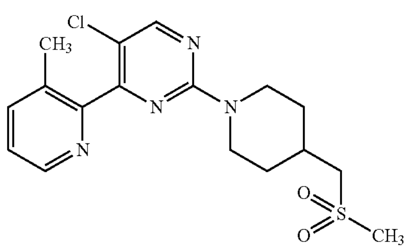 [SMILES: Cc1cccnc1-c1nc(N2CCC(CS(C)(=O)=O)CC2)ncc1Cl] | 5-chloro-4-(3-methylpyridin-2-yl)-2-{4-[(methylsulfonyl)methyl]piperidin-1-yl}pyrimidine | 381.4 | ¹H NMR (400 MHz, CDCl₃): δ 8.47-8.48 (d, 1H), 8.28 (s, 1H), 7.55-7.56 (dd, 1H), 7.20-7.24 (m, 1H), 4.66-4.69 (d, 1H), 2.88-2.92 (m, 7H), 2.30-2.34 (m, 1H), 2.18 (s, 3H), 1.94-1.97 (m, 2 H)?1.26-1.37 (m, 2H). |
| A-98 | 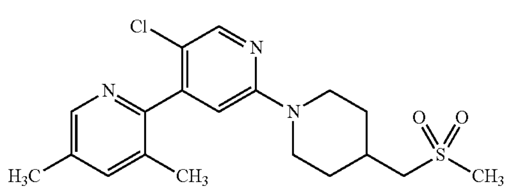 | 5'-chloro-3,5-dimethyl-2'-{4-[(methylsulfonyl)methyl]piperidin-1-yl}-2,4'-bipyridine | 394.3 | ¹H NMR (400 MHz, CDCl₃) δ ppm 8.30 (s, 1H), 8.13 (s, 1H), 7.40 (s, 1H), 6.53 (s, 1H), 4.21-4.18 (m, 2H), 2.92-2.82 (m, 7H), 2.32-2.28 (m, 4H), 2.11 (s, 3H), 1.98-1.95 (m, 2H), 1.43-1.33 (m, 2H) |
| A-99 | 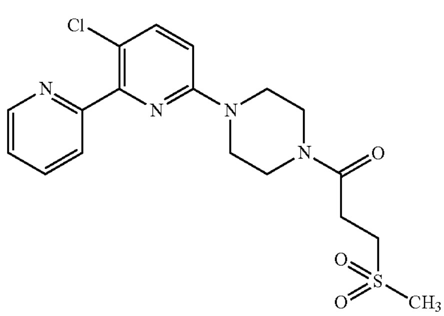 [SMILES: CS(=O)(=O)CCC(=O)N1CCN(c2ccc(Cl)c(-c3ccccn3)n2)CC1] | 3-chloro-6-{4-[3-(methylsulfonyl)propanoyl]piperazin-1-yl}-2,2'-bipyridine | 409.2 | ¹H NMR (400 MHz, DMSO-d₆) δ ppm 8.65 (d, J = 4.04 Hz, 1 H) 7.92 (td, J = 7.71, 1.77 Hz, 1 H) 7.74 (d, J = 8.84 Hz, 1 H) 7.70 (d, J = 7.83 Hz, 1 H) 7.44 (ddd, J = 7.52, 4.86, 1.26 Hz, 1 H) 6.98 (d, J = 9.09 Hz, 1 H) 3.57-3.65 (m, 6 H) 3.54 (d, J = 5.56 Hz, 2 H) 3.31-3.38 (m, 2 H) 3.01 (s, 3 H) 2.81-2.89 (m, 2 H) |
| A-100 | 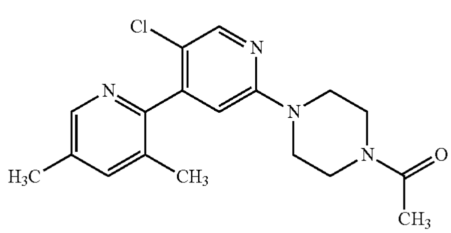 [SMILES: CC(=O)N1CCN(c2cc(-c3ncc(C)cc3C)c(Cl)cn2)CC1] | 2'-(4-acetylpiperazin-1-yl)-5'-chloro-3,5-dimethyl-2,4'-bipyridine | 345.3 | ¹H NMR (400 MHz, CD₃OD) δ ppm 8.27 (s, 1H), 8.21 (s, 1H), 7.65 (s, 1H), 6.79 (m, 1H), 3.71-3.66 (m, 6H), 3.59-3.56 (m, 2H), 2.40 (s, 3H), 2.17-2.15 (m, 6H) |

TABLE 1-continued

| Example Number | Structure | Compound Name | LRMS m/z (M + H) | ¹H NMR |
|---|---|---|---|---|
| A-101 | 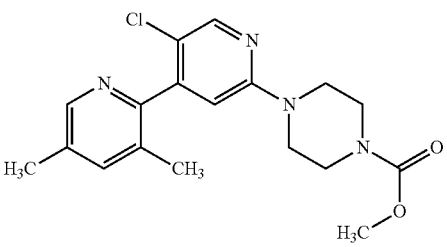 [SMILES: COC(=O)N1CCN(c2cc(-c3ncc(C)cc3C)c(Cl)cn2)CC1] | methyl 4-(5'-chloro-3,5-dimethyl-2,4'-bipyridin-2'-yl)piperazine-1-carboxylate | 361.3 | ¹H NMR (400 MHz, CD₃OD) δ ppm 8.26 (s, 1H), 8.20 (s, 1H), 7.64 (s, 1H), 6.78 (s, 1H), 3.71 (s, 3H), 3.58-3.56 (m, 8H), 2.39 (s, 3H), 2.16 (s, 3H |
| A-102 | 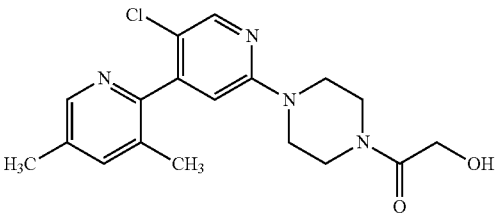 [SMILES: Cc1cnc(-c2cc(N3CCN(C(=O)CO)CC3)ncc2Cl)c(C)c1] | 2-[4-(5'-chloro-3,5-dimethyl-2,4'-bipyridin-2'-yl)piperazin-1-yl]-2-oxoethanol | 361.3 | ¹H NMR (400 MHz, CDCl₃) δ ppm 8.33 (s, 1H), 8.20 (s, 1H), 7.41 (s, 1H), 6.59 (s, 1H), 4.21-4.20 (m, 2H), 3.77-3.75 (m, 2H), 3.62-3.54 (m, 5H), 3.38-3.36 (m, 2H), 2.36 (s, 3H), 2.15 (s, 3H) |
| A-103 | 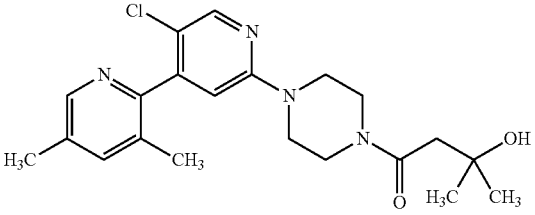 [SMILES: Cc1cnc(-c2cc(N3CCN(C(=O)CC(C)(C)O)CC3)ncc2Cl)c(C)c1] | 4-[4-(5'-chloro-3,5-dimethyl-2,4'-bipyridin-2'-yl)piperazin-1-yl]-2-methyl-4-oxobutan-2-ol | 425.1 (M + Na) | ¹H NMR (400 MHz, CDCl3) δ ppm 8.28 (s, 1H), 8.15 (s, 1H), 7.36 (s, 1H), 6.53 (s, 1H), 3.71-3.68 (m, 2H), 3.63-3.44 (m, 6H), 2.46-2.42 (m, 2H), 2.31 (s, 3H), 2.10 (s, 3H), 1.37 (s, 6H) |
| A-104 | 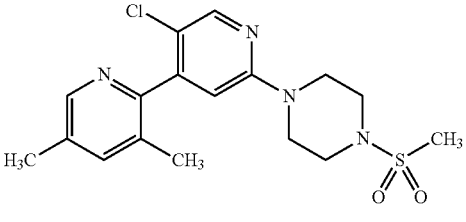 | 5'-chloro-3,5-dimethyl-2'-[4-(methylsulfonyl)piperazin-1-yl]-2,4'-bipyridine | 381.10/383.05 | ¹H NMR (400 MHz, CDCl₃) δ ppm 8.34 (s, 1H), 8.21 (s, 1H), 7.42 (s, 1H), 6.61 (s, 1H), 3.69-3.67 (m, 4H), 3.34-3.32 (m, 4H), 2.83 (s, 3H), 2.36 (s, 3H), 2.16 (s, 3H) |
| A-105 | 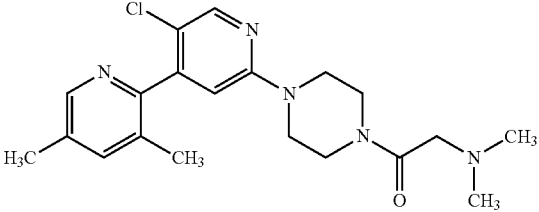 | 2-[4-(5'-chloro-3,5-dimethyl-2,4'-bipyridin-2'-yl)piperazin-1-yl]-N,N-dimethyl-2-oxoethanamine | 388.3 | ¹H NMR (400 MHz, CD₃OD) δ ppm 8.28 (s, 1H), 8.23 (s, 1H), 7.66 (s, 1H), 6.87 (s, 1H), 4.08 (s, 2H), 3.75-3.68 (m, 4H), 3.64-3.54 (m, 4H), 2.83 (s, 6H), 2.41 (s, 3H), 2.17 (s, 3H) |
| A-106 | 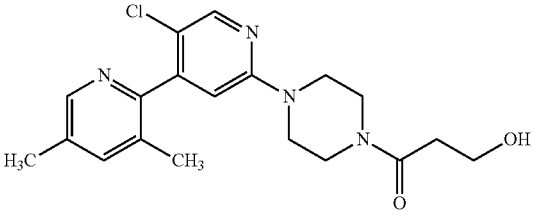 [SMILES: Cc1cnc(-c2cc(N3CCN(C(=O)CCO)CC3)ncc2Cl)c(C)c1] | 3-[4-(5'-chloro-3,5-dimethyl-2,4'-bipyridin-2'-yl)piperazin-1-yl]-3-oxopropan-1-ol | 397.2 (M + Na) | ¹H NMR (400 MHz, CDCl₃) δ ppm 8.33 (s, 1H), 8.20 (s, 1H), 7.50 (s, 1H), 6.58 (s, 1H), 3.90-3.89 (m, 2H), 3.74-3.72 (m, 2H), 3.62-3.51 (m, 6H), 2.53-2.51 (m, 2H), 2.36 (s, 3H), 2.15 (s, 3H) |

TABLE 1-continued

| Example Number | Structure | Compound Name | LRMS m/z (M + H) | ¹H NMR |
|---|---|---|---|---|
| A-107 | 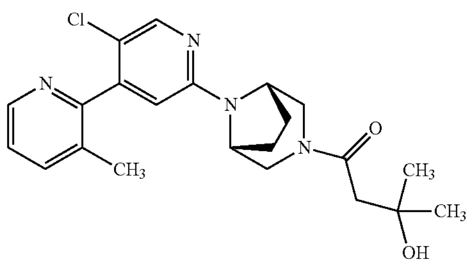 [SMILES: Cc1cccnc1-c1cc(N2[C@@H]3CC[C@H]2CN(C(=O)CC(C)(C)O)C3)ncc1Cl] | 1-[(1R,5S)-8-(5'-chloro-3-methyl-2,4'-bipyridin-2'-yl)-3,8-diazabicyclo[3.2.1]oct-3-yl]-3-hydroxy-3-methylbutan-1-one | 397.2 | ¹H NMR (400 MHz, CDCl$_3$): δ 8.56-8.58 (d, 1H), 8.27 (s, 1H), 7.66-7.68 (d, 1H), 7.32-7.35 (m, 1H), 6.62 (s, 1H), 5.26 (s, 1H), 4.67 (s, 1H), 4.52 (s, 1H), 4.35-4.38 (d, 2H), 3.55 (s, 2H), 3.06-3.09 (d, 1H), 2.51-2.55 (d, 1H), 2.36-2.40 (d, 1H), 2.26 (s, 3H), 2.04-2.15 (m, 2H), 1.78-1.92 (m, 2 H), 1.77-1.78 (m, 3H), 1.31-1.34 (d, 6H) |
| A-108 | 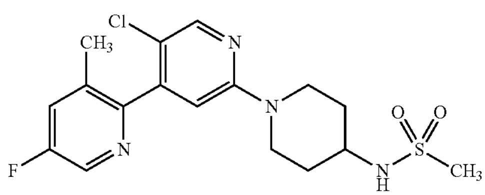 [SMILES: Cc1cc(F)cnc1-c1cc(N2CCC(NS(C)(=O)=O)CC2)ncc1Cl] | N-[1-(5'-chloro-5-fluoro-3-methyl-2,4'-bipyridin-2'-yl)piperidin-4-yl]methanesulfonamide | 399.10 | ¹H NMR (400 MHz, DMSO-d$_6$) δppm 8.50 (s, 1 H) 8.22 (d, J = 1.26 Hz, 1 H) 7.77 (s, 1 H) 7.10 (d, J = 7.58 Hz, 1 H) 6.84 (s, 1 H) 4.20 (d, J = 13.64 Hz, 2 H) 3.43 (br. s., 2 H) 2.95-3.08 (m, 2 H) 2.95 (d, J = 1.52 Hz, 3 H) 2.16 (s, 3 H) 1.79-1.93 (m, 2 H) 1.33-1.49 (m 2 H) |
| A-109 | 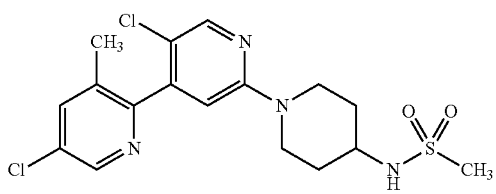 [SMILES: Cc1cc(Cl)cnc1-c1cc(N2CCC(NS(C)(=O)=O)CC2)ncc1Cl] | N-[1-(5,5'-dichloro-3-methyl-2,4'-bipyridin-2'-yl)piperidin-4-yl]methanesulfonamide | 415.0 | ¹H NMR (400 MHz, DMSO-d$_6$) δ ppm 8.54 (d, J = 2.02 Hz, 1 H) 8.21 (s, 1 H) 7.98 (d, J = 1.77 Hz, 1 H) 7.09 (d, J = 7.33 Hz, 1 H) 6.85 (s, 1 H) 4.18 (d, J = 14.15 Hz, 2 H) 3.43 (br. s., 1 H) 2.95-3.09 (m, 2 H) 2.93 (s, 3 H) 2.13 (s, 3 H) 1.80-1.91 (m, 2 H) 1.30-1.46 (m, 2 H) |
| A-110 | 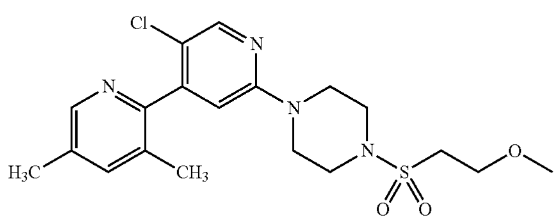 | 5'-chloro-2'-{4-[(2-methoxyethyl)sulfonyl]piperazin-1-yl}-3,5-dimethyl-2,4'-bipyridine | 425.0 | ¹H NMR (400 MHz, CDCl$_3$) δ ppm 8.34 (s, 1H), 8.21 (s, 1H), 7.42 (s, 1H), 6.60 (s, 1H), 3.77-3.74 (m, 2H), 3.65-3.64 (m, 4H), 3.38-3.36 (m, 7H), 3.23-3.20 (m, 2H), 2.37 (s, 3H), 2.17 (s, 3H) |
| A-111 | 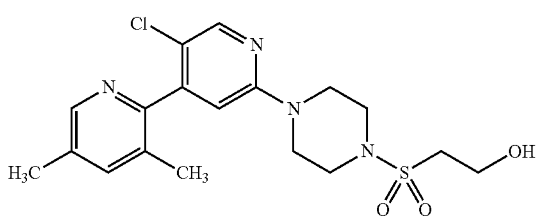 [SMILES: Cc1cnc(-c2cc(N3CCN(S(=O)(=O)CCO)CC3)ncc2Cl)c(C)c1] | 2-{[4-(5'-chloro-3,5-dimethyl-2,4'-bipyridin-2'-yl)piperazin-1-yl]sulfonyl}ethanol | 411.3 | ¹H NMR (400 MHz, CDCl$_3$) δ ppm 8.47 (s, 1H), 8.26 (s, 1H), 7.81 (s, 1H), 6.70 (s, 1H), 6.03-6.02 (m, 2H), 3.89-3.64 (m, 4H), 3.45-3.38 (m, 4H), 3.23-3.20 (m, 2H), 2.50 (s, 3H), 2.31 (s, 3H) |
| A-112 | 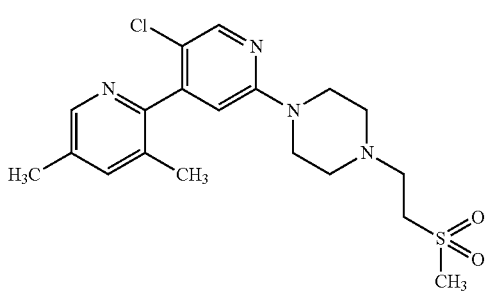 [SMILES: Cc1cnc(-c2cc(N3CCN(CCS(C)(=O)=O)CC3)ncc2Cl)c(C)c1] | 5'-chloro-3,5-dimethyl-2'-{4-[2-(methylsulfonyl)ethyl]piperazin-1-yl}-2 4'-bipyridine | 431.3 (M + Na) | ¹H NMR (400 MHz, CDCl$_3$) δ ppm 8.33 (s, 1H), 8.19 (s, 1H), 7.41 (s, 1H), 6.57 (s, 1H), 3.54-3.51 (m, 4H), 3.26-3.24 (m, 2H), 3.04 (s, 3H), 2.93-2.91 (m, 2H), 2.61-2.59 (m, 4H), 2.36 (s, 3H), 2.15 (s, 3H) |

TABLE 1-continued

| Example Number | Structure | Compound Name | LRMS m/z (M + H) | ¹H NMR |
|---|---|---|---|---|
| A-113 | 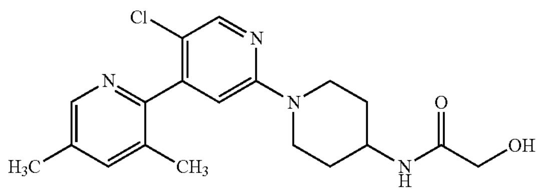 [SMILES: Cc1cnc(-c2cc(N3CCC(NC(=O)CO)CC3)ncc2Cl)c(C)c1] | N-[1-(5'-chloro-3,5-dimethyl-2,4'-bipyridin-2'-yl)piperidin-4-yl]-2-hydroxyacetamide | 375.10/ 377.20 | ¹H NMR (400 MHz, DMSO-d₆) δ ppm 8.30 (s, 1 H) 8.19 (s, 1 H) 7.62 (d, J = 8.1 Hz, 1 H) 7.57 (s, 1 H) 6.77 (s, 1 H) 5.37 (t, J = 5.8 Hz, 1 H) 4.24 (d, J = 13.4 Hz, 2 H) 3.82-3.95 (m, 1 H) 3.78 (d, J = 5.8 Hz, 2 H) 2.94 (t, J = 11.6 Hz, 2 H) 2.32 (s, 3 H) 2.09 (s, 3 H) 1.72 (d, J = 10.1 Hz, 2 H) 1.48 (m, J = 11.9, 11.8, 11.8, 3.7 Hz, 2 H) |
| A-114 | 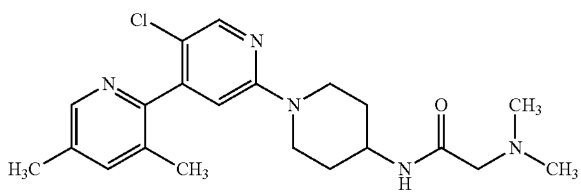 | N-(1-(5'-chloro-3,5-dimethyl-[2,4'-bipyridin]-2'-yl)piperidin-4-yl)-2-(dimethylamino)acetamide | 402.3 | ¹H NMR (400 MHz, CD₃OD) δ ppm 8.25 (s, 1H), 8.16 (s, 1H), 7.63 (s, 1H), 6.76 (s, 1H), 4.28-4.25 (m, 2H), 3.98-3.96 (brs, 1H), 3.07-3.01(m, 2H), 2.53 (s, 3H), 2.37 (s, 3H), 2.16 (s, 3H), 1.94-1.91 (m, 2H), 1.54-1.45 (m, 2H) |
| A-115 | 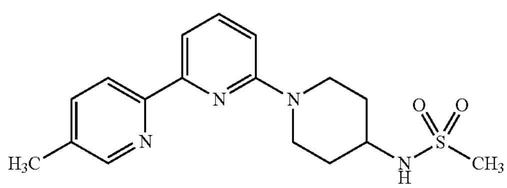 | N-[1-(5'-methyl-2,2'-bipyridin-6-yl)piperidin-4-yl]methanesulfonamide | 347.2 | ¹H NMR (400 MHz, DMSO-d₆) δ ppm 8.47 (d, J = 1.52 Hz, 1 H) 8.20 (d, J = 8.08 Hz, 1 H) 7.72 (dd, J = 8.08, 2.02 Hz, 1 H) 7.59-7.66 (m, 2 H) 7.11 (d, J = 7.07 Hz, 1 H) 6.89 (dd, J = 7.71, 1.14 Hz, 1 H) 4.32 (d, J = 13.39 Hz, 2 H) 3.38-3.50 (m, 1 H) 2.98-3.07 (m, 2 H) 2.95 (s, 3 H) 2.34 (s, 3 H) 1.93 (dd, J = 12.76, 2.65 Hz, 2 H) 1.39-1.53 (m, 2 H) |
| A-116 | 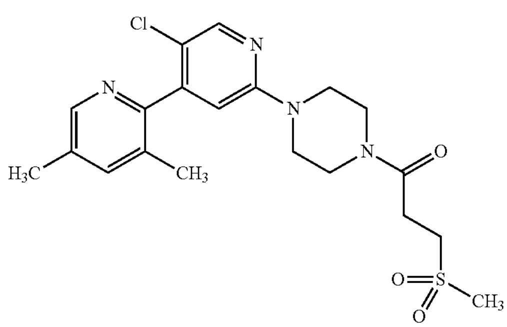 | 5'-chloro-3,5-dimethyl-2'-{4-[3-(methylsulfonyl)propanoyl]piperazin-1-yl}-2,4'-bipyridine | 437.20 | ¹H NMR (400 MHz, DMSO-d₆) δ ppm 8.31 (s, 1 H) 8.24 (s, 1 H) 7.58 (s, 1 H) 6.81 (s, 1 H) 3.43-3.69 (m, 8 H) 3.23-3.39 (m, 2 H) 3.02 (s, 3 H) 2.79-2.91 (m, 2 H) 2.33 (s, 3 H) 2.09 (s, 3 H) |
| A-117 | 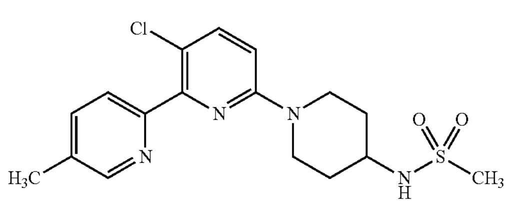 | N-[1-(3-chloro-5'-methyl-2,2'-bipyridin-6-yl)piperidin-4-yl]methanesulfonamide | 381.2 | ¹H NMR (400 MHz, DMSO-d₆) δ ppm 8.47 (s, 1 H) 7.72 (dd, J = 7.96, 1.64 Hz, 1 H) 7.65 (d, J = 9.09 Hz, 1 H) 7.58 (d, J = 8.08 Hz, 1 H) 7.10 (d, J = 7.33 Hz, 1 H) 6.93 (d, J = 9.09 Hz, 1 H) 4.19 (d, J = 13.39 Hz, 2 H) 3.35-3.47 (m, 1 H) 2.95-3.04 (m, 2 H) 2.94 (s, 3 H) 2.36 (s, 3 H) 1.88 (dd, J = 12.51, 2.91 Hz, 2 H) 1.35-1.46 (m, 2 H) |

TABLE 1-continued

| Example Number | Structure | Compound Name | LRMS m/z (M + H) | ¹H NMR |
|---|---|---|---|---|
| A-118 | 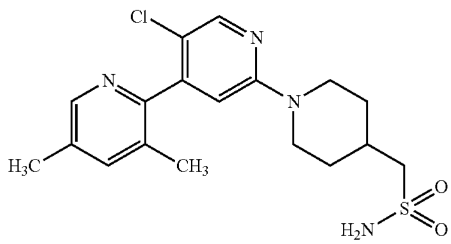 [SMILES: Cc1cnc(-c2cc(N3CCC(CS(N)(=O)=O)CC3)ncc2Cl)c(C)c1] | 1-[1-(5'-chloro-3,5-dimethyl-2,4'-bipyridin-2'-yl)piperidin-4-yl]methanesulfonamide | 395.2 | ¹H NMR (400 MHz, DMSO-d₆) δ ppm 8.30 (s, 1 H) 8.18 (s, 1 H) 7.57 (s, 1 H) 6.82 (s, 2 H) 6.76 (s, 1 H) 4.25 (d, J = 14.15 Hz, 2 H) 2.95 (d, J = 6.32 Hz, 2 H) 2.85 (t, J = 11.87 Hz, 2 H) 2.32 (s, 3 H) 2.10-2.19 (m, 1 H) 2.08 (s, 3 H) 1.90 (d, J = 11.37 Hz, 2 H) 1.28 (m, J = 12.25, 12.25, 12.25, 3.16 Hz, 2 H) |
| A-119 | 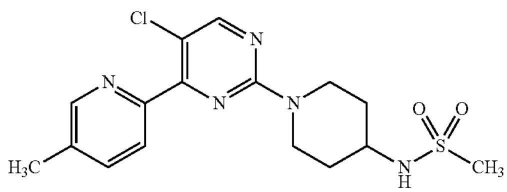 | N-{1-[5-chloro-4-(5-methylpyridin-2-yl)pyrimidin-2-yl]piperidin-4-yl}methanesulfonamide | 382.3 | ¹H NMR (400 MHz, CDCl₃) δ ppm 8.60 (s, 1H), 8.29 (s, 1H), 7.63-7.72 (m, 2H), 4.62-4.65 (m, 2H), 4.14-4.16 (d, 2H), 3.52-3.56 (m, 1H), 3.01-3.08 (m, 2H), 2.95 (s, 3H), 2.38(s, 3H), 2.00-2.03 (m, 2H), 1.40-1.50 (m, 2H) |
| A-120 | 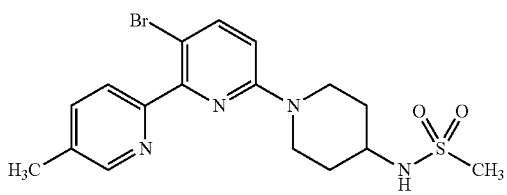 | N-[1-(3-bromo-5'-methyl-2,2'-bipyridin-6-yl)piperidin-4-yl]methanesulfonamide | 425.0/ 427.0 | ¹H NMR (400 MHz, DMSO-d₆) δ ppm 8.47 (br. s., 1 H) 7.78 (d, J = 9.09 Hz, 1 H) 7.69-7.73 (m, 1 H) 7.54 (d, J = 7.83 Hz, 1 H) 7.09 (d, J = 7.58 Hz, 1 H) 6.86 (d, J = 9.09 Hz, 1 H) 4.18 (d, J = 13.14 Hz, 2 H) 3.36-3.47 (m, 1 H) 2.94-3.03 (m, 2 H) 2.94 (s, 3 H) 2.36 (s, 3 H) 1.83-1.92 (m, 2 H) 1.34-1.46 (m, 2 H) |
| A-121 | 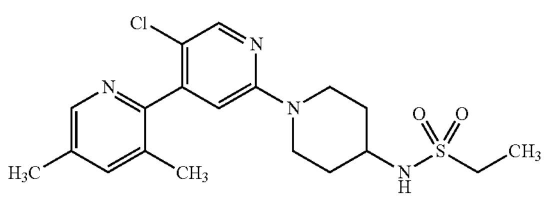 [SMILES: CCS(=O)(=O)NC1CCN(c2cc(-c3ncc(C)cc3C)c(Cl)cn2)CC1] | N-[1-(5'-chloro-3,5-dimethyl-2,4'-bipyridin-2'-yl)piperidin-4-yl]ethanesulfonamide | 409.20 | ¹H NMR (400 MHz, DMSO-d₆) δ ppm 8.30 (d, J = 1.3 Hz, 1 H) 8.19 (s, 1 H) 7.57 (s, 1 H) 7.12 (d, J = 7.8 Hz, 1 H) 6.78 (s, 1 H) 4.19 (d, J = 13.4 Hz, 2 H) 3.33-3.46 (m, 1 H) 2.85-3.10 (m, 4 H) 2.32 (s, 3 H) 2.09 (s, 3 H) 1.70-1.90 (m, 2 H) 1.33-1.54 (m, 2 H) 1.19 (t, J = 7.3 Hz, 3 H) |
| A-122 | 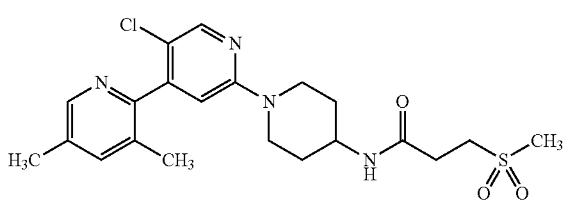 | N-[1-(5'-chloro-3,5-dimethyl-2,4'-bipyridin-2'-yl)piperidin-4-yl]-3-(methylsulfonyl)propanamide | 451.20 | ¹H NMR (400 MHz, DMSO-d₆) δ ppm 8.30 (d, J = 1.3 Hz, 1 H) 8.20 (s, 1 H) 8.03 (d, J = 7.6 Hz, 1 H) 7.57 (s, 1 H) 6.78 (s, 1 H) 4.16 (d, J = 13.4 Hz, 2 H) 3.76-3.89 (m, 1 H) 3.25-3.37 (m, 2 H) 2.98-3.09 (m, 2 H) 2.97 (s, 3 H) 2.52-2.58 (m, 2 H) 2.32 (s, 3 H) 2.09 (s, 3 H) 1.77 (dd, J = 12.9, 3.0 Hz, 2 H) 1.28-1.45 (m, 2 H) |
| A-123 | 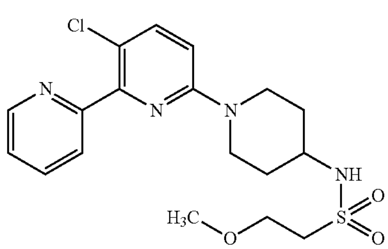 [SMILES: COCCS(=O)(=O)NC1CCN(c2ccc(Cl)c(-c3ccccn3)n2)CC1] | N-[1-(3-chloro-2,2'-bipyridin-6-yl)piperidin-4-yl]-2-methoxyethanesulfonamide | 411.0 | ¹H NMR (400 MHz, DMSO-d₆) δ ppm 8.62-8.67 (m, 1 H) 7.91 (td, J = 7.71, 1.77 Hz, 1 H) 7.64-7.71 (m, 2 H) 7.43 (ddd, J = 7.52, 4.86, 1.26 Hz, 1 H) 7.17 (d, J = 7.33 Hz, 1 H) 6.95 (d, J = 8.84 Hz, 1 H) 4.19 (d, J = 13.14 Hz, 2 H) 3.65 (t, J = 6.44 Hz, 2 H) 3.41 (dd, J = 10.99, 4.17 Hz, 1 H) 3.31 (d, J = 12.88 Hz, 2 H) 3.25-3.27 (m, 3 H) 2.98 (t, J = 11.24 Hz, 2 H) 1.87 (dd, J = 13.26, 3.41 Hz, 2 H) 1.33-1.49 (m, 2 H) |

TABLE 1-continued

| Example Number | Structure | Compound Name | LRMS m/z (M + H) | $^1$H NMR |
|---|---|---|---|---|
| A-124 | 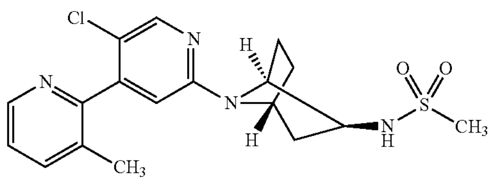 [SMILES: Cc1cccnc1-c1cc(N2[C@@H]3CC[C@H]2[C@@H](NS(C)(=O)=O)C3)ncc1Cl] | N-[(3-endo)-8-(5'-chloro-3-methyl-2,4'-bipyridin-2'-yl)-8-azabicyclo[3.2.1]oct-3-yl]methanesulfonamide | 407.5 | $^1$H NMR (400 MHz, CDCl$_3$): δ 8.45-8.46 (d, 1H), 8.14 (s, 1H), 7.54-7.56 (d, 1H), 7.21-7.23 (m, 1H), 6.41 (s, 1H), 4.43-4.53 (m, 3H), 3.59-3.60 (d, 1H), 2.89 (s, 3H), 2.18 (m, 2H), 2.15 (s, 3H), 2.09-2.13 (m, 2H), 2.00-2.04 (m, 2H), 1.68-1.72 (m, 2H) |
| A-125 | 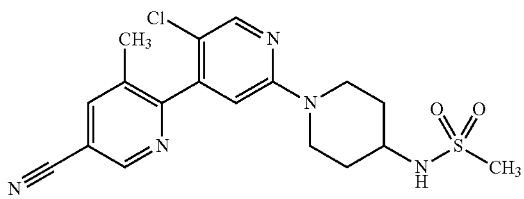 [SMILES: Cc1cc(C#N)cnc1-c1cc(N2CCC(NS(C)(=O)=O)CC2)ncc1Cl] | N-[1-(5'-chloro-5-cyano-3-methyl-2,4'-bipyridin-2'-yl)piperidin-4-yl]methanesulfonamide | 406.0 | $^1$H NMR (400 MHz, DMSO-d$_6$) δ ppm 8.95 (d, J = 1.52 Hz, 1 H) 8.35 (d, J = 1.26 Hz, 1 H) 8.23 (s, 1 H) 7.09 (d, J = 7.33 Hz, 1 H) 6.88 (s, 1 H) 4.16 (br. s., 2 H) 3.43 (br. s., 1 H) 2.95-3.10 (m, 2 H) 2.93 (s, 3 H) 2.17 (s, 3 H) 1.82-1.90 (m, 2 H) 1.31-1.46 (m, 2 H) |
| A-126 | 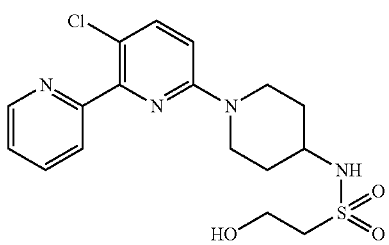 [SMILES: O=S(=O)(CCO)NC1CCN(c2ccc(Cl)c(-c3ccccn3)n2)CC1] | N-[1-(3-chloro-2,2'-bipyridin-6-yl)piperidin-4-yl]-2-hydroxyethanesulfonamide | 397.0 | $^1$H NMR (400 MHz, DMSO-d$_6$) δ ppm 8.64 (d, J = 4.80 Hz, 1 H) 7.91 (td, J = 7.71, 1.77 Hz, 1 H) 7.67 (d, J = 8.84 Hz, 2 H) 7.40-7.47 (m, 1 H) 7.10 (d, J = 6.82 Hz, 1 H) 6.96 (d, J = 9.09 Hz, 1 H) 4.88 (t, J = 5.94 Hz, 1 H) 4.19 (d, J = 13.64 Hz, 2 H) 3.69-3.79 (m, 2 H) 3.42 (m, J = 8.59 Hz, 1 H) 3.20 (t, J = 6.82 Hz, 2 H) 2.92-3.05 (m, 2 H) 1.87 (dd, J = 13.14, 3.03 Hz, 2 H) 1.33-1.48 (m, 2 H) |
| A-127 | 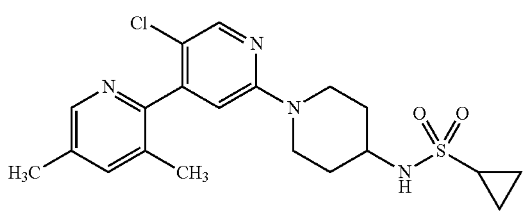 [SMILES: Cc1cnc(-c2cc(N3CCC(NS(=O)(=O)C4CC4)CC3)ncc2Cl)c(C)c1] | N-[1-(5'-chloro-3,5-dimethyl-2,4'-bipyridin-2'-yl)piperidin-4-yl]cyclopropanesulfonamide | 421.15/ 423.10 | $^1$H NMR (400 MHz, DMSO-d$_6$) δ ppm 8.30 (s, 1 H) 8.19 (s, 1 H) 7.57 (s, 1 H) 7.12 (d, J = 7.8 Hz, 1 H) 6.78 (s, 1 H) 4.19 (d, J = 13.4 Hz, 2 H) 3.38-3.52 (m, 1 H) 2.99 (t, J = 11.6 Hz, 2 H) 2.53-2.64 (m, 1 H) 2.32 (s, 3 H) 2.09 (s, 3 H) 1.88 (d, J = 10.6 Hz, 2 H) 1.36-1.53 (m, 2 H) 0.85-1.00 (m, 4 H) |
| A-128 | 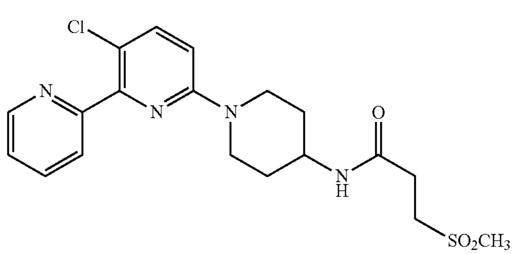 [SMILES: CS(=O)(=O)CCC(=O)NC1CCN(c2ccc(Cl)c(-c3ccccn3)n2)CC1] | N-[1-(3-chloro-2,2'-bipyridin-6-yl)piperidin-4-yl]-3-(methylsulfonyl)propanamide | 423.0 | $^1$H NMR (400 MHz, DMSO-d$_6$) δ ppm 8.65 (d, J = 4.04 Hz, 1 H) 8.03 (d, J = 7.58 Hz, 1 H) 7.91 (td, J = 7.71, 1.77 Hz, 1 H) 7.64-7.72 (m, 2 H) 7.43 (ddd, J = 7.58, 4.80, 1.01 Hz, 1 H) 6.96 (d, J = 8.84 Hz, 1 H) 4.18 (d, J = 13.39 Hz, 2 H) 3.75-3.91 (m, 1 H) 3.24-3.36 (m, 2 H) 2.98-3.09 (m, 2 H) 2.97 (s, 3 H) 2.49-2.57 (m, 2 H) 1.80 (dd, J = 13.01, 2.91 Hz, 2 H) 1.28-1.44 (m, 2 H) |

TABLE 1-continued

| Example Number | Structure | Compound Name | LRMS m/z (M + H) | ¹H NMR |
|---|---|---|---|---|
| A-129 | 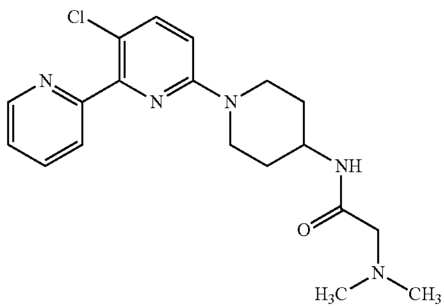 [SMILES: CN(C)CC(=O)NC1CCN(c2ccc(Cl)c(-c3ccccn3)n2)CC1] | N-(1-(3-chloro-[2,2'-bipyridin]-6-yl)piperidin-4-yl)-2-(dimethylamino)acetamide | 374.1 | ¹H NMR (400 MHz, DMSO-$d_6$) δ ppm 8.64 (d, J = 4.04 Hz, 1 H) 7.91 (td, J = 7.71, 1.77 Hz, 1 H) 7.65-7.70 (m, 2 H) 7.64 (d, J = 8.34 Hz, 1 H) 7.43 (ddd, J = 7.58, 4.80, 1.26 Hz, 1 H) 6.95 (d, J = 9.09 Hz, 1 H) 4.23 (d, J = 13.39 Hz, 2 H) 3.80-3.94 (m, 1 H) 2.89-3.01 (m, 2 H) 2.83 (s, 1 H) 2.18 (s, 6 H) 1.74 (dd, J = 12.51, 2.91 Hz, 2 H) 1.47 (qd, J = 11.92, 3.92 Hz, 2 H) |
| A-130 | 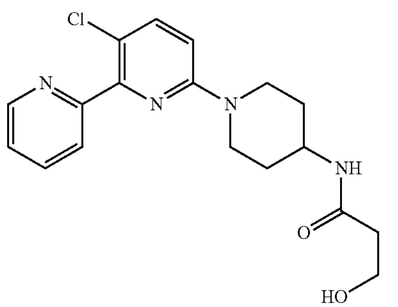 [SMILES: O=C(CCO)NC1CCN(c2ccc(Cl)c(-c3ccccn3)n2)CC1] | N-[1-(3-chloro-2,2'-bipyridin-6-yl)piperidin-4-yl]-3-hydroxypropanamide | 360.1 | ¹H NMR (400 MHz, DMSO-$d_6$) δ ppm 8.64 (d, J = 4.04 Hz, 1 H) 7.91 (td, J = 7.71, 1.77 Hz, 1 H) 7.65-7.73 (m, 3 H) 7.43 (ddd, J = 7.58, 4.80, 1.26 Hz, 1 H) 6.96 (d, J = 9.09 Hz, 1 H) 4.26 (d, J = 13.39 Hz, 2 H) 3.83-3.97 (m, 1 H) 3.77 (s, 2 H) 3.28 (s, 3 H) 2.88-2.99 (m, 2 H) 1.73 (dd, J = 12.38, 2.78 Hz, 2 H) 1.49 (qd, J = 12.00, 3.92 Hz, 2 H) |
| A-131 | 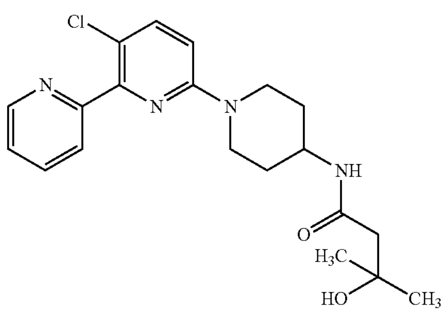 [SMILES: CC(C)(O)CC(=O)NC1CCN(c2ccc(Cl)c(-c3ccccn3)n2)CC1] | N-[1-(3-chloro-2,2'-bipyridin-6-yl)piperidin-4-yl]-3-hydroxy-3-methylbutanamide | 389.2 | ¹H NMR (400 MHz, DMSO-$d_6$) δ ppm 8.64 (d, J = 4.80 Hz, 1 H) 7.91 (td, J = 7.71, 1.77 Hz, 1 H) 7.83 (d, J = 7.58 Hz, 1 H) 7.67 (d, J = 8.84 Hz, 2 H) 7.43 (ddd, J = 7.58, 4.80, 1.26 Hz, 1 H) 6.96 (d, J = 9.09 Hz, 1 H) 4.79 (s, 1 H) 4.18 (d, J = 13.39 Hz, 2 H) 3.85 (m, J = 11.87 Hz, 1 H) 2.96-3.08 (m, 2 H) 2.17 (s, 2 H) 1.79 (m, J = 10.11 Hz, 2 H) 1.30-1.45 (m, 2 H) 1.13 (s, 6 H) |
| A-132 | 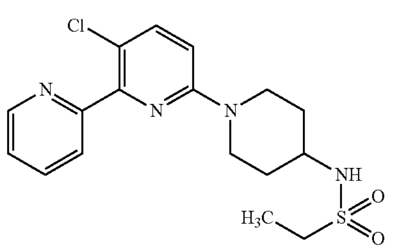 [SMILES: CCS(=O)(=O)NC1CCN(c2ccc(Cl)c(-c3ccccn3)n2)CC1] | N-[1-(3-chloro-2,2'-bipyridin-6-yl)piperidin-4-yl]ethanesulfonamide | 381.1 | ¹H NMR (400 MHz, DMSO-$d_6$) δ ppm 8.64 (d, J = 4.04 Hz, 1 H) 7.91 (td, J = 7.71, 1.77 Hz, 1 H) 7.67 (d, J = 9.09 Hz, 2 H) 7.43 (ddd, J = 7.58, 4.80, 1.01 Hz, 1 H) 7.12 (d, J = 7.58 Hz, 1 H) 6.95 (d, J = 9.09 Hz, 1 H) 4.20 (d, J = 13.39 Hz, 2 H) 3.34-3.45 (m, 1 H) 2.92-3.06 (m, 4 H) 1.86 (dd, J = 12.63, 2.78 Hz, 2 H) 1.35-1.49 (m, 2 H) 1.19 (d, J = 7.33 Hz, 3 H) |

TABLE 1-continued

| Example Number | Structure | Compound Name | LRMS m/z (M + H) | ¹H NMR |
|---|---|---|---|---|
| A-133 | 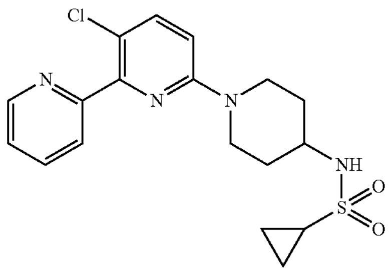 [SMILES: O=S(=O)(NC1CCN(c2ccc(Cl)c(-c3ccccn3)n2)CC1)C1CC1] | N-[1-(3-chloro-2,2'-bipyridin-6-yl)piperidin-4-yl]cyclopropane-sulfonamide | 379.0 | ¹H NMR (400 MHz, DMSO-d₆) δ ppm 8.65 (d, J = 3.79 Hz, 1 H) 7.91 (td, J = 7.71, 1.77 Hz, 1 H) 7.67 (d, J = 8.84 Hz, 2 H) 7.43 (ddd, J = 7.58, 4.80, 1.26 Hz, 1 H) 7.13 (d, J = 7.83 Hz, 1 H) 6.96 (d, J = 8.84 Hz, 1 H) 4.20 (d, J = 13.39 Hz, 2 H) 3.37-3.51 (m, 1 H) 2.95-3.07 (m, 2 H) 2.57 (tt, J = 7.71, 5.18 Hz, 1 H) 1.90 (dd, J = 12.63, 3.03 Hz, 2 H) 1.38-1.52 (m, 2 H) 0.90-0.96 (m, 4 H) |
| A-134 | 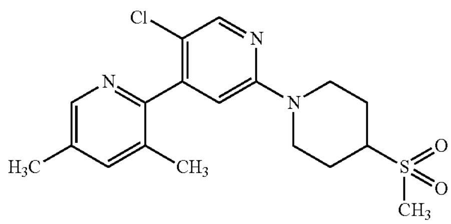 [SMILES: Cc1cnc(-c2cc(N3CCC(S(C)(=O)=O)CC3)ncc2Cl)c(C)c1] | 5'-chloro-3,5-dimethyl-2'-[4-(methylsulfonyl)piperidin-1-yl]-2,4'-bipyridine | 380.4 | ¹H NMR (400 MHz, CDCl₃) δ ppm 8.35 (s, 1H), 8.21 (s, 1H), 7.46 (s, 1H), 6.63 (s, 1H), 4.51-4.48 (m, 2H), 3.09-3.03 (m, 1H), 2.94-2.85 (m, 5H), 2.38 (s, 3H), 2.24-2.08 (m, 5H), 1.89-1.83 (m, 2H) |
| A-135 | 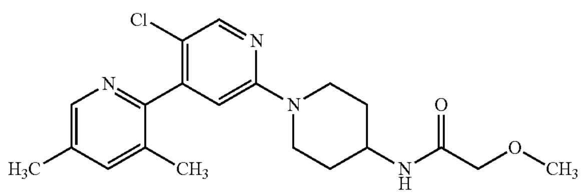 | N-[1-(5'-chloro-3,5-dimethyl-2,4'-bipyridin-2'-yl)piperidin-4-yl]-2-methoxyacetamide | 389.2 | ¹H NMR (400 MHz, DMSO-d₆) δ ppm 8.30 (s, 1 H) 8.19 (s, 1 H) 7.70 (d, J = 8.08 Hz, 1 H) 7.57 (s, 1 H) 6.78 (s, 1 H) 4.24 (d, J = 13.14 Hz, 2 H) 3.84-3.96 (m, 1 H) 3.77 (s, 2 H) 3.28 (s, 3 H) 2.89-2.98 (m, 2 H) 2.32 (s, 3 H) 2.09 (s, 3 H) 1.71 (dd, J = 12.51, 2.65 Hz, 2 H) 1.42-1.54 (m, 2 H) |
| A-136 | 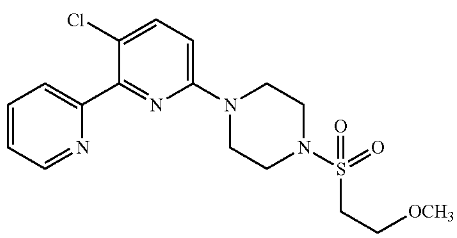 [SMILES: COCCS(=O)(=O)N1CCN(c2ccc(Cl)c(-c3ccccn3)n2)CC1] | 3-chloro-6-{4-[(2-methoxyethyl)sulfonyl]piperazin-1-yl}-2,2'-bipyridine | 397.0 | ¹H NMR (400 MHz, DMSO-d₆) δ ppm 8.65 (d, J = 4.80 Hz, 1 H) 7.92 (td, J = 7.71, 1.77 Hz, 1 H) 7.75 (d, J = 9.09 Hz, 1 H) 7.69 (d, J = 7.83 Hz, 1 H) 7.44 (ddd, J = 7.52, 4.86, 1.01 Hz, 1 H) 7.00 (d, J = 8.84 Hz, 1 H) 3.57-3.70 (m, 8 H) 3.35 (t, J = 5.94 Hz, 2 H) 3.30 (s, 3 H) 3.22-3.27 (m, 2 H) |
| A-137 | 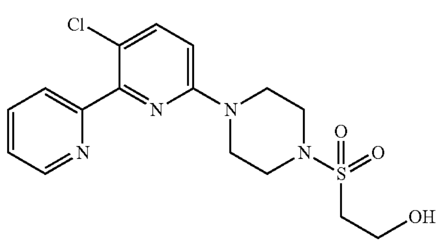 [SMILES: O=S(=O)(CCO)N1CCN(c2ccc(Cl)c(-c3ccccn3)n2)CC1] | 2-{[4-(3-chloro-2,2'-bipyridin-6-yl)piperazin-1-yl]sulfonyl}ethanol | 383.0 | ¹H NMR (400 MHz, DMSO-d₆) δ ppm 8.65 (d, J = 4.80 Hz, 1 H) 7.92 (td, J = 7.71, 1.77 Hz, 1 H) 7.75 (d, J = 9.09 Hz, 1 H) 7.69 (d, J = 7.83 Hz, 1 H) 7.44 (td, J = 6.19, 1.01 Hz, 1 H) 6.99 (d, J = 8.84 Hz, 1 H) 5.02 (t, J = 5.43 Hz, 1 H) 3.75 (q, J = 6.06 Hz, 2 H) 3.59-3.67 (m, 4 H) 3.24-3.30 (m, 4 H) 3.21 (t, J = 6.19 |
| A-138 | 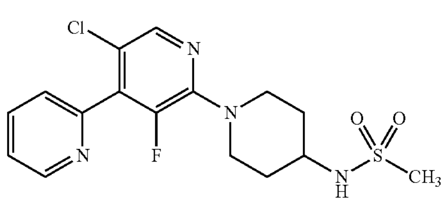 [SMILES: CS(=O)(=O)NC1CCN(c2ncc(Cl)c(-c3ccccn3)c2F)CC1] | N-(1-(5'-chloro-3'-fluoro-2,4'-bipyridin-2'-yl)piperidin-4-yl)methanesulfonamide | 385.0 | ¹H NMR (400 MHz, CDCl₃) δ 1.59-1.73 (m, 2 H), 2.10 (d, J = 10.36 Hz, 2 H), 2.95-3.12 (m, 5 H), 3.47-3.66 (m, 1 H), 4.02 (d, J = 13.39 Hz, 2 H), 4.28 (d, J = 7.58 Hz, 1 H), 7.34-7.49 (m, 2 H), 7.84 (td, J = 7.71, 1.77 Hz, 1 H), 8.12 (s, 1 H), 8.78 (d, J = 4.55 Hz, 1 H). |

TABLE 1-continued

| Example Number | Structure | Compound Name | LRMS m/z (M + H) | ¹H NMR |
|---|---|---|---|---|
| A-139 | 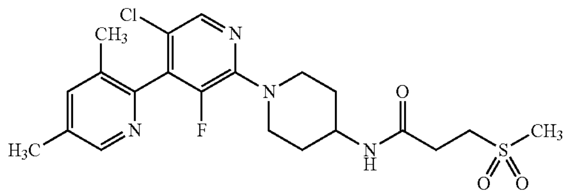 | N-(1-(5'-chloro-3'-fluoro-3,5-dimethyl-2,4'-bipyridin-2'-yl)piperidin-4-yl)-3-(methylsulfonyl)propanamide | 469.1 | ¹H NMR (400 MHz, CDCl₃) δ 1.52 (dd, J = 12.51, 3.66 Hz, 2 H), 2.02 (d, J = 12.38 Hz, 2 H), 2.15 (s, 3 H), 2.39 (s, 3 H), 2.74 (t, J = 6.95 Hz, 2 H), 2.96 (s, 3 H), 2.97-3.12 (m, 2 H), 3.42 (t, J = 7.07 Hz, 2 H), 3.89-4.12 (m, 3 H), 5.63 (d, J = 7.33 Hz, 1 H), 7.47 (d, J = 0.76 Hz, 1 H), 8.10 (s, 1 H), 8.40 (d, J = 1.26 Hz, 1 H). |
| A-140 | 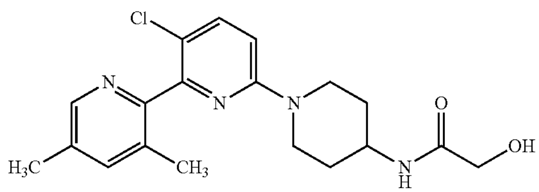 [SMILES: Cc1cnc(-c2nc(N3CCC(NC(=O)CO)CC3)ccc2Cl)c(C)c1] | N-[1-(3-chloro-3',5'-dimethyl-2,2'-bipyridin-6-yl)piperidin-4-yl]-2-hydroxyacetamide | 375.10 | ¹H NMR (400 MHz, DMSO-d6) δ ppm 8.26 (s, 1 H) 7.67 (d, J = 9.09 Hz, 1 H) 7.62 (d, J = 8.34 Hz, 1 H) 7.53 (s, 1 H) 6.93 (d, J = 9.35 Hz, 1 H) 5.37 (t, J = 5.94 Hz, 1 H) 4.18 (d, J = 13.64 Hz, 2 H) 3.82-3.94 (m, 1 H) 3.78 (d, J = 5.81 Hz, 2 H) 2.91 (t, J = 11.49 Hz, 2 H) 2.32 (s, 3 H) 2.08 (s, 3 H) 1.72 (dd, J = 12.76, 2.91 Hz, 2 H) 1.41-1.54 (m, 2 H) |
| A-141 | 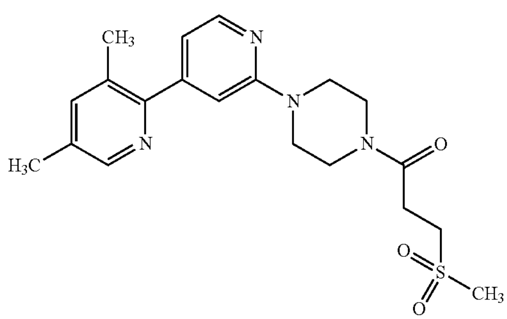 | 1-[4-(3,5-dimethyl-2,4'-bipyridin-2'-yl)piperazin-1-yl]-3-(methylsulfonyl)propan-1-one | 403.1 | ¹H NMR (400 MHz, chloroform-d) δ ppm 8.36 (s, 1 H) 8.24-8.29 (m, 1 H) 7.42 (s, 1 H) 6.79-6.84 (m, 2 H) 3.75-3.81 (m, 4 H) 3.58-3.66 (m, 4 H) 3.47 (t, J = 7.33 Hz, 2 H) 3.00 (s, 3 H) 2.93-2.99 (m, 2 H) 2.37 (s, 3 H) 2.33 (s, 3 H) |
| A-142 | 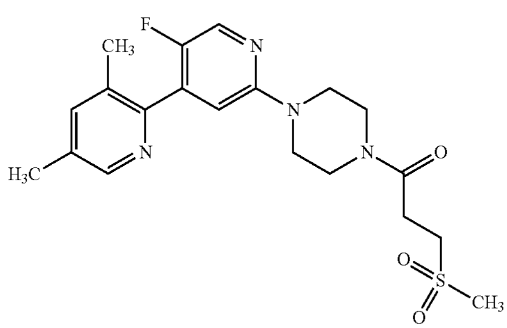 | 1-[4-(5'-fluoro-3,5-dimethyl-2,4'-bipyridin-2'-yl)piperazin-1-yl]-3-(methylsulfonyl)propan-1-one | 421.2 | ¹H NMR (400 MHz, chloroform-d) δ ppm 8.34 (s, 1 H) 8.08 (d, J = 5.05 Hz, 1 H) 7.44 (s, 1 H) 6.87 (t, J = 4.80 Hz, 1 H) 3.74-3.81 (m, 2 H) 3.61-3.68 (m, 2 H) 3.53-3.58 (m, 2 H) 3.51 (d, J = 5.31 Hz, 2 H) 3.47 (t, J = 7.45 Hz, 2 H) 3.00 (s, 3 H) 2.96 (t, J = 7.20 Hz, 2 H) 2.38 (s, 3 H) 2.22 (s, 3 H) |
| A-143 | 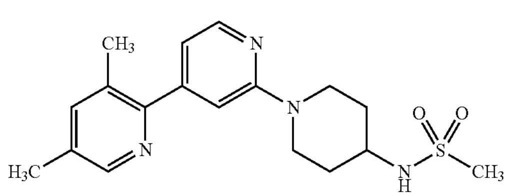 | N-[1-(3,5-dimethyl-2,4'-bipyridin-2'-yl)piperidin-4-yl]methanesulfonamide | 361.1 | ¹H NMR (400 MHz, chloroform-d) δ ppm 8.35 (s, 1 H) 8.24 (d, J = 5.05 Hz, 1 H) 7.42 (s, 1 H) 6.80 (s, 1 H) 6.74 (d, J = 5.05 Hz, 1 H) 4.21-4.37 (m, 4 H) 3.52-3.66 (m, 1 H) 3.05-3.06 (m, 2 H) 3.02 (s, 3 H) 2.36 (s, 3 H) 2.32 (s, 3 H) 2.06-2.14 (m, 2 H) |

TABLE 1-continued

| Example Number | Structure | Compound Name | LRMS m/z (M + H) | ¹H NMR |
|---|---|---|---|---|
| A-144 | 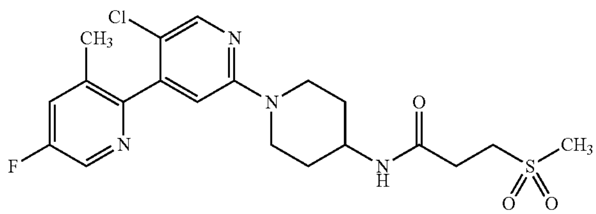 [SMILES: Cc1cc(F)cnc1-c1cc(N2CCC(NC(=O)CCS(C)(=O)=O)CC2)ncc1Cl] | N-[1-(5'-chloro-5-fluoro-3-methyl-2,4'-bipyridin-2'-yl)piperidin-4-yl]-3-(methylsulfonyl)propanamide | 455.0 | ¹H NMR (400 MHz, DMSO-$d_6$): δ 8.50-8.49 (d, 1H), 8.22(s, 1H), 8.06-8.04 (d, 1H), 7.80-7.77 (q, 1H), 6.85 (s, 1H), 4.19-4.16 (m, 2H), 3.84-3.81 (m, 1H), 3.32-3.30 (m, 2H), 3.05-3.00 (m, 2H), 2.97 (s, 3H), 2.55-2.53 (m, 2H), 2.15 (s, 3H), 1.79-1.76 (m, 2H), 1.36-1.33 (m, H) |
| A-145 | 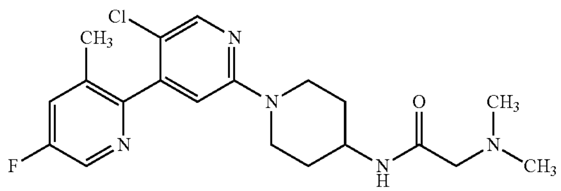 [SMILES: Cc1cc(F)cnc1-c1cc(N2CCC(NC(=O)CN(C)C)CC2)ncc1Cl] | N-[1-(5'-chloro-5-fluoro-3-methyl-2,4'-bipyridin-2'-yl)piperidin-4-yl]-$N^2,N^2$-dimethyl-glycinamide | 406.6 | ¹H NMR (400 MHz, CDCl$_3$): δ 8.38-8.37 (d, 1H), 8.19 (s, 1H), 7.70-7.68 (d, 1H), 7.36-7.33 (q, 1H), 6.57 (s, 1H), 4.20-4.17 (m, 2H), 4.01 (broad, 1H), 3.26 (s, 2H), 3.08-3.02 (m, 2H), 2.52 (s, 6H), 2.22 (s, 3H), 1.99-1.97 (m, 2H), 1.53-1.51 (m, 2H) |
| A-146 | 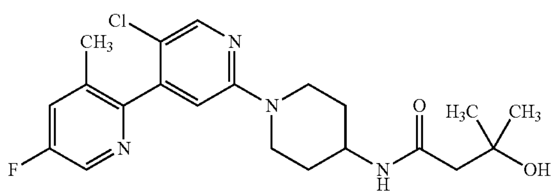 [SMILES: Cc1cc(F)cnc1-c1cc(N2CCC(NC(=O)CC(C)(C)O)CC2)ncc1Cl] | N-[1-(5'-chloro-5-fluoro-3-methyl-2,4'-bipyridin-2'-yl)piperidin-4-yl]-3-hydroxy-3-methylbutanamide | 420.9 | ¹H NMR (400 MHz, CDCl$_3$): δ 8.38-8.37 (d, 1H), 8.19 (s, 1H), 7.36-7.33 (q, 1H), 6.57 (s, 1H), 5.92-5.90 (d, 1H), 4.08-4.05 (m, 4H), 3.06-2.99 (m, 2H), 2.31 (s, 2H), 2.21 (s, 3H), 2.02-2.00 (m, 2H), 1.46-1.42 (m, 2H), 1.27 (s, 6H) |
| A-147 | 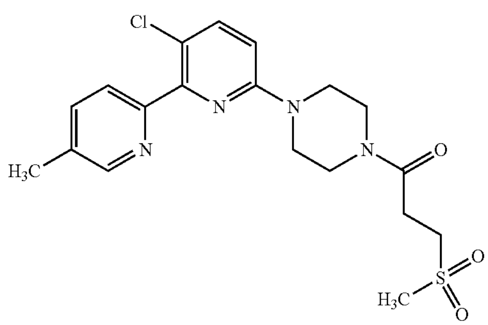 [SMILES: Cc1ccc(-c2nc(N3CCN(C(=O)CCS(C)(=O)=O)CC3)ccc2Cl)nc1] | 1-[4-(3-chloro-5'-methyl-2,2'-bipyridin-6-yl)piperazin-1-yl]-3-(methylsulfonyl)propan-1-one | 361.1 | ¹H NMR (400 MHz, DMSO-$d_6$) δ ppm 8.39-8.58 (m, 1 H) 7.68-7.76 (m, 2 H) 7.60 (d, J = 7.83 Hz, 1 H) 6.95 (d, J = 9.09 Hz, 1 H) 3.50-3.64 (m, 8 H) 3.35 (d, J = 7.07 Hz, 2 H) 3.01 (s, 3 H) 2.81-2.91 (m, 2 H) 2.36 (s, 3 H) |
| A-148 | 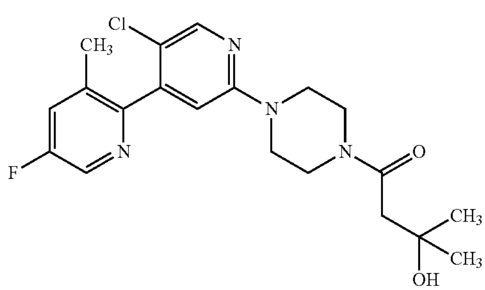 [SMILES: Cc1cc(F)cnc1-c1cc(N2CCN(C(=O)CC(C)(C)O)CC2)ncc1Cl] | 1-[4-(3-chloro-5'-methyl-2,2'-bipyridin-6-yl)piperazin-1-yl]-3-(methylsulfonyl)propan-1-one | ND | ¹H NMR (400 MHz, CDCl$_3$): δ 8.37 (s, 1H), 8.22 (s, 1H), 7.37-7.34 (d, 1H), 6.57 (s, 1H), 3.77-3.75 (m, 2H), 3.65-3.64 (m, 2H), 3.60-3.58 (m, 2H), 3.53-3.51 (m, 2H), 2.49 (s, 2H), 2.22 (s, 3H), 1.30 (s, 6H) |

TABLE 1-continued

| Example Number | Structure | Compound Name | LRMS m/z (M + H) | ¹H NMR |
|---|---|---|---|---|
| A-149 | 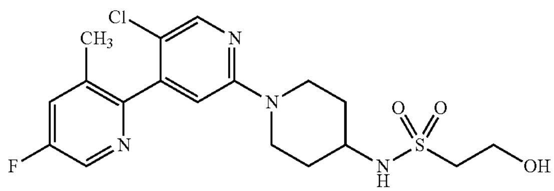 [SMILES: Cc1cc(F)cnc1-c1cc(N2CCC(NS(=O)(=O)CCO)CC2)ncc1Cl] | N-[1-(5'-chloro-5-fluoro-3-methyl-2,4'-bipyridin-2'-yl)piperidin-4-yl]-2-hydroxyethanesulfonamide | 429.20 | ¹H NMR (400 MHz, CDCl₃): δ 8.38-8.37 (d, 1H), 8.20 (s, 1H), 7.38-7.36 (d, 1H), 6.67 (s, 1H), 4.97-4.96 (d, 1H), 4.23-4.19 (d, 2H), 4.09-4.06 (m, 2H), 3.62-3.58 (m, 1H), 3.29-3.27 (m, 2H), 3.19-3.13 (m, 2H), 2.23 (s, 3H), 2.12-2.09 (m, 2H), 1.70-1.65 (m, 2H) |
| A-150 | 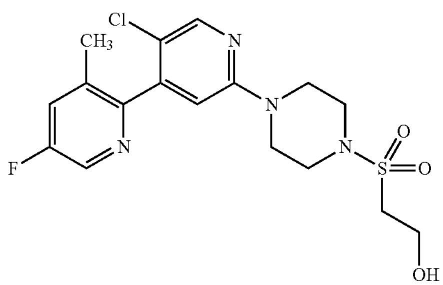 [SMILES: Cc1cc(F)cnc1-c1cc(N2CCN(S(=O)(=O)CCO)CC2)ncc1Cl] | 2-{[4-(5'-chloro-5-fluoro-3-methyl-2,4'-bipyridin-2'-yl)piperazin-1-yl]sulfonyl}ethanol | 415.3 | ¹H NMR (400 MHz, CDCl₃): δ 8.37 (s, 1H), 8.23(s, 1H), 7.36-7.35 (d, 1H), 6.58 (s, 1H), 4.09-4.06 (t, 2H), 3.67-3.60 (m, 4H), 3.40-3.38 (m, 4H), 3.18-3.16 (t, 2H), 2.55-2.52 (t, 1H), 2.22 (s, 3H) |
| A-151 | 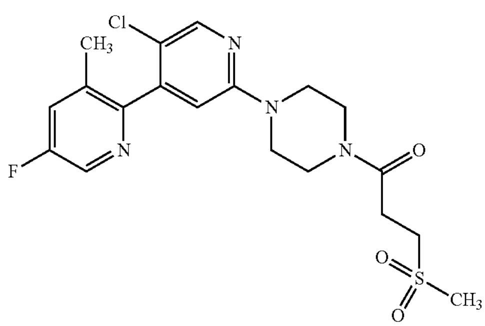 [SMILES: Cc1cc(F)cnc1-c1cc(N2CCN(C(=O)CCS(C)(=O)=O)CC2)ncc1Cl] | 1-[4-(5'-chloro-5-fluoro-3-methyl-2,4'-bipyridin-2'-yl)piperazin-1-yl]-3-(methylsulfonyl)propan-1-one | 411.2 | ¹H NMR (400 MHz, CDCl₃): δ 8.37 (s, 1H), 8.23(s, 1H), 7.37-7.34 (d, 1H), 6.57 (s, 1H), 3.75-3.73 (t, 2H), 3.66-3.60 (m, 4H), 3.55-3.52 (m, 2H), 3.49-3.43 (t, 2H), 2.99 (s, 3H), 2.95-2.92 (t, 2H), 2.22 (s, 3H) |
| A-152 | 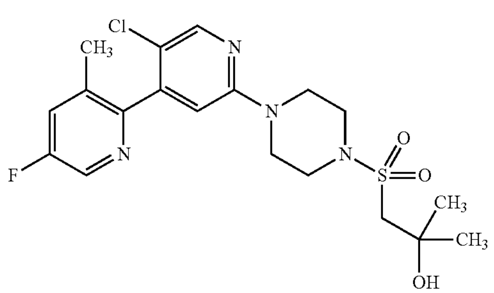 [SMILES: Cc1cc(F)cnc1-c1cc(N2CCN(S(=O)(=O)CC(C)(C)O)CC2)ncc1Cl] | 1-{[4-(5'-chloro-5-fluoro-3-methyl-2,4'-bipyridin-2'-yl)piperazin-1-yl]sulfonyl}-2-methylpropan-2-ol | 457.2 | ¹H NMR (400 MHz, CDCl₃): δ 8.37 (s, 1H), 8.23 (s, 1H), 7.37-7.34 (d, 1H), 6.59 (s, 1H), 3.68 (m, 4H), 3.43 (s, 1H), 3.35-3.30 (m, 4H), 2.22 (s, 3H), 1.45 (s, 6H) |
| A-153 | 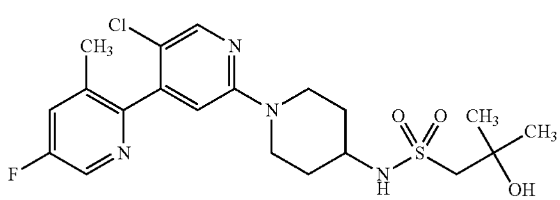 [SMILES: Cc1cc(F)cnc1-c1cc(N2CCC(NS(=O)(=O)CC(C)(C)O)CC2)ncc1Cl] | N-[1-(5'-chloro-5-fluoro-3-methyl-2,4'-bipyridin-2'-yl)piperidin-4-yl]-2-hydroxy-2-methylpropane-1-sulfonamide | 457.20 | ¹H NMR (400 MHz, CDCl₃): δ 8.37 (s, 1H), 8.19 (s, 1H), 7.36-7.33 (q, 1H), 6.57 (s, 1H), 4.41-4.39 (d, 1H), 4.22-4.20 (d, 2H), 3.58-3.56 (m, 1H), 3.29 (s, 1H), 3.25 (s, 2H), 3.05-2.98 (m, 2H), 2.21 (s, 3H), 2.08-2.05 (d, 2H), 1.51-1.50 (m, 2H), 1.43(s, 6H) |

TABLE 1-continued

| Example Number | Compound Name | LRMS m/z (M + H) | ¹H NMR |
|---|---|---|---|
| A-154 | N-[1-(3-chloro-5'-fluoro-3'-methyl-2,2'-bipyridin-6-yl)piperidin-4-yl]methanesulfonamide | 399.0 | ¹H NMR (400 MHz, DMSO-$d_6$) δ ppm 8.44 (d, J = 2.78 Hz, 1 H) 7.72 (dd, J = 9.73, 2.91 Hz, 1 H) 7.68 (d, J = 9.09 Hz, 1 H) 7.09 (d, J = 7.07 Hz, 1 H) 6.95 (d, J = 9.09 Hz, 1 H) 4.12 (d, J = 13.64 Hz, 2 H) 3.40 (d, J = 11.12 Hz, 1 H) 2.94-3.01 (m, 2 H) 2.92 (s, 3 H) 2.13 (s, 3 H) 1.85 (d, J = 13.39 Hz, 2 H) 1.28-1.46 (m, 2 H) |
| A-155 | 2'-{4-[(2-methoxyethyl)sulfonyl]piperazin-1-yl}-3,5-dimethyl-2,4'-bipyridine | 391.1 | ¹H NMR (400 MHz, chloroform-d) δ ppm 8.36-8.39 (m, 1 H) 8.08 (d, J = 5.05 Hz, 1 H) 7.44 (s, 1 H) 6.87 (t, J = 4.80 Hz, 1 H) 3.74-3.81 (m, 2 H) 3.61-3.68 (m, 2 H) 3.53-3.58 (m, 2 H) 3.51 (d, J = 5.31 Hz, 2 H) 3.47 (t, J = 7.45 Hz, 2 H) 3.00 (s, 3 H) 2.96 (t, J = 7.20 Hz, 2 H) 2.38 (s, 3 H) 2.22 (s, 3 H) |
| A-156 | 1-[4-(3,5-dimethyl-2,4'-bipyridin-2'-yl)piperazin-1-yl]-2-[(2R,6S)-2,6-dimethylmorpholin-4-yl]ethanone | 424.2 | ¹H NMR (400 MHz, DMSO-$d_6$) δ ppm 8.27-8.37 (m, 1 H) 8.18 (d, J = 5.05 Hz, 1 H) 7.53-7.62 (m, 1 H) 6.90 (s, 1 H) 6.79 (dd, J = 5.05, 1.01 Hz, 1 H) 3.64 (br. s., 2 H) 3.49-3.60 (m, 8 H) 3.16 (s, 2 H) 2.70 (s, 2 H) 2.23-2.35 (m, 6 H) 1.71 (t, J = 10.74 Hz, 2 H) 1.03 (d, J = 6.32 Hz, 6 H) |
| A-157 | 1-[4-(3,5-dimethyl-2,4'-bipyridin-2'-yl)piperazin-1-yl]-2-(morpholin-4-yl)ethanone | 396.2 | ¹H NMR (400 MHz, DMSO-$d_6$) δ ppm 8.33 (d, J = 1.77 Hz, 1 H) 8.19 (d, J = 5.05 Hz, 1 H) 7.57 (s, 1 H) 6.91 (s, 1 H) 6.80 (dd, J = 5.05, 1.01 Hz, 2 H) 3.54-3.63 (m, 10 H) 3.52 (br. s., 2 H) 3.20 (s, 2 H) 2.39-2.45 (m, 4 H) 2.31 (d, J = 6.32 Hz, 6 H) |

Smo Radioligand Competition Binding Assay

Membranes were prepared from a stable cell line created in HEK293FlpIn-TetR cells (Invitrogen) using Flp recombinase-mediated insertion of the pSecTag-FRT/V5-His vector containing a cDNA encoding amino acids 181-787 of human Smo fused to the murine Igk leader sequence to produce a cell surface expressed Smo 181-781 protein. Hygromycin-resistant clones were obtained and stained for LacZ expression (no expression indicates a correct knock-in of fusion cDNA). LacZ-negative cells were analyzed for binding tritiated Smo antagonists. For membrane preparation, the HEK293 cells expressing Smo 181-781 were grown to 90% confluence in nine to fifteen 245 mm×245 mm×22 mm dishes, washed with Dulbecco's PBS (15 mL per dish) and harvested via scraping in 10 mL of DPBS. The cells were collected and centrifuged at 1500 rpm (400×g) for 10 min at 4° C. The cell pellets were re-suspended in 40 mL of cold DPBS and washed by centrifugation at 2300 rpm (950×g max) for 10 minutes at 4° C. The supernatant was aspirated and the cell pellet was snap frozen in a methanol/dry ice bath and stored at −70° C. For membrane preparation, 15 mL of Membrane Preparation Buffer (50 mM Tris-HCl pH 7.5, 250 mM sucrose with Roche complete protease cocktail tablets) was added to the tube containing the cell pellet, then cells are rapidly thawed, and homogenized using an Ultra-Turrax T8 (IKA Labortechnik) set on "6" for 15 seconds for 5-6 times in icy water bath. This homogenate was diluted up to 50 mL using Membrane Preparation Buffer and centrifuged at 35,000 rpm in a Beckman Ti45 rotor (140,000×g) for 35 minutes at 4° C. followed by aspiration of the supernatant and re-suspension of the pellet in 5 mL of Assay Buffer (50 mM Tris-HCl pH 7.5, 100 mM NaCl, 25 mM $MgCl_2$, 1 mM EDTA, and 0.1% protease free bovine serum albumin). The re-suspended pellet was then homogenized in a glass tissue grinder. The re-suspended membranes were aliquoted (0.5 mL aliquots), snap frozen and stored at −70° C. Total protein in the membrane preparation was determined using the Pierce BCA protein assay (Pierce Chemical).

For the binding competition assay, 100 μL of Assay Buffer was added to all the wells of a 96 well GF/B filter plate (Millipore MultiScreen-HTS-FB cat# MSFBN6B50) for 10 minutes to pre-wet the filter prior to evacuation of the buffer (8 inches Hg for 8 seconds). To the pre-wet wells is added: 20 μL of Assay Buffer, 10 μL diluted test agent, 20 μL of a tritiated Smo antagonist (15 nM stock solution), and 50 μL of membrane preparation (40 μg total protein per well). The plates are sealed and mixed at room temperature for 5 min, incubated at room temperature for 2 hours, then washed 5 times with 100 μL/each of wash buffer and vacuum dried for 8 seconds at 8 inches Hg. The plate is then dried for one hour in a 60° C. oven prior to the addition of 45 μL of Microscint 20 (Packard, #6013621) to each well and incubation at RT for 30 minutes to 1 hour. The plate is counted in a TopCount scintillation counter (Perkin Elmer).

Data analysis uses Excel for % Inhibition and Graphpad Prism for $IC_{50}$ calculation. Total binding (TB, in the absence of inhibitors)=average of tritiated Smo antagonist 3 nM+Smo membrane (40 μg/wells (approx 5000-7000 CPM)). Non-specific binding (NSB)=average of tritiated Smo antagonist (3 nM)+cold Smo antagonist (30 μM)+Smo membrane (approx 600-1200 CPM). Specific binding (SB)=(total binding−non-specific binding). % Inhibition=[1−(compound Specific binding/control Specific binding)]×100%. $IC_{50}$ is calculated by fitting the data to the four parameter sigmoidal dose-response curve (variable slope) Y=Bottom+(Top-Bottom)/(1+10^(($LogEC_{50}$−X)*HillSlope)). X is the logarithm of the inhibitor concentration. Y is the response; Y starts at Bottom and goes to Top with a sigmoid shape.

Gli-Luc/MEF Assay

The Gli-Luc/MEF cells obtained from Gli-Luc transgenic mice contain a luciferase reporter gene under the control of the Gli response element. Luciferase activity stimulated with Sonic hedgehog ligand was inhibited by Smo inhibitors, and $IC_{50}$ was subsequently calculated.

Gli-Luc/MEF cells were grown in Knockout DMEM media (Invitrogen 10829-18) supplemented with 10% Heat inactive Fetal Bovine Serum (FBS, Hyclone), 2 mM L-glutamine (Invitrogen 25030-80), and 0.55 mM β-mercaptoethanol) until 90° A) confluence. On day one, cells were trypsinized and seeded into white 384-well plates (corning #3704) in 20 μL/well of OptiMEM media (Invitrogen 11058-021) that was supplemented with 1% heat inactive FBS and 1 mM sodium pyruvate at a concentration of 7,500 cells/well. Plates were incubated at 37° C. and 5% $CO_2$ overnight. On day two, cells were dosed with test compounds at a final concentration ranging from 3 μM to 50 μM at a 3-time series dilution. Immediately after dosing cells with compounds, recombinant mouse sonic hedgehog (Shh, R&D Systems 464-SH) was added to a final concentration of 2 μg/mL. The cells were incubated with compounds and Shh for 48 hours at 37° C. and 5% $CO_2$. Luciferase assays were conducted on Day 4 using the Bright-Glo Luciferase assay system (Promega E2620) according to Promega's protocol. Briefly, Bright-Glo luciferase reagent was made up and 25 μL were added to each well of the 384-well plate containing media. Plates were kept at room temperature for 5 minutes, and then read on an Envision Luminescence plate reader (Perkin-Elmer). $IC_{50}$ of the inhibition was calculated by using GraphPad Prism.

The results of the Smo radioligand competition binding assay (Smo % inhibition (inh.) and Smo $IC_{50}$ values) and the Gli-Luc/MEF assay (Gli $IC_{50}$ values) for the compounds tested are listed in Table 2.

TABLE 2

| Example Number | Smo % inh. @ 0.05 μM | Smo $IC_{50}$ (nM) | Gli $IC_{50}$ (nM) | Example Number | Smo % inh. @ 0.05 μM | Smo $IC_{50}$ (nM) | Gli $IC_{50}$ (nM) |
|---|---|---|---|---|---|---|---|
| A-7 | 45 | ND | ND | A-12 | 88 | 18.8 | 53.4 |
| A-8 | 92 | 18.7 | 39.2 | A-13 | 56 | 110 | 404 |
| A-9 | 65 | 75 | 226 | A-14 | 95 | 6.40 | 16.4 |
| A-10 | 75 | 32.1 | 209 | A-15 | 83 | 34.3 | 78.5 |
| A-11 | 78 | 32.9 | 152 | A-16 | 97.80 | 20.6 | 14.5 |
| A-17 | 63.00 | 511 | 60.0 | A-34 | 94.80 | 24.4 | 20.9 |
| A-18 | 58.90 | 343 | 82.0 | A-35 | 70.60 | 199 | 67.7 |
| A-19 | 91.50 | 37.5 | 10.1 | A-36 | 72.70 | 246 | 109 |
| A-20 | 64.60 | 407 | 109 | A-37 | 71.6 | 209 | 98.0 |
| A-21 | 65.90 | 297 | 114 | A-38 | 78.5 | 164 | 60.2 |
| A-22 | 81.50 | 110 | 42.0 | A-39 | 80.7 | 109 | 48.5 |
| A-23 | 59.50 | 417 | 194 | A-40 | 70.2 | 254 | 114 |
| A-24 | 69.30 | 243 | 126 | A-41 | 82.3 | 131 | 28.5 |
| A-25 | 72.10 | 239 | 197 | A-42 | 80.5 | 125 | 37.1 |
| A-26 | 69.90 | 359 | 189 | A-43 | 95.0 | 25.5 | 19.1 |
| A-27 | 75.70 | 107 | 21.1 | A-44 | 82.9 | 128 | 80.2 |
| A-28 | 68.90 | 212 | 146 nM | A-45 | 80.10 | 83.7 | 58.2 |
| A-29 | 89.30 | 52.3 | 42.5 | A-46 | 97.60 | 40.3 | 21.1 |
| A-30 | 77.70 | 160 | 246 | A-47 | 95.20 | 21.7 | 36.3 |
| A-31 | 89.20 | 43.4 | 20.8 | A-48 | 82 | 57 | 48 |
| A-32 | 86.60 | 77.9 | 27.4 | A-49 | 87 | 39 | 44 |
| A-33 | 76.90 | 172 | 113 | A-50 | 97.10 | 17.7 | 27.4 |
| A-51 | 87.8 | 35.8 | 23.6 | A-68 | 88.8 | 120 | 54.4 |
| A-52 | 90.6 | 54.3 | 28.0 | A-69 | 74.4 | 189 | 148 |
| A-53 | 93.3 | 38.2 | 27.3 | A-70 | 105 | 42.4 | 27.3 |
| A-54 | 86.1 | 64.9 | 55.4 | A-71 | 85.7 | 72.9 | 39.4 |
| A-55 | 83.7 | 63.3 | 25.2 | A-72 | 96.3 | 28.3 | 22.5 |
| A-56 | 80.5 | 106 | 41.6 | A-73 | 76.1 | 154 | 55.8 |
| A-57 | 87.9 | 90.7 | 78.2 | A-74 | 97.8 | 25.5 | 23 |
| A-58 | 70.3 | 184 | 38.8 | A-75 | 88.6 | 93.3 | 47.9 |
| A-59 | 89.5 | 71.4 | 21.2 | A-76 | 91.6 | 25.8 | 18.3 |
| A-60 | 83.8 | 67.0 | 57.4 | A-77 | 87.7 | 52.5 | 48.4 |
| A-61 | 91.9 | 40.9 | 37.1 | A-78 | 70.1 | 295 | 87.3 |
| A-62 | 72.4 | 234 | 106 | A-79 | 78.4 | 161 | 30.5 |
| A-63 | 82.5 | 137 | 83.6 | A-80 | 101 | 33.6 | 16.5 |
| A-64 | 78.1 | 157 | 109 | A-81 | 97.9 | 32.6 | 15.7 |
| A-65 | 78.5 | 145 | 124 | A-82 | 92.6 | 39.2 | 38.8 |
| A-66 | 81.7 | 162 | 94.0 | A-83 | 78.9 | 138 | 48.5 |
| A-67 | 70.4 | 217 | 164 | A-84 | 71.5 | 283 | 92.0 |
| A-85 | 92.7 | 42.4 | 116 | A-102 | 84 | 57.9 | 60.1 |
| A-86 | 81.5 | 112 | 116 | A-103 | 98 | 19.4 | 11.7 |
| A-87 | 81.8 | 134 | 123 | A-104 | 92.9 | 36 | 12.7 |
| A-88 | 85.6 | 49 | 53 | A-105 | 84.5 | 82.4 | 12.3 |
| A-89 | 94.6 | 28.5 | 24.4 | A-106 | 86 | 65.7 | 36.5 |
| A-90 | 82.5 | 111 | 66.9 | A-107 | 82.7 | 92.2 | 41.5 |
| A-91 | 92.7 | 26.3 | 28.6 | A-108 | 91.5 | 20.8 | 11.2 |
| A-92 | 79.8 | 132 | 59 | A-109 | 97.4 | 20.5 | 6.81 |
| A-93 | 97.5 | 9.84 | 12.4 | A-110 | 94.4 | 29.2 | 12.4 |
| A-94 | 88.0 | 44.2 | 28.4 | A-111 | 95 | 23.3 | 10.2 |
| A-95 | 94 | 37 | 32 | A-112 | 72.9 | 124 | 25.3 |
| A-96 | 84.1 | 102 | 62.5 | A-113 | 84 | 55.6 | 11.7 |
| A-97 | 95.4 | 30 | 13.3 | A-114 | 94.5 | 19.2 | 3.86 |
| A-98 | 96.6 | 12.4 | 9.4 | A-115 | 93 | 22 | 16 |
| A-99 | 94.4 | 33.1 | 23.9 | A-116 | 101 | 6.8 | 2.76 |
| A-100 | 85.6 | 113 | 50.2 | A-117 | 96 | 17 | 11 |
| A-101 | 89 | 72.4 | 30.2 | A-118 | 93.8 | 11.1 | 8.46 |
| A-119 | 88.5 | 58.9 | 22.9 | A-136 | 58.8 | 328 | 117 |
| A-120 | 93 | 40 | 29 | A-137 | 45.8 | ND | ND |
| A-121 | 101 | 11.6 | 4.25 | A-138 | 80.5 | 84.6 | 29.4 |

TABLE 2-continued

| Example Number | Smo % inh. @ 0.05 µM | Smo IC$_{50}$ (nM) | Gli IC$_{50}$ (nM) | Example Number | Smo % inh. @ 0.05 µM | Smo IC$_{50}$ (nM) | Gli IC$_{50}$ (nM) |
|---|---|---|---|---|---|---|---|
| A-122 | 103 | 14.7 | 5.49 | A-139 | 101 | 17.8 | 1.96 |
| A-123 | 90.4 | 26.7 | 14.1 | A-140 | 92 | 47.7 | 19.5 |
| A-124 | 79.9 | 100 | 25.3 | A-141 | 96.3 | 11.6 | 8.42 |
| A-125 | 82.3 | 95.6 | 32.3 | A-142 | 92.7 | 20.4 | 16.6 |
| A-126 | 96.1 | 15.2 | 10.3 | A-143 | 96.3 | 12.2 | 10.4 |
| A-127 | 97.8 | 11.5 | 5.03 | A-144 | 91.3 | 29.8 | 16.6 |
| A-128 | 95.0 | 31.3 | 15.2 | A-145 | 88.9 | 66.2 | 11.3 |
| A-129 | 88.4 | 54.3 | 8.12 | A-146 | 87.4 | 52.2 | 20.7 |
| A-130 | 81.3 | 110 | 35.5 | A-147 | 94.7 | 22.5 | 14.4 |
| A-131 | 92.7 | 30.5 | 20.7 | A-148 | 91.7 | 33.4 | 18.4 |
| A-132 | 92.0 | 38.2 | 33.7 | A-149 | 90.6 | 20.7 | 10.1 |
| A-133 | 94.3 | 16.5 | 11.7 | A-150 | 76.9 | 80.9 | 29.5 |
| A-134 | 80.8 | 114 | 37.7 | A-151 | 101% | 7.11 | 8.76 |
| A-135 | 94 | 40 | 7.6 | A-152 | 95.9 | 11.4 | 11.2 |
| A-153 | 96.4 | 10.6 | 4.71 | A-156 | 102 | 12.1 | 6.57 |
| A-154 | 94.3 | 29.2 | 39.5 | A-157 | 101 | 14.8 | 3.58 |
| A-155 | 77.1 | 97 | 45 | | | | |

Down Regulation of Smo Targeted Gene Gli1 in the Brain by A-116

The following study demonstrated the inhibition of Smo in the brain by A-116 in a primary medulloblastoma model.

In this study, 6-week-old Ptch1+/−p53−/− primary medulloblastoma mice (n=3 per group) were treated with 30 mg/kg of A-116 or vehicle (0.5% methylcellulose (MC)) once daily for 4 days by oral gavage. On day 4, at 6 hours post last dose, mice were euthanized and tumor bearing cerebella were removed. Total RNA was extracted from the tumor tissue together with the cerebella using the RNeasy Mini Kit (Qiagen). Subsequently, cDNA was synthesized from the RNA using High Capacity cDNA Reverse Transcription Kit (Applied Biosystems) according to the protocol provided by the vendor. Quantitative real-time PCR analysis of Smo targeted gene Gli1 expression level was performed using RT-PCR ABI Prism 7900 sequence detection system (Applied Biosystems). The results showed that in the A-116-treated group, the Gli1 level was significantly decreased to 4.5±0.4% of vehicle control (Gli1 in the vehicle treated group is normalized to 100%). This study demonstrated that A-116 was able to target Smo in the brain leading to the down regulation of Gli1.

Assessment of Brain Penetration of A-116 in Rats

The following study demonstrated brain penetration of A-116 in rats.

An in vivo study in rats was conducted to assess the extent of brain penetration of A-116. In this study, approximately 10-week-old (250 grams body weight) Wistar rats were dosed once with 10 mg/kg of A-116 subcutaneously. Three rats per group were euthanized 1 hour, 4 hours, and 7 hours post dose. The plasma, the whole brain, and the cerebral spinal fluid (CSF) were collected to determine the tissue concentrations using HPLC-MS/MS. At 1 hour, 4 hours and 7 hours, the respective brain concentrations were 201±52 ng/g, 224±231 ng/g, and 28 ng/g of tissue. The total plasma concentrations were 2240±296 ng/mL, 2220±1780 ng/mL, and 287±75 ng/mL at 1 hour, 4 hours and 7 hours, respectively. To calculate the unbound plasma concentrations, the total plasma concentrations were multiplied by 0.067, a previously determined unbound fraction of rat plasma protein binding. The resulting unbound plasma concentrations were 150±20 ng/mL (1 hour), 149±119 ng/mL (4 hours), and 19.2±5.0 ng/mL (7 hours). The respective CSF concentrations were 64.4±12.0 ng/mL, 72.1±71.9 ng/mL, and 3.9±2.3 ng/mL at 1 hour, 4 hours, and 7 hours post dose. Since A-116 is not a P-glycoprotein substrate, the CSF concentration was used as a surrogate for unbound concentrations in the brain. To determine the extent of brain penetration, a ratio of the CSF concentration to the unbound plasma concentration was calculated. At 1 hour, 4 hours, and 7 hours, the ratios were 0.43±0.03, 0.44±0.1, and 0.19±0.06, respectively. The study demonstrated that a significant amount of A-116, approximately 40% of unbound A-116 in the plasma, was able to cross the blood brain barrier in rats (within 4 hours post dose).

What is claimed is:

1. A compound of formula (1),

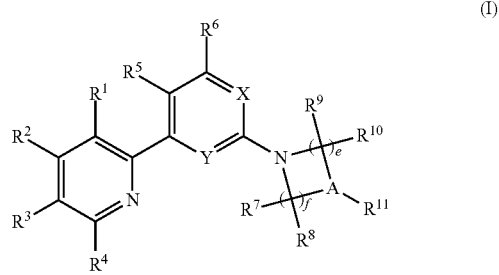

(I)

wherein:
A is selected from N and C—$R^{13}$;
X is N and Y is C—$R^{12}$;
$R^1$, $R^2$, $R^3$, $R^4$, $R^6$, $R^{12}$ and $R^{13}$ are independently selected from the group consisting of hydrogen, —$(CR^{14}R^{15})_n$halo, —$(CR^{14}R^{15})_n$CN, —$(CR^{14}R^{15})_n$CF$_3$, —$(CR^{14}R^{15})_n$($C_1$-$C_{10}$alkyl), —$(CR^{14}R^{15})_n$($C_2$-$C_6$alkenyl), —$(CR^{14}R^{15})_n$($CR^{14}R^{15})_n$($C_2$-$C_6$alkynyl), —$CR^{14}R^{15})_n$NR$^{16}$R$^{17}$, —$(CR^{14}R^{15})_n$OR$^{16}$, —$(CR^{14}R^{15})_n$C(O)R$^{16}$, —$(CR^{14}R^{15})_n$C(O)R$^{16}$, —$(CR^{14}R^{15})_n$S(O)R$^{16}$, —$(CR^{14}R^{15})_n$S(O)$_2$R$^{16}$, —$(CR^{14}R^{15})_n$S(O)$_2$NR$^{16}$R$^{17}$, —$(CR^{14}R^{15})_n$NR$^{16}$S(O)$_2$R$^{17}$, —$(CR^{14}R^{15})_n$($C_3$-$C_{10}$cycloalkyl), —$(CR^{14}R^{15})_n$(3-12 membered heterocyclyl), —$(CR^{14}R^{15})_n$($C_6$-$C_{10}$aryl), and —$(CR^{14}R^{15})_n$(5-12 membered heteroaryl);
$R^5$ is selected from the group consisting of halo, $C_1$-$C_{10}$ alkyl, and —CF$_3$;
each $R^7$, $R^8$, $R^9$, and $R^{10}$ is independently selected from the group consisting of hydrogen, —$(CR^{14}R^{15})_n$halo, —$(CR^{14}R^{15})_n$CN, —$(CR^{14}R^{15})_n$CF$_3$, —$(CR^{14}R^{15})_n$($C_1$-$C_{10}$alkyl), —$(CR^{14}R^{15})_n$($C_2$-$C_6$alkenyl), —$(CR^{14}R^{15})_n$($C_2$-$C_6$alkenyl), —$(CR^{14}R^{15})_n$NR$^{16}$R$^{17}$, —$(CR^{14}R^{15})_n$OR$^{16}$, —$(CR^{14}R^{15})_n$C(O)R$^{16}$, 13 $(CR^{14}R^{15})_n$C(O))R$^{16}$, —$(CR^{15}R^{15})_n$S(O)$_2$R$^{16}$, —$(CR^{14}R^{15})_n$S(O)$_2$NR$^{16}$R$^{17}$, —$(CR^{13}R^{15})_n$NR$^{16}$S(O)$_2$R$^{17}$, —$(CR^{14}R^{15})_n$($C_3$-$C_{10}$cycloalkyl), —$(CR^{14}R^{15})_n$(3-12 membered heterocyclyl), —$(CR^{14}R^{15})_n$($C_6$-$C_{10}$aryl), and —$(CR^{14}R^{15})_n$(5-12 membered heteroaryl); or each $R^7$ and $R^8$, or $R^9$ and $R^{10}$, together with the carbon to which they are attached, may combine to form a carbonyl group; or each $R^7$ and $R^9$, or $R^8$ and $R^{10}$, may combine to form a 5 or 6 membered ring when said $R^7$ and said $R^9$, or said $R^8$ and said $R^{10}$, are each —$(CR^{14}R^{15})_n$($C_1$-$C_{10}$alkyl);
$R^{11}$ is selected from the group consisting of hydrogen —$(CR^{14}R^{15})_n$halo, —$(CR^{14}R^{15})$—$_n$CN, —$(CR^{14}R^{15})_n$CF$_3$, —$(CR_{14}R^{15})_n$($C_1$-$C_{10}$alkyl), —$(CR^{14}R^{15})_n$($C_2$-$C_6$alkenyl), —$(CR^{14}R^{15})_n$($C_2$-$C_6$alkynyl), —$(CR^{14}R^{15})_n$NR$^A$R$^B$, —$(CR^{14}R^{15})_n$NR$^A$OR$^B$, —$(CR^{14}R^{15})_n$NR$^A$C(O)R$^B$, —$(CR^{14}R^{15})_n$NR$^A$C(O)

OR$^B$, —(CR$^{14}$R$^{15}$)$_n$OR$^A$, —(CR$^{14}$R$^{15}$)$_n$C(O)R$^A$, —(CR$^{14}$R$^{15}$)$_n$C(O)OR$^A$, —(CR$^{14}$R$^{15}$)$_n$S(O)R$^A$, —(CR$^{14}$R$^{15}$)$_n$S(O)$_2$R$^A$, —(CR$^{14}$R$^{15}$)$_n$S(O)$_2$NR$^A$R$^B$, —(CR$^{14}$R$^{15}$)$_n$NR$^A$S(O)$_2$R$^B$, —(CR$^{14}$R$^{15}$)$_n$C(O)NR$^A$R$^B$, —(CR$^{14}$R$^{15}$)$_n$(C$_3$-C$_{10}$cycloalkyl), —(CR$^{14}$R$^{15}$)$_n$(3-12 membered heterocyclyl), —(CR$^{14}$R$^{15}$)$_n$(C$_6$-C$_{10}$aryl), and —(CR$^{14}$R$^{15}$)$_n$(5-12 membered heteroaryl wherein each of said C$_3$-C$_{10}$cycloalkyl, said 3-12 membered heterocyclyl, said C$_6$-C$_{10}$aryl, and said 5-12 membered heteroaryl groups is substituted with one or more R$^{14}$ groups; or R$^{11}$ and R$^{13}$, together with the carbon to which they are attached, may combine to form a 3-12 membered heterocyclyl group which is substituted with one or more R$^{14}$ groups;

R$^A$ and R$^B$ are independently selected from the group consisting of hydrogen, —(CR$^{14}$R$^{15}$)$_n$halo, —(CR$^{14}$R$^{15}$)$_n$CN, —(CR$^{14}$R$^{15}$)$_n$CF$_3$, —(CR$^{14}$R$^{15}$)$_n$(C$_1$-C$_{10}$alkyl), —(CR$^{14}$R$^{15}$)$_n$(C$_2$-C$_5$alkenyl), —(CR$^{14}$R$^{15}$)$_n$(C$_2$-C$_6$alkynyl), —(CR$^{14}$R$^{15}$)$_n$NR$^{16}$R$^{17}$, —(CR$^{14}$R$^{15}$)$_n$NR$^{16}$OR$^{17}$, —(CR$^{14}$R$^{15}$)$_n$NR$^{16}$C(O)R$^{17}$, —(CR$^{14}$R$^{15}$)$_n$NR$^{16}$C(O)OR$^{17}$, —(CR$^{14}$R$^{15}$)$_n$OR$^{16}$, —(CR$^{14}$R$^{15}$)$_n$C(O)R$^{16}$, —(CR$^{14}$R$^{15}$)$_n$C(O)OR$^{16}$, —(CR$^{14}$R$^{15}$)$_n$S(O)R$^{16}$, —(CR$^{14}$R$^{15}$)$_n$S(O)$_2$R$^{16}$, —(CR$^{14}$R$^{15}$)$_n$S(O)$_2$NR$^{16}$R$^{17}$, —(CR$^{14}$R$^{15}$)$_n$NR$^{16}$S(O)$_2$R$^{17}$, —(CR$^{14}$R$^{15}$)$_n$(C$_3$-C$_{10}$cycloalkyl), —(CR$^{14}$R$^{15}$)$_n$(3-12 membered heterocyclyl), —(CR$^{14}$R$^{15}$)$_n$(C$_6$-C$_{10}$aryl), and —(CR$^{14}$R$^{15}$)$_n$-(5-12 membered heteroaryl), wherein each of said C$_3$-C$_{10}$cycloalkyl, said 3-12 membered heterocyclyl, said C$_6$-C$_{10}$aryl, and said 5-12 membered heteroaryl groups is substituted with one or more R$^{14}$ groups;

each R$^{14}$, R$^{15}$, R$^{16}$ and R$^{17}$ is independently selected from the group consisting of hydrogen, —(CR$^{24}$R$^{25}$)$_n$halo, —(CR$^{24}$R$^{25}$)$_n$CF$_3$, —(CR$^{24}$R$^{25}$)$_n$(C$_1$-C$_{10}$alkyl), —(CR$^{24}$R$^{25}$)$_n$(C$_2$-C$_6$alkenyl), —(CR$^{24}$R$^{25}$)$_n$(C$_2$-C$_6$alkynyl), —(CR$^{24}$R$^{25}$)$_n$OR$^{18}$, —(CR$^{24}$R$^{25}$)$_n$NR$^{18}$R$^{19}$, —(CR$^{24}$R$^{25}$)$_n$CN, —(CR$^{24}$R$^{25}$)$_n$S(O)$_2$R$^{18}$, —CR$^{24}$R$^{25}$)$_n$S(O)$_2$NR$^{18}$R$^{19}$, —(CR$^{24}$R$^{25}$)$_n$(C$_3$-C$_{10}$cycloalkyl), —CR$^{24}$R$^{25}$)$_n$(3-12 membered heterocyclyl), —(CR$^{24}$R$^{25}$)$_n$(C$_6$-C$_{10}$aryl), and —(CR$^{24}$R$^{25}$)$_n$(5-12 membered heteroaryl), wherein each of said C$_3$-C$_{10}$cycloalkyl, said 3-12 membered heterocyclyl, said C$_6$-C$_{10}$aryl, and said 5-12 membered heteroaryl groups is substituted with one or more R$^{18}$ groups;

each R$^{18}$, R$^{19}$, R$^{24}$ and R$^{25}$ is independently selected from the group consisting of hydrogen, —(CH$_2$)$_n$(C$_1$-C$_{10}$alkyl), —(CH$_2$)$_n$(C$_3$-C$_{10}$cycloalkyl), —(CH$_2$)$_n$(3-12 membered heterocyclyl), —(CH$_2$)$_n$(C$_6$-C$_{10}$aryl), and —(CH$_2$)$_n$(5-12 membered heteroaryl):

e is 2;
f is 2; and
each n is independently 0, 1, 2, 3, 4, 5, or 6; or
a pharmaceutically acceptable salt thereof.

2. The compound of claim 1, or a pharmaceutically acceptable salt thereof, wherein R$^1$, R$^2$, R$^3$, R$^4$, and R$^6$ are independently selected from the group consisting of hydrogen, -halo, —CN, —CF$_3$, and —(C$_1$-C$_{10}$alkyl).

3. The compound of claim 1, or a pharmaceutically acceptable salt thereof, wherein each R$^7$, R$^8$, R$^9$, and R$^{10}$ is independently selected from the group consisting of hydrogen, -halo, —CN, —CF$_3$, and —(C$_1$-C$_{10}$alkyl).

4. The compound of claim 1, or a pharmaceutically acceptable salt thereof, wherein R$^5$ is halo.

5. The compound of claim 1, or a pharmaceutically acceptable salt thereof, wherein R$^{12}$ is selected from the group consisting of hydrogen, -halo, —CN, —CF$_3$ and —(C$_1$-C$_{10}$alkyl).

6. The compound of claim 1, or a pharmaceutically acceptable salt thereof, wherein R$^{11}$ is selected from the group consisting of —(CR$^{14}$R$^{15}$)$_n$C(O)R$^A$, —(CR$^{14}$R$^{15}$)$_n$NR$^A$C(O)R$^B$, —(CR$^{14}$R$^{15}$)$_n$S(O)$_2$R$^A$, —(CR$^{14}$R$^{15}$)$_n$S(O)$_2$NR$^A$R$^B$, and —(CR$^{14}$R$^{15}$)$_n$NR$^A$S(O)$_2$R$^B$.

7. The compound of claim 1, or a pharmaceutically acceptable salt thereof, wherein A is N.

8. The compound of claim 7, or a pharmaceutically acceptable salt thereof, wherein R$^{11}$ is —C(O)R$^A$ or —S(O)$_2$R$^A$.

9. The compound of claim 8, or a pharmaceutically acceptable salt thereof, wherein:
R$^5$ is F or Cl;
R$^{11}$ is C(O)R$^A$; and
R$^A$ is —(CR$_{14}$R$^{15}$)$_n$S(O)$_2$R$^{16}$.

10. A compound which is:

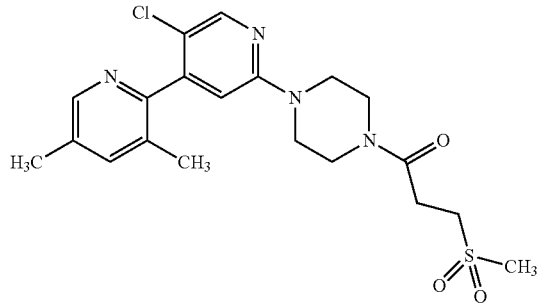

or a pharmaceutically acceptable salt thereof.

11. A compound of formula (II),

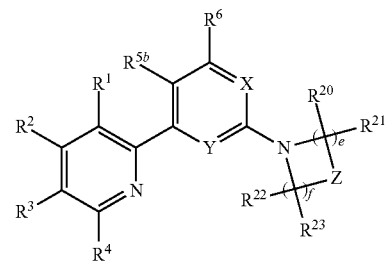

wherein:
X is N and Y is C—R$^{12}$;
Z is NR$^{11b}$ or CR$^{13}$NR$^{14}$R$^{11b}$;
R$^1$, R$^2$, R$^3$, R$^4$, R$^{5b}$, R$^6$, R$^{12}$ and R$^{13}$ are independently selected from the group comsisting of hydrogen, —(CR$^{14}$R$^{15}$)$_n$halo, —(CR$^{14}$R$^{15}$)$_n$CN, —(CR$^{14}$R$^{15}$)$_n$CF$_3$, —(CR$^{14}$R$^{15}$)$_n$(C$_1$-C$_{10}$alkyl), —(CR$^{14}$R$^{15}$)$_n$(C$_2$-C$_6$alkenyl), —(CR$^{14}$R$^{15}$)$_n$(C$_2$-C$_6$alkynyl), —(CR$^{14}$R$^{15}$)$_n$NR$^{16}$R$^{17}$, —(CR$^{14}$R$^{15}$)$_n$OR$^{16}$, —(CR$^{14}$R$^{15}$)$_n$C(O)R$^{16}$, —(CR$^{14}$R$^{15}$)$_n$C(O)OR$^{16}$, —(CR$^{14}$R$^{15}$)$_n$S(O)R$^{16}$, —(CR$^{14}$R$^{15}$)$_n$S(O)$_2$R$^{16}$, —(CR$^{14}$R$^{15}$)$_n$S(O)$_2$NR$^{16}$R$^{17}$, —(CR$^{14}$R$^{15}$)$_n$NR$^{16}$S(O)$_2$R$^{17}$, —(CR$^{14}$R$^{15}$)$_n$(C$_3$-C$_{10}$cycloalkyl), —(CR$^{14}$R$^{15}$)$_n$(3-12 membered heterocyclyl), —(CR$^{14}$R$^{15}$)$_n$(C$_6$-C$_{10}$aryl), and —(CR$^{14}$R$^{15}$)$_n$(5-12 membered heteroaryl);

each $R^{20}$, $R^{21}$, $R^{22}$ and $R^{23}$ is indpendently selected from the group consisting of hydrogen, $-(CR^{14}R^{15})_n$halo, $-(CR^{14}R^{15})_n$CN, $-(CR^{14}R^{15})_n$CF$_3$, $-(CR^{14}R^{15})_n$(C$_1$-C$_{10}$alkyl), $-(CR^{14}R^{15})_n$(C$_2$-C$_6$alkenyl), $-(CR^{14}R^{15})_n$(C$_2$-C$_6$alkynyl), $-(CR^{14}R^{15})_n$NR$^{16}$R$^{17}$, $-(CR^{14}R^{15})_n$OR$^{16}$, $-(CR^{14}R^{15})_n$C(O)R$^{16}$, $-(CR^{14}R^{15})_n$C(O)OR$^{16}$, $-(CR^{14}R^{15})_n$S(O)R$^{16}$, $-(CR^{14}R^{15})_n$S(O)$_2$R$^{16}$, $-(CR^{14}R^{15})_n$S(O)$_2$NR$^{16}$R$^{17}$, $-(CR^{14}R^{15})_n$NR$^{16}$S(O)$_2$R$^{17}$, $-(CR^{14}R^{15})_n$(C$_3$-C$_{10}$cycloalkyl), $-(CR^{14}R^{15})_n$(3-12 membered heterocyclyl), $-(CR^{14}R^{15})_n$(C$_6$-C$_{10}$aryl), and $-(CR^{14}R^{15})_n$(5-12 membered heteroaryl); or each $R^{20}$ and $R^{21}$, or $R^{22}$ and $R^{23}$, together with the carbon to which they are attached, may combine to form a carbonyl group; or each $R^{20}$ and $R^{22}$, or $R^{21}$ and $R^{23}$, may combine to form a 5 or 6 membered ring when said $R^{20}$ and said $R^{22}$, or said $R^{21}$ and said $R^{23}$, are each $-(CR^{14}R^{15})_n$(C$_1$-C$_{10}$alkyl);

$R^{11b}$ is C(O)R$^A$ or S(O)$_2$R$^A$;

$R^A$ is selected from the a group consisting of $-(CR^{14}R^{15})_n$CF$_3$, $-(CR^{14}R^{15})_n$(C$_1$-C$_{10}$alkyl), $-(CR^{14}R^{15})_n$(C$_2$-C$_6$alkenyl), $-(CR^{14}R^{15})_n$(C$_2$-C$_6$alkynyl), $-(CR^{14}R^{15})_n$NR$^{16}$R$^{17}$, $-(CR^{14}R^{15})_n$NR$^{16}$OR$^{17}$, $-(CR^{14}R^{15})_n$NR$^{16}$C(O)R$^{17}$, $-(CR^{14}R^{15})_n$NR$^{16}$C(O)OR$^{17}$, $-(CR^{14}R^{15})_n$NR$^{16}$S(O)$_2$R$^{17}$, $-(CR^{14}R^{15})_n$(C$_3$-C$_{10}$cycloalkyl), $-(CR^{14}R^{15})_n$(3-12 membered heterocyclyl), $-(CR^{14}R^{15})_n$(C$_6$-C$_{10}$aryl), and $-(CR^{14}R^{15})_n$(5-12 membered heteroaryl), $-(CR^{14}R^{15})_m$halo, $-(CR^{14}R^{15})_m$CN, $-(CR^{14}R^{15})_m$OR$^{16}$, $-(CR^{14}R^{15})_m$C(O)R$^{16}$, $-(CR^{14}R^{15})_m$C(O)OR$^{16}$, $-(CR^{14}R^{15})_m$S(O)R$^{16}$, $-(CR^{14}R^{15})_m$S(O)$_2$R$^{16}$, and $-(CR^{14}R^5)_m$S(O)$_2$NR$^{16}$R$^{17}$, wherein said C$_3$-C$_{10}$cycloalkyl, said 3-12 membered heterocyclyl, said C$_6$-C$_{10}$aryl, and said 5-12 membered heteroaryl are each substituted with one or more R$^{14}$ groups;

each $R^{14}$, $R^{15}$, $R^{16}$ and $R^{17}$ is independently selected from the group consisting of hydrogen, $-(CR^{24}R^{25})_n$halo, $-(CR^{24}R^{25})_n$CF$_3$, $-(CR^{24}R^{25})_n$CF$_3$, $-(CR^{24}R^{25})_n$C$_1$-C$_{10}$alkyl, $-(CR^{24}R^{25})_n$C$_2$-C$_6$alkenyl, $-(CR^{24}R^{25})_n$C$_2$-C$_6$alynyl, $-(CR^{24}R^{25})_n$OR$^{18}$, $-(CR^{24}R^{25})_n$NR$^{18}$R$^{19}$, $-(CR^{24}R^{25})_n$CN, $-(CR^{24}R^{25})_n$S(O)$_2$R$^{18}$, $-(CR^{24}R^{25})_n$S(O)$_2$NR$^{18}$R$^{19}$, $-(CR^{24}R^{25})_n$C$_3$-C$_{10}$cycloalkyl, $-(CR^{24}R^{25})_n$3-12 membered heterocyclyl, $-(CR^{24}R^{25})_n$C$_6$-C$_{10}$aryl, and $-(CR^{24}R^{25})_n$5-12 membered heteroaryl, wherein each of said C$_3$-C$_{10}$cycloalkyl, said 3-12 memebered heterocyclyl, said C$_6$-C$_{10}$aryl, and said 5-12 membered heteroaryl groups is substituted with one or more R$^{18}$ groups;

each $R^{18}$, $R^{19}$, $R^{24}$ and $R^{25}$ is independently selected from the group consisting of hydrogen, $-(CH_2)_n$(C$_1$-C$_{10}$alkyl), $-(CH_2)_n$(C$_3$-C$_{10}$cycloalkyl), $-(CH_2)_n$(3-12 membered heterocyclyl), $-(CH_2)_n$(C$_6$-C$_{10}$aryl), and $-(CH_2)_n$(5-12 membered heteroaryl);

e is 2;

f is 2;

each n is independently 0, 1, 2, 3, 4, 5, or 6; and each m is independently 0, 1, 2, 3, 4, 5, or 6; or a pharmaceutically acceptable salt thereof.

12. The compound of claim 11, or a pharmaceutically acceptable salt thereof, wherein R$^1$, R$^2$, R$^3$, R$^4$, and R$^6$ are independently selected from the group consisting of hydrogen, -halo, $-$CN, $-$CF$_3$, and $-$(C$_1$-C$_{10}$alkyl).

13. The compound of claim 11, or a pharmaceutically acceptable salt thereof, wherein each R$^{20}$, R$^{21}$, R$^{22}$, and R$_{23}$ is independently selected from the group consisting of hydrogen, -halo, $-$CN, $-$CF$_3$, and $-$(C$_1$-C$_{10}$alkyl).

14. The compound of claim 11, or a pharmaceutically acceptable salt thereof, wherein R$^{5b}$ is selected from the group consisting of hydrogen, -halo, $-$CN, $-$CF$_3$, and $-$(C$_1$-C$_{10}$alkyl).

15. The compound of claim 11, or a pharmaceutically acceptable salt thereof, wherein R$^{12}$ is selected from the group consisting of hydrogen, -halo, $-$CN, $-$CF$_3$, and $-$(C$_1$-C$_{10}$alkyl).

16. The compound of claim 11, or a pharmaceutically acceptable salt thereof, wherein Z is NR$^{11b}$.

17. The compound of claim 16, or a pharmaceutically acceptable salt thereof, wherein:

R$^{5b}$ is hydrogen, chloro, or fluoro;

R$^{11b}$ is C(O)R$^A$; and

R$^A$ is selected from the group consisting of $-(CR^{14}R^{15})_n$(C$_1$-C$_{10}$alkyl), $-(CR^{14}R^{15})_n$NR$^{16}$R$^{17}$, $-(CR^{14}R^{15})_m$OR$^{16}$, $-(CR^{14}R^{15})_m$C(O)R$^{16}$, and $-(CR^{14}R^{15})_m$S(O)$_2$R$^{16}$.

18. A pharmaceutical composition comprising a compound of claim 1, or a pharmaceutically acceptable salt thereof, and a pharmaceutically acceptable carrier or diluent.

\* \* \* \* \*

UNITED STATES PATENT AND TRADEMARK OFFICE
CERTIFICATE OF CORRECTION

PATENT NO. : 9,056,865 B2  
APPLICATION NO. : 13/880298  
DATED : June 16, 2015  
INVENTOR(S) : Sajiv Krishnan Nair and Simon Paul Planken Page 1 of 1

It is certified that error appears in the above-identified patent and that said Letters Patent is hereby corrected as shown below:

In the claims:

Column 132, line 34, delete "-$(CR^{14}R^{15})_n(CR^{14}R^{15})_n$ ($C_2$-$C_6$alkynyl)" and insert -- -$(CR^{14}R^{15})_n$ ($C_2$-$C_6$alkynyl) --

Column 132, line 36, delete duplicate "-$(CR^{14}R^{15})_nC(O)R^{16}$" and insert -- -$(CR^{14}R^{15})_nC(O)OR^{16}$ --

Column 132, line 49, delete "-$(CR^{14}R^{15})_n(C_2$-$C_6$alkenyl)" and insert -- -$(CR^{14}R^{15})_n(C_2$-$C_6$alkynyl) --

Column 132, line 50, delete "13"

Column 132, line 51, delete "$(CR^{14}R^{15})_nC(O))R^{16}$" and insert -- -$(CR^{14}R^{15})_nC(O)OR^{16}$ --

Column 133, line 41, delete "-$CR^{24}R^{25)}{}_nS(O)_2NR^{18}R^{19}$" and insert -- -$(CR^{24}R^{25})_nS(O)_2NR^{18}R^{19}$ --

Column 135, line 38, delete duplicate "-$(CR^{24}R^{25})_nCF_3$,"

Column 135, line 40, delete "$C_2$-$C_6$alynyl," and insert -- $C_2$-$C_6$alkynyl, --

Column 136, line 2, delete "memebered" and insert -- membered --

Column 136, line 20, delete "$R_{23}$" and insert -- $R^{23}$ --

Signed and Sealed this  
Twelfth Day of July, 2016

Michelle K. Lee  
*Director of the United States Patent and Trademark Office*